(12) United States Patent
Gohimukkula et al.

(10) Patent No.: US 8,741,900 B2
(45) Date of Patent: Jun. 3, 2014

(54) PHENYL-HETEROARYL DERIVATIVES AND METHODS OF USE THEREOF

(71) Applicant: TransTech Pharma, LLC, High Point, NC (US)

(72) Inventors: Devi R. Gohimukkula, Jamestown, NC (US); David Jones, Milford, OH (US); Ghassan Qabaja, Jamestown, NC (US); Jeff J. Zhu, Winston-Salem, NC (US); Jeremy T. Cooper, High Point, NC (US); William K. Banner, Greensboro, NC (US); Kurt Sundermann, Summerfield, NC (US); Muralidhar Bondlela, Greensboro, NC (US); Mohan Rao, Greensboro, NC (US); Pingzhen Wang, Kernersville, NC (US); Raju B. Gowda, Oak Ridge, NC (US); Robert C. Andrews, Jamestown, NC (US); Suparna Gupta, Greensboro, NC (US); Anitha Hari, High Point, NC (US); Rongyuan Xie, Greensboro, NC (US)

(73) Assignee: TransTech Pharma, LLC, High Point, NC (US)

( * ) Notice: Subject to any disclaimer, the term of this patent is extended or adjusted under 35 U.S.C. 154(b) by 0 days.

(21) Appl. No.: 13/772,685

(22) Filed: Feb. 21, 2013

(65) Prior Publication Data

US 2013/0197007 A1    Aug. 1, 2013

Related U.S. Application Data

(62) Division of application No. 13/028,036, filed on Feb. 15, 2011, now Pat. No. 8,431,575.

(60) Provisional application No. 61/305,572, filed on Feb. 18, 2010.

(51) Int. Cl.
*A61K 31/50* (2006.01)
*A61K 31/501* (2006.01)

(52) U.S. Cl.
USPC ..................... 514/252.03; 544/224

(58) Field of Classification Search
USPC ..................... 514/252.03; 544/238
See application file for complete search history.

(56) References Cited

U.S. PATENT DOCUMENTS

| | | |
|---|---|---|
| 2,728,768 A | 12/1955 | Leanza et al. |
| 4,008,232 A | 2/1977 | Lacefield |
| 4,265,874 A | 5/1981 | Bonsen et al. |
| 4,356,108 A | 10/1982 | Schwab et al. |
| 5,202,424 A | 4/1993 | Vlassara et al. |
| 5,449,676 A | 9/1995 | Amschler et al. |
| 5,585,344 A | 12/1996 | Vlassara et al. |
| 5,864,018 A | 1/1999 | Morser et al. |
| 5,939,526 A | 8/1999 | Gaugler et al. |
| 5,965,578 A | 10/1999 | Graham et al. |
| 6,221,667 B1 | 4/2001 | Reiner et al. |
| 6,274,615 B1 | 8/2001 | Pappolla et al. |
| 6,472,145 B2 | 10/2002 | Reiner et al. |
| 6,613,801 B2 | 9/2003 | Mjalli et al. |
| 6,664,256 B1 | 12/2003 | Ohkuchi et al. |
| 6,677,299 B2 | 1/2004 | Stern et al. |
| 6,825,164 B1 | 11/2004 | Stern et al. |
| 7,067,554 B2 | 6/2006 | Mjalli et al. |
| 7,087,632 B2 | 8/2006 | Mjalli et al. |
| 7,300,931 B2 | 11/2007 | Hangauer, Jr. |
| 7,329,684 B2 | 2/2008 | Mjalli et al. |
| 7,361,678 B2 | 4/2008 | Mjallii et al. |
| 7,423,177 B2 | 9/2008 | Mjalli et al. |
| 7,714,013 B2 | 5/2010 | Mjalli et al. |
| 7,737,285 B2 | 6/2010 | Mjalli et al. |
| 7,776,919 B2 | 8/2010 | Mjalli et al. |
| 7,994,179 B2 | 8/2011 | Johannesson et al. |
| 2001/0039256 A1 | 11/2001 | Stern et al. |

(Continued)

FOREIGN PATENT DOCUMENTS

| | | |
|---|---|---|
| CA | 2296102 A1 | 1/1999 |
| CA | 2507026 A1 | 6/2004 |

(Continued)

OTHER PUBLICATIONS

M. Spite et al., 107 Circulation Research, 1170-1184, 1171 (2010).*

(Continued)

*Primary Examiner* — Deepak Rao
*Assistant Examiner* — Alexander R Pagano
(74) *Attorney, Agent, or Firm* — Samuel B. Rollins

(57) ABSTRACT

The present invention provides phenyl-heteroaryl derivatives of Formula (I) and pharmaceutically acceptable salts thereof

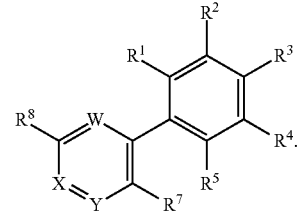

Formula (I)

These compounds are useful in the treatment of RAGE-mediated diseases such as Alzheimer's Disease.

The present invention further relates to methods for the preparation of compounds of Formula (I) and pharmaceutically acceptable salts thereof, pharmaceutical compositions comprising such compounds, and the use of such compounds and/or pharmaceutical compositions in treating RAGE-mediated diseases.

8 Claims, No Drawings

(56) References Cited

U.S. PATENT DOCUMENTS

| | | |
|---|---|---|
| 2002/0122799 A1 | 9/2002 | Stern et al. |
| 2005/0026811 A1 | 2/2005 | Mjalli et al. |
| 2005/0272777 A1 | 12/2005 | Doherty et al. |
| 2006/0069102 A1 | 3/2006 | Leban et al. |
| 2006/0160804 A1 | 7/2006 | Ohkuchi et al. |
| 2006/0247253 A1 | 11/2006 | Leban et al. |
| 2006/0258672 A1 | 11/2006 | Barbosa et al. |
| 2006/0281712 A1 | 12/2006 | Yen et al. |
| 2007/0004736 A1 | 1/2007 | Kubo et al. |
| 2007/0015752 A1 | 1/2007 | Hangauer, Jr. |
| 2007/0032481 A1 | 2/2007 | Dvorak et al. |
| 2007/0135437 A1 | 6/2007 | Benjamin et al. |
| 2008/0275050 A1 | 11/2008 | Morishita et al. |
| 2009/0275589 A1 | 11/2009 | Manabe |
| 2010/0210590 A1 | 8/2010 | Watterson et al. |
| 2011/0137032 A1 | 6/2011 | Endo et al. |
| 2011/0160187 A1 | 6/2011 | Yoon et al. |
| 2012/0088778 A1 | 4/2012 | Mjalli et al. |

FOREIGN PATENT DOCUMENTS

| | | |
|---|---|---|
| CA | 2602467 A1 | 10/2006 |
| EP | 1887000 A1 | 2/2008 |
| JP | 10-007572 A | 1/1998 |
| JP | 2006-008664 A | 1/2006 |
| WO | WO 92/02513 A1 | 2/1992 |
| WO | WO 9202513 A1 * | 2/1992 |
| WO | WO 92/18089 A2 | 10/1992 |
| WO | WO 95/06037 A1 | 3/1995 |
| WO | WO 97/26913 A1 | 7/1997 |
| WO | WO 97/39121 A1 | 10/1997 |
| WO | WO 97/39125 A1 | 10/1997 |
| WO | WO 98/22138 A1 | 5/1998 |
| WO | WO 98/27108 A2 | 6/1998 |
| WO | WO 99/07402 A1 | 2/1999 |
| WO | WO 99/18987 A1 | 4/1999 |
| WO | WO 99/54485 A1 | 10/1999 |
| WO | WO 99/65881 A1 | 12/1999 |
| WO | WO 00/20458 A1 | 4/2000 |
| WO | WO 00/20621 A1 | 4/2000 |
| WO | WO 00/31065 A1 | 6/2000 |
| WO | WO 00/51547 A2 | 9/2000 |
| WO | WO 00/51611 A1 | 9/2000 |
| WO | WO 00/51612 A1 | 9/2000 |
| WO | WO 00/51614 A1 | 9/2000 |
| WO | WO 00/52134 A2 | 9/2000 |
| WO | WO 01/12598 A2 | 2/2001 |
| WO | WO 01/60368 A1 | 8/2001 |
| WO | WO 01/60815 A1 | 8/2001 |
| WO | WO 01/74898 A2 | 10/2001 |
| WO | WO 02/50045 A1 | 6/2002 |
| WO | WO 03/066604 A2 | 8/2003 |
| WO | WO 2004/002983 A2 | 1/2004 |
| WO | WO 2004/011441 A1 | 2/2004 |
| WO | WO 2004/012736 A1 | 2/2004 |
| WO | WO 2004/029031 A2 | 4/2004 |
| WO | WO 2004/043380 A2 | 5/2004 |
| WO | WO 2004/110350 A2 | 12/2004 |
| WO | WO 2004/111032 A1 | 12/2004 |
| WO | WO 2005/066130 A1 | 7/2005 |
| WO | WO 2005/089502 A2 | 9/2005 |
| WO | WO 2005/113522 A1 | 12/2005 |
| WO | WO 2006/034446 A2 | 3/2006 |
| WO | WO 2006/071960 A2 | 7/2006 |
| WO | WO 2006/124897 A2 | 11/2006 |
| WO | WO 2007/089336 A2 | 8/2007 |
| WO | WO 2007/127375 A2 | 11/2007 |
| WO | WO 2008/002676 A2 | 1/2008 |
| WO | WO 2008/067121 A2 | 6/2008 |
| WO | WO 2008/098892 A1 | 8/2008 |
| WO | WO 2009/081195 A1 | 7/2009 |

OTHER PUBLICATIONS

N. A. Bishop et al., 464 Nature, 529-535, 534 (2010).*
J.E. Donahu et al., 112 Acta Neuropath, 405-415 (2006).*
K. Takuma et al., 106 PNAS 20021-20026 (2009).*
European Patent Office Search Report for related EP Application No. 11745116.1, dated Jun. 26, 2013.
Tanaka et al., "Studies on Anti-platelet Agents. V. Synthesis and Structure-Activity Relationship of 3-Substituted 5,6-Bis(4-methoxyphenyl)-1,2,4-triazines," Chemical and Pharmaceutical Bulletin 42(9):1835-1840 (1994).
Wustrow et al., "Aminopyrazine CB1 receptor inverse agonists," Bioorganic & Medicinal Chemistry Letters 18(11):3376-3381 (2008).
Behl et al., "Amyloid beta peptide induces necrosis rather than apoptosis," Brain Research 645:253-264 (1994).
Behl et al., "Hydrogen Peroxide Mediates Amyloid beta Protein Toxicity," Cell 77:817-827 (1994).
Berge et al., "Pharmaceutical Salts," Journal of Pharmaceutical Sciences 66(1):1-19 (1977).
Bierhaus et al., "Advanced Glycation End Product (AGE)-Mediated Induction of Tissue Factor in Cultured Endothelial Cells Is Dependent on RAGE," Circulation 96:2262-2271 (1997).
Blacker et al., "Reliability and Validity of NINCDS-ADRDA Criteria for Alzheimer's Disease," Arch. Neurol. 51:1198-1204 (1994).
Bonnardel-Phu et al., "Acute Modulation of Albumin Microvascular Leakage by Advanced Glycation End Products in Microcirculation of Diabetic Rats in Vivo," Diabetes 48:2052-2058 (1999).
Bonnaud et al., Journal of Labelled Compounds and Radiopharmaceuticals 22(1):95-100 (1985).
Chartier-Harlin et al., "Early-onset Alzheimer's disease caused by mutations at codon 717 of the beta-amyloid precursor protein gene," Nature 353:844-846 (1991).
Checler, "Processing of the beta-Amyloid Precursor Protein and Its Regulation in Alzheimer's Disease," Journal of Neurochemistry 65(4):1431-1444 (1995).
Chitaley et al., "Antagonism of Rho-kinase stimulates rat penile erection via a nitric oxide-independent pathway," Nature Medicine 7(1):119-122 (2001).
Crall, Jr. et al., "The Extramural and Intramural Coronary Arteries in Juvenile Diabetes Mellitus," The American Journal of Medicine 64:221-230 (1978).
Deane et al., "RAGE mediates amyloid-beta peptide transport across the blood-brain barrier and accumulation in brain," Nature Medicine 9(7):907-913 (2003).
Degenhardt et al., "Chemical Modification of Proteins by Methylglyoxal," Cellular and Molecular Biology 44(7):1139-1145 (1998).
Dyer et al., "Accumulation of Maillard Reaction Products in Skin Collagen in Diabetes and Aging," J. Clin. Invest. 91:2463-2469 (1993).
Dyer et al., "Formation of Pentosidine during Nonenzymatic Browning of Proteins by Glucose," The Journal of Biological Chemistry 266(18):11654-11660 (1991).
Fang et al., "RAGE-dependent signaling in microglia contributes to neuroinflammation, A-beta accumulation, and impaired learning/memory in a mouse model of Alzheimer's disease," The FASEB Journal 24:1043-1055 (2010).
Galasko et al., "Clinical-Neuropathological Correlations in Alzheimer's Disease and Related Dementias," Arch. Neurol. 51:888-895 (1994).
Games et al., "Alzheimer-type neuropathology in transgenic mice overexpressing V717F beta-amyloid precursor protein," Nature 373:523-527 (1995).
Girouard et al., "Neurovascular coupling in the normal brain and in hypertension, stroke, and Alzheimer disease," J. Appl. Physiol. 100:328-335 (2006).
Goova et al., "Blockade of Receptor for Advanced Glycation End-Products Restores Effective Wound Healing in Diabetic Mice," The American Journal of Pathology 159:513-525 (2001).
Haass et al., "Cellular Processing of beta-Amyloid Precursor Protein and the Genesis of Amyloid beta-Peptide," Cell 75:1039-1042 (1993).
Hambly et al., "Reappraisal of the role of the diabetic state in coronary artery disease," Chest 70(2):251-257 (1976).

(56) References Cited

OTHER PUBLICATIONS

Hammes et al., "Diabetic retinopathy risk correlates with intracellular concentrations of the glycoxidation product N(epsilon)-(carboxymethyl) lysine independently of glycohaemoglobin concentrations," Diabetologia 42:603-607 (1999).
Hofmann et al., "RAGE Mediates a Novel Proinflammatory Axis: A Central Cell Surface Receptor for S100/Calgranulin Polypeptides," Cell 97:889-901 (1999).
Hori et al., "The Receptor for Advanced Glycation End Products (RAGE) Is a Cellular Binding Site for Amphoterin," The Journal of Biological Chemistry 270(43):25752-25761 (1995).
Huttunen et al., "Receptor for Advanced Glycation End Products (RAGE)-mediated Neurite Outgrowth and Activation of NF-kB Require the Cytoplasmic Domain of the Receptor but Different Downstream Signaling Pathways," The Journal of Biological Chemistry 274(28):19919-19924 (1999).
International Preliminary Report on Patentability for related International Application No. PCT/US2011/024886 mailed Aug. 30, 2012.
International Search Report and Written Opinion for related International Application No. PCT/US2011/024886 mailed Apr. 20, 2011.
Kamboh, "Molecular Genetics of Late-Onset Alzheimer's Disease," Annals of Human Genetics 68:381-404 (2004).
Kannel et al., "Diabetes and Cardiovascular Disease: The Framingham Study," JAMA 241(19):2035-2038 (1979).
Kannel et al., "Diabetes and Glucose Tolerance as Risk Factors for Cardiovascular Disease: The Framingham Study," Diabetes Care 2(2):120-126 (1979).
Kennedy et al., "Familial Alzheimer's disease," Brain 116:309-324 (1993).
Kislinger et al., "Receptor for Advanced Glycation End Products Mediates Inflammation and Enhanced Expression of Tissue Factor in Vasculature of Diabetic Apolipoprotein E-Null Mice," Arterioscler Thromb Vasc Biol. 21:905-910 (2001).
Kumar et al., "RAGE at the Blood-Brain Barrier Mediates Neurovascular Dysfunction Caused by Amyloid-beta1-40 Peptide," Neurosci. Program, p141-#275.19 (2000).
Lander et al., "Activation of the Receptor for Advanced Glycation End Products Triggers a p21ras-dependent Mitogen-activated Protein Kinase Pathway Regulated by Oxidant Stress," The Journal of Biological Chemistry 272(28):17810-17814 (1997).
Leder et al., "v-Ha-ras transgene abrogates the initiation step in mouse skin tumorigenesis: Effects of phorbol esters and retinoic acid," Proc. Natl. Acad. Sci. USA 87:9178-9182 (1990).
Levy-Lahad et al., "Candidate Gene for the Chromosome 1 Familial Alzheimer's Disease Locus," Science, New Series 269(5226):973-977 (1995).
Li et al., "Characterization and Functional Analysis of the Promoter of RAGE, the Receptor for Advanced Glycation End Products," The Journal of Biological Chemistry 272(26):16498-16506 (1997).
Li et al., "Sp1-binding Elements in the Promoter of RAGE Are Essential for Amphoterin-mediated Gene Expression in Cultured Neuroblastoma Cells," The Journal of Biological Chemistry 273(47):30870-30878 (1998).
Lugering et al., "The myeloic related protein MRP8/14 (27E10 antigen)—usefulness as a potential marker for disease activity in ulcerative colitis and putative biological function," European Journal of Clinical Investigation 25:659-664 (1995).
Mackic et al., "Human Blood-Brain Barrier Receptors for Alzheimer's Amyloid-beta 1-40: Asymmetrical Binding, Endocytosis, and Transcytosis at the Apical Side of Brain Microvascular Endothelial Cell Monolayer," J. Clin. Invest. 102(4):734-743 (1998).
McIntyre et al., "Pryidazine Based Inhibitors of p38 MAPK," Bioorganic & Medicinal Chemistry Letters 12:689-692 (2002).
McKhann et al., "Clinical diagnosis of Alzheimer's disease: Report of the NINCDS-ADRDA Work Group under the auspices of Department of Health and Human Services Task Force on Alzheimer's Disease," Neurology 34:939-944 (1984).

Miyata et al., "Beta2-Microglobulin Modified with Advanced Glycation End Products Is a Major Component of Hemodialysis-associated Amyloidosis," J. Clin. Invest. 92:1243-1252 (1993).
Miyata et al., "The Receptor for Advanced Glycation End Products (RAGE) Is a Central Mediator of the Interaction of AGE-beta2-Microglobulin with Human Mononuclear Phagocytes Via an Oxidant-sensitive Pathway," J. Clin. Invest. 98(5):1088-1094 (1996).
Morcos et al., "Activation of Tubular Epithelial Cells in Diabetic Nephropathy," Diabetes 51:3532-3544 (2002).
Morris et al., "Place navigation impaired in rats with hippocampal lesions," Nature 297:681-683 (1982).
Neeper et al., "Cloning and Expression of a Cell Surface Receptor for Advanced Glycosylation End Products of Proteins," The Journal of Biological Chemistry 267(21):14998-15004 (1992).
Oldfield et al., "Advanced glycation end products cause epithelial-myofibroblast transdifferentiation via the receptor for advanced glycation end products (RAGE)," The Journal of Clinical Investigation 108(12):1853-1863 (2001).
Pappolla et al., "The Heat Shock/Oxidative Stress Connection: Relevance to Alzheimer Disease," Molecular and Chemical Neuropathology 28:21-24 (1996).
Park et al., "Suppression of accelerated diabetic atherosclerosis by the soluble receptor for advanced glycation endproducts," Nature Medicine 4(9):1025-1031 (1998).
Parkkinen et al., "Amphoterin, the 30-kDa Protein in a Family of HMG1-type Polypeptides: Enhanced Expression in Transformed Cells, Leading Edge Localization, and Interactions with Plasminogen Activation," The Journal of Biological Chemistry 268(25):19726-19738 (1993).
Pastor et al., "Molecular Genetics of Alzheimer's Disease," Current Psychiatry Reports 6:125-133 (2004).
Pike et al., "Neurodegeneration Induced by beta-Amyloid Peptides in vitro: The Role of Peptide Assembly State," The Journal of Neuroscience 13(4):1676-1687 (1993).
Pyorala et al., "Diabetes and Atherosclerosis: An Epidemiologic View," Diabetes/Metabolism Reviews 3(2):463-524 (1987).
Rammes et al., "Myeloid-related Protein (MRP) 8 and MRP14, Calcium-binding Proteins of the S100 Family, Are Secreted by Activated Monocytes via a Novel, Tubulin-dependent Pathway," The Journal of Biological Chemistry 272(14):9496-9502 (1997).
Ranginwala et al., "Clinical Criteria for the Diagnosis of Alzheimer Disease: Still Good After All These Years," Am. J. Geriatr. Psychiatry 16(5):384-388 (2008).
Rauvala et al., "Isolation and Some Characteristics of an Adhesive Factor of Brain That Enhances Neurite Outgrowth in Central Neurons," The Journal of Biological Chemistry 262(34):16625-16635 (1987).
Reddy et al., "N(epsilon)-(Carboxymethyl)lysine Is a Dominant Advanced Glycation End Product (AGE) Antigen in Tissue Proteins," Biochemistry 34:10872-10878 (1995).
Ritthaler et al., "Expression of Receptors for Advanced Glycation End Products in Peripheral Occlusive Vascular Disease," American Journal of Pathology 146(3):688-694 (1995).
Robertson et al., "Atherosclerosis in persons with Hypertension and Diabetes Mellitus," Laboratory Investigation 18(5):538-551 (1968).
Rogaev et al., "Familial Alzheimer's disease in kindreds with missense mutations in a gene on chromosome 1 related to the Alzheimer's disease type 3 gene," Nature 376:775-778 (1995).
Schafer et al., "The S100 family of EF-hand calcium-binding proteins: functions and pathology," TIBS 21:134-140 (1996).
Schleicher et al., "Increased Accumulation of the Glycoxidation Product N-epsilon-(carboxymethyl)lysine in Human Tissues in Diabetes and Aging," J. Clin. Invest. 99(3):457-468 (1997).
Schmidt et al., "Advanced Glycation Endproducts Interacting with Their Endothelial Receptor Induce Expression of Vascular Cell Adhesion Molecule-1 (VCAM-1) in Cultured Human Endothelial Cells and in Mice," J. Clin. Invest. 96:1395-1403 (1995).
Schmidt et al., "Isolation and Characterization of Two Binding Proteins for Advanced Glycosylation End Products from Bovine Lung Which Are Present on the Endothelial Cell Surface," The Journal of Biological Chemistry 267(21):14987-14977 (1992).

(56) References Cited

OTHER PUBLICATIONS

Schmidt et al., "Receptor for advanced glycation end products (AGEs) has a central role in vessel wall interactions and gene activation in response to circulating AGE proteins," Proc. Natl. Acad. Sci. USA 91:8807-8811 (1994).

Schmidt et al., "The dark side of glucose," Nature Medicine 1(10):1002-1004 (1995).

Schmidt et al., "The role of RAGE in amyloid-beta peptide-mediated pathology in Alzheimer's disease," Current Opinion in Investigational Drugs 10(7):672-680 (2009).

Schmidt et al., "The V-Domain of Receptor for Advanced Glycation Endproducts (RAGE) Mediates Binding of AGEs: A Novel Target for Therapy of Diabetic Complications," Supplement to Circulation 96(8):Abstract No. 194 (1997).

Selkoe, "Normal and Abnormal Biology of the beta-Amyloid Precursor Protein," Annual Review of Neuroscience 17:489-517 (1994).

Selkoe, "The Molecular Pathology of Alzheimer's Disease," Neuron 6:487-498 (1991).

Selkoe, "Translating cell biology into therpeutic advances in Alzheimer's disease," Nature 399:A23-31 (1999).

Semprini et al., "Evidence for differential S100 gene over-expression in psoriatic patients from genetically heterogeneous pedigrees," Hum. Genet. 111:310-313 (2002).

Sherrington et al., "Cloning of a gene bearing missense mutations in early-onset familial Alzheimer's disease," Nature 375:754-760 (1995).

Snowdon, "Healthy Aging and Dementia: Findings from the Nun Study," Annals of Internal Medicine 139(5):450-454 (2003).

Sousa et al., "Interaction of the Receptor for Advanced Glycation End Products (RAGE) with Transthyretin Triggers Nuclear Transcription Factor kB (NF-kB) Activation," Laboratory Investigation 80(7):1101-1110 (2000).

Taguchi et al., "Blockade of RAGE-amphoterin signalling suppresses tumour growth and metastases," Nature 405:354-360 (2000).

Tanaka et al., "The Receptor for Advanced Glycation End Products Is Induced by the Glycation Products Themselves and Tumor Necrosis Factor-alpha through Nuclear Factor-kB, and by 17-beta-Estradiol through Sp-1 in Human Vascular Endothelial Cells," The Journal of Biological Chemistry 275(33):25781-25790 (2000).

Teillet et al., "Food Restriction Prevents Advanced Glycation End Product Accumulation and Retards Kidney Aging in Lean Rats," J. Am. Soc. Nephrol. 11:1488-1497 (2000).

Vlassara, "Advanced Glycation End-products and Atherosclerosis," Annals of Medicine 28:419-426 (1996).

Waller et al., "Status of the Coronary Arteries at Necropsy in Diabetes Mellitus with Onset After Age 30 Years: Analysis of 229 Diabetic Patients With and Without Clinical Evidence of Coronary Heart Disease and Comparison to 183 Control Subjects," The American Journal of Medicine 69:498-506 (1980).

Wang et al., "The Profile of Soluble Amyloid beta Protein in Cultured Cell Media: Detection and Quantification of Amyloid beta Protein and Variants by Immunoprecipitation-mass Spectrometry," The Journal of Biological Chemistry 271(50):31894-31902 (1996).

Wautier et al., "Advanced glycation end products (AGEs) on the surface of diabetic erythrocytes bind to the vessel wall via a specific receptor inducing oxidant stress in the vasculature: A link between surface-associated AGEs and diabetic complications," Proc. Natl. Acad. Sci. USA 91:7742-7746 (1994).

Wautier et al., "Receptor-mediated Endothelial Cell Dysfunction in Diabetic Vasculopathy: Soluble Receptor for Advanced Glycation End Products Blocks Hyperpermeability in Diabetic Rats," J. Clin. Invest. 97(1):238-243 (1996).

Wisniewski et al., "Apolipoprotein E: a pathological chaperone protein in patients with cerebral and systemic amyloid," Neuroscience Letters 135:235-238 (1992).

Yan et al., "Amyloid-beta peptide-Receptor for Advanced Glycation Endproduct interaction elicits neuronal expression of macrophage-colony stimulating factor: A proinflammatory pathway in Alzheimer disease," Proc. Natl. Acad. Sci. USA 94:5296-5301 (1997).

Yan et al., "An intracellular protein that binds amyloid-beta peptide and mediates neurotoxicity in Alzheimer's disease," Nature 389:689-695 (1997).

Yan et al., "Enhanced Cellular Oxidant Stress by the Interaction of Advanced Glycation End Products with Their Receptors/Binding Proteins," The Journal of Biological Chemistry 269(13):9889-9897 (1994).

Yan et al., "RAGE and Alzheimer's Disease: A Progression Factor for Amyloid-beta-Induced Cellular Perturbation?" Journal of Alzheimer's Disease 16:833-843 (2009).

Yan et al., "RAGE and amyloid-beta peptide neurotoxicity in Alzheimer's disease," Nature 382:685-691 (1996).

Yan et al., "Receptor-dependent cell stress and amyloid accumulation in systemic amyloidosis," Nature Medicine 6(6):643-651 (2000).

Yankner et al., "Neurotrophic and Neurotoxic Effects of Amyloid beta Protein: Reversal by Tachykinin Neuropeptides," Science, New Series 250(4978):279-282 (1990).

Yeh et al., "Requirement for p38 and p44/p42 Mitogen-Activated Protein Kinases in RAGE-Mediated Nuclear Factor-kB Transcriptional Activation and Cytokine Secretion," Diabetes 50:1495-1504 (2001).

Zimmer et al., "The S100 Protein Family: History, Function, and Expression," Brain Research Bulletin 37(4):417-429 (1995).

\* cited by examiner

PHENYL-HETEROARYL DERIVATIVES AND METHODS OF USE THEREOF

STATEMENT REGARDING FEDERALLY SPONSORED RESEARCH

Not applicable

FIELD OF THE INVENTION

This invention relates to compounds which are inhibitors of the interaction between the receptor for advanced glycation endproducts (RAGE) and its physiological ligands such as advanced glycated end products (AGEs), S100/calgranulin/EN-RAGE, β-amyloid, and amphoterin, for the treatment of RAGE mediated diseases.

BACKGROUND OF THE INVENTION

The Receptor for Advanced Glycated Endproducts (RAGE) is a member of the immunoglobulin super family of cell surface molecules. The extracellular (N-terminal) domain of RAGE includes three immunoglobulin-type regions, one V (variable) type domain followed by two C-type (constant) domains (Neeper et al., J. Biol. Chem. 267:14998-15004 (1992)). A single transmembrane spanning domain and a short, highly charged cytosolic tail follow the extracellular domain. The N-terminal, extracellular domain can be isolated by proteolysis of RAGE to generate soluble RAGE (sRAGE) comprised of the V and C domains.

RAGE is expressed in most tissues, and in particular, is found in cortical neurons during embryogenesis (Hon et al. (1995)). Increased levels of RAGE are also found in aging tissues (Schleicher et al., J. Clin. Invest. 99 (3): 457-468 (1997)), and the diabetic retina, vasculature and kidney (Schmidt et al., Nature Med. 1:1002-1004 (1995)). Activation of RAGE in different tissues and organs leads to a number of pathophysiological consequences. RAGE has been implicated in a variety of conditions including: acute and chronic inflammation (Hofmann et al., Cell 97:889-901 (1999)), the development of diabetic late complications such as increased vascular permeability (Wautier et al., J. Clin. Invest. 97:238-243 (1996)), nephropathy (Teillet et al., J. Am. Soc. Nephrol. 11:1488-1497 (2000)), atherosclerosis (Vlassara et al., The Finnish Medical Society DUODECIM, Ann. Med. 28:419-426 (1996)), and retinopathy (Hammes et al., Diabetologia 42:603-607 (1999)). RAGE has also been implicated in Alzheimer's disease (Yan et al., Nature 382: 685-691 (1996)), erectile dysfunction, and in tumor invasion and metastasis (Taguchi et al., Nature 405: 354-357 (2000)).

Advanced glycation endproducts (AGEs) have been implicated in a variety of disorders including complications associated with diabetes and normal aging. Incubation of proteins or lipids with aldose sugars results in nonenzymatic glycation and oxidation of amino groups on proteins to form Amadori adducts. Over time, the adducts undergo additional rearrangements, dehydrations, and cross-linking with other proteins to form complexes known as AGEs. Factors which promote formation of AGEs include delayed protein turnover (e.g. as in amyloidoses), accumulation of macromolecules having high lysine content, and high blood glucose levels (e.g. as in diabetes) (Hori et al., J. Biol. Chem. 270: 25752-761, (1995)).

AGEs display specific and saturable binding to cell surface receptors on endothelial cells of the microvasculature, monocytes and macrophages, smooth muscle cells, mesengial cells, and neurons.

In addition to AGEs, other compounds can bind to, and inhibit the interaction of physiological ligands with RAGE. In normal development, RAGE interacts with amphoterin, a polypeptide which mediates neurite outgrowth in cultured embryonic neurons (Hori et al., (1995)). RAGE has also been shown to interact with EN-RAGE, a protein having substantial similarity to calgranulin (Hofmann et al. (1999)). RAGE has also been shown to interact with β-amyloid (Yan et al., Nature 389:689-695 (1997); Yan et al., Nature 382:685-691 (1996); Yan et al., Proc. Natl. Acad. Sci., 94:5296-5301 (1997)).

Binding of ligands such as AGEs, S100/calgranulin/EN-RAGE, β-amyloid, CML (Nε-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like. In addition, several other regulatory pathways, such as those involving p21ras, MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Inhibiting binding of physiological ligands to RAGE provides for the down-regulation of the pathophysiological changes brought about by excessive concentrations of AGEs and other ligands for RAGE as described above.

Thus, there is a need for the development of compounds that inhibit the binding of physiological ligands to RAGE.

SUMMARY OF THE INVENTION

The present invention relates to compounds of Formula (I):

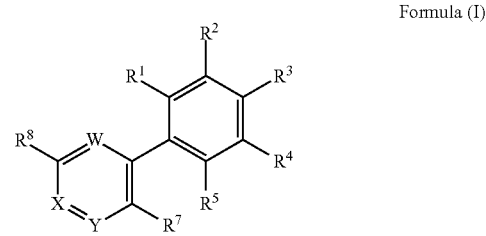

Formula (I)

or pharmaceutically acceptable salts thereof as described herein. This invention also provides for methods of preparation of compounds of Formula (I) or pharmaceutically acceptable salts thereof, pharmaceutical compositions comprising compounds of Formula (I) or pharmaceutically acceptable salts thereof; and methods for the use of compounds of Formula (I) or pharmaceutically acceptable salts thereof in treating diseases mediated by RAGE.

Compounds of Formula (I) or pharmaceutically acceptable salts thereof are useful as inhibitors of the interaction of the receptor for advanced glycation endproducts (RAGE) with ligands such as advanced glycated end products (AGEs), S100/calgranulin/EN-RAGE, β-amyloid, and amphoterin. The compounds are also useful in treating a variety of diseases or conditions in humans that may be responsive to the inhibition of RAGE. Such diseases or conditions include, but are not limited to, acute and chronic inflammation, the development of diabetic late complications such as increased vascular permeability, nephropathy, atherosclerosis, and retinopathy, the development of Alzheimer's disease and related disorders, erectile dysfunction, tumor invasion and metastasis, and osteoporosis.

The scope of the present invention includes combinations of the various aspects, embodiments, and preferences as herein described.

BRIEF DESCRIPTION OF DRAWINGS

Not applicable

DETAILED DESCRIPTION OF THE INVENTION

The following definitions are meant to clarify, but not limit, the terms defined. If a particular term used herein is not specifically defined, such term should not be considered indefinite. Rather, such terms are used within their plain and ordinary meanings.

As used herein the term "alkyl" refers to a straight or branched chain hydrocarbon having one to ten carbon atoms, which may be optionally substituted as herein further described, with multiple degrees of substitution being allowed. Examples of "alkyl" as used herein include, but are not limited to, methyl, ethyl, propyl, isopropyl, isobutyl, n-butyl, tert-butyl, isopentyl, and n-pentyl.

As used throughout this specification, the number of atoms, such as carbon atoms in an alkyl group, for example, will be represented by the phrase "$C_x$-$C_y$ alkyl," which refers to an alkyl group, as herein defined, containing the from x to y, inclusive, carbon atoms. Similar terminology will apply for other terms and ranges as well. Thus, $C_1$-$C_6$ alkyl represents an alkyl chain having from 1 to 6 carbons as described above.

As used herein the term "alkenyl" refers to a straight or branched chain aliphatic hydrocarbon having two to ten carbon atoms and containing one or more carbon-to-carbon double bonds, which may be optionally substituted as herein further described, with multiple degrees of substitution being allowed. Examples of "alkenyl" as used herein include, but are not limited to, vinyl, and allyl.

As used herein the term "alkynyl" refers to a straight or branched chain aliphatic hydrocarbon having two to ten carbon atoms and containing one or more carbon-to-carbon triple bonds, which may be optionally substituted as herein further described, with multiple degrees of substitution being allowed. Examples of "alkynyl" as used herein include, but are not limited to, acetylene.

As used herein, the term "alkylene" refers to a straight or branched chain divalent hydrocarbon radical having from one to ten carbon atoms, which may be optionally substituted as herein further described, with multiple degrees of substitution being allowed. Examples of "alkylene" as used herein include, but are not limited to, methylene, ethylene, n-propylene, and n-butylene.

As used herein, the term "cycloalkyl" refers to a saturated, three- to ten-membered, cyclic hydrocarbon ring, which may be optionally substituted as herein further described, with multiple degrees of substitution being allowed. Exemplary "cycloalkyl" groups as used herein include, but are not limited to, cyclopropyl, cyclobutyl, cyclopentyl, cyclohexyl, and cycloheptyl.

As used herein, the term "cycloalkenyl" refers to an a non-aromatic, three- to twelve-membered, cyclic hydrocarbon ring containing one or more degrees of unsaturation, which may be optionally substituted as herein further described, with multiple degrees of substitution being allowed. Examples of "cycloalkenyl" as used herein include, but are not limited to, cyclopropenyl, cyclobutenyl, cyclopentenyl, cyclohexenyl, and cycloheptenyl.

As used herein, the term "heterocycle" or "heterocyclyl" refers to an optionally substituted mono- or polycyclic ring system, optionally containing one or more degrees of unsaturation and also containing one or more heteroatoms, which may be optionally substituted as herein further described, with multiple degrees of substitution being allowed. Exemplary heteroatoms include nitrogen, oxygen, or sulfur atoms, including N-oxides, sulfur oxides, and sulfur dioxides. Typically, the ring is three to twelve-membered and is either fully saturated or has one or more degrees of unsaturation. Such rings may be optionally fused to one or more of another heterocyclic ring(s), cycloalkyl ring(s), aryl groups (as defined below) or heteroaryl groups (as defined below). Examples of "heterocyclic" groups as used herein include, but are not limited to, tetrahydrofuran, pyran, 1,4-dioxane, 1,3-dioxane, piperidine, pyrrolidine, morpholine, tetrahydrothiopyran, and tetrahydrothiophene.

As used herein the term "halogen" refers to fluorine, chlorine, bromine, or iodine.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include groups such as —$CF_3$, —$CH_2$—$CF_3$, and —$CF_2Cl$.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrase "substituted with one or more . . . " refers to a number of substituents that equals from one to the maximum number of substituents possible based on the number of available bonding sites, provided that the above conditions of stability and chemical feasibility are met As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left.

When any variable occurs more than one time in any one constituent (e.g., $R^{22}$), or multiple constituents, its definition on each occurrence is independent of its definition on every other occurrence.

In a first embodiment, the present invention provides a compound of Formula (I) or a pharmaceutically acceptable salt thereof,

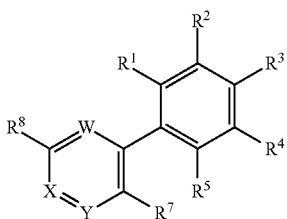

(I)

wherein

W, X, and Y are independently selected from the group consisting of $CR^6$, N, and N(O), wherein at least one of W, X, and Y is N or N(O), and $R^6$ is selected from the group consisting of —H, -halogen, —$(C_1$-$C_6)$alkyl, and —$(C_1$-$C_6)$haloalkyl;

$R^1$, $R^2$, $R^4$, and $R^5$ are independently selected from the group consisting of —H, -halogen, -cyano, —$NO_2$, —$OR^9$, —$SR^9$, —$S(O)_sR^9$, —$S(O)_2OR^9$, —$S(O)_sNR^9R^{10}$, —$NR^9S(O)_2R^{10}$, —$NHC(O)NHR^9$, —$NR^9C(O)R^{10}$, —$(CR^{11}R^{12})_tNR^9R^{10}$, —$C(O)R^9$, —$C(O)OR^9$, —$C(O)O(CR^{11}R^{12})_tNR^9R^{10}$, —$CONR^9R^{10}$, —$C(O)NR^9R^{10}$, —$(C_1$-$C_{10})$alkyl, —$(C_2$-$C_{10})$alkenyl, —$(C_2$-$C_{10})$alkynyl, -phenyl, —$(C_3$-$C_{10})$cycloalkyl, -pyrazolyl, -isoxazolyl, -tetrazolyl, -oxazolyl, -dihydro-oxazolyl, wherein the alkyl, alkenyl, phenyl, cycloalkyl, pyrazolyl, isoxazolyl, tetrazolyl, oxazolyl, and dihydro-oxazolyl groups are optionally substituted one or more times with substituents independently selected from $R^{39}$, wherein $R^9$ and $R^{10}$ are independently selected from the group consisting of —H, —$(C_1$-$C_6)$alkyl, —$(C_3$-$C_{10})$cycloalkyl, -phenyl, —$(C_1$-$C_6)$alkylene-$(C_3$-$C_{10})$cycloalkyl, and —$(C_1$-$C_6)$alkylene-phenyl, wherein the alkyl, alkylene, cycloalkyl, phenyl groups of $R^9$ and $R^{10}$ are optionally substituted one or more times with substituents independently selected from $R^{39}$, or $R^9$ and $R^{10}$ together with the atoms to which they are attached form a heterocyclic ring of 5 to 7 members containing 0 to 2 additional heteroatoms independently selected from oxygen, sulfur and nitrogen and the ring is optionally substituted one or more times with substituents independently selected from $R^{39}$, and $R^{11}$ and $R^{12}$ are independently selected from the group consisting of —H, —$(C_1$-$C_6)$alkyl, —$(C_3$-$C_{10})$cycloalkyl, -phenyl, —$(C_1$-$C_6)$alkylene-$(C_3$-$C_{10})$cycloalkyl, and —$(C_1$-$C_6)$alkylene-phenyl, wherein the alkyl, alkylene, cycloalkyl, phenyl groups of $R^{11}$ and $R^{12}$ are optionally substituted one or more times with substituents independently selected from $R^{39}$, or $R^{11}$ and $R^{12}$ together with the carbon to which they are attached form a ring of 5 to 7 members containing 0 to 2 heteroatoms independently selected from oxygen, sulfur and nitrogen and the ring is optionally substituted one or more times with substituents independently selected from $R^{39}$;

$R^3$ is selected from the group consisting of —$X^1$-$L^1$-$R^{13}$ and -$L^1$-$X^1$—$R^{13}$ wherein $X^1$ is selected from the group consisting of a direct bond, —O—, —C(O)—, —C(O)O—, —OC(O)—, —S(O)$_2$—, —S(O)$_2$NH—, —NHS(O)$_2$—, —C(O)NH—, and —NHC(O)—, $L^1$ is selected from the group consisting of a direct bond and —$(C_1$-$C_6)$alkylene-, and $R^{13}$ is selected from the group consisting of —$(C_1$-$C_6)$alkyl, —$(C_3$-$C_{10})$cycloalkyl, —$(C_6$-$C_{10})$cycloalkenyl, -phenyl, -pyridyl, -pyridazinyl, -piperidinyl, and -tetrahydropyranyl, wherein the alkyl, cycloalkyl, cycloalkenyl, phenyl, pyridyl, pyridazinyl, piperidinyl, tetrahydropyranyl groups of $R^{13}$ are optionally substituted one or more times with $R^{14}$, wherein each $R^{14}$ is independently selected from the group $R^{39}$;

$R^7$ is the group -$L^2$-$X^2$—$R^{15}$ wherein $L^2$ is selected from the group consisting of a direct bond and —$(C_1$-$C_6)$alkylene-, $X^2$ is selected from the group consisting of a direct bond and —O—, and $R^{15}$ is selected from the group consisting of —$(C_1$-$C_{10})$alkyl, —$(C_3$-$C_{10})$cycloalkyl, —$(C_1$-$C_6)$alkylene-$(C_3$-$C_{10})$cycloalkyl, -phenyl, and —$(C_1$-$C_6)$alkylene-phenyl, wherein the alkyl, alkylene, cycloalkyl, and phenyl groups of $R^{15}$ are optionally substituted one or more times with $R^{16}$, wherein each $R^{16}$ is independently selected from the group $R^{39}$;

$R^8$ is selected from the group consisting of —$X^3$-$L^3$-$R^{17}$ and -$L^3$-$X^3$—$R^{17}$ and wherein $X^3$ is selected from the group consisting of direct bond, —O—, —C(O)—, —C(O)O—, —C(O)NH—, —C(O)N($R^{18}$)—, —NHC(O)—, and —N($R^{18}$)C(O)— wherein $R^{18}$ is selected from the group consisting of —$(C_1$-$C_6)$alkyl, —$(C_3$-$C_6)$cycloalkyl, —$(C_1$-$C_6)$alkylene-O—$(C_1$-$C_6)$alkyl, —$(C_1$-$C_6)$alkylene-$(C_3$-$C_6)$cycloalkyl, $L^3$ is selected from the group consisting of a direct bond and —$(C_1$-$C_6)$alkylene-wherein the alkylene group is optionally substituted one or more times with $R^{19}$, wherein each $R^{19}$ is independently selected from the group consisting of —OH, —$NH_2$, —O—$(C_1$-$C_6)$alkyl, —$(C_1$-$C_6)$alkylene-$NH_2$, —$(C_1$-$C_6)$alkylene-NH($(C_1$-$C_6)$alkyl), and —$(C_1$-$C_6)$alkylene-N($(C_1$-$C_6)$alkyl)$_2$, wherein the alkyl and alkylene groups of $R^{19}$ are optionally substituted one or more times with -halogen, $R^{17}$ is selected from the group consisting of

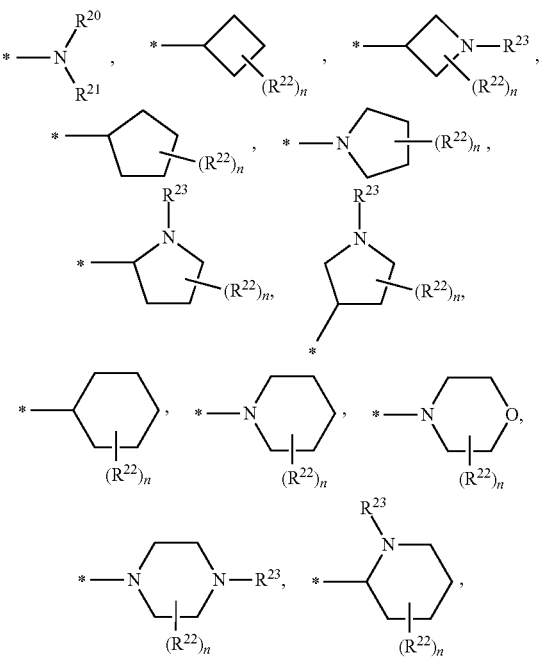

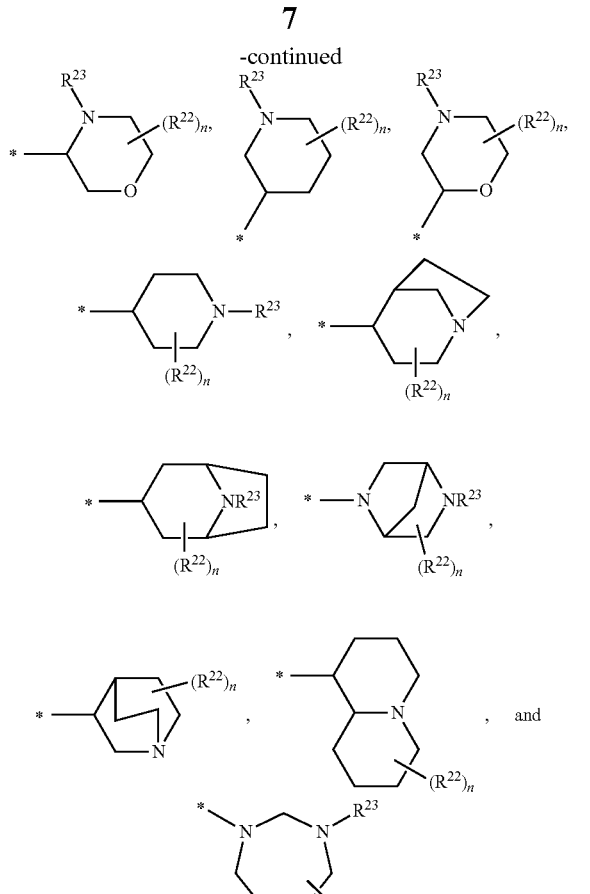

wherein
each $R^{22}$ may be attached to any of the ring carbon atoms of $R^{17}$, and
wherein
$R^{20}$ and $R^{21}$ are independently selected from the group consisting of —H, —($C_1$-$C_6$)alkyl, and —($C_1$-$C_6$)haloalkyl,
each $R^{22}$ is independently selected from the group consisting of -cyano, -halogen, —$X^4$—$R^{24}$, —($C_1$-$C_6$)alkylene-$R^{24}$, —$X^4$—($C_1$-$C_6$)alkylene-$R^{24}$, —($C_1$-$C_6$)alkylene-$X^5$—$R^{24}$, —$X^4$—($C_1$-$C_6$)alkylene-$X^5$—$R^{24}$, and —$X^4$—($C_1$-$C_6$)alkylene-$NR^{25}R^{26}$, wherein
$X^4$ and $X^5$ are independently selected from the group consisting of: direct bond, —O—, —N($R^{27}$)—, —C(O)—, —C(O)O—, —OC(O)—, —S(O)$_2$—, —C(O)N($R^{27}$)—, —N($R^{27}$)C(O)—, —S(O)$_2$N($R^{27}$)—, —N($R^{27}$)S(O)$_2$—, and —C(O)N($R^{27}$)—S(O)$_2$—,
wherein $R^{27}$ is selected from the group consisting of —H and —($C_1$-$C_6$)alkyl,
$R^{24}$ is selected from the group consisting of —H, —($C_1$-$C_6$)alkyl, -phenyl, and —($C_3$-$C_{10}$)cycloalkyl, wherein the alkyl, phenyl, and cycloalkyl groups of $R^{24}$ are optionally substituted one or more times with $R^{28}$, wherein each $R^{28}$ is independently selected from $R^{39}$,
$R^{25}$ and $R^{26}$ are independently selected from the group consisting of —H, —($C_1$-$C_6$)alkyl, and —($C_1$-$C_6$)haloalkyl,
wherein the alkylene groups of $R^{22}$ are optionally substituted one or more times with $R^{29}$, wherein each $R^{29}$ is independently selected from the group consisting of -halogen, —OH, —$NH_2$, —O—($C_1$-$C_6$)alkyl, —($C_1$-$C_6$)alkylene-$NH_2$, —($C_1$-$C_6$)alkylene-NH(($C_1$-$C_6$)alkyl), and —($C_1$-$C_6$)alkylene-N(($C_1$-$C_6$)alkyl)$_2$, wherein the alkyl and alkylene groups of $R^{29}$ are optionally substituted one or more times with halogen;

$R^{23}$ is selected from the group consisting of —H, —$R^{30}$, —($C_1$-$C_6$)alkylene-$R^{31}$, —($C_1$-$C_6$)alkylene-$NR^{32}R^{33}$, —$X^8$—($C_2$-$C_6$)alkylene-$NR^{32}R^{33}$, and —($C_1$-$C_6$)alkylene-$X^7$—$R^{31}$, wherein $X^6$ is selected from the group consisting of —C(O)—, —C(O)O—, —S(O)$_2$—, —C(O)N($R^{34}$)—, and —S(O)$_2$N($R^{34}$)—, wherein $R^{34}$ is selected from the group consisting of —H, —($C_1$-$C_6$)alkyl, and —($C_1$-$C_6$)haloalkyl, $X^7$ is selected from the group consisting of —O—, —N($R^{35}$)—, —C(O)—, —C(O)O—, —O—C(O)—, —C(O)N($R^{35}$)—, —N($R^{35}$)C(O)—, —S(O)$_2$N($R^{35}$)—, and —N($R^{35}$)S(O)$_2$—, wherein $R^{35}$ is selected from the group consisting of —H, —($C_1$-$C_6$)alkyl, and —($C_1$-$C_6$)haloalkyl, $R^{30}$ is selected from the group consisting of —H, —($C_1$-$C_6$)alkyl, -phenyl, and —($C_3$-$C_{10}$)cycloalkyl, wherein the alkyl, phenyl, and cycloalkyl groups of $R^{30}$ are optionally substituted one or more times with $R^{36}$, wherein each $R^{36}$ is independently selected from $R^{39}$, $R^{31}$ is selected from the group consisting of —H, —($C_1$-$C_6$)alkyl, -phenyl, —($C_3$-$C_{10}$)cycloalkyl, -tetrazolyl, -1,3-dioxanyl, 1,3,4-oxadiazolyl, and piperidinyl, wherein the alkyl, phenyl, cycloalkyl, tetrazolyl, 1,3-dioxanyl, 1,3,4-oxadiazolyl, and piperidinyl groups of $R^{31}$ are optionally substituted one or more times with $R^{37}$, wherein each $R^{37}$ is independently selected from $R^{39}$, $R^{32}$ and $R^{33}$ are independently selected from the group consisting of —H, —($C_1$-$C_6$)alkyl, and —($C_1$-$C_6$)haloalkyl, wherein the alkylene groups of $R^{23}$ are optionally substituted one or more times with $R^{38}$, wherein each $R^{38}$ is independently selected from the group consisting of halogen, —OH, —$NH_2$, —O—($C_1$-$C_6$)alkyl, —($C_1$-$C_6$)alkylene-$NH_2$, —($C_1$-$C_6$)alkylene-NH(($C_1$-$C_6$)alkyl), and —($C_1$-$C_6$)alkylene-N(($C_1$-$C_6$)alkyl)$_2$, wherein the alkyl and alkylene groups of $R^{38}$ are optionally substituted one or more times with halogen;

each $R^{39}$ is independently selected from the group consisting of -halogen, —($C_1$-$C_6$)haloalkyl, —C(O)OH, —($C_1$-$C_6$)alkyl, —O—($C_1$-$C_6$)alkyl, —O—($C_1$-$C_6$)haloalkyl, —C(O)—($C_1$-$C_6$)alkyl, —($C_3$-$C_{10}$)cycloalkyl, —O—($C_3$-$C_{10}$)cycloalkyl, —OH, —$NH_2$, —($C_1$-$C_6$)alkylene-OH, —($C_1$-$C_6$)alkylene-$NH_2$, —NH(($C_1$-$C_6$)alkyl), —N(($C_1$-$C_6$)alkyl)$_2$, —($C_1$-$C_6$)alkylene-NH(($C_1$-$C_6$)alkyl), —($C_1$-$C_6$)alkylene-N(($C_1$-$C_6$)alkyl)$_2$, -phenyl, —O-phenyl, —($C_1$-$C_6$)alkylene-phenyl, —O—($C_1$-$C_6$)alkylene-phenyl, —C(O)$NH_2$, —C(O)NH—($C_1$-$C_6$)alkyl, —C(O)N(($C_1$-$C_6$)alkyl)$_2$, —S(O)$_2$—($C_1$-$C_6$)alkyl, —C(O)O—($C_1$-$C_6$)alkyl, and —C(O)O—($C_1$-$C_6$)alkylene-phenyl, n is an integer from 0 to 5,
s is an integer from 1 to 2, and
t is an integer from 1 to 10.

Other embodiments of the present invention are illustrated in the following list of embodiments.

Embodiment 2

A compound according to embodiment 1, wherein W is $CR^6$, X is $CR^6$, and Y is N.

Embodiment 3

A compound according to embodiment 1, wherein W is $CR^6$, X is $CR^6$, and Y is N(O).

Embodiment 4

A compound according to embodiment 1, wherein W is $CR^6$, X is N, and Y is C.

Embodiment 5

A compound according to embodiment 1, wherein W is $CR^6$, X is N, and Y is N.

Embodiment 6

A compound according to embodiment 1, wherein W is $CR^6$, X is N, and Y is N(O).

Embodiment 7

A compound according to embodiment 1, wherein W is $CR^6$, X is N(O), and Y is $CR^6$.

Embodiment 8

A compound according to embodiment 1, wherein W is $CR^6$, X is N(O), and Y is N.

Embodiment 9

A compound according to embodiment 1, wherein W is N, X is $CR^6$, and Y is $CR^6$.

Embodiment 10

A compound according to embodiment 1, wherein W is N, X is $CR^6$, and Y is N.

Embodiment 11

A compound according to embodiment 1, wherein W is N, X is $CR^6$, and Y is N(O).

Embodiment 12

A compound according to embodiment 1, wherein W is N, X is N, and Y is $CR^6$.

Embodiment 13

A compound according to embodiment 1, wherein W is N, X is N, and Y is N.

Embodiment 14

A compound according to embodiment 1, wherein W is N, X is N, and Y is N(O).

Embodiment 15

A compound according to embodiment 1, wherein W is N, X is N(O), and Y is $CR^6$.

Embodiment 16

A compound according to embodiment 1, wherein W is N, X is N(O), and Y is N.

Embodiment 17

A compound according to embodiment 1, wherein W is N(O), X is $CR^6$, and Y is $CR^6$.

Embodiment 18

A compound according to embodiment 1, wherein W is N(O), X is $CR^6$, and Y is N.

Embodiment 19

A compound according to embodiment 1, wherein W is N(O), X is N, and Y is $CR^6$.

Embodiment 20

A compound according to embodiment 1, wherein W is N(O), X is N, and Y is N.

Embodiment 21

A compound according to any one of the previous embodiments,
wherein $R^6$ is selected from the group consisting of —H and —$CF_3$.

Embodiment 22

A compound according to any one of the previous embodiments,
wherein $R^6$ is —H.

Embodiment 23

A compound according to any one of the previous embodiments,
wherein $R^1$, $R^2$, $R^4$, and $R^5$ are independently selected from the group consisting of —H, -halogen, -cyano, —$OR^9$, —$S(O)_sR^9$, —$S(O)_2OR^9$, —$S(O)_sNR^9R^{10}$, —$NR^9S(O)_2R^{10}$, —$NHC(O)NHR^9$, —$NR^9C(O)R^{10}$, —$(CR^{11}R^{12})_tNR^9R^{10}$, —$C(O)R^9$, —$C(O)OR^9$, —$C(O)OR^9$, —$C(O)O(CR^{11}R^{12})_tCONR^9R^{10}$, —$C(O)NR^9R^{10}$, —$(C_1$-$C_{10})$alkyl, —$(C_2$-$C_{10})$alkenyl, —$(C_2$-$C_{10})$alkynyl, -phenyl, —$(C_3$-$C_{10})$cycloalkyl, -pyrazol-5-yl, -pyrazol-4-yl, -isoxazol-4-yl, -tetrazol-5-yl, -oxazol-2-yl, and -4,5-dihydro-oxazol-2-yl, wherein the alkyl, alkenyl, phenyl, cycloalkyl, pyrazolyl, isoxazolyl, tetrazolyl, oxazolyl, and dihydro-oxazolyl groups are optionally substituted one or more times with substituents independently selected from $R^{39}$.

Embodiment 24

A compound according to embodiment 23, wherein $R^1$ and $R^5$ are independently selected from the group consisting of —H, -halogen, —$(C_1$-$C_6)$alkyl, —$OR^9$, wherein $R^9$ is selected from the group consisting of —$(C_1$-$C_6)$alkyl, —$(C_3$-$C_6)$cycloalkyl, -phenyl, —$(C_1$-$C_6)$alkylene-$(C_3$-$C_6)$cycloalkyl, and —$(C_1$-$C_6)$alkylene-phenyl, wherein the alkyl, alkylene, cycloalkyl, and phenyl groups of $R^9$ are optionally substituted one or more times with substituents independently selected from $R^{39}$, and wherein the alkyl group of $R^1$ and $R^5$ is optionally substituted one or more times with substituents independently selected from $R^{39}$.

Embodiment 25

A compound according to embodiment 24, wherein
$R^1$ and $R^5$ are independently selected from the group consisting of —H, -halogen, —$(C_1$-$C_6)$alkyl, —$OR^9$, wherein $R^9$ is selected from the group consisting of —$(C_1$-$C_6)$alkyl, —$(C_3$-$C_6)$cycloalkyl, -phenyl, —$(C_1$-$C_6)$alkylene-$(C_3$-$C_6)$cycloalkyl, and —$(C_1$-$C_6)$alkylene-phenyl, wherein the alkyl, alkylene, cycloalkyl, phenyl groups of $R^9$ are optionally substituted one or more times with substituents independently selected from halogen, and wherein the alkyl group of $R^1$ and $R^5$ is optionally substituted one or more times with substituents independently selected from $R^{39}$.

Embodiment 26

A compound according to embodiment 25, wherein
$R^1$ and $R^5$ are independently selected from the group consisting of —H and -halogen.

Embodiment 27

A compound according to embodiment 26, wherein
$R^1$ and $R^5$ are —H.

Embodiment 28

A compound according to any one of the previous embodiments,
wherein $R^2$ and $R^4$ are —H.

Embodiment 29

A compound according to any one embodiments 1 to 27, wherein
$R^2$ is —H, and $R^4$ is selected from the group consisting of -halogen, —$OR^9$, —$SR^9$, —$S(O)_sR^9$, —$S(O)_2OR^9$, —$S(O)_sNR^9R^{10}$, —$NR^9S(O)_2R^{10}$, —NHC(O)NHR$^9$, —$NR^9C(O)R^{10}$, —$(CR^{11}R^{12})_tNR^9R^{10}$, —$C(O)R^9$, —$C(O)OR^9$, —$C(O)O(CR^{11}R^{12})_tCONR^9R^{10}$, —$C(O)NR^9R^{10}$, —$(C_1$-$C_6)$alkyl, —$(C_2$-$C_6)$alkenyl, —$(C_2$-$C_6)$alkynyl, -phenyl, —$(C_3$-$C_6)$cycloalkyl, -pyrazol-5-yl, -pyrazol-4-yl, -isoxazol-4-yl, -tetrazol-5-yl, -oxazol-2-yl, and -4,5-dihydro-oxazol-2-yl, wherein the alkyl, alkenyl, phenyl, cycloalkyl, pyrazolyl, isoxazolyl, tetrazolyl, oxazolyl, and dihydro-oxazolyl groups are optionally substituted one or more times with substituents independently selected from $R^{39}$, wherein
$R^9$ and $R^{10}$ are independently selected from the group consisting of —H, —$(C_1$-$C_6)$alkyl, —$(C_3$-$C_6)$cycloalkyl, -phenyl, —$(C_1$-$C_6)$alkylene-$(C_3$-$C_6)$cycloalkyl, and —$(C_1$-$C_6)$alkylene-phenyl, wherein the alkyl, alkylene, cycloalkyl, phenyl groups of $R^9$ and $R^{10}$ are optionally substituted one or more times with substituents independently selected from $R^{39}$, or $R^9$ and $R^{10}$ together with the atoms to which they are attached form a heterocyclic ring of 5 to 7 members containing 0 to 2 additional heteroatoms independently selected from oxygen, sulfur and nitrogen and the ring is optionally substituted one or more times with substituents independently selected from $R^{39}$, and
$R^{11}$ and $R^{12}$ are independently selected from the group consisting of —H, —$(C_1$-$C_6)$alkyl, —$(C_3$-$C_6)$cycloalkyl, -phenyl, —$(C_1$-$C_6)$alkylene-$(C_3$-$C_6)$cycloalkyl, and —$(C_1$-$C_6)$alkylene-phenyl, wherein the alkyl, alkylene, cycloalkyl, phenyl groups of $R^{11}$ and $R^{12}$ are optionally substituted one or more times with substituents independently selected from $R^{39}$, or $R^{11}$ and $R^{12}$ together with the carbon to which they are attached form a ring of 5 to 7 members containing 0 to 2 heteroatoms independently selected from oxygen, sulfur and nitrogen and the ring is optionally substituted one or more times with substituents independently selected from $R^{39}$.

Embodiment 30

A compound according to embodiment 29, wherein
$R^2$ is —H, and $R^4$ is selected from the group consisting of -halogen, —$OR^9$, —$SR^9$, —$S(O)_sR^9$, —$S(O)_2OR^9$, —$S(O)_sNR^9R^{10}$, —$NR^9S(O)_2R^{10}$, —NHC(O)NHR$^9$, —$NR^9C(O)R^{10}$, —$C(O)R^9$, —$C(O)OR^9$, —$C(O)NR^9R^{10}$, —$(C_1$-$C_6)$alkyl, —$(C_2$-$C_6)$alkenyl, —$(C_2$-$C_6)$alkynyl, -phenyl, —$(C_3$-$C_6)$cycloalkyl, -pyrazol-5-yl, -pyrazol-4-yl, -isoxazol-4-yl, -tetrazol-5-yl, -oxazol-2-yl, and -4,5-dihydro-oxazol-2-yl, wherein the alkyl, alkenyl, phenyl, cycloalkyl, pyrazolyl, isoxazolyl, tetrazolyl, oxazolyl, and dihydro-oxazolyl groups are optionally substituted one or more times with substituents independently selected from $R^{39}$, wherein
$R^9$ and $R^{10}$ are independently selected from the group consisting of —H, —$(C_1$-$C_6)$alkyl, —$(C_3$-$C_6)$cycloalkyl, -phenyl, —$(C_1$-$C_6)$alkylene-$(C_3$-$C_6)$cycloalkyl, and —$(C_1$-$C_6)$alkylene-phenyl, wherein the alkyl, alkylene, cycloalkyl, phenyl groups of $R^9$ and $R^{10}$ are optionally substituted one or more times with substituents independently selected from $R^{39}$, or $R^9$ and $R^{10}$ together with the atoms to which they are attached form a heterocyclic ring of 5 to 7 members containing 0 to 2 additional heteroatoms independently selected from oxygen, sulfur and nitrogen and the ring is optionally substituted one or more times with substituents independently selected from $R^{39}$.

Embodiment 31

A compound according to embodiment 29, wherein
$R^2$ is —H, and $R^4$ is selected from the group consisting of -halogen, —$OR^9$, —$(C_1$-$C_6)$alkyl, -phenyl, —$(C_3$-$C_6)$cycloalkyl, -pyrazol-5-yl, -pyrazol-4-yl, -isoxazol-4-yl, -tetrazol-5-yl, -oxazol-2-yl, and -4,5-dihydro-oxazol-2-yl, wherein the alkyl, alkenyl, phenyl, cycloalkyl, pyrazolyl, isoxazolyl, tetrazolyl, oxazolyl, and dihydro-oxazolyl groups are optionally substituted one or more times with substituents independently selected from $R^{39}$, and
$R^9$ is selected from the group consisting of —H, —$(C_1$-$C_6)$alkyl, —$(C_3$-$C_6)$cycloalkyl, -phenyl, —$(C_1$-$C_6)$alkylene-$(C_3$-$C_6)$cycloalkyl, and —$(C_1$-$C_6)$alkylene-phenyl, wherein the alkyl, alkylene, cycloalkyl,

Embodiment 32

A compound according to embodiment 29, wherein
$R^2$ is —H, and $R^4$ is selected from the group consisting of -halogen, —O—$(C_1$-$C_6)$alkyl, —$(C_1$-$C_6)$alkyl, -phenyl, —$(C_3$-$C_6)$cycloalkyl, -pyrazol-5-yl, -pyrazol-4-yl, -isoxazol-4-yl, -tetrazol-5-yl, -oxazol-2-yl, and -4,5-dihydro-oxazol-2-yl, wherein the alkyl, alkenyl, phenyl, cycloalkyl, pyrazolyl, isoxazolyl, tetrazolyl, oxazolyl, and dihydro-oxazolyl groups are optionally substituted one or more times with substituents independently selected from the group consisting of halogen, —$(C_1$-$C_6)$haloalkyl, and —$(C_1$-$C_6)$alkyl.

Embodiment 33

A compound according to embodiment 29, wherein
$R^2$ is —H, and $R^4$ is selected from the group consisting of —$SR^9$, —$S(O)_sR^9$, —$S(O)_2OR^9$, —$S(O)_sNR^9R^{10}$, —$NR^9S(O)_2R^{10}$, —$NHC(O)NHR^9$, —$NR^9C(O)R^{10}$, —$(CR^{11}R^{12})_tNR^9R^{10}$, —$C(O)R^9$, —$C(O)OR^9$, and —$C(O)NR^9R^{10}$.

Embodiment 34

A compound according to embodiment 33, wherein
$R^9$ and $R^{10}$ are independently selected from the group consisting of —H, —$(C_1$-$C_6)$alkyl, —$(C_3$-$C_6)$cycloalkyl, -phenyl, —$(C_1$-$C_6)$alkylene-$(C_3$-$C_6)$cycloalkyl, and —$(C_1$-$C_6)$alkylene-phenyl, wherein the alkyl, alkylene, cycloalkyl, phenyl groups of $R^9$ and $R^{10}$ are optionally substituted one or more times with substituents independently selected from $R^{39}$.

Embodiment 35

A compound according to embodiment 34, wherein
$R^9$ and $R^{10}$ are independently selected from the group consisting of —H, —$(C_1$-$C_6)$alkyl, —$(C_3$-$C_6)$cycloalkyl, -phenyl, —$(C_1$-$C_6)$alkylene-$(C_3$-$C_6)$cycloalkyl, and —$(C_1$-$C_6)$alkylene-phenyl, wherein the alkyl, alkylene, cycloalkyl, phenyl groups of $R^9$ and $R^{10}$ are optionally substituted one or more times with halogen.

Embodiment 36

A compound according to embodiment 33, wherein
$R^4$ is selected from the group consisting of —$S(O)_sNR^9R^{10}$, —$NR^9S(O)_2R^{10}$, —$NR^9C(O)R^{10}$, —$(CH_2)_tNR^9R^{10}$, and —$C(O)NR^9R^{10}$, wherein
$R^9$ and $R^{10}$ together with the atoms to which they are attached form a heterocyclic ring of 5 to 7 members containing 0 to 2 additional heteroatoms independently selected from oxygen, sulfur and nitrogen and the ring is optionally substituted one or more times with substituents independently selected from $R^{39}$.

Embodiment 37

A compound according to embodiment 36, wherein
$R^9$ and $R^{10}$ together with the atoms to which they are attached form a heterocyclic ring of 5 to 6 members containing 0 additional heteroatoms and the ring is optionally substituted one or more times with substituents independently selected from -halogen, —$(C_1$-$C_6)$alkyl, and —$(C_1$-$C_6)$haloalkyl.

Embodiment 38

A compound according to any one of the previous embodiments, wherein $R^3$ is the group —$X^1$-$L^1$-$R^{13}$ wherein
$X^1$ is selected from the group consisting of a direct bond, —O—, —C(O)—, —C(O)O—, —OC(O)—, —$S(O)_2$—, —$S(O)_2NH$—, —$NHS(O)_2$—, —C(O)NH—, and —NHC(O)—,
$L^1$ is selected from the group consisting of a direct bond and —$(C_1$-$C_6)$alkylene-, and
$R^{13}$ is selected from the group consisting of —$(C_1$-$C_6)$alkyl, —$(C_3$-$C_6)$cycloalkyl, —$(C_5$-$C_6)$cycloalkenyl, -phenyl, -pyridyl, -pyridazinyl, -piperidinyl, and -tetrahydropyranyl, wherein the alkyl, cycloalkyl, cycloalkenyl, phenyl, pyridyl, pyridazinyl, piperidinyl, tetrahydropyranyl groups of $R^{13}$ are optionally substituted one or more times with $R^{14}$, wherein each $R^{14}$ is independently selected from the group $R^{39}$.

Embodiment 39

A compound according to embodiment 38, wherein
$X^1$ is a direct bond.

Embodiment 40

A compound according to embodiment 38, wherein
$X^1$ is —O—.

Embodiment 41

A compound according to embodiment 38, wherein
$X^1$ is —$SO_2$—.

Embodiment 42

A compound according to embodiment 38, wherein
$X^1$ is selected from the group consisting of —C(O)—, —C(O)O—, —OC(O)—, —$S(O)_2NH$—, —$NHS(O)_2$—, —C(O)NH—, and —NHC(O)—.

Embodiment 43

A compound according to any one of embodiments 38 to 42, wherein
$L^1$ is a direct bond.

Embodiment 44

A compound according to any one of embodiments 38 to 42, wherein
$L^1$ is —$(C_1$-$C_6)$alkylene-.

Embodiment 45

A compound according to any one of embodiments 38 to 42, wherein
$L^1$ is —$CH_2$—.

Embodiment 46

A compound according to any one of embodiments 38 to 45, wherein
$R^{13}$ is —$(C_1-C_6)$alkyl optionally substituted one or more times with $R^{14}$, wherein each $R^{14}$ is independently selected from the group $R^{39}$.

Embodiment 47

A compound according to embodiment 46, wherein
$R^{13}$ is —$(C_1-C_6)$alkyl optionally substituted one or more times with $R^{14}$, wherein each $R^{14}$ is independently selected from the group consisting of halogen and —$(C_1-C_6)$haloalkyl.

Embodiment 48

A compound according to any one of embodiments 38 to 45, wherein
$R^{13}$ is —$(C_3-C_6)$cycloalkyl optionally substituted one or more times with $R^{14}$, wherein each $R^{14}$ is independently selected from the group $R^{39}$.

Embodiment 49

A compound according to embodiment 48, wherein
$R^{13}$ is —$(C_3-C_6)$cycloalkyl optionally substituted one or more times with $R^{14}$, wherein each $R^{14}$ is independently selected from the group consisting of halogen, —$(C_1-C_6)$haloalkyl, —$(C_1-C_6)$alkyl, —O—$(C_1-C_6)$alkyl, and —O—$(C_1-C_6)$haloalkyl.

Embodiment 50

A compound according to embodiment 49, wherein
$R^{13}$ is -cyclohexyl.

Embodiment 51

A compound according to any one of embodiments 38 to 45, wherein
$R^{13}$ is —$(C_5-C_6)$cycloalkenyl optionally substituted one or more times with $R^{14}$, wherein each $R^{14}$ is independently selected from the group $R^{39}$.

Embodiment 52

A compound according to embodiment 51, wherein
$R^{13}$ is -cyclohexenyl optionally substituted one or more times with $R^{14}$, wherein each $R^{14}$ is independently selected from the group consisting of halogen, —$(C_1-C_6)$haloalkyl, —$(C_1-C_6)$alkyl, —O—$(C_1-C_6)$alkyl, and —O—$(C_1-C_6)$haloalkyl.

Embodiment 53

A compound according to any one of embodiments 38 to 45, wherein
$R^{13}$ is -phenyl optionally substituted one or more times with $R^{14}$, wherein each $R^{14}$ is independently selected from the group $R^{39}$.

Embodiment 54

A compound according to embodiment 53, wherein
$R^{13}$ is -phenyl optionally substituted one or more times with $R^{14}$, wherein each $R^{14}$ is independently selected from the group consisting of -halogen, —$(C_1-C_6)$haloalkyl, —$(C_1-C_6)$alkyl, —O—$(C_1-C_6)$alkyl, and —O—$(C_1-C_6)$haloalkyl.

Embodiment 55

A compound according to embodiment 54, wherein
$R^{13}$ is -phenyl optionally substituted one or more times with $R^{14}$, wherein each $R^{14}$ is independently selected from the group consisting of halogen.

Embodiment 56

A compound according to any one of embodiments 38 to 45, wherein
$R^{13}$ is -pyridyl, optionally substituted one or more times with $R^{14}$, wherein each $R^{14}$ is independently selected from the group $R^{39}$.

Embodiment 57

A compound according to embodiment 56, wherein
$R^{13}$ is selected from the group consisting of -pyrid-2-yl, -3-yl, or -4-yl optionally substituted one or more times with $R^{14}$, wherein each $R^{14}$ is independently selected from the group consisting of -halogen, —$(C_1-C_6)$haloalkyl, —$(C_1-C_6)$alkyl, —O—$(C_1-C_6)$alkyl, and —O—$(C_1-C_6)$haloalkyl.

Embodiment 58

A compound according to any one of embodiments 38 to 45, wherein
$R^{13}$ is -pyridazinyl, optionally substituted one or more times with $R^{14}$, wherein each $R^{14}$ is independently selected from the group $R^{39}$.

Embodiment 59

A compound according to embodiment 58, wherein
$R^{13}$ is -pyridazinyl optionally substituted one or more times with $R^{14}$, wherein each $R^{14}$ is independently selected from the group consisting of -halogen, —$(C_1-C_6)$haloalkyl, —$(C_1-C_6)$alkyl, —O—$(C_1-C_6)$alkyl, and —O—$(C_1-C_6)$haloalkyl.

Embodiment 60

A compound according to any one of embodiments 38 to 45, wherein
$R^{13}$ is -piperidinyl, optionally substituted one or more times with $R^{14}$, wherein each $R^{14}$ is independently selected from the group $R^{39}$.

Embodiment 61

A compound according to embodiment 60, wherein
$R^{13}$ is -piperidin-4-yl optionally substituted one or more times with $R^{14}$, wherein each $R^{14}$ is independently selected from the group consisting of -halogen, —$(C_1-C_6)$haloalkyl, —$(C_1-C_6)$alkyl, —O—$(C_1-C_6)$alkyl, and —O—$(C_1-C_6)$haloalkyl.

Embodiment 62

A compound according to any one of embodiments 38 to 45, wherein
$R^{13}$ is tetrahydropyranyl, optionally substituted one or more times with $R^{14}$, wherein each $R^{14}$ is independently selected from the group $R^{39}$.

Embodiment 63

A compound according to embodiment 62, wherein $R^{13}$ is tetrahydropyran-4-yl.

Embodiment 64

A compound according to any one of the previous embodiments, wherein $R^7$ is the group -$L^2$-$X^2$—$R^{15}$ wherein
$L^2$ is selected from the group consisting of a direct bond and —$(C_1$-$C_6)$alkylene-,
$X^2$ is selected from the group consisting of a direct bond and —O—, and
$R^{15}$ is selected from the group consisting of —$(C_1$-$C_6)$alkyl, —$(C_3$-$C_6)$cycloalkyl, —$(C_1$-$C_6)$alkylene-$(C_3$-$C_6)$cycloalkyl, -phenyl, and —$(C_1$-$C_6)$alkylene-phenyl, wherein the alkyl, alkylene, cycloalkyl, and phenyl groups of $R^{15}$ are optionally substituted one or more times with $R^{16}$, wherein each $R^{16}$ is independently selected from the group $R^{39}$.

Embodiment 65

A compound according to embodiment 64, wherein $L^2$ is a direct bond.

Embodiment 66

A compound according to embodiment 64, wherein $L^2$ is —$(C_1$-$C_6)$alkylene-.

Embodiment 67

A compound according to any one of embodiments 64 to 66, wherein
$X^2$ is a direct bond.

Embodiment 68

A compound according to any one of embodiments 64 to 66, wherein
$X^2$ is —O—.

Embodiment 69

A compound according to any one of embodiments 64 to 68, wherein
$R^{15}$ is —$(C_1$-$C_6)$alkyl optionally substituted one or more times with $R^{16}$, wherein each $R^{16}$ is independently selected from the group $R^{39}$.

Embodiment 70

A compound according to embodiment 69, wherein
$R^{15}$ is —$(C_1$-$C_6)$alkyl optionally substituted one or more times with $R^{16}$, wherein each $R^{16}$ is independently selected from the group consisting of halogen and —$(C_1$-$C_3)$haloalkyl.

Embodiment 71

A compound according to embodiment 70, wherein
$R^{15}$ is —$CH_2CH_2CH_2CH_3$.

Embodiment 72

A compound according to any one of embodiments 64 to 68, wherein
$R^{15}$ is —$(C_3$-$C_6)$cycloalkyl optionally substituted one or more times with $R^{16}$, wherein each $R^{16}$ is independently selected from the group $R^{39}$.

Embodiment 73

A compound according to any one of embodiments 64 to 68, wherein
$R^{15}$ is —$(C_3$-$C_6)$cycloalkyl optionally substituted one or more times with $R^{16}$, wherein each $R^{16}$ is independently selected from the group consisting of -halogen, —$(C_1$-$C_3)$alkyl, —$(C_1$-$C_3)$haloalkyl, —O—$(C_1$-$C_3)$alkyl, and —O—$(C_1$-$C_3)$haloalkyl.

Embodiment 74 (R8)

A compound according to any one of the previous embodiments,
wherein $R^8$ is the group —$X^3$-$L^3$-$R^{17}$.

Embodiment 75

A compound according to embodiment 74, wherein $X^3$ is a direct bond.

Embodiment 76

A compound according to embodiment 74, wherein $X^3$ is a —O—.

Embodiment 77

A compound according to embodiment 74, wherein $X^3$ is a —C(O)NH—.

Embodiment 78

A compound according to embodiment 74, wherein $X^3$ is a —C(O)—.

Embodiment 79

A compound according to any one of embodiments 74 to 78, wherein
$L^3$ is a direct bond.

Embodiment 80

A compound according to any one of embodiments 74 to 78, wherein
$L^3$ is a —$(C_2$-$C_6)$alkylene-, wherein the alkylene group is optionally substituted one or more times with $R^{19}$, wherein each $R^{19}$ is independently selected from the group consisting of —OH, —$NH_2$, —O—$(C_1$-$C_6)$alkyl, —$(C_1$-$C_6)$alkylene-$NH_2$, —$(C_1$-$C_6)$alkylene-NH(($C_1$-$C_6)$alkyl), and —$(C_1$-$C_6)$alkylene-N(($C_1$-$C_6)$alkyl)$_2$, wherein the alkyl and alkylene groups of $R^{19}$ are optionally substituted one or more times with -halogen.

Embodiment 81

A compound according to embodiment 80, wherein
$L^3$ is a —CH$_2$CH$_2$CH$_2$— group optionally substituted once with $R^{19}$, wherein $R^{19}$ is selected from the group consisting of —OH, —O—(C$_1$-C$_6$)alkyl, —(C$_1$-C$_6$)alkylene-NH((C$_1$-C$_6$)alkyl), and —(C$_1$-C$_6$)alkylene-N((C$_1$-C$_6$)alkyl)$_2$.

Embodiment 82

A compound according to embodiment 74 to 81, wherein $R^{17}$ is selected from the group consisting of

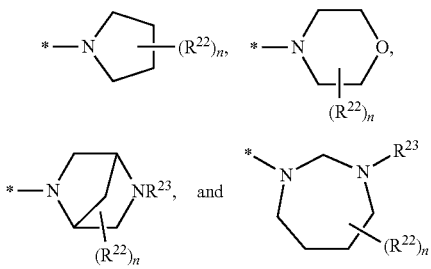

Embodiment 83

A compound according to any one of embodiments 74 to 81, wherein $R^{17}$ is selected from the group consisting of

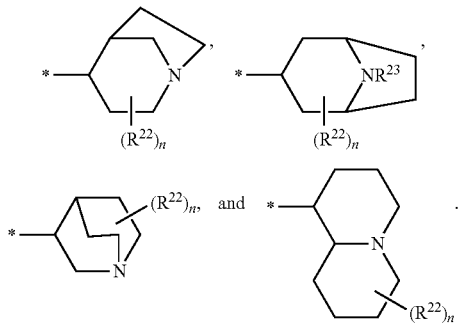

Embodiment 84

A compound according to any one of embodiments 74 to 81, wherein $R^{17}$ is selected from the group consisting of

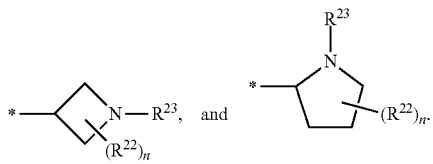

Embodiment 85

A compound according to any one of embodiments 74 to 81, wherein $R^{17}$ is

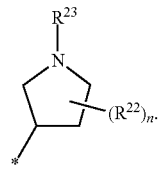

Embodiment 86

A compound according to any one of embodiments 74 to 81, wherein $R^{17}$ is selected from the group consisting of

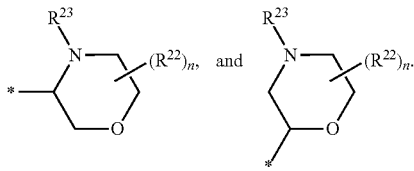

Embodiment 87

A compound according to any one of embodiments 74 to 81, wherein $R^{17}$ is

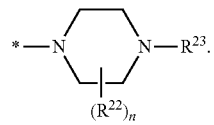

Embodiment 88

A compound according to any one of embodiments 74 to 81, wherein $R^{17}$ is

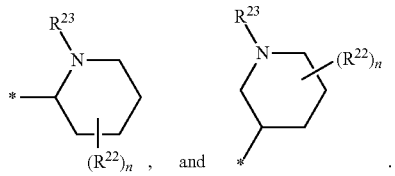

Embodiment 89

A compound according to any one of embodiments 74 to 81, wherein $R^{17}$ is

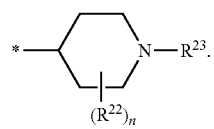

Embodiment 90

A compound according to any one of embodiments 74 to 81, wherein $R^{17}$ is

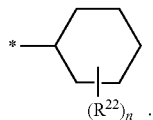

Embodiment 91

A compound according to any one of embodiments 74 to 81, wherein $R^{17}$ is

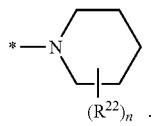

Embodiment 92

A compound according to any one of embodiments 74 to 81, wherein $R^{17}$ is selected from the group consisting of

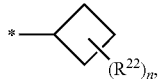 and 

Embodiment 93

A compound according to any one of embodiments 74 to 89, wherein
$R^{23}$ is selected from the group consisting of —H, —$R^{30}$, —$(C_1$-$C_6)$alkylene-$R^{31}$, —$(C_1$-$C_6)$alkylene-$NR^{32}R^{33}$, —$X^6$—$(C_2$-$C_6)$alkylene-$NR^{32}R^{33}$, and —$(C_2$-$C_6)$alkylene-$X^7$—$R^{31}$, wherein
  $X^6$ is selected from the group consisting of —C(O)—, —C(O)O—, —S(O)$_2$—, —C(O)N($R^{34}$)—, and —S(O)$_2$N($R^{34}$)—, wherein $R^{34}$ is selected from the group consisting of —H, —$(C_1$-$C_6)$alkyl, and —$(C_1$-$C_6)$haloalkyl,
  $X^7$ is selected from the group consisting of —O—, —N($R^{35}$)—, —C(O)—, —C(O)O—, —O—C(O)—, —C(O)N($R^{35}$)—, —N($R^{35}$)C(O)—, —S(O)$_2$N($R^{35}$)—, and —N($R^{35}$)S(O)$_2$—,
    wherein $R^{35}$ is selected from the group consisting of —H, —$(C_1$-$C_6)$alkyl, and —$(C_1$-$C_6)$haloalkyl,
  $R^{30}$ is selected from the group consisting of —H, —$(C_1$-$C_6)$alkyl, -phenyl, and —$(C_3$-$C_6)$cycloalkyl, wherein the alkyl, phenyl, and cycloalkyl groups of $R^{30}$ are optionally substituted one or more times with $R^{36}$, wherein each $R^{36}$ is independently selected from $R^{39}$,
  $R^{31}$ is selected from the group consisting of —H, —$(C_1$-$C_6)$alkyl, -phenyl, —$(C_3$-$C_6)$cycloalkyl, -tetrazolyl, -1,3-dioxanyl, 1,3,4-oxadiazolyl, and piperidinyl, wherein the alkyl, phenyl, cycloalkyl, tetrazolyl, 1,3-dioxanyl, 1,3,4-oxadiazolyl, and piperidinyl groups of $R^{31}$ are optionally substituted one or more times with $R^{37}$, wherein each $R^{37}$ is independently selected from $R^{39}$,
  $R^{32}$ and $R^{33}$ are independently selected from the group consisting of —H, —$(C_1$-$C_6)$alkyl, and —$(C_1$-$C_6)$haloalkyl,
wherein the alkylene groups of $R^{23}$ are optionally substituted one or more times with $R^{38}$, wherein each $R^{38}$ is independently selected from the group consisting of halogen, —OH, —$NH_2$, —O—$(C_1$-$C_6)$alkyl, —$(C_1$-$C_6)$alkylene-$NH_2$, —$(C_1$-$C_6)$alkylene-NH(($C_1$-$C_6)$alkyl), and —$(C_1$-$C_6)$alkylene-N(($C_1$-$C_6)$alkyl)$_2$, wherein the alkyl and alkylene groups of $R^{38}$ are optionally substituted one or more times with halogen.

Embodiment 94

A compound according to any one of embodiments 74 to 89, wherein
  $R^{23}$ is —H.

Embodiment 95

A compound according to any one of embodiments 74 to 89, wherein
  $R^{23}$ is —$(C_1$-$C_3)$alkyl.

Embodiment 96

A compound according to any one of embodiments 74 to 89, wherein
  $R^{23}$ is selected from the group consisting of —$(C_1$-$C_6)$alkylene-$NR^{32}R^{33}$, and —$X^6$—$(C_2$-$C_6)$alkylene-$NR^{32}R^{33}$, wherein
    $X^6$ is selected from the group consisting of —C(O)—, —C(O)O—, —S(O)$_2$—, —C(O)N($R^{34}$)—, and —S(O)$_2$N($R^{34}$)—, wherein $R^{34}$ is selected from the group consisting of —H, —$(C_1$-$C_6)$alkyl, and —$(C_1$-$C_6)$haloalkyl,
    $R^{32}$ and $R^{33}$ are independently selected from the group consisting of —H, —$(C_1$-$C_6)$alkyl, and —$(C_1$-$C_6)$haloalkyl,
  wherein the alkylene groups of $R^{23}$ are optionally substituted one or more times with $R^{38}$, wherein each $R^{38}$ is independently selected from the group consisting of halogen, —OH, —$NH_2$, —O—$(C_1$-$C_6)$alkyl, —$(C_1$-$C_6)$alkylene-$NH_2$, —$(C_1$-$C_6)$alkylene-NH(($C_1$-$C_6)$alkyl), and —$(C_1$-$C_6)$alkylene-N(($C_1$-$C_6)$alkyl)$_2$, wherein the alkyl and alkylene groups of $R^{38}$ are optionally substituted one or more times with halogen.

Embodiment 97

A compound according to any one of embodiments 74 to 89, wherein
  $R^{23}$ is —$(C_1$-$C_6)$alkylene-$NR^{32}R^{33}$, wherein $R^{32}$ and $R^{33}$ are independently selected from the group consisting of —H, —$(C_1$-$C_6)$alkyl, and —$(C_1$-$C_6)$haloalkyl.

Embodiment 98

A compound according to any one of embodiments 74 to 89, wherein
  $R^{23}$ is selected from the group consisting of —$R^{30}$, —($C_1$-$C_6$)alkylene-$R^{31}$, and —($C_2$-$C_6$)alkylene-$X^7$—$R^{31}$, wherein
    $X^7$ is selected from the group consisting of —O—, —N($R^{35}$)—, —C(O)—, —C(O)O—, —O—C(O)—, —C(O)N($R^{35}$)—, —N($R^{35}$)C(O)—, —S(O)$_2$N($R^{35}$)—, and —N($R^{35}$)S(O)$_2$—,
      wherein $R^{35}$ is selected from the group consisting of —H, —($C_1$-$C_6$)alkyl, and —($C_1$-$C_6$)haloalkyl,
    $R^{30}$ is selected from the group consisting of —H, —($C_1$-$C_6$)alkyl, -phenyl, and —($C_3$-$C_6$)cycloalkyl, wherein the alkyl, phenyl, and cycloalkyl groups of $R^{30}$ are optionally substituted one or more times with $R^{36}$, wherein each $R^{36}$ is independently selected from -halogen, —($C_1$-$C_6$)alkyl, and —($C_1$-$C_6$)haloalkyl,
    $R^{31}$ is selected from the group consisting of —H, —($C_1$-$C_6$)alkyl, -phenyl, —($C_3$-$C_6$)cycloalkyl, -tetrazolyl, -1,3-dioxan-2-yl, 1,3,4-oxadiazol-2-yl, and piperidinyl, wherein the alkyl, phenyl, cycloalkyl, tetrazolyl, 1,3-dioxanyl, 1,3,4-oxadiazolyl, and piperidinyl groups of $R^{31}$ are optionally substituted one or more times with $R^{37}$, wherein each $R^{37}$ is independently selected from $R^{39}$,
  wherein the alkylene groups of $R^{23}$ are optionally substituted one or more times with $R^{38}$, wherein each $R^{38}$ is independently selected from the group consisting of halogen, —OH, —NH$_2$, —O—($C_1$-$C_6$)alkyl, —($C_1$-$C_6$)alkylene-NH$_2$, —($C_1$-$C_6$)alkylene-NH(($C_1$-$C_6$)alkyl), and —($C_1$-$C_6$)alkylene-N(($C_1$-$C_6$)alkyl)$_2$, wherein the alkyl and alkylene groups of $R^{38}$ are optionally substituted one or more times with halogen.

Embodiment 99

A compound according to any one of embodiments 74 to 89, wherein
  $R^{23}$ is selected from the group consisting of —$R^{30}$, —($C_1$-$C_6$)alkylene-$R^{31}$, and —($C_2$-$C_6$)alkylene-$X^7$—$R^{31}$, wherein
    $X^7$ is selected from the group consisting of —O—, —N($R^{35}$)—, —C(O)—, —C(O)O—, —O—C(O)—, —C(O)N($R^{35}$)—, —N($R^{35}$)C(O)—, —S(O)$_2$N($R^{35}$)—, and —N($R^{35}$)S(O)$_2$—,
      wherein $R^{35}$ is selected from the group consisting of —H, —($C_1$-$C_6$)alkyl, and —($C_1$-$C_6$)haloalkyl,
    $R^{30}$ is selected from the group consisting of —H, —($C_1$-$C_6$)alkyl, -phenyl, and —($C_3$-$C_6$)cycloalkyl, wherein the alkyl, phenyl, and cycloalkyl groups of $R^{30}$ are optionally substituted one or more times with $R^{36}$, wherein each $R^{36}$ is independently selected from -halogen, —($C_1$-$C_6$)alkyl, and —($C_1$-$C_6$)haloalkyl,
    $R^{31}$ is selected from the group consisting of —H, —($C_1$-$C_6$)alkyl, -phenyl, —($C_3$-$C_6$)cycloalkyl, -tetrazolyl, -1,3-dioxan-2-yl, 1,3,4-oxadiazol-2-yl, and piperidinyl, wherein the alkyl, phenyl, cycloalkyl, tetrazolyl, 1,3-dioxanyl, 1,3,4-oxadiazolyl, and piperidinyl groups of $R^{31}$ are optionally substituted one or more times with $R^{37}$, wherein each $R^{37}$ is independently selected from -halogen, —($C_1$-$C_6$)alkyl, and —($C_1$-$C_6$)haloalkyl.

Embodiment 100

A compound according to any one of embodiments 74 to 89, wherein
  $R^{23}$ is selected from the group consisting of —$R^{30}$, and —($C_1$-$C_6$)alkylene-$R^{31}$, wherein
    $R^{30}$ is selected from the group consisting of —H, —($C_1$-$C_6$)alkyl, -phenyl, and —($C_3$-$C_6$)cycloalkyl, wherein the alkyl, phenyl, and cycloalkyl groups of $R^{30}$ are optionally substituted one or more times with $R^{36}$, wherein each $R^{36}$ is independently selected from -halogen, —($C_1$-$C_6$)alkyl, and —($C_1$-$C_6$)haloalkyl,
    $R^{31}$ is selected from the group consisting of —H, —($C_1$-$C_6$)alkyl, -phenyl, —($C_3$-$C_6$)cycloalkyl, -tetrazolyl, -1,3-dioxan-2-yl, 1,3,4-oxadiazol-2-yl, and piperidinyl, wherein the alkyl, phenyl, cycloalkyl, tetrazolyl, 1,3-dioxanyl, 1,3,4-oxadiazolyl, and piperidinyl groups of $R^{31}$ are optionally substituted one or more times with $R^{37}$, wherein each $R^{37}$ is independently selected from -halogen, —($C_1$-$C_6$)alkyl, and —($C_1$-$C_6$)haloalkyl.

Embodiment 101

A compound according to any one of embodiments 74 to 89, wherein
  $R^{23}$ is selected from the group consisting of —($C_2$-$C_6$)alkylene-$X^7$—$R^{31}$, wherein
    $X^7$ is —O—, and
    $R^{31}$ is selected from the group consisting of —H and —($C_1$-$C_6$)alkyl.

Embodiment 102

A compound according to any one of embodiments 74 to 101, wherein
  each $R^{22}$ is independently selected from the group consisting of -halogen, —$X^4$—$R^{24}$, —($C_1$-$C_6$)alkylene-$R^{24}$, —$X^4$—($C_1$-$C_6$)alkylene-$R^{24}$, —($C_1$-$C_6$)alkylene-$X^5$—$R^{24}$, —$X^4$—($C_1$-$C_6$)alkylene-$X^5$—$R^{24}$, and —$X^4$—($C_1$-$C_6$)alkylene-N$R^{25}R^{26}$, wherein
    $X^4$ and $X^5$ are independently selected from the group consisting of direct bond, —O—, —N($R^{27}$)—, —C(O)—, —C(O)O—, —OC(O)—, —S(O)$_2$—, —C(O)N($R^{27}$)—, —N($R^{27}$)C(O)—, —S(O)$_2$N($R^{27}$)—, —N($R^{27}$)S(O)$_2$—, and —C(O)N($R^{27}$)—S(O)$_2$—,
      wherein $R^{27}$ is selected from the group consisting of —H and —($C_1$-$C_6$)alkyl,
    $R^{24}$ is selected from the group consisting of —H, —($C_1$-$C_6$)alkyl, -phenyl, and —($C_3$-$C_6$)cycloalkyl, wherein the alkyl, phenyl, and cycloalkyl groups of $R^{24}$ are optionally substituted one or more times with $R^{28}$, wherein each $R^{28}$ is independently selected from $R^{39}$,
    $R^{25}$ and $R^{26}$ are independently selected from the group consisting of —H, —($C_1$-$C_6$)alkyl, and —($C_1$-$C_6$)haloalkyl,
  wherein the alkylene groups of $R^{22}$ are optionally substituted one or more times with $R^{29}$, wherein each $R^{29}$ is independently selected from the group consisting of -halogen, —OH, —NH$_2$, —O—($C_1$-$C_6$)alkyl, —($C_1$-$C_6$)alkylene-NH$_2$, —($C_1$-$C_6$)alkylene-NH(($C_1$-$C_6$)alkyl), and —($C_1$-$C_6$)alkylene-N(($C_1$-$C_6$)alkyl)$_2$, wherein the alkyl and alkylene groups of $R^{29}$ are optionally substituted one or more times with halogen.

Embodiment 103

A compound according to any one of embodiments 74 to 101, wherein
each $R^{22}$ is independently selected from the group consisting of -halogen and $-X^4-(C_1-C_6)$alkylene-$NR^{25}R^{26}$, wherein
$X^4$ is selected from the group consisting of direct bond, $-O-$, $-N(R^{27})-$, $-C(O)-$, $-C(O)O-$, $-OC(O)-$, $-S(O)_2-$, $-C(O)N(R^{27})-$, and $-S(O)_2N(R^{27})-$,
wherein $R^{27}$ is selected from the group consisting of $-H$ and $-(C_1-C_6)$alkyl,
$R^{25}$ and $R^{26}$ are independently selected from the group consisting of $-H$, $-(C_1-C_6)$alkyl, and $-(C_1-C_6)$haloalkyl,
wherein the alkylene group of $R^{22}$ is optionally substituted once with $R^{29}$, wherein $R^{29}$ is selected from the group consisting of -halogen, $-OH$, $-NH_2$, $-O-(C_1-C_6)$alkyl, $-(C_1-C_6)$alkylene-$NH_2$, $-(C_1-C_6)$alkylene-$NH((C_1-C_6)$alkyl)$, and $-(C_1-C_6)$alkylene-$N((C_1-C_6)$alkyl)$_2$, wherein the alkyl and alkylene groups of $R^{29}$ are optionally substituted one or more times with halogen.

Embodiment 104

A compound according to any one of embodiments 74 to 101, wherein
each $R^{22}$ is independently selected from the group consisting of -halogen and $-X^4-(C_1-C_6)$alkylene-$NR^{25}R^{26}$, wherein
$X^4$ is selected from the group consisting of direct bond and $-O-$,
$R^{25}$ and $R^{26}$ are independently selected from the group consisting of $-H$, $-(C_1-C_6)$alkyl, and $-(C_1-C_6)$haloalkyl.

Embodiment 105

A compound according to any one of embodiments 74 to 101, wherein
each $R^{22}$ is independently selected from the group consisting of -halogen, $-X^4-R^{24}$, $-(C_1-C_6)$alkylene-$R^{24}$, $-X^4-(C_1-C_6)$alkylene-$R^{24}$, $-(C_1-C_6)$alkylene-$X^5-R^{24}$, and $-X^4-(C_1-C_6)$alkylene-$X^5-R^{24}$, wherein
$X^4$ and $X^5$ are independently selected from the group consisting of: direct bond, $-O-$, $-N(R^{27})-$, $-C(O)-$, $-C(O)O-$, $-OC(O)-$, $-S(O)_2-$, $-C(O)N(R^{27})-$, $-N(R^{27})C(O)-$, $-S(O)_2N(R^{27})-$, $-N(R^{27})S(O)_2-$, and $-C(O)N(R^{27})-S(O)_2-$,
wherein $R^{27}$ is selected from the group consisting of $-H$ and $-(C_1-C_6)$alkyl,
$R^{24}$ is selected from the group consisting of $-H$, $-(C_1-C_6)$alkyl, -phenyl, and $-(C_3-C_{10})$cycloalkyl, wherein the alkyl, phenyl, and cycloalkyl groups of $R^{24}$ are optionally substituted one or more times with $R^{28}$, wherein each $R^{28}$ is independently selected from $R^{39}$,
wherein the alkylene groups of $R^{22}$ are optionally substituted one or more times with $R^{29}$, wherein each $R^{29}$ is independently selected from the group consisting of -halogen, $-OH$, $-NH_2$, $-O-(C_1-C_6)$alkyl, $-(C_1-C_6)$alkylene-$NH_2$, $-(C_1-C_6)$alkylene-$NH((C_1-C_6)$alkyl)$, and $-(C_1-C_6)$alkylene-$N((C_1-C_6)$alkyl)$_2$, wherein the alkyl and alkylene groups of $R^{29}$ are optionally substituted one or more times with halogen.

Embodiment 106

A compound according to any one of embodiments 74 to 101, wherein
each $R^{22}$ is independently selected from the group consisting of -halogen, $-X^4-R^{24}$, $-(C_1-C_6)$alkylene-$R^{24}$, $-X^4-(C_1-C_6)$alkylene-$R^{24}$, $-(C_1-C_6)$alkylene-$X^5-R^{24}$, and $-X^4-(C_1-C_6)$alkylene-$X^5-R^{24}$, wherein
$X^4$ and $X^5$ are independently selected from the group consisting of: direct bond, $-O-$, $-N(H)-$, $-C(O)-$, and $-C(O)O-$,
$R^{24}$ is selected from the group consisting of $-H$, and $-(C_1-C_6)$alkyl, wherein the alkyl group of $R^{24}$ is optionally substituted one or more times with $R^{28}$, wherein each $R^{28}$ is independently selected from halogen.

Embodiment 107

A compound according to any one of embodiments 74 to 101, wherein
each $R^{22}$ is independently selected from the group consisting of halogen, $-X^4-R^{24}$, $-(C_1-C_6)$alkylene-$X^5-R^{24}$, and $-X^4-(C_1-C_6)$alkylene-$NR^{25}R^{26}$, wherein
$X^4$ and $X^5$ are independently selected from the group consisting of: direct bond, $-O-$, and $-N(R^{27})-$,
wherein $R^{27}$ is selected from the group consisting of $-H$ and $-(C_1-C_6)$alkyl,
$R^{24}$ is selected from the group consisting of $-H$, and $-(C_1-C_6)$alkyl, wherein the alkyl group of $R^{24}$ is optionally substituted one or more times with $R^{28}$, wherein each $R^{28}$ is independently selected from halogen,
$R^{25}$ and $R^{26}$ are independently selected from the group consisting of $-H$, and $-(C_1-C_6)$alkyl.

Embodiment 108

A compound according to any one of embodiments 74 to 102, wherein
n is 0.

Embodiment 109

A compound according to any one of embodiments 74 to 107, wherein
n is 1, 2 or 3.

Embodiment 110

A compound according to any one of embodiments 74 to 81, wherein
$R^{17}$ is

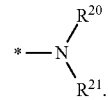

Embodiment 111

A compound according to embodiment 1, wherein
W is $CR^6$, and X and Y are N, and $R^6$ is —H,
$R^1$, $R^2$, $R^4$, and $R^5$ are —H,
$R^3$ is the group —$X^1$-$L^1$-$R^{13}$ wherein
  $X^1$ is selected from the group consisting of a direct bond and —O—,
  $L^1$ is selected from the group consisting of a direct bond, —$CH_2$—, and —$CH_2CH_2$—, and
  $R^{13}$ is selected from the group consisting of -phenyl and -cyclohexyl, wherein the cyclohexyl and phenyl groups of $R^{13}$ are optionally substituted one or more times with $R^{14}$, wherein each $R^{14}$ is independently selected from the group consisting of -halogen, —($C_1$-$C_6$)alkyl, and —($C_1$-$C_6$)haloalkyl,
$R^7$ is the group -$L^2$-$X^2$—$R^{15}$ wherein
  $L^2$ is —($C_1$-$C_4$)alkylene-,
  $X^2$ is selected from the group consisting of a direct bond and —O—, and
  $R^{15}$ is selected from the group consisting of —($C_1$-$C_4$)alkyl, optionally substituted one or more times with $R^{16}$, wherein each $R^{16}$ is independently selected from the group consisting of -halogen,
$R^8$ is the group —$X^3$-$L^3$-$R^{17}$, wherein
  $X^3$ is selected from the group consisting of direct bond, —O—, and —C(O)NH—,
  $L^3$ is selected from the group consisting of a direct bond and —$CH_2$—,
  $R^{17}$ is selected from the group consisting of

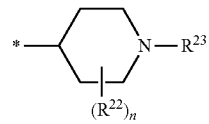

wherein
  each $R^{22}$ may be attached to any of the ring carbon atoms of $R^{17}$, and wherein
  each $R^{22}$ is independently selected from the group consisting of -halogen, —$X^4$—$R^{24}$, —($C_1$-$C_6$)alkylene-$R^{24}$, —($C_1$-$C_6$)alkylene-$X^5$—$R^{24}$, and —$X^4$—($C_1$-$C_6$)alkylene-$NR^{25}R^{26}$, wherein
    $X^4$ and $X^5$ are independently selected from the group consisting of: direct bond, —O—, and —N($R^{27}$)—, wherein $R^{27}$ is selected from the group consisting of —H and —($C_1$-$C_6$)alkyl,
    $R^{24}$ is selected from the group consisting of —H, —($C_1$-$C_6$)alkyl, wherein the alkyl groups of $R^{24}$ is optionally substituted one or more times with $R^{28}$, wherein each $R^{28}$ is independently selected from the group consisting of halogen,
    $R^{25}$ and $R^{26}$ are independently selected from the group consisting of —H, and —($C_1$-$C_6$)alkyl,
  $R^{23}$ is selected from the group consisting of —H and —($C_1$-$C_6$)alkyl, and
  n is 0, 1, 2, or 3.

Specific embodiments of the compound of Formula (I) or a pharmaceutically acceptable salt thereof include:

| Ex. | Structure | Name |
|---|---|---|
| 1 | 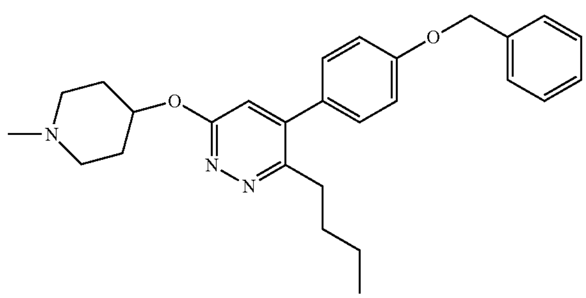 [SMILES: CCCCc1nnc(OC2CCN(C)CC2)cc1-c1ccc(OCc2ccccc2)cc1] | 4-(4-Benzyloxy-phenyl)-3-butyl-6-(1-methyl-piperidin-4-yloxy)-pyridazine |
| 2 | 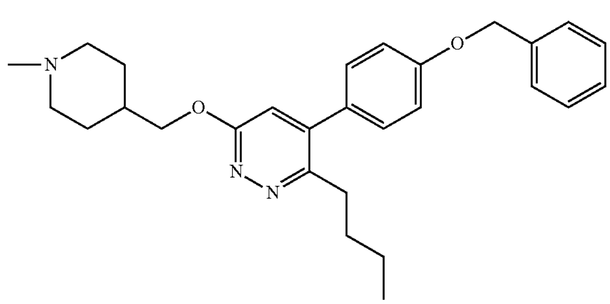 [SMILES: CCCCc1nnc(OCC2CCN(C)CC2)cc1-c1ccc(OCc2ccccc2)cc1] | 4-(4-Benzyloxy-phenyl)-3-butyl-6-(1-methyl-piperidin-4-ylmethoxy)-pyridazine |

| Ex. | Structure | Name |
|---|---|---|
| 3 | 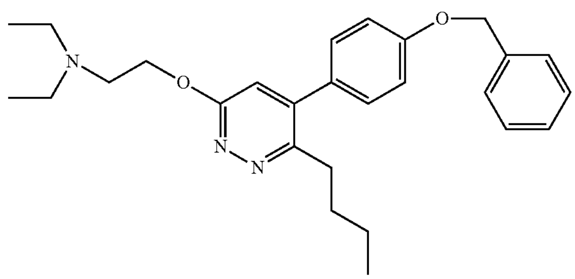 [SMILES: CCCCc1nnc(OCCN(CC)CC)cc1-c1ccc(OCc2ccccc2)cc1] | {2-[5-(4-Benzyloxy-phenyl)-6-butyl-pyridazin-3-yloxy]-ethyl}-diethyl-amine |
| 4 | 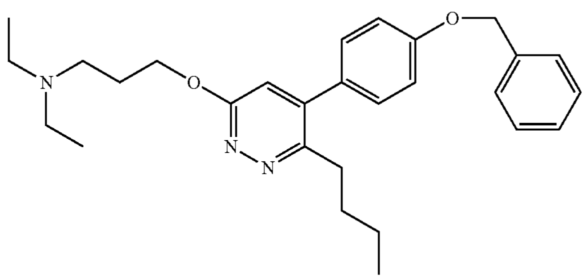 [SMILES: CCCCc1nnc(OCCCN(CC)CC)cc1-c1ccc(OCc2ccccc2)cc1] | {3-[5-(4-Benzyloxy-phenyl)-6-butyl-pyridazin-3-yloxy]-propyl}-diethyl-amine |
| 5 | 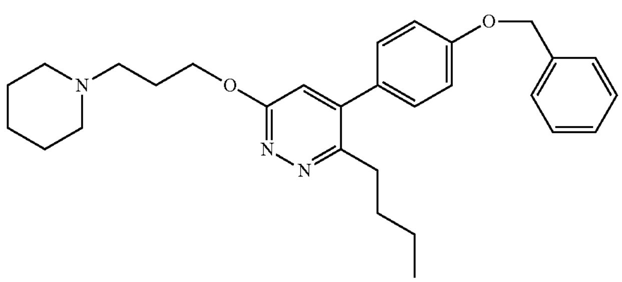 [SMILES: CCCCc1nnc(OCCCN2CCCCC2)cc1-c1ccc(OCc2ccccc2)cc1] | 4-(4-Benzyloxy-phenyl)-3-butyl-6-(3-piperidin-1-yl-propoxy)-pyridazine |
| 6 | 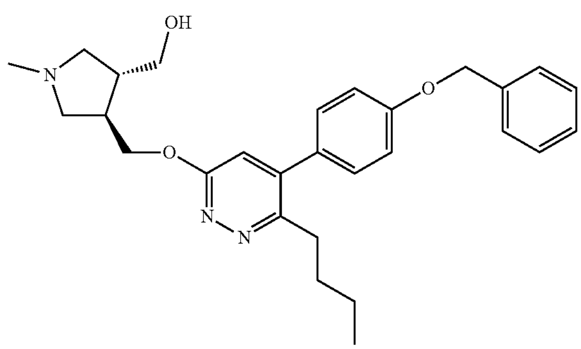 [SMILES: CCCCc1nnc(OC[C@H]2CN(C)C[C@@H]2CO)cc1-c1ccc(OCc2ccccc2)cc1] | {trans-(±)-4-[5-(4-Benzyloxy-phenyl)-6-butyl-pyridazin-3-yloxymethyl]-1-methyl-pyrrolidin-3-yl}-methanol |
| 7 | 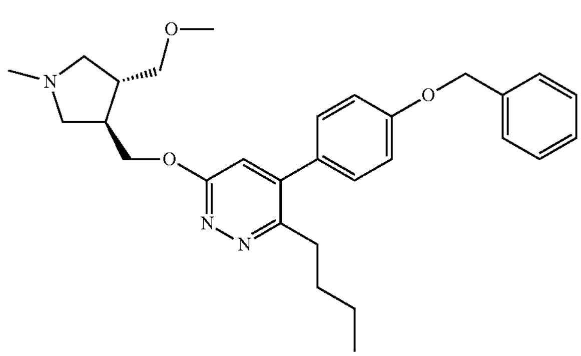 [SMILES: CCCCc1nnc(OC[C@H]2CN(C)C[C@@H]2COC)cc1-c1ccc(OCc2ccccc2)cc1] | trans-(±)-4-(4-Benzyloxy-phenyl)-3-butyl-6-(4-methoxymethyl-1-methyl-pyrrolidin-3-ylmethoxy)-pyridazine |

| Ex. | Structure | Name |
|---|---|---|
| 8 | 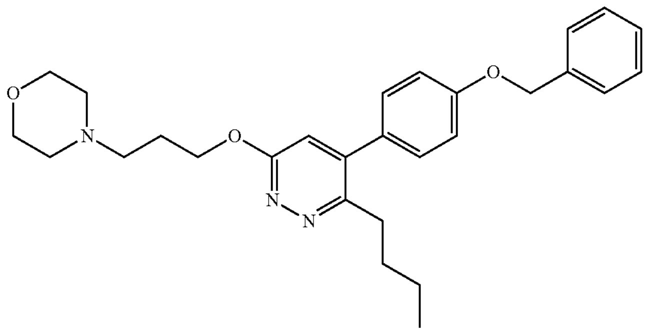 [SMILES: CCCCc1nnc(OCCCN2CCOCC2)cc1-c1ccc(OCc2ccccc2)cc1] | 4-{3-[5-(4-Benzyloxy-phenyl)-6-butyl-pyridazin-3-yloxy]-propyl}-morpholine |
| 9 | 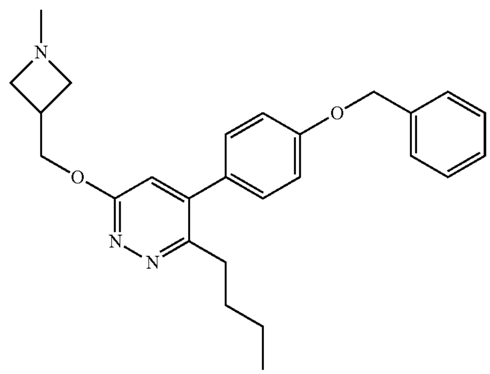 [SMILES: CCCCc1nnc(OCC2CN(C)C2)cc1-c1ccc(OCc2ccccc2)cc1] | 4-(4-Benzyloxy-phenyl)-3-butyl-6-(1-methyl-azetidin-3-ylmethoxy)-pyridazine |
| 10 | 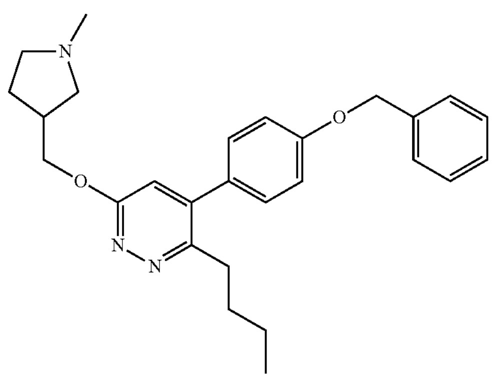 [SMILES: CCCCc1nnc(OCC2CCN(C)C2)cc1-c1ccc(OCc2ccccc2)cc1] | 4-(4-Benzyloxy-phenyl)-3-butyl-6-(1-methyl-pyrrolidin-3-ylmethoxy)-pyridazine |
| 11 | 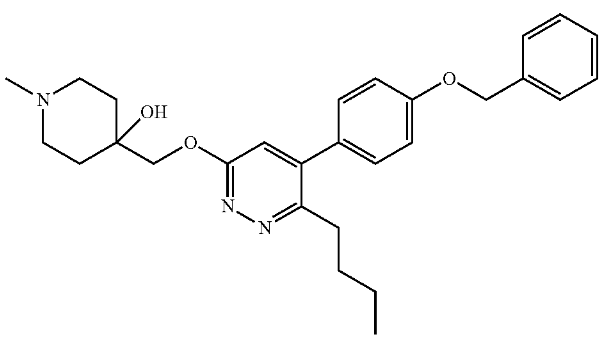 [SMILES: CCCCc1nnc(OCC2(O)CCN(C)CC2)cc1-c1ccc(OCc2ccccc2)cc1] | 4-[5-(4-Benzyloxy-phenyl)-6-butyl-pyridazin-3-yloxymethyl]-1-methyl-piperidin-4-ol |

| Ex. | Structure | Name |
|---|---|---|
| 12 | 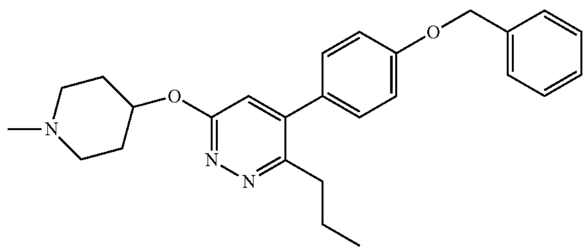 [SMILES: CCCc1nnc(OC2CCN(C)CC2)cc1-c1ccc(OCc2ccccc2)cc1] | 4-(4-Benzyloxy-phenyl)-6-(1-methyl-piperidin-4-yloxy)-3-propyl-pyridazine |
| 13 | 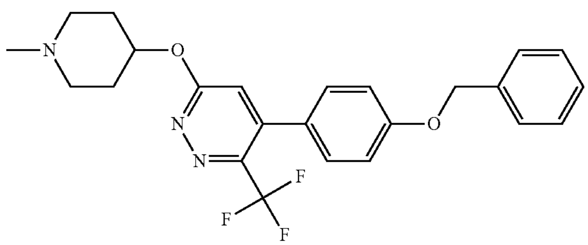 [SMILES: CN1CCC(Oc2cc(-c3ccc(OCc4ccccc4)cc3)c(C(F)(F)F)nn2)CC1] | 4-(4-Benzyloxy-phenyl)-6-(1-methyl-piperidin-4-yloxy)-3-trifluoromethyl-pyridazine |
| 14 | 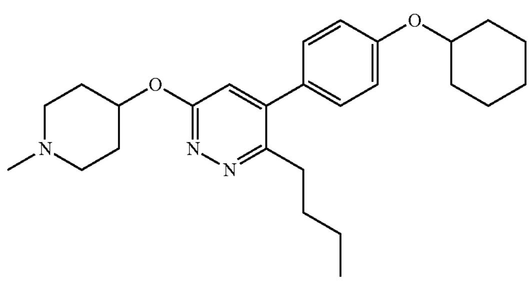 [SMILES: CCCCc1nnc(OC2CCN(C)CC2)cc1-c1ccc(OC2CCCCC2)cc1] | 3-Butyl-4-(4-cyclohexyloxy-phenyl)-6-(1-methyl-piperidin-4-yloxy)-pyridazine |
| 15 | 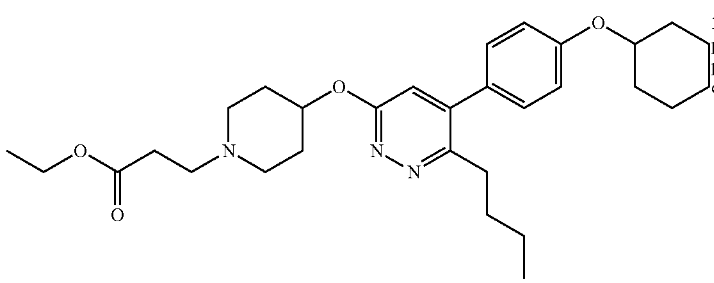 [SMILES: CCCCc1nnc(OC2CCN(CCC(=O)OCC)CC2)cc1-c1ccc(OC2CCCCC2)cc1] | 3-{4-[6-Butyl-5-(4-cyclohexyloxy-phenyl)-pyridazin-3-yloxy]-piperidin-1-yl}-propionic acid ethyl ester |
| 16 | 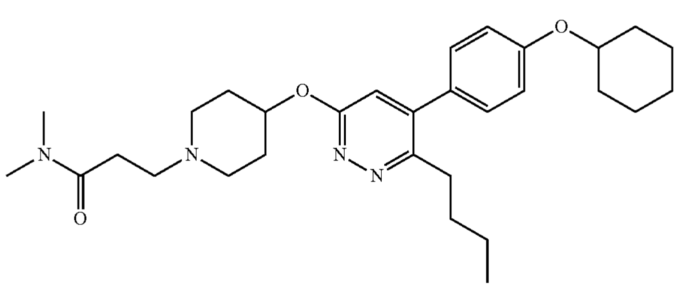 [SMILES: CCCCc1nnc(OC2CCN(CCC(=O)N(C)C)CC2)cc1-c1ccc(OC2CCCCC2)cc1] | 3-{4-[6-Butyl-5-(4-cyclohexyloxy-phenyl)-pyridazin-3-yloxy]-piperidin-1-yl}-N,N-dimethyl-propionamide |

-continued

| Ex. | Structure | Name |
|---|---|---|
| 17 | 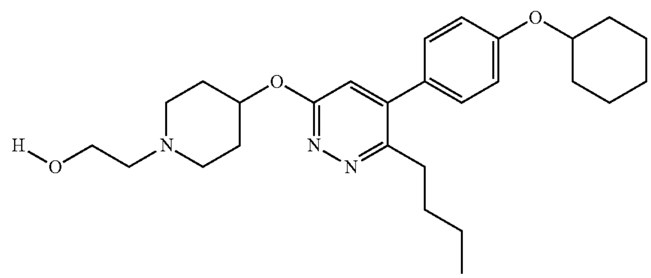 [SMILES: CCCCc1nnc(OC2CCN(CCO)CC2)cc1-c1ccc(OC2CCCCC2)cc1] | 2-{4-[6-Butyl-5-(4-cyclohexyloxy-phenyl)-pyridazin-3-yloxy]-piperidin-1-yl}-ethanol |
| 18 | 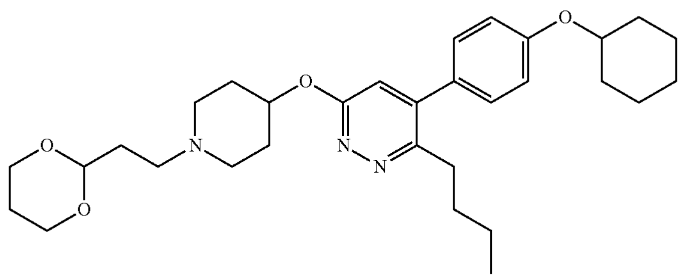 [SMILES: CCCCc1nnc(OC2CCN(CCC3OCCCO3)CC2)cc1-c1ccc(OC2CCCCC2)cc1] | 3-Butyl-4-(4-cyclohexyloxy-phenyl)-6-[1-(2-[1,3]dioxan-2-yl-ethyl)-piperidin-4-yloxy]-pyridazine |
| 19 | 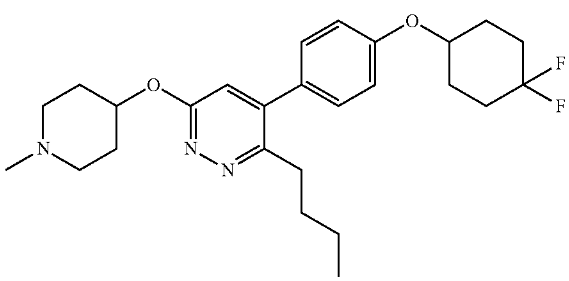 [SMILES: CCCCc1nnc(OC2CCN(C)CC2)cc1-c1ccc(OC2CCC(F)(F)CC2)cc1] | 3-Butyl-4-[4-(4,4-difluoro-cyclohexyloxy)-phenyl]-6-(1-methylpiperidin-4-yloxy)-pyridazine |
| 20 | 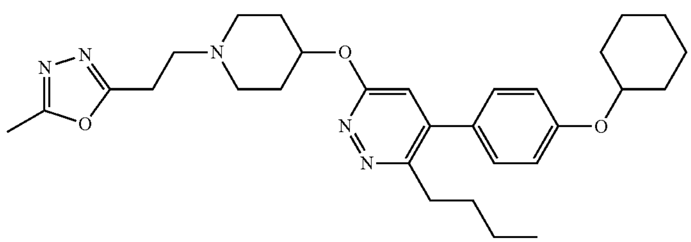 [SMILES: CCCCc1nnc(OC2CCN(CCc3nnc(C)o3)CC2)cc1-c1ccc(OC2CCCCC2)cc1] | 3-Butyl-4-(4-cyclohexyloxy-phenyl)-6-{1-[2-(5-methyl-[1,3,4]oxadiazol-2-yl)-ethyl]-piperidin-4-yloxy}-pyridazine |
| 21 | 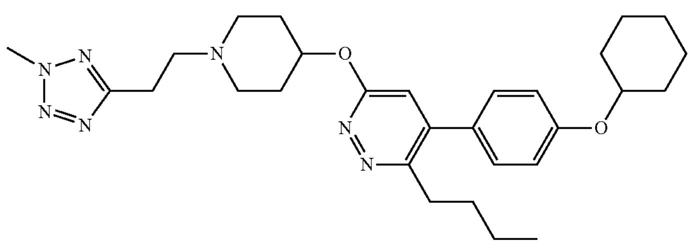 [SMILES: CCCCc1nnc(OC2CCN(CCc3nnn(C)n3)CC2)cc1-c1ccc(OC2CCCCC2)cc1] | 3-Butyl-4-(4-cyclohexyloxy-phenyl)-6-{1-[2-(2-methyl-2H-tetrazol-5-yl)-ethyl]-piperidin-4-yloxy}-pyridazine |
| 22 | 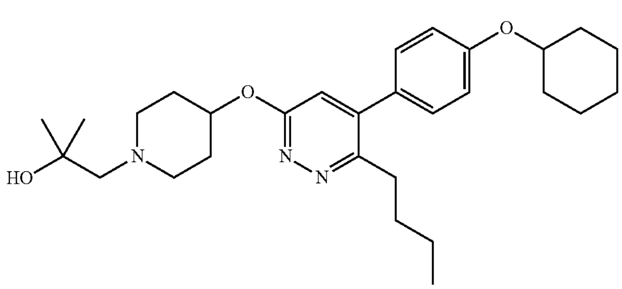 [SMILES: CCCCc1nnc(OC2CCN(CC(C)(C)O)CC2)cc1-c1ccc(OC2CCCCC2)cc1] | 1-{4-[6-Butyl-5-(4-cyclohexyloxy-phenyl)-pyridazin-3-yloxy]-piperidin-1-yl}-2-methyl-propan-2-ol |

| Ex. | Structure | Name |
|---|---|---|
| 23 | 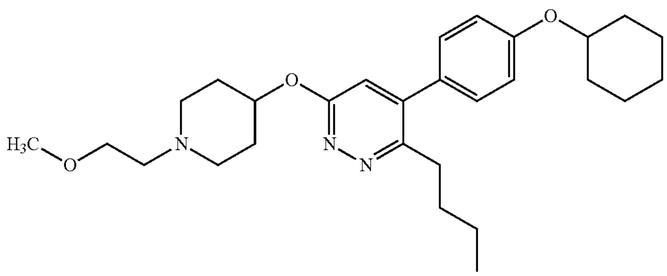 [SMILES: CCCCc1nnc(OC2CCN(CCOC)CC2)cc1-c1ccc(OC2CCCCC2)cc1] | 3-Butyl-4-(4-cyclohexyloxy-phenyl)-6-[1-(2-methoxy-ethyl)-piperidin-4-yloxy]-pyridazine |
| 24 | 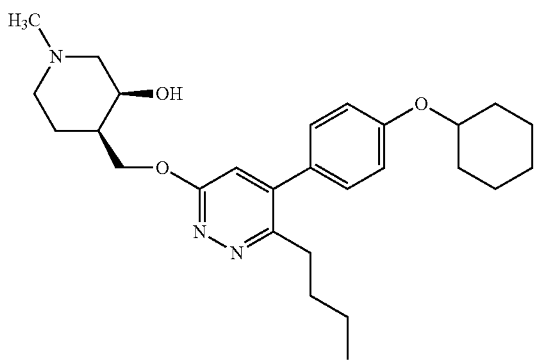 [SMILES: CCCCc1nnc(OC[C@H]2CCN(C)C[C@H]2O)cc1-c1ccc(OC2CCCCC2)cc1] | cis-(±)-4-[6-Butyl-5-(4-cyclohexyloxy-phenyl)-pyridazin-3-yloxymethyl]-1-methyl-piperidin-3-ol |
| 25 | 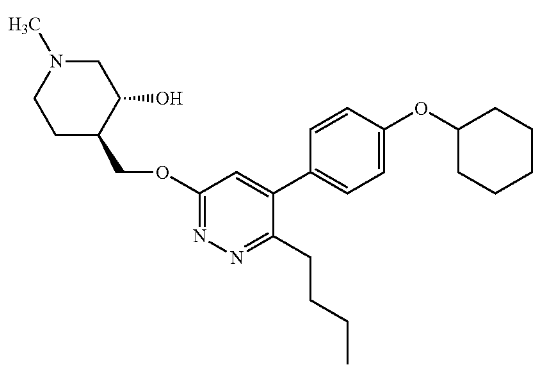 [SMILES: CCCCc1nnc(OC[C@H]2CCN(C)C[C@@H]2O)cc1-c1ccc(OC2CCCCC2)cc1] | trans-(±)-4-[6-Butyl-5-(4-cyclohexyloxy-phenyl)-pyridazin-3-yloxymethyl]-1-methyl-piperidin-3-ol |
| 26 | 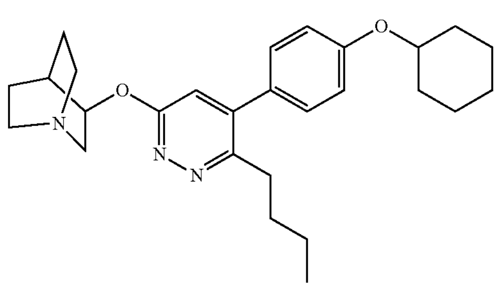 [SMILES: CCCCc1nnc(OC2CN3CCC2CC3)cc1-c1ccc(OC2CCCCC2)cc1] | 3-[6-Butyl-5-(4-cyclohexyloxy-phenyl)-pyridazin-3-yloxy]-1-aza-bicyclo[2.2.2]octane |

| Ex. | Structure | Name |
|---|---|---|
| 27 | 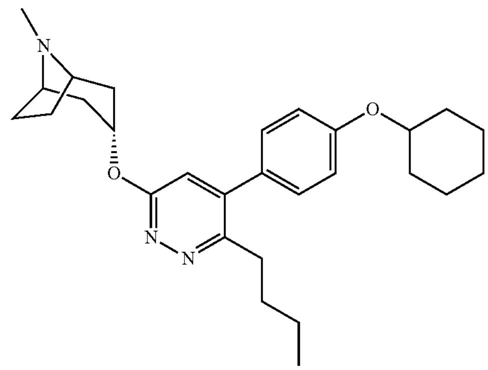 | 3-[6-Butyl-5-(4-cyclohexyloxy-phenyl)-pyridazin-3-yloxy]-8-methyl-8-aza-bicyclo[3.2.1]octane |
| 28 | 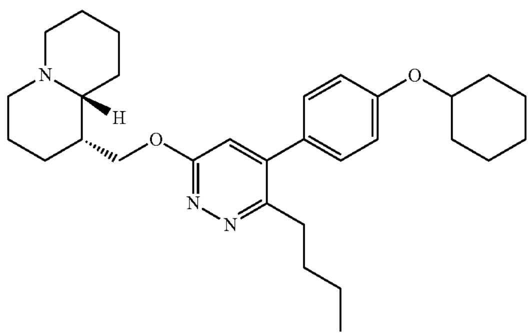 [SMILES: CCCCc1nnc(OC[C@@H]2CCCN3CCCC[C@H]23)cc1-c1ccc(OC2CCCCC2)cc1] | (1R,9aR)-1-[6-Butyl-5-(4-cyclohexyloxy-phenyl)-pyridazin-3-yloxymethyl]-octahydro-quinolizine |
| 29 | 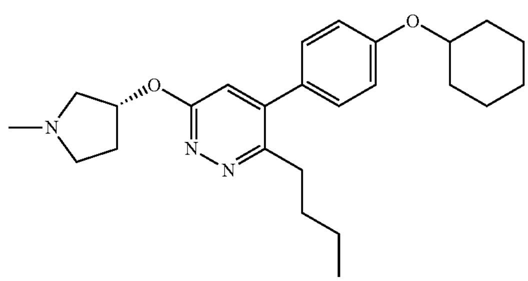 [SMILES: CCCCc1nnc(O[C@@H]2CCN(C)C2)cc1-c1ccc(OC2CCCCC2)cc1] | 3-Butyl-4-(4-cyclohexyloxy-phenyl)-6-((R)-1-methyl-pyrrolidin-3-yloxy)-pyridazine |
| 30 | 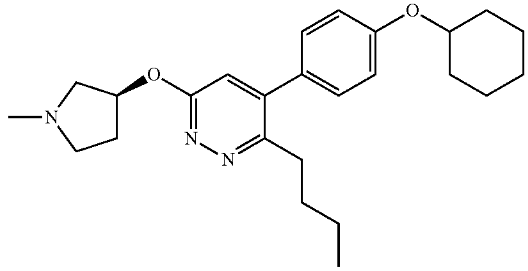 [SMILES: CCCCc1nnc(O[C@H]2CCN(C)C2)cc1-c1ccc(OC2CCCCC2)cc1] | 3-Butyl-4-(4-cyclohexyloxy-phenyl)-6-((S)-1-methyl-pyrrolidin-3-yloxy)-pyridazine |

-continued

| Ex. | Structure | Name |
|---|---|---|
| 31 | 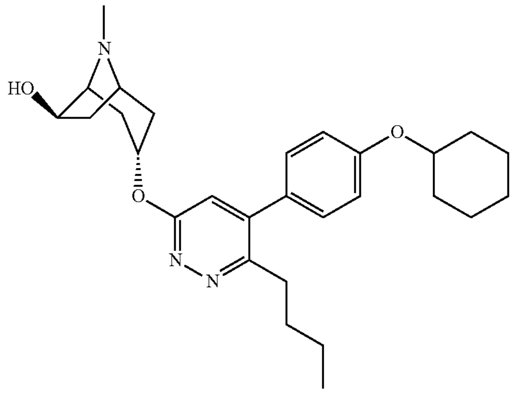 [SMILES: CCCCc1nnc(O[C@H]2CC3C[C@@H](O)C(C2)N3C)cc1-c1ccc(OC2CCCCC2)cc1] | (3S,6R)-3-[6-Butyl-5-(4-cyclohexyloxy-phenyl)-pyridazin-3-yloxy]-8-methyl-8-aza-bicyclo[3.2.1]octan-6-ol |
| 32 | 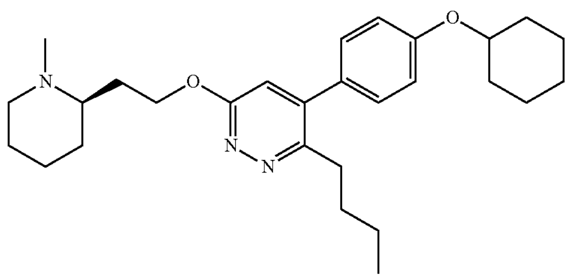 [SMILES: CCCCc1nnc(OCC[C@H]2CCCCN2C)cc1-c1ccc(OC2CCCCC2)cc1] | 3-Butyl-4-(4-cyclohexyloxy-phenyl)-6-[2-((R)-1-methyl-piperidin-2-yl)-ethoxy]-pyridazine |
| 33 | 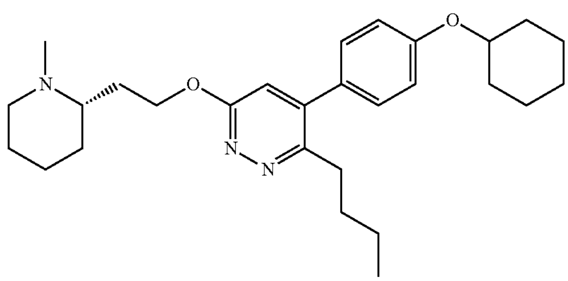 [SMILES: CCCCc1nnc(OCC[C@@H]2CCCCN2C)cc1-c1ccc(OC2CCCCC2)cc1] | 3-Butyl-4-(4-cyclohexyloxy-phenyl)-6-[2-((S)-1-methyl-piperidin-2-yl)-ethoxy]-pyridazine |
| 34 | 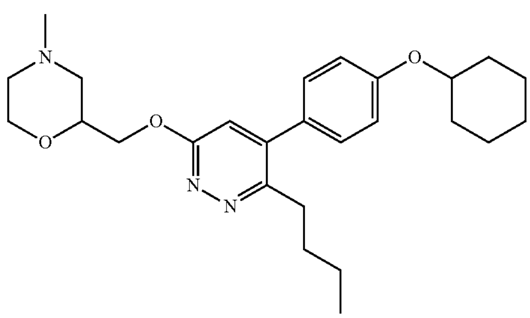 [SMILES: CCCCc1nnc(OCC2CN(C)CCO2)cc1-c1ccc(OC2CCCCC2)cc1] | 2-[6-Butyl-5-(4-cyclohexyloxy-phenyl)-pyridazin-3-yloxymethyl]-4-methyl-morpholine |
| 35 | 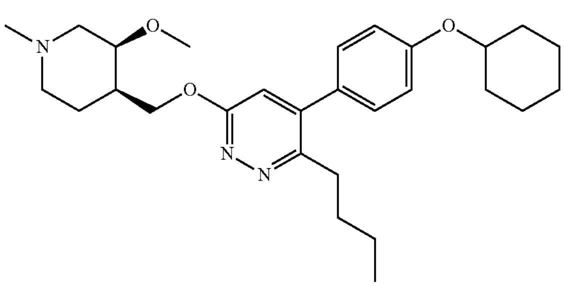 [SMILES: CCCCc1nnc(OC[C@H]2CCN(C)C[C@H]2OC)cc1-c1ccc(OC2CCCCC2)cc1] | cis-(±)-3-Butyl-4-(4-cyclohexyloxy-phenyl)-6-(-3-methoxy-1-methyl-piperidin-4-ylmethoxy)-pyridazine |

| Ex. | Structure | Name |
|---|---|---|
| 36 | 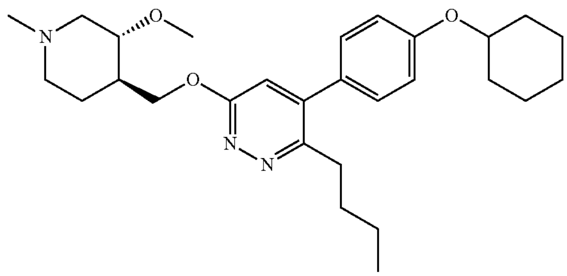 [SMILES: CCCCc1nnc(OC[C@H]2CCN(C)C[C@@H]2OC)cc1-c1ccc(OC2CCCCC2)cc1] | trans-(±)-3-Butyl-4-(4-cyclohexyloxy-phenyl)-6-(3-methoxy-1-methyl-piperidin-4-ylmethoxy)-pyridazine |
| 37 | 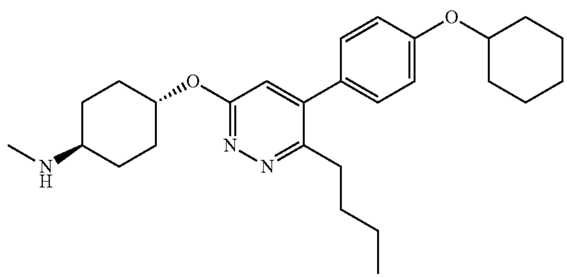 [SMILES: CCCCc1nnc(O[C@H]2CC[C@H](NC)CC2)cc1-c1ccc(OC2CCCCC2)cc1] | trans-{4-[6-Butyl-5-(4-cyclohexyloxy-phenyl)-pyridazin-3-yloxy]-cyclohexyl}-methyl-amine |
| 38 | 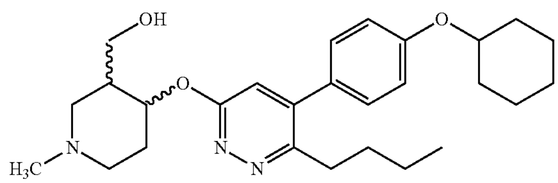 [SMILES: CCCCc1nnc(OC2CCN(C)CC2CO)cc1-c1ccc(OC2CCCCC2)cc1] | {4-[6-Butyl-5-(4-cyclohexyloxy-phenyl)-pyridazin-3-yloxy]-1-methyl-piperidin-3-yl}-methanol |
| 39 | 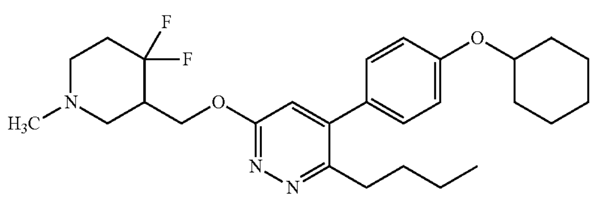 [SMILES: CCCCc1nnc(OCC2CN(C)CCC2(F)F)cc1-c1ccc(OC2CCCCC2)cc1] | 3-Butyl-4-(4-cyclohexyloxy-phenyl)-6-(4,4-difluoro-1-methyl-piperidin-3-ylmethoxy)-pyridazine |
| 40 | 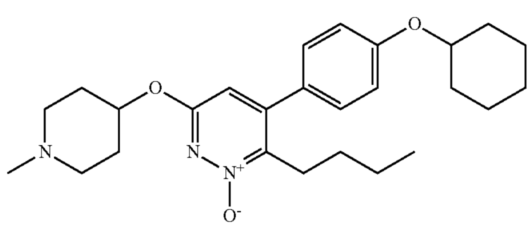 [SMILES: CCCCc1c(-c2ccc(OC3CCCCC3)cc2)cc(OC2CCN(C)CC2)n[n+]1[O-]] | 3-Butyl-4-(4-cyclohexyloxy-phenyl)-6-(1-methyl-piperidin-4-yloxy)-pyridazine 2-oxide |
| 41 | 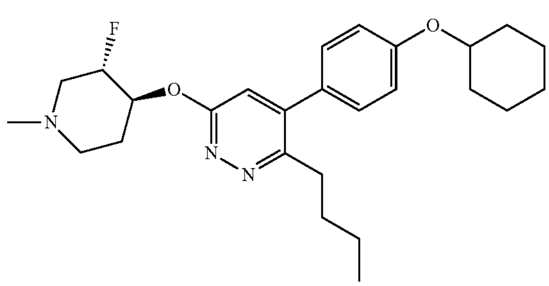 [SMILES: CCCCc1nnc(O[C@H]2CCN(C)C[C@@H]2F)cc1-c1ccc(OC2CCCCC2)cc1] | trans-(±)-3-Butyl-4-(4-cyclohexyloxy-phenyl)-6-(3-fluoro-1-methyl-piperidin-4-yloxy)-pyridazine |

-continued

| Ex. | Structure | Name |
|---|---|---|
| 42 | 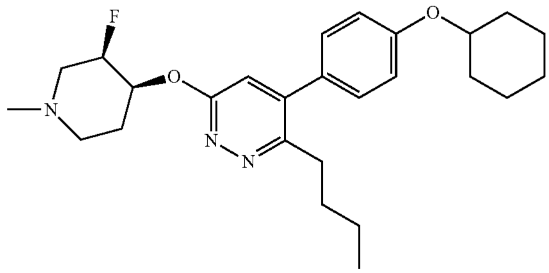 [SMILES: CCCCc1nnc(O[C@H]2CCN(C)C[C@H]2F)cc1-c1ccc(OC2CCCCC2)cc1] | cis-(±)-3-Butyl-4-(4-cyclohexyloxy-phenyl)-6-(-3-fluoro-1-methyl-piperidin-4-yloxy)-pyridazine |
| 43 | 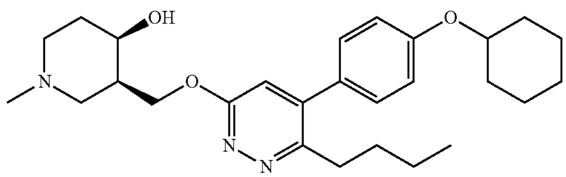 [SMILES: CCCCc1nnc(OC[C@H]2CN(C)CC[C@H]2O)cc1-c1ccc(OC2CCCCC2)cc1] | cis-(±)-3-[6-Butyl-5-(4-cyclohexyloxy-phenyl)-pyridazin-3-yloxymethyl]-1-methyl-piperidin-4-ol |
| 44 | 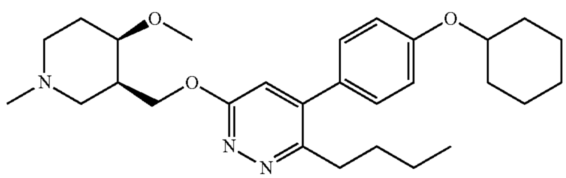 [SMILES: CCCCc1nnc(OC[C@H]2CN(C)CC[C@H]2OC)cc1-c1ccc(OC2CCCCC2)cc1] | cis-(±)-3-Butyl-4-(4-cyclohexyloxy-phenyl)-6-(4-methoxy-1-methyl-piperidin-3-ylmethoxy)-pyridazine |
| 45 | 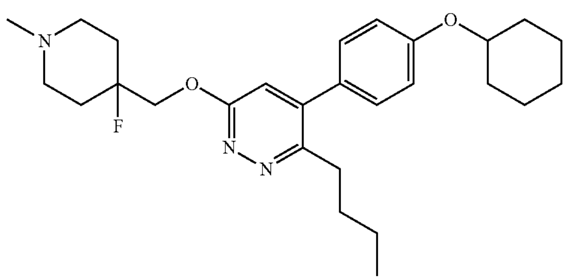 [SMILES: CCCCc1nnc(OCC2(F)CCN(C)CC2)cc1-c1ccc(OC2CCCCC2)cc1] | 3-Butyl-4-(4-cyclohexyloxy-phenyl)-6-(4-fluoro-1-methyl-piperidin-4-ylmethoxy)-pyridazine |
| 46 | 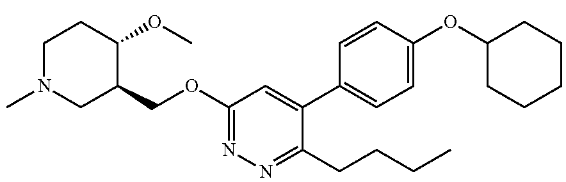 [SMILES: CCCCc1nnc(OC[C@H]2CN(C)CC[C@@H]2OC)cc1-c1ccc(OC2CCCCC2)cc1] | trans-(±)-3-Butyl-4-(4-cyclohexyloxyphenyl)-6-(4-methoxy-1-methyl-piperidin-3-ylmethoxy)-pyridazine |
| 47 | 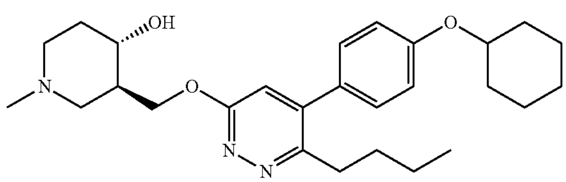 [SMILES: CCCCc1nnc(OC[C@H]2CN(C)CC[C@@H]2O)cc1-c1ccc(OC2CCCCC2)cc1] | trans-(±)-3-[6-Butyl-5-(4-cyclohexyloxy-phenyl)-pyridazin-3-yloxymethyl]-1-methyl-piperidin-4-ol |
| 48 | 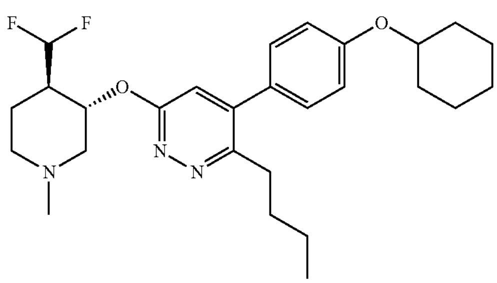 [SMILES: CCCCc1nnc(O[C@@H]2CN(C)CC[C@H]2C(F)F)cc1-c1ccc(OC2CCCCC2)cc1] | trans-(±)-3-Butyl-4-(4-cyclohexyloxy-henyl)-6-(4-difluoromethyl-1-methyl-piperidin-3-yloxy)-pyridazine |

| Ex. | Structure | Name |
|---|---|---|
| 49 | 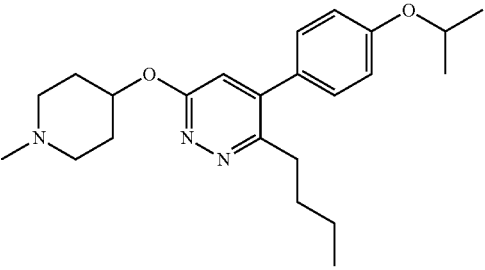 [SMILES: CCCCc1nnc(OC2CCN(C)CC2)cc1-c1ccc(OC(C)C)cc1] | 3-Butyl-4-(4-isopropoxy-phenyl)-6-(1-methyl-piperidin-4-yloxy)-pyridazine |
| 50 | 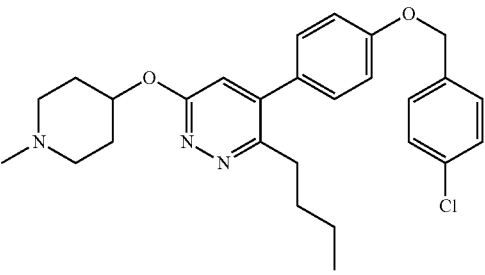 [SMILES: CCCCc1nnc(OC2CCN(C)CC2)cc1-c1ccc(OCc2ccc(Cl)cc2)cc1] | 3-Butyl-4-[4-(4-chloro-benzyloxy)-phenyl]-6-(1-methyl-piperidin-4-yloxy)-pyridazine |
| 51 | 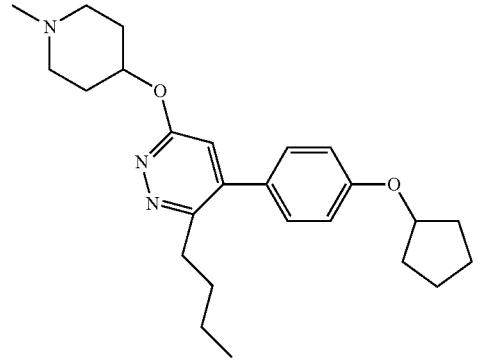 [SMILES: CCCCc1nnc(OC2CCN(C)CC2)cc1-c1ccc(OC2CCCC2)cc1] | 3-Butyl-4-(4-cyclopentyloxy-phenyl)-6-(1-methyl-piperidin-4-yloxy)-pyridazine |
| 52 | 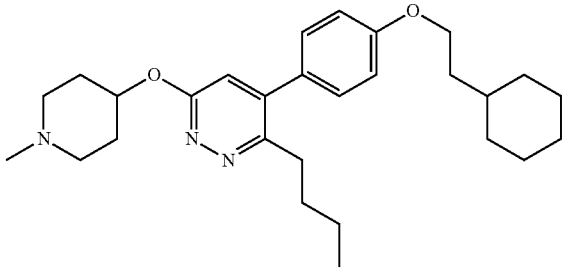 [SMILES: CCCCc1nnc(OC2CCN(C)CC2)cc1-c1ccc(OCCC2CCCCC2)cc1] | 3-Butyl-4-[4-(2-cyclohexyl-ethoxy)-phenyl]-6-(1-methyl-piperidin-4-yloxy)-pyridazine |
| 53 | 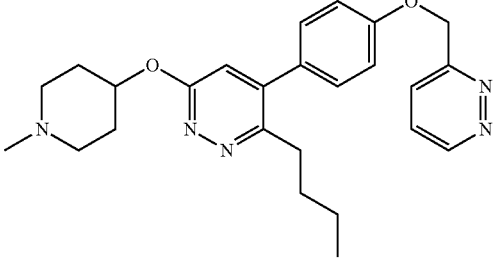 | 3-Butyl-6-(1-methyl-piperidin-4-yloxy)-4-[4-(pyridazin-3-ylmethoxy)-phenyl]-pyridazine |

| Ex. | Structure | Name |
|---|---|---|
| 54 | 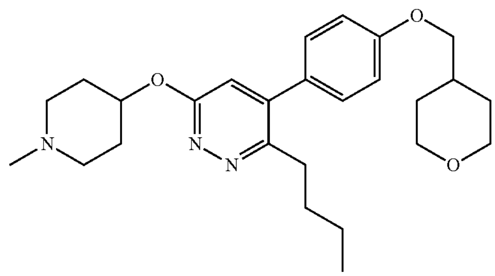 [SMILES: CCCCc1nnc(OC2CCN(C)CC2)cc1-c1ccc(OCC2CCOCC2)cc1] | 3-Butyl-6-(1-methyl-piperidin-4-yloxy)-4-[4-(tetrahydro-pyran-4-ylmethoxy)-phenyl]-pyridazine |
| 55 | 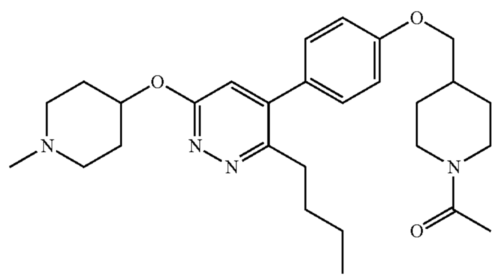 [SMILES: CCCCc1nnc(OC2CCN(C)CC2)cc1-c1ccc(OCC2CCN(C(C)=O)CC2)cc1] | 1-(4-{4-[3-Butyl-6-(1-methyl-piperidin-4-yloxy)-pyridazin-4-yl]-phenoxymethyl}-piperidin-1-yl)-ethanone |
| 56 | 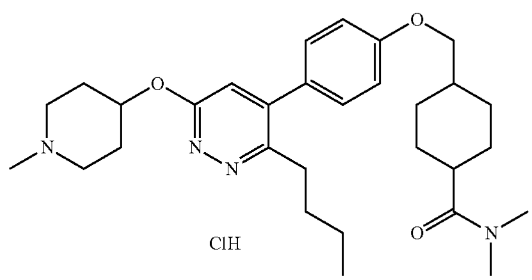 | 4-{4-[3-Butyl-6-(1-methyl-piperidin-4-yloxy)-pyridazin-4-yl]-phenoxymethyl}-cyclohexanecarboxylic acid diethylamide |
| 57 | 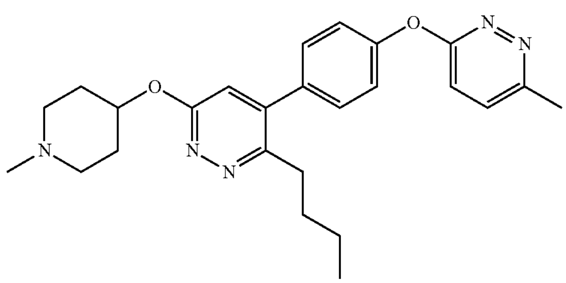 | 3-Butyl-6-(1-methyl-piperidin-4-yloxy)-4-[4-(6-methyl-pyridazin-3-yloxy)-phenyl]-pyridazine |
| 58 | 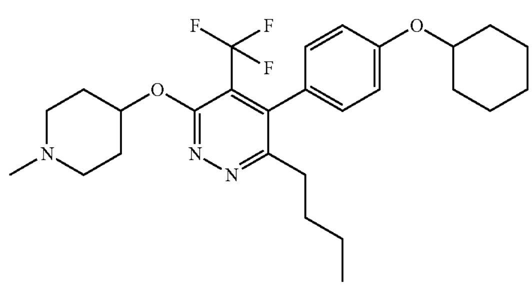 [SMILES: CCCCc1nnc(OC2CCN(C)CC2)c(C(F)(F)F)c1-c1ccc(OC2CCCCC2)cc1] | 3-Butyl-4-(4-cyclohexyloxy-phenyl)-6-(1-methyl-piperidin-4-yloxy)-5-trifluoromethyl-pyridazine |
| 59 | 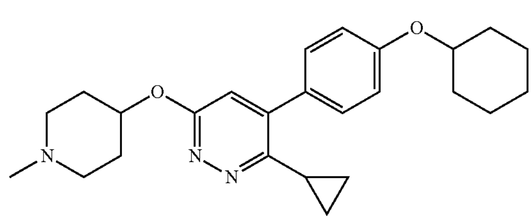 [SMILES: CN1CCC(Oc2cc(-c3ccc(OC4CCCCC4)cc3)c(C3CC3)nn2)CC1] | 4-(4-Cyclohexyloxy-phenyl)-3-cyclopropyl-6-(1-methyl-piperidin-4-yloxy)-pyridazine |

-continued

| Ex. | Structure | Name |
|---|---|---|
| 60 | 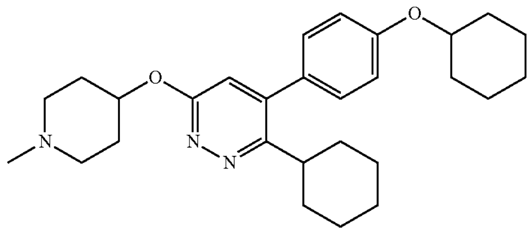 [SMILES: CN1CCC(Oc2cc(-c3ccc(OC4CCCCC4)cc3)c(C3CCCCC3)nn2)CC1] | 3-Cyclohexyl-4-(4-cyclohexyloxy-phenyl)-6-(1-methyl-piperidin-4-yloxy)-pyridazine |
| 61 | 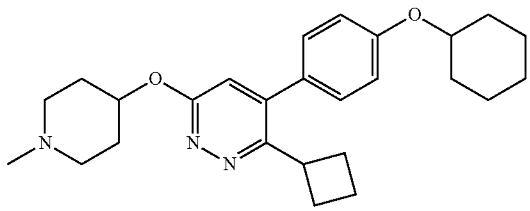 [SMILES: CN1CCC(Oc2cc(-c3ccc(OC4CCCCC4)cc3)c(C3CCC3)nn2)CC1] | 3-Cyclobutyl-4-(4-cyclohexyloxy-phenyl)-6-(1-methyl-piperidin-4-yloxy)-pyridazine |
| 62 | 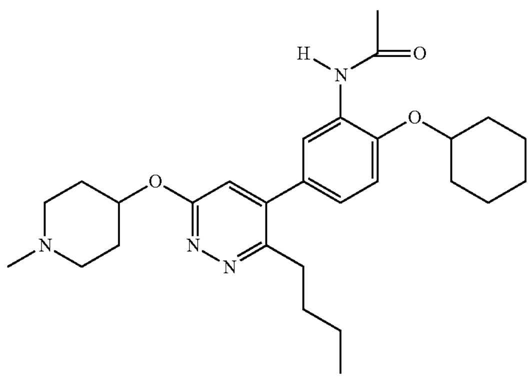 [SMILES: CCCCc1nnc(OC2CCN(C)CC2)cc1-c1ccc(OC2CCCCC2)c(NC(C)=O)c1] | N-{5-[3-Butyl-6-(1-methyl-piperidin-4-yloxy)-pyridazin-4-yl]-2-cyclohexyloxy-phenyl}-acetamide |
| 63 | 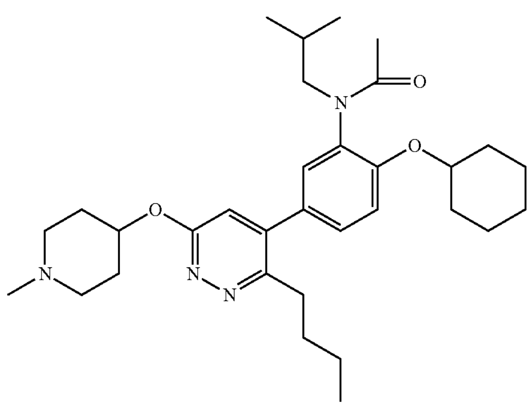 [SMILES: CCCCc1nnc(OC2CCN(C)CC2)cc1-c1ccc(OC2CCCCC2)c(N(CC(C)C)C(C)=O)c1] | N-{5-[3-butyl-6-(1-methyl-piperidin-4-yloxy)-pyridazin-4-yl]-2-cyclohexyloxy-phenyl}-N-isobutyl-acetamide |

| Ex. | Structure | Name |
|---|---|---|
| 64 | 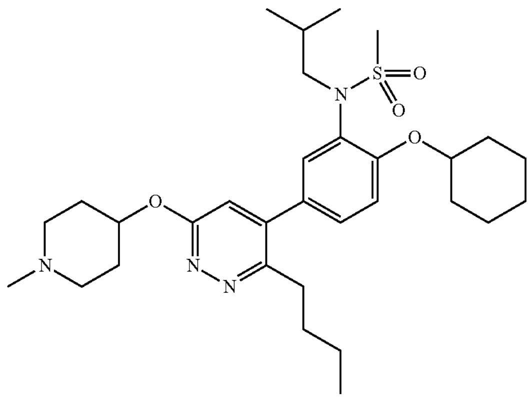 [SMILES: CCCCc1nnc(OC2CCN(C)CC2)cc1-c1ccc(OC2CCCCC2)c(N(CC(C)C)S(C)(=O)=O)c1] | N-{5-[3-Butyl-6-(1-methyl-piperidin-4-yloxy)-pyridazin-4-yl]-2-cyclohexyloxy-phenyl}-N-isobutyl-methanesulfonamide |
| 65 | 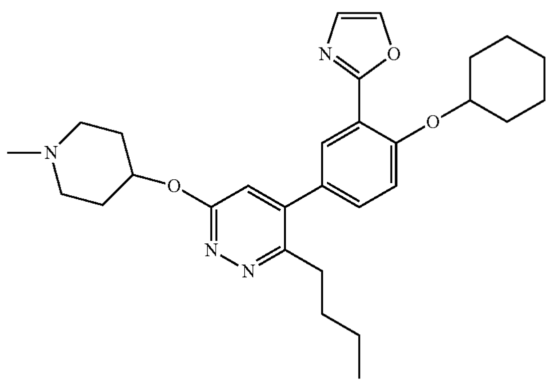 [SMILES: CCCCc1nnc(OC2CCN(C)CC2)cc1-c1ccc(OC2CCCCC2)c(-c2ncco2)c1] | 3-Butyl-4-(4-cyclohexyloxy-3-oxazol-2-yl-phenyl)-6-(1-methyl-piperidin-4-yloxy)-pyridazine |
| 66 | 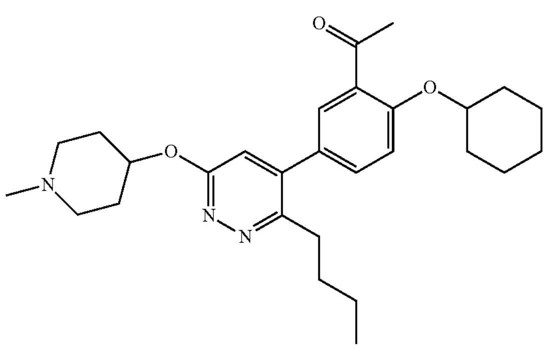 [SMILES: CCCCc1nnc(OC2CCN(C)CC2)cc1-c1ccc(OC2CCCCC2)c(C(C)=O)c1] | 1-{5-[3-Butyl-6-(1-methyl-piperidin-4-yloxy)-pyridazin-4-yl]-2-cyclohexyloxy-phenyl}-ethanone |
| 67 | 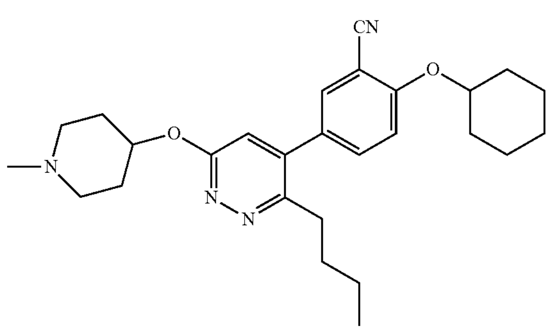 [SMILES: CCCCc1nnc(OC2CCN(C)CC2)cc1-c1ccc(OC2CCCCC2)c(C#N)c1] | 5-[3-Butyl-6-(1-methyl-piperidin-4-yloxy)-pyridazin-4-yl]-2-cyclohexyloxy-benzonitrile |

| Ex. | Structure | Name |
|---|---|---|
| 68 | 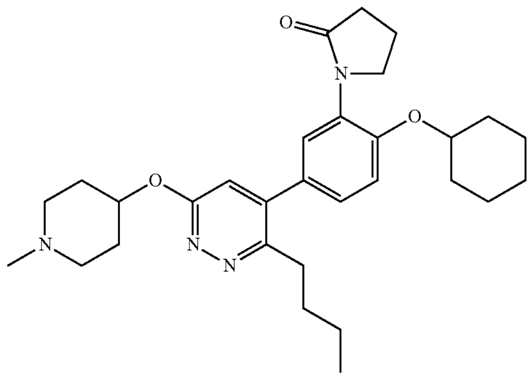 [SMILES: CCCCc1nnc(OC2CCN(C)CC2)cc1-c1ccc(OC2CCCCC2)c(N2CCCC2=O)c1] | 1-{5-[3-Butyl-6-(1-methyl-piperidin-4-yloxy)-pyridazin-4-yl]-2-cyclohexyloxy-phenyl}-pyrrolidin-2-one |
| 69 | 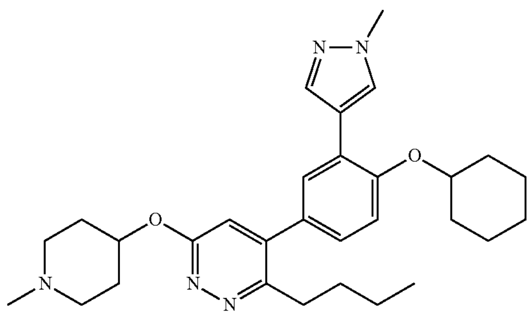 [SMILES: CCCCc1nnc(OC2CCN(C)CC2)cc1-c1ccc(OC2CCCCC2)c(-c2cnn(C)c2)c1] | 3-Butyl-4-[4-cyclohexyloxy-3-(1-methyl-1H-pyrazol-4-yl)-phenyl]-6-(1-methyl-piperidin-4-yloxy)-pyridazine |
| 70 | 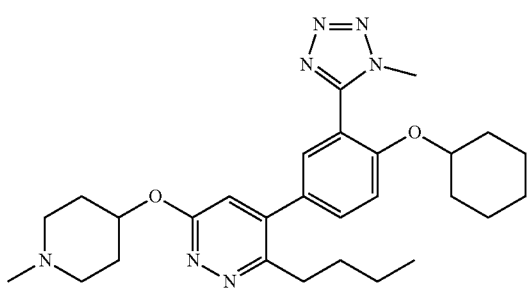 [SMILES: CCCCc1nnc(OC2CCN(C)CC2)cc1-c1ccc(OC2CCCCC2)c(-c2nnnn2C)c1] | 3-Butyl-4-[4-cyclohexyloxy-3-(1-methyl-1H-tetrazol-5-yl)-phenyl]-6-(1-methyl-piperidin-4-yloxy)-pyridazine |
| 71 | 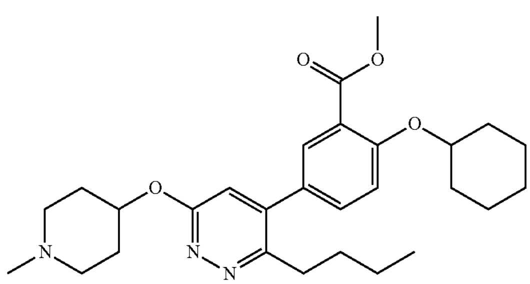 [SMILES: CCCCc1nnc(OC2CCN(C)CC2)cc1-c1ccc(OC2CCCCC2)c(C(=O)OC)c1] | 5-[3-Butyl-6-(1-methyl-piperidin-4-yloxy)-pyridazin-4-yl]-2-cyclohexyloxy-benzoic acid methyl ester |
| 72 | 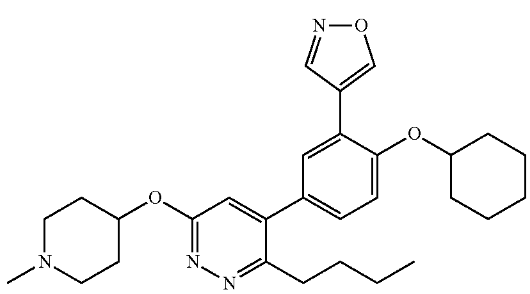 [SMILES: CCCCc1nnc(OC2CCN(C)CC2)cc1-c1ccc(OC2CCCCC2)c(-c2cnoc2)c1] | 3-Butyl-4-(4-cyclohexyloxy-3-isoxazol-4-yl-phenyl)-6-(1-methyl-piperidin-4-yloxy)-pyridazine |

| Ex. | Structure | Name |
|---|---|---|
| 73 | 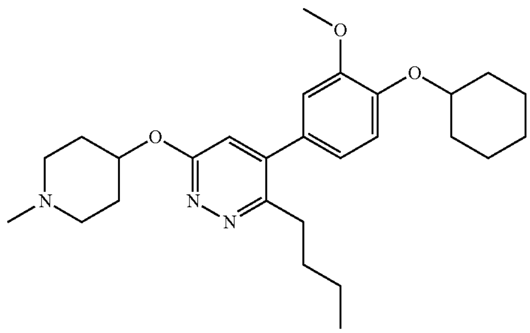 [SMILES: CCCCc1nnc(OC2CCN(C)CC2)cc1-c1ccc(OC2CCCCC2)c(OC)c1] | 3-Butyl-4-(4-cyclohexyloxy-3-methoxy-phenyl)-6-(1-methyl-piperidin-4-yloxy)-pyridazine |
| 74 | 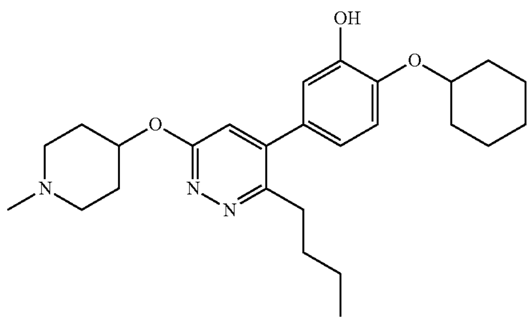 [SMILES: CCCCc1nnc(OC2CCN(C)CC2)cc1-c1ccc(OC2CCCCC2)c(O)c1] | 5-[3-Butyl-6-(1-methyl-piperidin-4-yloxy)-pyridazin-4-yl]-2-cyclohexyloxy-phenol |
| 75 | 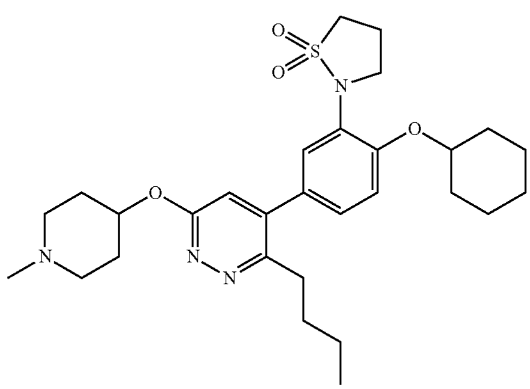 [SMILES: CCCCc1nnc(OC2CCN(C)CC2)cc1-c1ccc(OC2CCCCC2)c(N2CCCS2(=O)=O)c1] | 3-Butyl-4-[4-cyclohexyloxy-3-(1,1-dioxo-1lambda*6*-isothiazolidin-2-yl)-phenyl]-6-(1-methyl-piperidin-4-yloxy)-pyridazine |
| 76 | 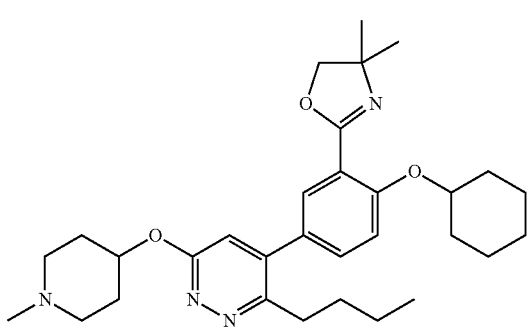 [SMILES: CCCCc1nnc(OC2CCN(C)CC2)cc1-c1ccc(OC2CCCCC2)c(C2=NC(C)(C)CO2)c1] | 3-Butyl-4-[4-cyclohexyloxy-3-(4,4-dimethyl-4,5-dihydro-oxazol-2-yl)-phenyl]-6-(1-methyl-piperidin-4-yloxy)-pyridazine |

| Ex. | Structure | Name |
|---|---|---|
| 77 | 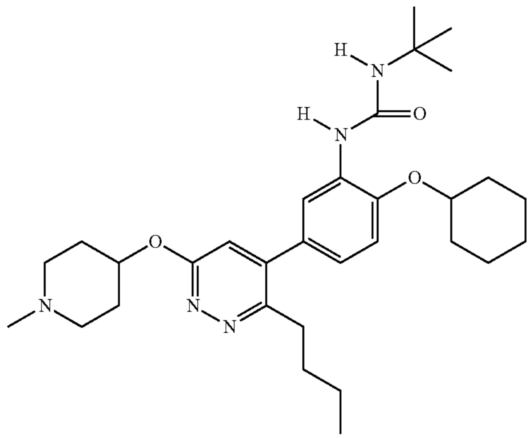 [SMILES: CCCCc1nnc(OC2CCN(C)CC2)cc1-c1ccc(OC2CCCCC2)c(NC(=O)NC(C)(C)C)c1] | 1-tert-Butyl-3-{5-[3-butyl-6-(1-methyl-piperidin-4-yloxy)-pyridazin-4-yl]-2-cyclohexyloxy-phenyl}-urea |
| 78 | 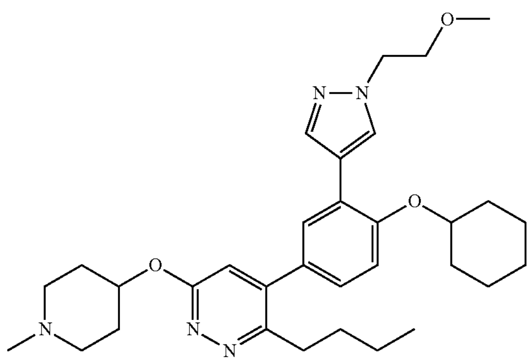 [SMILES: CCCCc1nnc(OC2CCN(C)CC2)cc1-c1ccc(OC2CCCCC2)c(-c2cnn(CCOC)c2)c1] | 3-Butyl-4-{4-cyclohexyloxy-3-[1-(2-methoxy-ethyl)-1H-pyrazol-4-yl]-phenyl}-6-(1-methyl-piperidin-4-yloxy)-pyridazine |
| 79 | 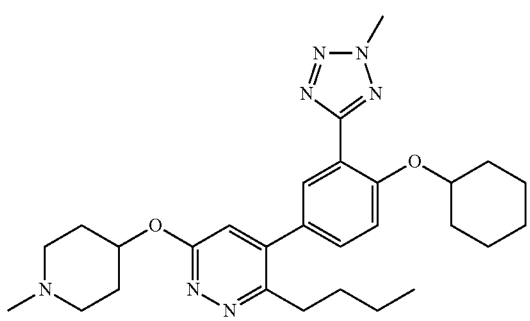 | 3-Butyl-4-[4-cyclohexyloxy-3-(2-methyl-2H-tetrazol-5-yl)-phenyl]-6-(1-methyl-piperidin-4-yloxy)-pyridazine |
| 80 | 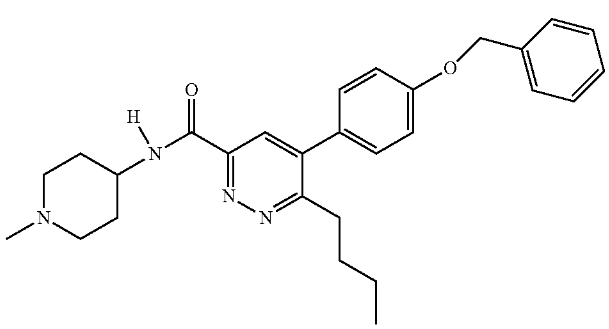 [SMILES: CCCCc1nnc(C(=O)NC2CCN(C)CC2)cc1-c1ccc(OCc2ccccc2)cc1] | 5-(4-Benzyloxy-phenyl)-6-butyl-pyridazine-3-carboxylic acid (1-methyl-piperidin-4-yl)-amide |

-continued

| Ex. | Structure | Name |
|---|---|---|
| 81 | 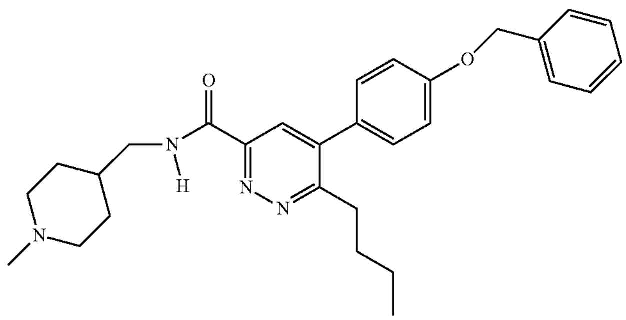 [SMILES: CCCCc1nnc(C(=O)NCC2CCN(C)CC2)cc1-c1ccc(OCc2ccccc2)cc1] | 5-(4-Benzyloxy-phenyl)-6-butyl-pyridazine-3-carboxylic acid (1-methyl-piperidin-4-ylmethyl)-amide |
| 82 | 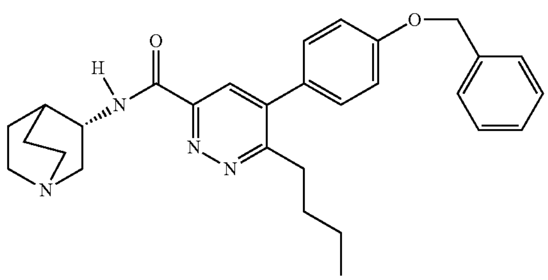 [SMILES: CCCCc1nnc(C(=O)N[C@@H]2CN3CCC2CC3)cc1-c1ccc(OCc2ccccc2)cc1] | 5-(4-Benzyloxy-phenyl)-6-butyl-pyridazine-3-carboxylic acid (S)-(1-aza-bicyclo[2.2.2]oct-3-yl)-amide |
| 83 | 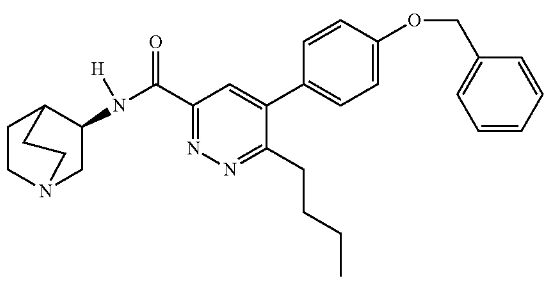 [SMILES: CCCCc1nnc(C(=O)N[C@H]2CN3CCC2CC3)cc1-c1ccc(OCc2ccccc2)cc1] | 5-(4-Benzyloxy-phenyl)-6-butyl-pyridazine-3-carboxylic acid (R)-(1-aza-bicyclo[2.2.2]oct-3-yl)-amide |
| 84 | 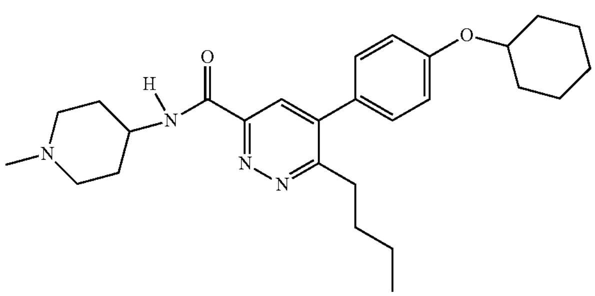 [SMILES: CCCCc1nnc(C(=O)NC2CCN(C)CC2)cc1-c1ccc(OC2CCCCC2)cc1] | 6-Butyl-5-(4-cyclohexyloxy-phenyl)-pyridazine-3-carboxylic acid (1-methyl-piperidin-4-yl)-amide |
| 85 | 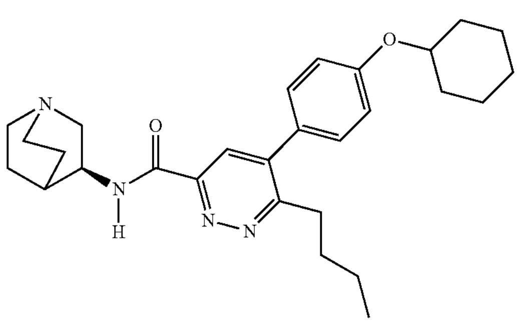 [SMILES: CCCCc1nnc(C(=O)N[C@@H]2CN3CCC2CC3)cc1-c1ccc(OC2CCCCC2)cc1] | (S)-6-Butyl-5-(4-cyclohexyloxy-phenyl)-pyridazine-3-carboxylic acid (1-aza-bicyclo[2.2.2]oct-3-yl)-amide |

-continued

| Ex. | Structure | Name |
|---|---|---|
| 86 | 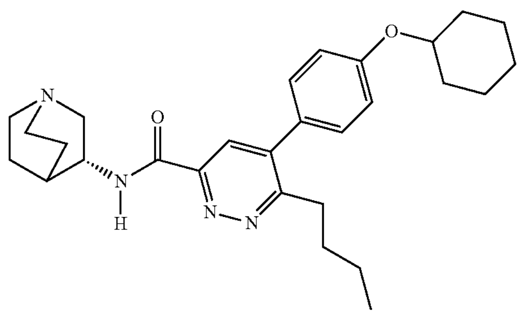 [SMILES: CCCCc1nnc(C(=O)N[C@H]2CN3CCC2CC3)cc1-c1ccc(OC2CCCCC2)cc1] | (R)-6-Butyl-5-(4-cyclohexyloxy-phenyl)-pyridazine-3-carboxylic acid (1-aza-bicyclo[2.2.2]oct-3-yl)-amide |
| 87 | 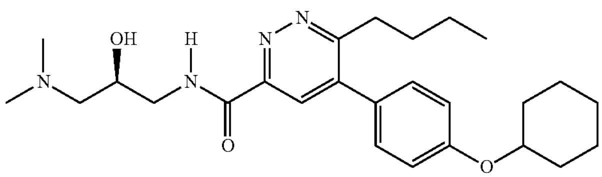 [SMILES: CCCCc1nnc(C(=O)NC[C@H](O)CN(C)C)cc1-c1ccc(OC2CCCCC2)cc1] | 6-Butyl-5-(4-cyclohexyloxy-phenyl)-pyridazine-3-carboxylic acid ((S)-3-dimethylamino-2-hydroxy-propyl)-amide |
| 88 | 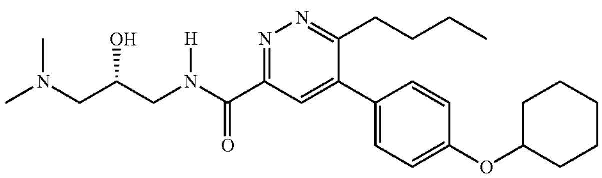 [SMILES: CCCCc1nnc(C(=O)NC[C@@H](O)CN(C)C)cc1-c1ccc(OC2CCCCC2)cc1] | 6-Butyl-5-(4-cyclohexyloxy-phenyl)-pyridazine-3-carboxylic acid ((R)-3-dimethylamino-2-hydroxy-propyl)-amide |
| 89 | 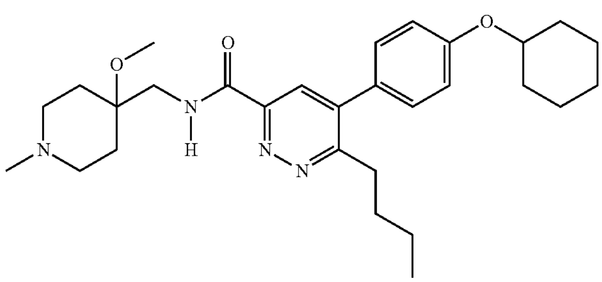 [SMILES: CCCCc1nnc(C(=O)NCC2(OC)CCN(C)CC2)cc1-c1ccc(OC2CCCCC2)cc1] | 6-Butyl-5-(4-cyclohexyloxy-phenyl)-pyridazine-3-carboxylic acid (4-methoxy-1-methyl-piperidin-4-ylmethyl)-amide |
| 90 | 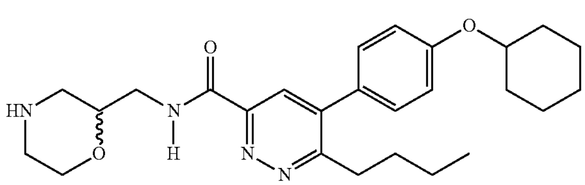 [SMILES: CCCCc1nnc(C(=O)NCC2CNCCO2)cc1-c1ccc(OC2CCCCC2)cc1] | 6-Butyl-5-(4-cyclohexyloxy-phenyl)-pyridazine-3-carboxylic acid (morpholin-2-ylmethyl)-amide |
| 91 | 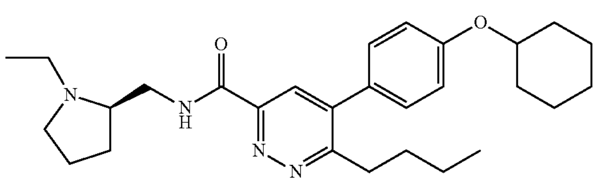 [SMILES: CCCCc1nnc(C(=O)NC[C@H]2CCCN2CC)cc1-c1ccc(OC2CCCCC2)cc1] | 6-Butyl-5-(4-cyclohexyloxy-phenyl)-pyridazine-3-carboxylic acid ((R)-1-ethyl-pyrrolidin-2-ylmethyl)-amide |
| 92 | 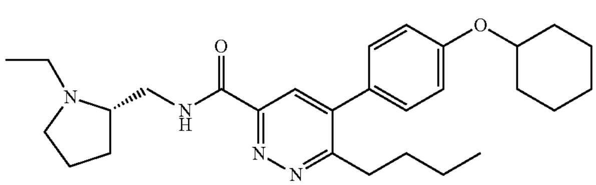 [SMILES: CCCCc1nnc(C(=O)NC[C@@H]2CCCN2CC)cc1-c1ccc(OC2CCCCC2)cc1] | 6-Butyl-5-(4-cyclohexyloxy-phenyl)-pyridazine-3-carboxylic acid ((S)-1-ethyl-pyrrolidin-2-ylmethyl)-amide dihydrochloride |

-continued

| Ex. | Structure | Name |
|---|---|---|
| 93 | 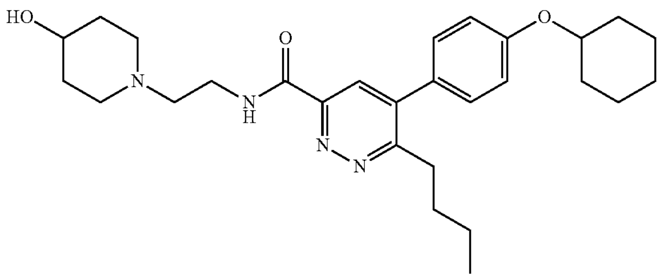 [SMILES: CCCCc1nnc(C(=O)NCCN2CCC(O)CC2)cc1-c1ccc(OC2CCCCC2)cc1] | 6-Butyl-5-(4-cyclohexyloxy-phenyl)-pyridazine-3-carboxylic acid [2-(4-hydroxy-piperidin-1-yl)-ethyl]-amide |
| 94 | 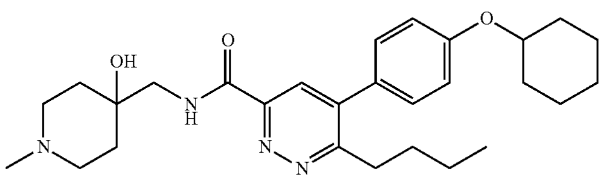 [SMILES: CCCCc1nnc(C(=O)NCC2(O)CCN(C)CC2)cc1-c1ccc(OC2CCCCC2)cc1] | 6-Butyl-5-(4-cyclohexyloxy-phenyl)-pyridazine-3-carboxylic acid (4-hydroxy-1-methyl-piperidin-4-ylmethyl)-amide |
| 95 | 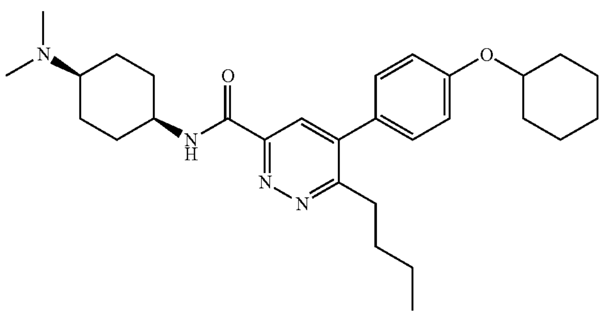 [SMILES: CCCCc1nnc(C(=O)N[C@H]2CC[C@@H](N(C)C)CC2)cc1-c1ccc(OC2CCCCC2)cc1] | (±)-(cis)-6-Butyl-5-(4-cyclohexyloxy-phenyl)-pyridazine-3-carboxylic acid (4-dimethylamino-cyclohexyl)-amide |
| 96 | 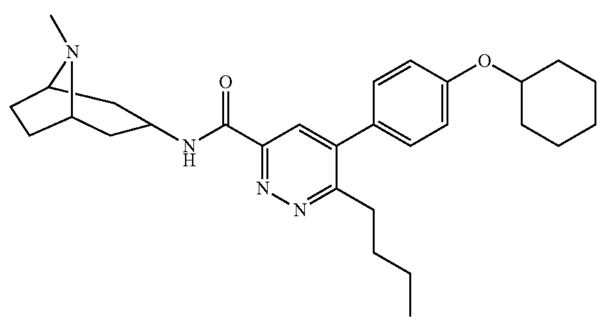 [SMILES: CCCCc1nnc(C(=O)NC2CC3CCC(C2)N3C)cc1-c1ccc(OC2CCCCC2)cc1] | 6-Butyl-5-(4-cyclohexyloxy-phenyl)-pyridazine-3-carboxylic acid (8-methyl-8-aza-bicyclo[3.2.1]oct-3-yl)-amide |
| 97 | 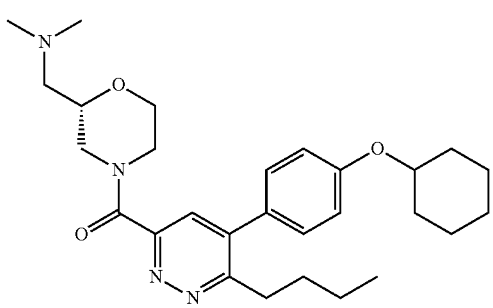 [SMILES: CCCCc1nnc(C(=O)N2CCO[C@@H](CN(C)C)C2)cc1-c1ccc(OC2CCCCC2)cc1] | [6-Butyl-5-(4-cyclohexyloxy-phenyl)-pyridazin-3-yl]-((S)-2-dimethylaminomethyl-morpholin-4-yl)-methanone |

| Ex. | Structure | Name |
|---|---|---|
| 98 | 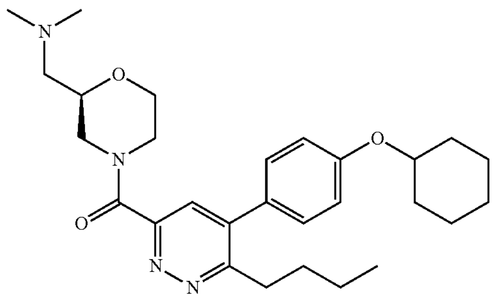 [SMILES: CCCCc1nnc(C(=O)N2CCO[C@H](CN(C)C)C2)cc1-c1ccc(OC2CCCCC2)cc1] | [6-Butyl-5-(4-cyclohexyloxy-phenyl)-pyridazin-3-yl]-((R)-2-dimethylaminomethyl-morpholin-4-yl)-methanone |
| 99 | 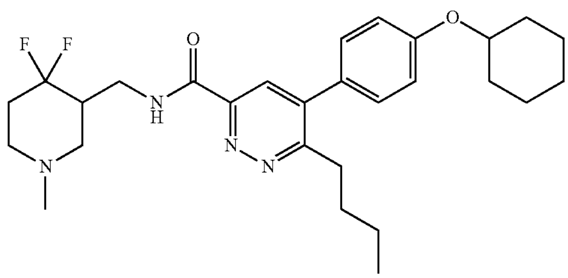 [SMILES: CCCCc1nnc(C(=O)NCC2CN(C)CCC2(F)F)cc1-c1ccc(OC2CCCCC2)cc1] | 6-Butyl-5-(4-cyclohexyloxy-phenyl)-pyridazine-3-carboxylic acid (4,4-difluoro-1-methyl-piperidin-3-ylmethyl)-amide |
| 100 | 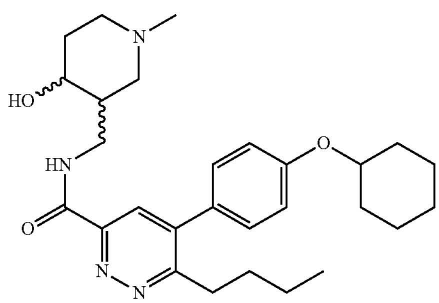 [SMILES: CCCCc1nnc(C(=O)NCC2CN(C)CCC2O)cc1-c1ccc(OC2CCCCC2)cc1] | 6-Butyl-5-(4-cyclohexyloxy-phenyl)-pyridazine-3-carboxylic acid (4-hydroxy-1-methyl-piperidin-3-ylmethyl)-amide |
| 101 | 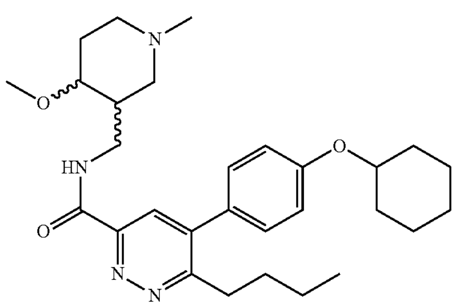 [SMILES: CCCCc1nnc(C(=O)NCC2CN(C)CCC2OC)cc1-c1ccc(OC2CCCCC2)cc1] | 6-Butyl-5-(4-cyclohexyloxy-phenyl)-pyridazine-3-carboxylic acid (4-methoxy-1-methyl-piperidin-3-ylmethyl)-amide |
| 102 | 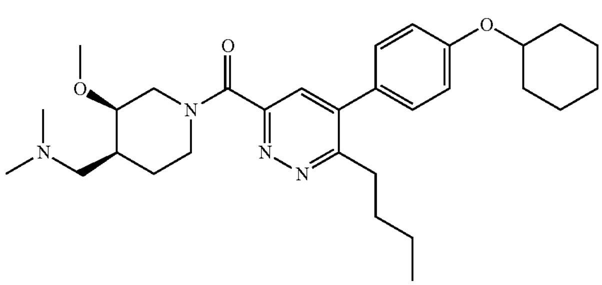 [SMILES: CCCCc1nnc(C(=O)N2CC[C@@H](CN(C)C)[C@@H](OC)C2)cc1-c1ccc(OC2CCCCC2)cc1] | (±)-cis-[6-Butyl-5-(4-cyclohexyloxy-phenyl)-pyridazin-3-yl]-((3R,4S)-4-dimethylaminomethyl-3-methoxy-pipertdin-1-yl)-methanone |

| Ex. | Structure | Name |
| --- | --- | --- |
| 103 | 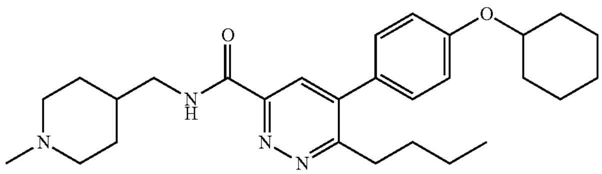 [SMILES: CCCCc1nnc(C(=O)NCC2CCN(C)CC2)cc1-c1ccc(OC2CCCCC2)cc1] | 6-Butyl-5-(4-cyclohexyloxy-phenyl)-pyridazine-3-carboxylic acid (1-methyl-piperidin-4-ylmethyl)-amide |
| 104 | 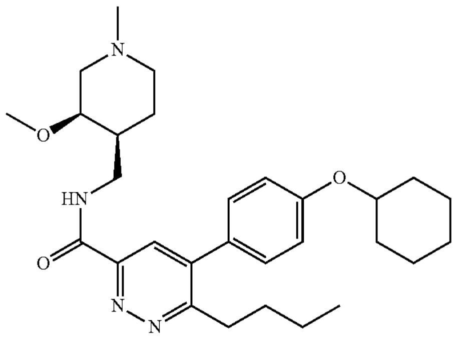 [SMILES: CCCCc1nnc(C(=O)NC[C@@H]2CCN(C)C[C@@H]2OC)cc1-c1ccc(OC2CCCCC2)cc1] | (±)-cis-6-Butyl-5-(4-cyclohexyloxy-phenyl)-pyridazine-3-carboxylic acid (3-methoxy-1-methyl-piperidin-4-ylmethyl)-amide |
| 105 | 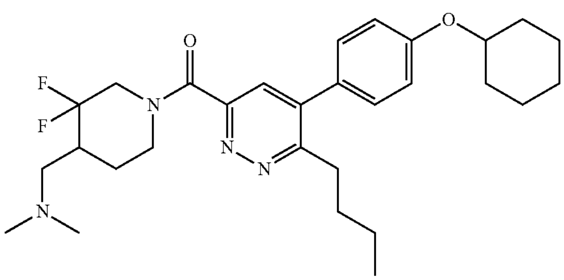 [SMILES: CCCCc1nnc(C(=O)N2CCC(CN(C)C)C(F)(F)C2)cc1-c1ccc(OC2CCCCC2)cc1] | [6-Butyl-5-(4-cyclohexyloxy-phenyl)-pyridazin-3-yl]-(4-dimethylaminomethyl-3,3-difluoro-piperidin-1-yl)-methanone |
| 106 | 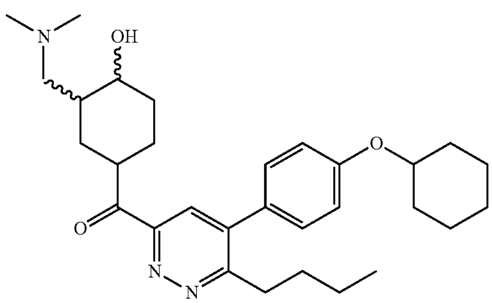 [SMILES: CCCCc1nnc(C(=O)C2CCC(O)C(CN(C)C)C2)cc1-c1ccc(OC2CCCCC2)cc1] | [6-Butyl-5-(4-cyclohexyloxy-phenyl)-pyridazin-3-yl]-(3-dimethylaminomethyl-4-hydroxyoxy-piperidin-1-yl)-methanone |
| 107 | 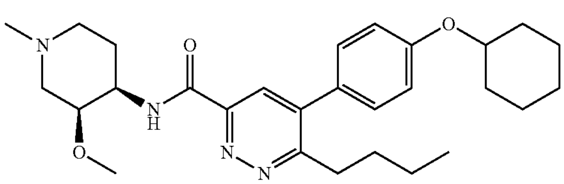 [SMILES: CCCCc1nnc(C(=O)N[C@@H]2CCN(C)C[C@@H]2OC)cc1-c1ccc(OC2CCCCC2)cc1] | 6-Butyl-5-(4-cyclohexyloxy-phenyl)-pyridazine-3-carboxylic acid (3-methoxy-1-methyl-piperidin-4-yl)-amide |
| 108 | 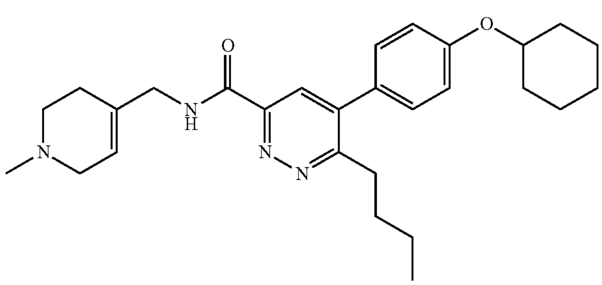 [SMILES: CCCCc1nnc(C(=O)NCC2=CCN(C)CC2)cc1-c1ccc(OC2CCCCC2)cc1] | 6-Butyl-5-(4-cyclohexyloxy-phenyl)-pyridazine-3-carboxylic acid (1-methyl-1,2,3,6-tetrahydro-pyridin-4-ylmethyl)-amide |

| Ex. | Structure | Name |
|---|---|---|
| 109 | 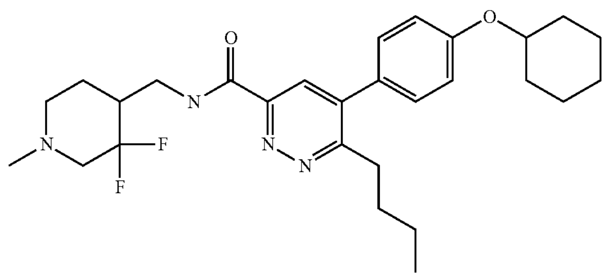 [SMILES: CCCCc1nnc(C(=O)NCC2CCN(C)CC2(F)F)cc1-c1ccc(OC2CCCCC2)cc1] | 6-Butyl-5-(4-cyclohexyloxy-phenyl)-pyridazine-3-carboxylic acid (4-fluoro-1-methyl-piperidin-4-ylmethyl)-amide |
| 110 | 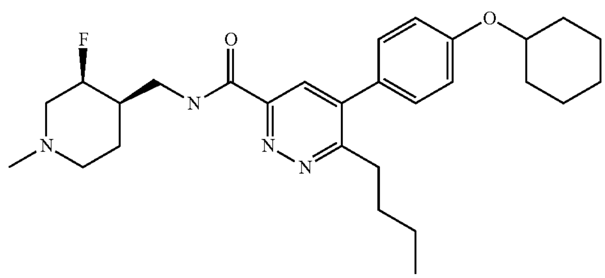 [SMILES: CCCCc1nnc(C(=O)NC[C@H]2CCN(C)C[C@H]2F)cc1-c1ccc(OC2CCCCC2)cc1] | (±)-cis-6-Butyl-5-(4-cyclohexyloxy-phenyl)-pyridazine-3-carboxylic acid (3-fluoro-1-methyl-piperidin-4-ylmethyl)-amide |
| 111 | 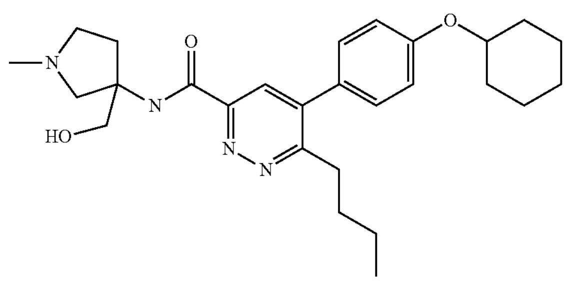 [SMILES: CCCCc1nnc(C(=O)NC2(CO)CCN(C)C2)cc1-c1ccc(OC2CCCCC2)cc1] | 6-Butyl-5-(4-cyclohexyloxy-phenyl)-pyridazine-3-carboxylic acid (3-hydroxymethyl-1-methyl-pyrrolidin-3-yl)-amide |
| 112 | 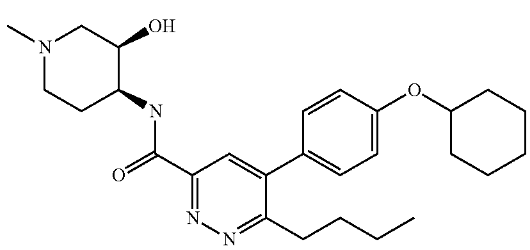 [SMILES: CCCCc1nnc(C(=O)N[C@H]2CCN(C)C[C@H]2O)cc1-c1ccc(OC2CCCCC2)cc1] | (±)-cis-6-Butyl-5-(4-cyclohexyloxy-phenyl)-pyridazine-3-carboxylic acid (3-hydroxy-1-methyl-piperidin-4-yl)-amide |
| 113 | 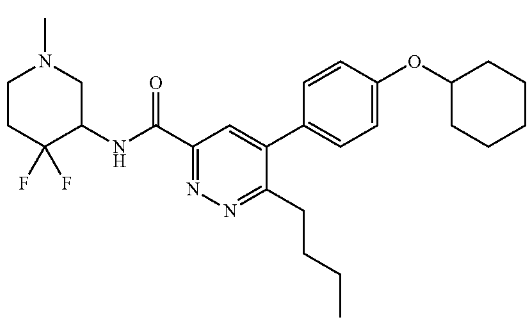 [SMILES: CCCCc1nnc(C(=O)NC2CN(C)CCC2(F)F)cc1-c1ccc(OC2CCCCC2)cc1] | 6-Butyl-5-(4-cyclohexyloxy-phenyl)-pyridazine-3-carboxylic acid (3,3-difluoro-1-methyl-piperidin-4-yl)-amide |

| Ex. | Structure | Name |
|---|---|---|
| 114 | 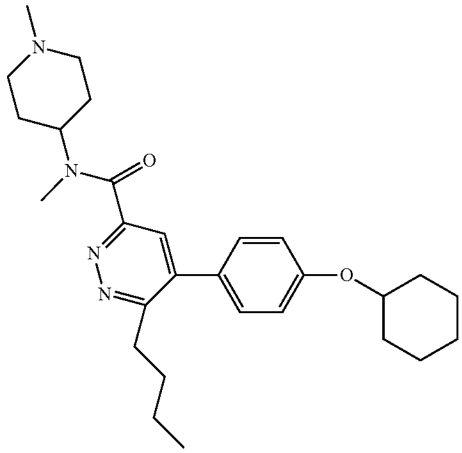 [SMILES: CCCCc1nnc(C(=O)N(C)C2CCN(C)CC2)cc1-c1ccc(OC2CCCCC2)cc1] | 6-Butyl-5-(4-cyclohexyloxy-phenyl)-pyridazine-3-carboxylic acid methyl-(1-methyl-piperidin-4-yl)-amide |
| 115 | 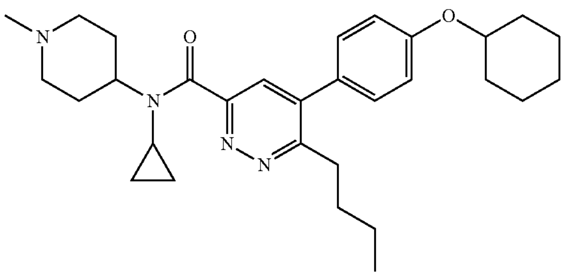 [SMILES: CCCCc1nnc(C(=O)N(C2CC2)C2CCN(C)CC2)cc1-c1ccc(OC2CCCCC2)cc1] | 6-Butyl-5-(4-cyclohexyloxy-phenyl)-pyridazine-3-carboxylic acid cyclopropyl-(1-methyl-piperidin-4-yl)-amide |

Another embodiment of the present invention includes a pharmaceutical composition comprising a compound of Formula (I) or a pharmaceutically acceptable salt thereof and a pharmaceutically acceptable carrier.

One embodiment of the present invention includes a method for treating a RAGE-mediated disease comprising administering to a subject a compound of Formula (I) or a pharmaceutically acceptable salt thereof. Another embodiment includes use of a compound of Formula (I) or a pharmaceutically acceptable salt thereof for the manufacture of a medicament for treating a RAGE-mediated disease. A still further embodiment includes a compound of Formula (I) or a pharmaceutically acceptable salt thereof for use in the treatment of a RAGE-mediated disease. In one embodiment, the disease is Alzheimer's Disease. In one embodiment, such treatment modifies the presentation of Alzheimer's Disease. In another embodiment, such treatment improves cognitive performance of a subject suffering from mild to moderate Alzheimer's Disease.

Pharmaceutically acceptable salts of the compounds of the present invention are also included within the scope of the invention. The term "pharmaceutically acceptable salt(s)" as used herein refers to non-toxic salts of a compound of Formula (I) which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartrate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

The compound of Formula (I) may contain one or more chiral centers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes any tautomers of the compounds represented by the formulas above.

Examples of compounds of Formula (I) or a pharmaceutically acceptable salt thereof having potentially useful biological activity are herein described. The ability of compounds of Formula (I) or pharmaceutically acceptable salts thereof to inhibit the interaction of RAGE with its physiological ligands was established with representative compounds of Formula (I) or a pharmaceutically acceptable salt thereof using the assay(s) described in the Examples section below.

The invention further provides pharmaceutical compositions comprising a compound of Formula (I) or a pharmaceutically acceptable salt thereof. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions or suspensions, lotions, eye ointments and eye or ear drops, impregnated dressings and aerosols etc., containing the compounds of the invention are contemplated. These topical formulations may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 0.1% up to about 99% of the formulation. More usually they will form up to about 80% of the formulation. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Compounds that antagonize the interaction of RAGE with its physiological ligands are potentially useful in treating diseases or conditions that may be responsive to the inhibiting of the RAGE receptor. The present invention provides a method of treatment comprising: administering to a subject a compound of Formula (I) or a pharmaceutically acceptable salt thereof. In an embodiment of this embodiment, the present invention provides a method for the inhibition of the interaction of RAGE with its physiological ligands. In another embodiment of this embodiment, the present invention provides a method for treating a disease state selected from the group consisting of acute and chronic inflammation including skin inflammation such as psoriasis, atopic dermatitis, inflammation associated with organ, tissue, or cell transplantation, and lung inflammation including, asthma and chronic obstructive pulmonary disease, sepsis, diabetes, diabetes related complications, renal failure, hyperlipidemic atherosclerosis associated with diabetes, neuronal cytotoxicity, restenosis, Down's syndrome, dementia associated with head trauma, amyotrophic lateral sclerosis, multiple sclerosis, amyloidosis, an autoimmune disease, wound healing, periodontal disease, neuropathy, neuronal degeneration, vascular permeability, nephropathy, atherosclerosis, retinopathy, Alzheimer's disease, erectile dysfunction, tumor invasion and/or metastasis, and osteoporosis which comprises administering to a subject a therapeutically effective amount of a compound of a compound of Formula (I) or a pharmaceutically acceptable salt thereof.

As noted above, the compounds of the present invention are useful in the treatment of the complications of diabetes. It has been shown that nonenzymatic glycoxidation of macromolecules ultimately resulting in the formation of advanced glycation endproducts (AGEs) is enhanced at sites of inflammation, in renal failure, in the presence of hyperglycemia and other conditions associated with systemic or local oxidant stress (Dyer, D., et al., J. Clin. Invest., 91:2463-2469 (1993); Reddy, S., et al., Biochem., 34:10872-10878 (1995); Dyer, D., et al., J. Biol. Chem., 266:11654-11660 (1991); Degenhardt, T., et al., Cell Mol. Biol., 44:1139-1145 (1998)). Accumulation of AGEs in the vasculature can occur focally, as in the joint amyloid composed of AGE-$\beta$2-microglobulin found in patients with dialysis-related amyloidosis (Miyata, T., et al., J. Clin. Invest., 92:1243-1252 (1993); Miyata, T., et al., J. Clin. Invest., 98:1088-1094 (1996)), or generally, as exemplified by the vasculature and tissues of patients with diabetes (Schmidt, A-M., et al., Nature Med., 1:1002-1004 (1995)). The progressive accumulation of AGEs over time in patients with diabetes suggests that endogenous clearance mechanisms are not able to function effectively at sites of AGE deposition. Such accumulated AGEs have the capacity to alter cellular properties by a number of mechanisms. Although RAGE is expressed at low levels in normal tissues and vasculature, in an environment where the receptor's ligands accumulate, it has been shown that RAGE becomes upregulated (Li, J. et al., J. Biol. Chem., 272:16498-16506 (1997); Li, J., et al., J. Biol. Chem., 273:30870-30878 (1998); Tanaka, N., et al., J. Biol. Chem., 275:25781-25790 (2000)). RAGE expression is increased in endothelium, smooth muscle cells and infiltrating mononuclear phagocytes in diabetic vasculature. Also, studies in cell culture have demonstrated that AGE-RAGE interaction caused changes in cellular properties important in vascular homeostasis.

Also as noted above, the compounds of the present invention are useful in treating amyloidoses and/or Alzheimer's Disease. RAGE appears to be a cell surface receptor which binds $\beta$-sheet fibrillar material regardless of the composition of the subunits (amyloid-$\beta$ peptide, A$\beta$, amylin, serum amyloid A, prion-derived peptide) (Yan, S.-D., et al., Nature, 382:685-691 (1996); Yan, S-D., et al., Nat. Med., 6:643-651 (2000)). Deposition of amyloid has been shown to result in enhanced expression of RAGE. For example, in the brains of patients with Alzheimer's disease (AD), RAGE expression increases in neurons and glia (Yan, S.-D., et al., Nature 382: 685-691 (1996)). The consequences of A$\beta$ interaction with RAGE appear to be quite different on neurons versus microglia. Whereas microglia become activated as a consequence of A$\beta$-RAGE interaction, as reflected by increased motility and expression of cytokines, early RAGE-mediated neuronal activation is superceded by cytotoxicity at later times. Further evidence of a role for RAGE in cellular interactions of A$\beta$ concerns inhibition of A$\beta$-induced cerebral vasoconstriction and transfer of the peptide across the blood-brain barrier to brain parenchyma when the receptor was blocked (Kumar, S., et al., Neurosci. Program, p 141 (2000)). Inhibition of RAGE-amyloid interaction has been shown to decrease expression of cellular RAGE and cell stress markers (as well as NF-kB activation), and diminish amyloid deposition (Yan, S-D., et al., Nat. Med., 6:643-651 (2000)) suggesting a role for RAGE-amyloid interaction in both perturbation of cellular properties in an environment enriched for amyloid (even at early stages) as well as in amyloid accumulation.

In other studies using a mouse model of Alzheimer's Disease, it has been shown that RAGE antagonists can reverse the formation of plaques and the loss of cognition. In U.S. Patent Publication No. US 2005/0026811, small molecule RAGE antagonists were used to inhibit the progression of Aβ deposition and reduced the volume of preexisting plaques in Alzheimer's Disease mice (US 2005/0026811 at ¶¶ 581-586). Furthermore, treatment with such small molecule RAGE antagonists improved cognition in these Alzheimer's Disease mouse models (US 2005/0026811 at ¶¶ 587-590). Thus, in a mouse model of Alzheimer's Disease, those mice who had developed Aβ plaques and cognitive loss and were treated with small molecule RAGE antagonists exhibited a reduction in plaque volume and an improvement in cognitive performance as compared to those Alzheimer's Disease mice who were not treated with the small molecule RAGE antagonists, showing that the RAGE antagonist compounds may delay or slow loss of cognitive performance, or may improve cognitive performance of a subject suffering from dementia of Alzheimer's type.

Also, it had been shown in both cellular assays and in animal studies that RAGE mediates the transcytosis of circulating Aβ across the blood-brain barrier (BBB). Such increased transcytosis of Aβ results in neuronal oxidant stress and sustained reductions in cerebral blood flow. The effects of RAGE can be inhibited by a RAGE modulator (e.g., anti-RAGE antibody or sRAGE) (see e.g., Mackic et al., J. Clin. Invest., 102:734-743 (1998); see also Kumar et al., Neurosci., Program, p 141 (2000)). These finding were confirmed by additional studies (see e.g., U.S. Pat. No. 6,825,164 at col. 17, line 48 to col. 18, line 43; Deane et al., Nature Medicine, 9:907-913 (2003)). Reduced cerebral perfusion can promote ischemic lesions which can act synergistically with Aβ to exacerbate dementia. Also, insufficient cerebral blood flow may alter Aβ trafficking across the blood brain barrier thereby reducing Aβ clearance and promoting accumulation of Aβ in brain (see Girouard and Iadecola, J. Appl. Physiol., 100, 328-335 (2006) at page 332). Thus, the increase in cerebral blood flow promoted by RAGE antagonists may reduce the symptoms or delay onset of development of Alzheimer's Disease, or both. For example, RAGE antagonists may delay or slow loss of cognitive performance, or may improve cognitive performance of a subject suffering from dementia of Alzheimer's type, or both.

As noted above, the compounds of the present invention are useful in treating inflammation. For example, S100/calgranulins have been shown to comprise a family of closely related calcium-binding polypeptides characterized by two EF-hand regions linked by a connecting peptide (Schafer, B. et al., TIBS, 21:134-140 (1996); Zimmer, D., et al., Brain Res. Bull., 37:417-429 (1995); Rammes, A., et al., J. Biol. Chem., 272:9496-9502 (1997); Lugering, N., et al., Eur. J. Clin. Invest., 25:659-664 (1995)). Although they lack signal peptides, it has long been known that 5100/calgranulins gain access to the extracellular space, especially at sites of chronic immune/inflammatory responses, as in cystic fibrosis and rheumatoid arthritis. RAGE is a receptor for many members of the S100/calgranulin family, mediating their proinflammatory effects on cells such as lymphocytes and mononuclear phagocytes. Also, studies on delayed-type hypersensitivity response, colitis in IL-10 null mice, collagen-induced arthritis, and experimental autoimmune encephalitis models suggest that RAGE-ligand interaction (presumably with S100/calgranulins) has a proximal role in the inflammatory cascade as implicated in the inflammatory diseases such as but not limited to rheumatoid arthritis and multiple sclerosis.

RAGE is also implicated in inflammatory diseases of the skin such as but not limited to atopic dermatitis, eczema, and psoriasis. Psoriasis in particular is characterized by inflamed itchy lesions. Psoriasis may be accompanied by arthropathic symptoms that are similar to those in seen in rheumatoid arthritis. There is considerable evidence that psoriasis is a polygenic autoimmune disorder. Psoriatic lesions are rich in cytokines, in particular IL-1 and IL-8, both potent proinflammatory mediators. IL-8 in particular is a chemotactic factor for neutrophils; neutrophils are also known to synthesize and secrete S100 proteins, one of the ligands for RAGE which is implicated in propagation of the immune and inflammatory response. Psoriasin, (S100A7) a new member of the S100 gene family, is a secreted protein isolated from psoriatic skin. Semprini et al. (Hum. Genet. 2002 October, 111(4-5), 310-3) have shown a linkage of psoriasis genetic susceptibility to distinct overexpression of S100 proteins in skin. Therefore, a modulator of RAGE would be expected to regulate the immune response in psoriasis.

As noted above, the compounds of the present invention are useful in treating tumor and tumor metastasis. For example, amphoterin is a high mobility group I nonhistone chromosomal DNA binding protein (Rauvala, H., et al., J. Biol. Chem., 262:16625-16635 (1987); Parkikinen, J., et al., J. Biol. Chem. 268:19726-19738 (1993)) which has been shown to interact with RAGE. It has been shown that amphoterin promotes neurite outgrowth, as well as serving as a surface for assembly of protease complexes in the fibrinolytic system (also known to contribute to cell mobility). In addition, a local tumor growth inhibitory effect of blocking RAGE has been observed in a primary tumor model (C6 glioma), the Lewis lung metastasis model (Taguchi, A., et al., Nature 405:354-360 (2000)), and spontaneously arising papillomas in mice expressing the v-Ha-ras transgene (Leder, A., et al., Proc. Natl. Acad. Sci., 87:9178-9182 (1990)).

Airway inflammation is important in the pathogenesis of asthma. Such inflammation may give rise to significant exacerbations and increases in asthma severity, as well as to be a major factor in a decline in asthmatic status. In severe exacerbations of asthma there is an intense, mechanistically heterogeneous inflammatory response involving neutrophil and eosinophil accumulation and activation. Neutrophils are a significant source of S100 proteins, key ligands for RAGE implicated in the propagation of the immune response and inflammation. Therefore, modulators of RAGE would be expected to possess therapeutic value in the treatment of asthma. Further, the propagation step in the immune response in the lung driven by S100-RAGE interaction would be expected to lead to the activation and/or recruitment of inflammatory cells, such as neutrophils, which in chronic obstructive pulmonary diseases such as emphysema, are significant sources of damaging proteases. Therefore, a RAGE modulator would be expected possess potential in the treatment of chronic obstructive pulmonary diseases.

As used herein, the phrase "therapeutically effective amount" shall mean that amount of a drug or pharmaceutical agent that will elicit the therapeutic response of an subject that is being sought.

In these methods, factors which may influence what constitutes a therapeutically effective amount include, but are not limited to, the size and weight of the subject, the biodegradability of the therapeutic agent, the activity of the therapeutic agent, the size of the effected area, as well as its bioavailability. The phrase includes amounts which, as compared to a corresponding subject who has not received such amount, results in improved treatment, healing, or amelioration of a side effect, or a decrease in the rate of advancement of a disease or disorder.

In an embodiment, the present invention provides a method for treating restenosis comprising: administering to a subject a therapeutically effective amount of a compound of Formula (I) or a pharmaceutically acceptable salt thereof. In an embodiment, the subject is suffering from diabetes.

In an embodiment, the present invention provides a method for treating acute or chronic inflammation comprising: administering to a subject a therapeutically effective amount of a compound of Formula (I) or a pharmaceutically acceptable salt thereof.

In an embodiment, the present invention provides a method for treating dementia associated with head trauma comprising: administering to a subject a therapeutically effective amount of a compound of Formula (I) or a pharmaceutically acceptable salt thereof. In an embodiment, the cognitive performance of the subject is improved. In another embodiment, the cognitive performance of the subject is maintained. In another embodiment, the rate of loss of cognitive performance of the subject is slowed.

In an embodiment, the present invention provides a method for treating Alzheimer's Disease comprising: administering to a subject a therapeutically effective amount of a compound of Formula (I) or a pharmaceutically acceptable salt thereof. With respect to Alzheimer's Disease, the present invention is believed useful in alteration the course of the underlying dementing process. Alzheimer's Disease may be diagnosed by NINCDS and DSM criteria, Mini-Mental State Examination, and Clinical Dementia Rating within particular limits. One embodiment of the present invention includes improving cognitive performance comprising administering a compound of Formula (I) or a pharmaceutically acceptable salt thereof. Cognitive performance may be assessed with the cognitive subscale of the Alzheimer's Disease Assessment Scale (ADAS-cog), as is known in the art, which scores cognitive function on a 0 to 70 scale, with higher scores indicating greater cognitive impairment. Thus, a reduction in score demonstrates cognitive improvement. One embodiment of the present invention includes administering to a subject a compound of Formula (I) or a pharmaceutically acceptable salt thereof to reduce an ADAS-cog score of a subject in need of such reduction. Such a subject may be a human be suffering from dementia of Alzheimer's type, mild to moderate Alzheimer's Diseases, or severe Alzheimer's Disease.

In addition, the progression of Alzheimer's Disease may also be assessed in a human through examination of four areas of function: General, Cognitive, Behavioral, and Activities of Daily Living. Such an assessment may be performed using a Clinician's Interview Based Impression of Change (CIBIC or CIBIC plus). One embodiment of the present invention includes improvement in subject's function comprising administering a compound of Formula (I) or a pharmaceutically acceptable salt thereof. In one embodiment, the subject's function is one or more of general, cognitive, behavioral, and activities of daily living.

In an embodiment, the present invention provides a method for improving wound healing in a diabetic subject comprising: administering to the subject a therapeutically effective amount of a compound of Formula (I) or a pharmaceutically acceptable salt thereof, so as to improve the rate of wound healing in the subject relative to an untreated wound.

In an embodiment, the present invention provides a method for treating in a subject inflammation associated with transplantation of an organ, a tissue or a plurality of cells from a first site to a second site comprising: administering to the subject a therapeutically effective amount of a compound of Formula (I) or a pharmaceutically acceptable salt thereof, so as to reduce inflammation in the subject. In an embodiment, the first and second sites are in different subjects. In another embodiment, the first and second sites are in the same subject. In another embodiment, the transplanted organ, cells or tissue comprise a cell or tissue of a pancreas, skin, liver, kidney, heart, bone marrow, blood, bone, muscle, artery, vein, cartilage, thyroid, nervous system, or stem cells.

In another embodiment, at least one compound of Formula (I) or a pharmaceutically acceptable salt thereof is utilized, either alone or in combination with one or more known therapeutic agents As used herein, the phrase "a subject" refers to mammalian subjects, and in one group of embodiments, humans, who either suffer from one or more of the aforesaid diseases or disease states or are at risk for such.

In a further embodiment of the present invention, the RAGE inhibitors of the invention may be used in adjuvant therapeutic or combination therapeutic treatments with other known therapeutic agents.

The following is a non-exhaustive listing of adjuvants and additional therapeutic agents which may be utilized in combination with the RAGE inhibitors of the present invention:

Pharmacologic Classifications of Anticancer Agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Methotrexate, Cytarabine, Fluorouracil
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins, Anti-tumor antibodies Pharmacologic Classifications of Treatment for Rheumatoid Arthritis (Inflammation)
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids Pharmacologic Classifications of Treatment for Diabetes Mellitus
1. Sulfonylureas: Tolbutamide, Tolazamide, Glyburide, Glipizide
2. Biguanides: Metformin
3. Miscellaneous oral agents: Acarbose, Troglitazone
4. Insulin Pharmacologic Classifications of Treatment for Alzheimer's Disease
1. Cholinesterase Inhibitor: Tacrine, Donepezil
2. Antipsychotics: Haloperidol, Thioridazine
3. Antidepressants: Desipramine, Fluoxetine, Trazodone, Paroxetine
4. Anticonvulsants: Carbamazepine, Valproic acid In a further embodiment, the present invention provides a method of treating a RAGE mediated disease, the method comprising administering to a subject a therapeutically effective amount of a compound of Formula (I) or a pharmaceutically acceptable salt thereof in combination with a therapeutic agent selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

In a further embodiment, the present invention provides the pharmaceutical composition of the invention as described above, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

Such other therapeutic agents may be administered by a like route or different route that the compound of Formula (I) or a pharmaceutically acceptable salt thereof. Where a compound of Formula (I) or a pharmaceutically acceptable salt thereof is used in combination with another therapeutic agent, the composition may contain the compound of Formula (I) or a pharmaceutically acceptable salt thereof in combination with the other therapeutic agent(s). Alternatively, where separate dosage formulations are used, the compound of Formula (I) or a pharmaceutically acceptable salt thereof and one or more additional therapeutic agents may be administered at essentially the same time (e.g., concurrently) or at separately staggered times (e.g., sequentially).

Generally speaking, a compound of Formula (I) or a pharmaceutically acceptable salt thereof may be administered at a dosage level of from about 0.003 to 500 mg/kg of the body weight of the subject being treated. In an embodiment, a compound of Formula (I) or a pharmaceutically acceptable salt thereof may be administered at a dosage range between about 0.003 and 200 mg/kg of body weight per day. In an embodiment, a compound of Formula (I) or a pharmaceutically acceptable salt thereof may be administered at a dosage range between about 0.1 to 100 mg/kg of body weight per day. The amount of active ingredient that may be combined with the carrier materials to produce a single dosage may vary depending upon the host treated and the particular mode of administration. For example, a formulation intended for oral administration to humans may contain 1 mg to 2 grams of a compound of Formula (I) or a pharmaceutically acceptable salt thereof with an appropriate and convenient amount of carrier material which may vary from about 5 to 95 percent of the total composition. A dosage form intended for topical administration to the skin may be prepared at 0.1% to 99% compound to topical excipient ratio. A dosage form intended for inhaled administration of 0.01 to 200 mg of compound in a suitable carrier to deliver an inhaled dosage of compound. Dosage unit forms of systemically delivered compound may generally contain between from about 5 mg to about 500 mg of active ingredient. This dosage may be individualized by the clinician based on the specific clinical condition of the subject being treated. Thus, it will be understood that the specific dosage level for any particular subject will depend upon a variety of factors including the activity of the specific compound employed, the age, body weight, general health, sex, diet, time of administration, route of administration, rate of excretion, drug combination, size of effected area and the severity of the particular disease undergoing therapy.

The compounds of this invention may be made by a variety of methods well known to those of ordinary skill in the art including the methods are set out below in the Examples.

In another embodiment, the present invention also provides a method for the synthesis of compounds useful as intermediates in the preparation of compounds of the present invention along with methods for their preparation.

In an embodiment, the present invention provides a method of synthesizing a compound of Formula (I) or a pharmaceutically acceptable salt thereof

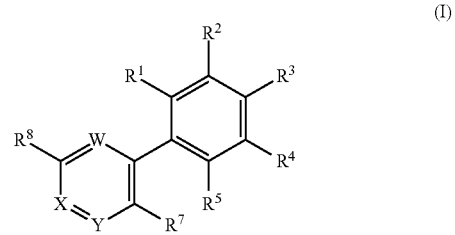

(I)

comprising mixing a base, a compound of Formula HO-L$^3$-R$^{17}$, and a compound of Formula (Ia)

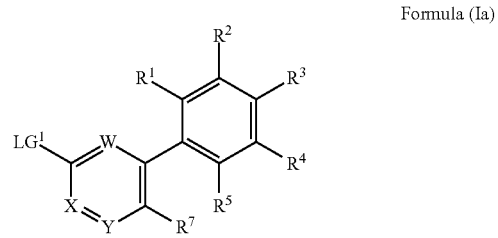

Formula (Ia)

wherein
R$^1$, R$^2$, R$^3$, R$^4$, R$^6$, R$^7$, W, X, and Y are as defined in any one of embodiments 1 to 73, R$^8$ is the group —X$^3$-L$^3$-R$^{17}$, X$^3$ is —O—, L$^3$ is selected from the group consisting of a direct bond or —(C$_1$-C$_6$)alkylene-, R$^{17}$ is as defined in any one of embodiments 82 to 111, and LG$^1$ is a leaving group. In a further embodiment, LG$^1$ is a halogen. In a further embodiment, the base is sodium hydride.

While the invention has been described and illustrated with reference to certain embodiments, the invention also provides other embodiments that may use any combination or subsets of elements as described in any of the above embodiments.

EXAMPLES

LC-MS data were obtained using gradient elution on a parallel MUX™ system, running four Waters 1525 binary HPLC pumps, equipped with a Mux-UV 2488 multichannel UV-Vis detector (recording at 215 and 254 nM) and a Leap Technologies HTS PAL Auto sampler using a Sepax GP-C18 4.6×50 mm column. A three minute gradient may be run from 25% of solution B (97.5% acetonitrile, 2.5% water, 0.05% TFA) and 75% of solution A (97.5% water, 2.5% acetonitrile, 0.05% TFA) to 100% of solution B. The system is interfaced with a Waters Micromass ZQ mass spectrometer using electrospray ionization. All MS data was obtained in the positive mode unless otherwise noted.

$^1$H NMR data was obtained on a Varian 400 MHz spectrometer.

Abbreviations used in the Examples and in other portions of the detailed description are as follows:

| | |
|---|---|
| d | = day |
| DCM | = dichloromethane |
| DIAD | = diisopropyl azodicarboxylate |
| DIEA or DIPEA | = diisopropylethylamine |
| DMAP | = 4-(dimethylamino)-pyridine |
| DME | = dimethoxyethane |
| DMF | = N,N-dimethylformamide |
| DMSO | = dimethylsulfoxide |
| DPPF | = 1,1'-Bis(diphenylphosphino) ferrocene |
| ELISA | = enzyme - linked immunosorbent assay |
| ether | = diethyl ether |
| EtOAc | = ethyl acetate |
| EtOH | = ethanol |
| g | = gram |
| h | = hour |
| HBTU | = O-benzotriazol-1-yl-N,N,N',N'-tetramethyluronium hexafluorophosphate |
| Hz | = hertz |
| L | = liter |
| LAH | = lithium aluminum hydride |
| LC | = liquid chromatography |
| M | = molar |
| m/z | = mass to charge ratio |
| m-CPBA | = meta chloroperbenzoic acid |
| MeOH | = methanol |
| mg | = milligram |
| min | = minute |
| mL | = milliliter |
| mM | = millimolar |
| mmol | = millimole |
| mol | = mole |
| MS | = mass spectrometry |
| N | = normal |
| NMP | = N-methylmorpholine |
| NMR | = nuclear magnetic resonance spectroscopy |
| ppm | = parts per million |
| rt or RT | = room temperature |
| TEA | = triethylamine |
| TFA | = trifluoroacetic acid |
| THF | = tetrahydrofuran |
| TLC | = thin layer chromatography |
| TMSCl | = trimethylsilyl chloride |

Example 1

4-(4-enzyloxy-phenyl)-3-butyl-6-(1-methyl-piperidin-4-yloxy)-pyridazine dihydrochloride To a stirred solution of (4-benzyloxy-phenyl)-acetic acid (61.9 mmol, 15.0 g), HBTU (74.3 mmol, 28.1 g), and N,O-dimethylhydroxylamine hydrochloride (92.9 mmol, 9.0 g) in DMF (100 mL) at 0° C. was added DIEA (136.3 mmol, 17.5 g) drop-wise. The reaction mixture was warmed to room temperature and stirred for 30 min. The mixture was diluted with ethyl acetate, washed with water, and 1.0 N HCl, followed by brine. The organic layer was dried (Na$_2$SO$_4$), filtered and concentrated under reduced pressure to provide 2-(4-benzyloxy-phenyl)-N-methoxy-N-methyl-acetamide.

To a stirred solution of 2-(4-benzyloxy-phenyl)-N-methoxy-N-methyl-acetamide (42.1 mmol, 12.0 g) in anhydrous THF at −10° C. was added n-butyl magnesium chloride (2.0 M solution in THF, 92.6 mmol, 46.3 mL) drop-wise. After completion of addition, the reaction mixture was warmed to room temperature and stirred for 30 min. The reaction mixture was cooled to 0° C. and quenched with 1.0 N HCl by adding drop-wise. The reaction mixture was poured into water, extracted with ethyl acetate, and the combined extract was washed with water followed by brine. The organic layer was dried (Na$_2$SO$_4$), filtered and concentrated under reduced pressure. The resultant residue was purified by column chromatography using 10% ethyl acetate in hexanes to provide 1-(4-benzyloxy-phenyl)-hexan-2-one.

A mixture of 1-(4-benzyloxy-phenyl)-hexan-2-one (40.36 mmol, 11.4 g), oxo-acetic acid ethyl ester solution in toluene (30 mL, 50% solution in toluene) and triethylamine (15 mL) was stirred at ambient temperature for 16 h. The reaction mixture was diluted with DCM (300 mL), washed with water (3×100 mL), and the organic layer was dried and concentrated under reduced pressure. The resultant residue was purified by flash silica gel chromatography eluting with 30% ethyl acetate in hexanes to provide 3-(4-benzyloxy-phenyl)-2-hydroxy-4-oxo-octanoic acid ethyl ester.

A mixture of 3-(4-benzyloxy-phenyl)-2-hydroxy-4-oxo-octanoic acid ethyl ester (28.08 mmol, 10.8 g) and hydrazine hydrate (15 mL) in acetic acid (45 mL) was stirred at 120° C. for 4 h. The reaction mixture was concentrated under reduced pressure and to the residue was added water (200 mL). This was extracted with DCM (3×200 mL), and the combined organic layer was dried and concentrated under reduced pressure. The resultant residue was purified by flash silica gel column chromatography eluting with 50% ethyl acetate in hexanes to afford 5-(4-benzyloxy-phenyl)-6-butyl-2H-pyridazin-3-one.

A suspension of 5-(4-benzyloxy-phenyl)-6-butyl-2H-pyridazin-3-one (5.4 g, 14.73 mmol) in POCl$_3$ (8 mL) was stirred at 70° C. for 2 h. The reaction mixture was concentrated under reduced pressure, and to the residue was added ice (50 g). The mixture was stirred for 1 h. This was extracted with DCM (3×50 mL), the combined organic layer was dried, filtered and concentrated under reduced pressure. The resultant residue was purified by flash silica gel column chromatography eluting with in 10% ethyl acetate in hexanes to provide 4-(4-benzyloxy-phenyl)-3-butyl-6-chloro-pyridazine.

To a stirred solution of 4-hydroxy-piperidine-1-carboxylic acid tert-butyl ester (227 mg, 1.13 mmol) in THF (4.0 mL) at room temperature was added NaH (100 mg, 4.5 mmol). Stirring was continued for 10 min. To this solution was added 4-(4-benzyloxy-phenyl)-3-butyl-6-chloro-pyridazine (200 mg, 0.56 mmol) and the resulting mixture was stirred at 50-55° C. overnight. The reaction was poured into water and extracted with ethyl acetate. The organic layer was washed with water followed by brine, dried (Na$_2$SO$_4$), filtered, and concentrated under reduced pressure. The crude product was purified by flash silica gel column chromatography using 30% ethyl acetate in hexanes to provide 4-[5-(4-benzyloxy-phenyl)-6-butyl-pyridazin-3-yloxy]-piperidine-1-carboxylic acid tert-butyl ester.

4-[5-(4-Benzyloxy-phenyl)-6-butyl-pyridazin-3-yloxy]-piperidine-1-carboxylic acid tert-butyl ester (0.50 mmol, 260 mg) was dissolved in 4.0 M HCl in dioxane and stirred for 45 min at room temperature. The solvent was evaporated, and the resultant solid was washed with ether and dried to provide 4-(4-benzyloxy-phenyl)-3-butyl-6-(piperidin-4-yloxy)-pyridazine dihydrochloride.

A stirred suspension of 4-(4-Benzyloxy-phenyl)-3-butyl-6-(piperidin-4-yloxy)-pyridazine dihydrochloride (0.34 mmol, 170 mg) and paraformaldehyde (6.1 mmol, 550 mg) in DCM was stirred for 20 min then sodiumtriacetoxyborohydride (6.1 mmol, 1.2 g) was added. Stirring was continued overnight. The solvent was evaporated and saturated NaHCO$_3$ solution was added to the residue. The mixture was extracted with ethyl acetate. The organic layer was washed with water, brine, dried (Na$_2$SO$_4$), filtered and concentrated under reduced pressure. The resultant product was purified by flash silica gel column chromatography using 5% methanolic solution of ammonia (2.0 M ammonia in methanol) in DCM to provide 4-(4-benzyloxy-phenyl)-3-butyl-6-(1-methyl-piperidin-4-yloxy)-pyridazine.

4-(4-Benzyloxy-phenyl)-3-butyl-6-(1-methyl-piperidin-4-yloxy)-pyridazine was dissolved in 4.0 M HCl in dioxane and the solvent evaporated. The resultant salt was washed with ether and dried to provide the title compound (100 mg). LCMS: m/z 433 [M+1]. $^1$H NMR (400 MHz, CD$_3$OD) δ 7.87 and 7.80 (1H, s), 7.45-7.52 (4H, m), 7.36-7.40 (2H, m), 7.30-7.34 (1H, m), 7.20-7.24 (2H, m), 5.47-5.49 (1H, m), 5.20 (2H, s), 3.65-3.69 (1H, m), 3.39-3.50 (2H, m), 3.20-3.31 (1H, m), 3.12-3.16 (2H, m), 2.93 (3H, s), 2.5 (1H, d), 2.4 (1H, d), 2.20 (1H, t), 2.00-2.17 (1H, m), 1.46-1.51 (2H, m), 1.25-1.30 (2H, m), 0.81 (3H, t).

Example 2

4-(4-Benzyloxy-phenyl)-3-butyl-6-(1-methyl-piperidin-4-ylmethoxy)-pyridazine

To a stirred solution of 4-hydroxymethyl-piperidine-1-carboxylic acid tert-butyl ester (1.13 mmol, 240 mg) in THF (10 mL) at room temperature was added NaH (100 mg, 4.5 mmol). Stirring continued for 10 min then 4-(4-benzyloxy-phenyl)-3-butyl-6-chloro-pyridazine (Example 1, 0.56 mmol, 200 mg) was added. The resulting mixture was stirred at 50-55° C. over night, then was poured into water and extracted with ethyl acetate. The organic layer was washed with water, brine, dried (Na$_2$SO$_4$), filtered and concentrated under reduced pressure. The product was purified by flash silica gel column chromatography using 30% ethyl acetate in hexanes to provide 4-[5-(4-benzyloxy-phenyl)-6-butyl-pyridazin-3-yloxymethyl]-piperidine-1-carboxylic acid tert-butyl ester 4-[5-(4-Benzyloxy-phenyl)-6-butyl-pyridazin-3-yloxymethyl]-piperidine-1-carboxylic acid tert-butyl ester (0.47 mmol, 250 mg) was dissolved in 4.0 M HCl in dioxane and stirred for 45 min at room temperature. The solvent was evaporated and the resultant solid was washed with ether and dried to provide 4-(4-benzyloxy-phenyl)-3-butyl-6-(piperidin-4-ylmethoxy)-pyridazine dihydrochloride.

A suspension of 4-(4-benzyloxy-phenyl)-3-butyl-6-(piperidin-4-ylmethoxy)-pyridazine dihydro chloride (0.37 mmol, 190 mg) and paraformaldehyde (6.7 mmol, 611 mg) in DCM was stirred for 20 min then sodium triacetoxyborohydride (6.7 mmol, 1.41 g) was added. Stirring was continued overnight. Solvent was evaporated, and to the residue was added saturated NaHCO$_3$. The mixture was extracted with ethyl acetate. The organic layer was washed with water, brine, dried (Na$_2$SO$_4$), filtered and concentrated under reduced pressure. The resultant product was purified by column chromatography using 5% methanolic solution of ammonia (2.0 M ammonia in methanol) in DCM to provide 4-(4-benzyloxy-phenyl)-3-butyl-6-(1-methyl-piperidin-4-ylmethoxy)-pyridazine.

4-(4-Benzyloxy-phenyl)-3-butyl-6-(1-methyl-piperidin-4-ylmethoxy)-pyridazine was dissolved in 4.0 M HCl in dioxane and evaporated the solvent. The resultant salt was washed with ether and dried to provide the title compound (79 mg). LCMS: m/z 447 [M+1]. $^1$H NMR (400 MHz, CD$_3$OD) δ 7.84 (1H, s), 7.45-7.50 (4H, m), 7.36-7.40 (2H, m), 7.30-7.33 (1H, m), 7.20 (2H, d), 5.19 (2H, s), 4.4 (2H, d), 3.58 (2H, d), 3.05-3.14 (4H, m), 2.88 (3H, s), 2.26 (1H, bs), 2.13 (2H, d), 1.67-1.80 (2H, m), 1.45-1.52 (2H, m), 1.24-1.33 (2H, m), 0.80 (3H, t).

Example 3

{2-[5-(4-Benzyloxy-phenyl)-6-butyl-pyridazin-3-yloxy]-ethyl}-diethyl-amine dihydrochloride To a stirred solution of 2-diethylamino-ethanol (0.42 mmol, 50 mg) in THF at room temperature was added NaH (0.85 mmol, 20 mg). Stirring continued for 10 min then 4-(4-benzyloxy-phenyl)-3-butyl-6-chloro-pyridazine (Example 1, 0.14 mmol, 50 mg) was added. The resulting mixture was stirred at 50-55° C. overnight. The reaction mixture was poured into water and extracted with ethyl acetate. The organic layer was washed with water, brine, dried (Na$_2$SO$_4$), filtered and concentrated under reduced pressure. The product was purified by column chromatography using 10% methanolic solution of ammonia (2.0 M ammonia in methanol) in ethyl acetate to provide {2-[5-(4-benzyloxy-phenyl)-6-butyl-pyridazin-3-yloxy]-ethyl}-diethyl-amine.

{2-[5-(4-Benzyloxy-phenyl)-6-butyl-pyridazin-3-yloxy]-ethyl}-diethyl-amine was dissolved in 4.0 M HCl in dioxane and the solvent was evaporated. The resultant salt was washed with ether and dried to provide the title compound (19 mg). LCMS: m/z 435 [M+1]. $^1$H NMR (400 MHz, CD$_3$OD) δ 7.89 (1H, s), 7.50-7.53 (2H, m), 7.45-7.47 (2H, m), 7.36-7.40 (2H, m), 7.30-7.34 (1H, m), 7.20-7.24 (2H, m), 5.20 (2H, S), 3.74 (2H, t), 3.35-3.42 (4H, m), 3.15 (2H, t), 1.48-1.53 (2H, m), 1.4 (6H, t), 1.21-1.32 (4H, m), 0.81 (3H, t).

Example 4

3-[5-(4-Benzyloxy-phenyl)-6-butyl-pyridazin-3-yloxy]-propyl}-diethyl-mine dihydrochloride To a stirred solution of 3-dethylamino-propan-1-ol (0.42 mmol, 55 mg) in THF at room temperature, was added NaH (0.85 mmol, 20 mg). Stirring continued for 10 min then 4-(4-benzyloxy-phenyl)-3-butyl-6-chloro-pyridazine (Example 1, 0.14 mmol, 50 mg) was added. The resulting mixture was stirred at 50-55° C. overnight. The reaction mixture was poured into water and extracted with ethyl acetate. The organic layer was washed with water, brine, dried (Na$_2$SO$_4$), filtered and concentrated under reduced pressure. The product was purified by flash silica gel column chromatography using 10% methanolic solution of ammonia (2.0 M ammonia in methanol) in ethyl acetate to provide 3-[5-(4-benzyloxy-phenyl)-6-butyl-pyridazin-3-yloxy]-propyl}-diethyl-amine.

3-[5-(4-Benzyloxy-phenyl)-6-butyl-pyridazin-3-yloxy]-propyl}-diethyl-mine was dissolved in 4.0 M HCl in dioxane and the solvent was evaporated. The resultant salt was washed with ether and dried to provide the title compound (22 mg). LCMS: m/z 449 [M+1]. $^1$H NMR (400 MHz, CD$_3$OD) δ 7.86 (1H, s), 7.49 (2H, d), 7.45-7.47 (2H, m), 7.36-7.40 (2H, m), 7.30-7.34 (1H, m), 7.21 (2H, d), 5.20 (2H, S), 4.63 (2H, t), 3.37-3.41 (2H, m), 3.23-3.32 (4H, m), 3.14 (2H, t), 2.32-2.36 (2H, m), 1.47-1.51 (2H, m), 1.36 (6H, t), 1.24-1.32 (2H, m), 0.80 (3H, t).

Example 5

4-(4-Benzyloxy-phenyl)-3-butyl-6-(3-piperidin-1-yl-propoxy)-pyridazine dihydrochloride To a stirred solution of 3-piperidin-1-yl-propan-1-ol (0.85 mmol, 121 mg) in THF at room temperature, NaH (1.2 mmol, 29 mg) was added and stirring continued for 10 min then 4-(4-benzyloxy-phenyl)-3-butyl-6-chloro-pyridazine (Example 1, 0.42 mmol, 150 mg) was added. The resulting mixture was stirred at 50-55° C. over night, poured into water and extracted with ethyl acetate. The organic layer was washed with water, brine dried (Na$_2$SO$_4$) filtered and concentrated under reduced pressure. The product was purified by column chromatography using 10% methanolic solution of ammonia (2.0 M ammonia in methanol) in DCM to get 4-(4-Benzyloxy-phenyl)-3-butyl-6-(3-piperidin-1-yl-propoxy)-pyridazine.

4-(4-Benzyloxy-phenyl)-3-butyl-6-(3-piperidin-1-yl-propoxy)-pyridazine was dissolved in 4.0 M HCl in dioxane and evaporated the solvent. The resultant salt was washed with ether and dried to provide the title compound (20 mg). LCMS: m/z 461 [M+1]. $^1$H NMR (400 MHz, CD$_3$OD) 7.35 (2H, d), 7.21-7.25 (5H, m), 7.03 (2H, d), 6.91 (1H, s), 5.06 (2H, s), 4.48 (2H, t), 3.48 (2H, d), 2.80-2.91 (4H, m), 2.23 (2H, s), 1.73-1.1.87 (6H, m), 1.36-1.41 (3H, m), 1.09-1.14 (3H, m), 0.68 (3H, t).

Example 6

(±)-trans-{4-[5-(4-Benzyloxy-phenyl)-6-butyl-pyridazin-3-yloxymethyl]-1-methyl-pyrrolidin-3-yl}-methanol dihydrochloride To a stirred solution of (E)-but-2-enedioic acid diethyl ester (23.23 mmol, 4 g) in DCM (50 mL) at 0° C. was added benzyl-methoxymethyl-trimethylsilanylmethyl-amine (21.06 mmol, 5 g) followed by drop wise addition of a solution of TFA in DCM (0.1 mL of TFA in 1 mL of DCM) over 10 min. After completion of addition, the cold bath was removed, and the reaction mixture was stirred at room temperature for 1 h. The reaction mixture was diluted with DCM, washed with a saturated solution of sodium bicarbonate, the organic layer was dried and concentrated under reduced pressure. The residue was dissolved in ethyl acetate (25 mL) and added di-tert-butyl dicarbonate (36.66 mmol, 8 g) followed by 10% palladium on carbon (1 g, wet). The resultant reaction mixture was subjected to catalytic hydrogenation using hydrogen gas at 55 psi for 18 h with stirring. The catalyst was filtered through a pad of celite, the celite pad was washed with ethyl acetate (200 mL), and the combined filtrate was concentrated. The residue was purified by flash silica gel column chromatography by eluting with 20% ethyl acetate in hexanes to provide (±)-trans-pyrrolidine-1,3,4-tricarboxylic acid 1-tert-butyl ester 3,4-diethyl ester.

To a stirred solution of (±)-trans-pyrrolidine-1,3,4-tricarboxylic acid 1-tert-butyl ester 3,4-diethyl ester (15.85 mmol, 5 g) in a mixture of THF (50 mL) and methanol (50 mL) was added NaBH$_4$ (4 g) portions wise over a period of 1 h. The volatiles were removed under reduced pressure. To the residue was added water and extracted with DCM. The organic layer was dried and concentrated under reduced pressure. The residue was purified by flash silica gel column chromatography by eluting with ethyl acetate to provide (±)-trans-3,4-bis-hydroxymethyl-pyrrolidine-1-carboxylic acid tert-butyl ester.

To a stirred solution of (±)-trans-3,4-bis-hydroxymethyl-pyrrolidine-1-carboxylic acid tert-butyl ester (2.0 mmol, 462 mg) in THF (4.0 mL) at 0° C. was added NaH (60% dispersion in mineral oil, 2.5 mmol, 100 mg) and stirring continued for 10 min at room temperature, then 4-(4-benzyloxy-phenyl)-3-butyl-6-chloro-pyridazine (Example 1, 1.0 mmol, 352 mg) was added. The resulting mixture was stirred at 50° C. for 1 hour, poured into water and extracted with ethyl acetate. The organic layers were combined and concentrated under reduced pressure. The product was purified by column chromatography using 1% methanol in ethyl acetate to give (±)-trans-3-[5-(4-benzyloxy-phenyl)-6-butyl-pyridazin-3-yloxymethyl]-4-hydroxymethyl-pyrrolidine-1-carboxylic acid tert-butyl ester, which was dissolved in dichloromethane (1.0 mL), added 4.0 M HCl in dioxane (1.0 mL) and stirred at room temperature for 1 hour. Solvents were evaporated to give (±)-trans-{4-[5-(4-benzyloxy-phenyl)-6-butyl-pyridazin-3-yloxymethyl]-pyrrolidin-3-yl}-methanol dihydrochloride.

To a solution of (±)-trans-{4-[5-(4-benzyloxy-phenyl)-6-butyl-pyridazin-3-yloxymethyl]-pyrrolidin-3-yl}-methanol dihydrochloride (0.2 mmol, 104 mg) in dichloromethane (2.0 mL) was added formaldehyde solution in water (37%, 2.0 mmol, 0.2 mL), and 1 drop of acetic acid. Then sodium triacetoxyborohydride (2.0 mmol, 424 mg) was added. The mixture was stirred at room temperature for 0.5 hour then condensed, diluted with water/ethyl acetate, and neutralized with NaHCO$_3$ powder. The solvent was removed in vacuo, and the residue was purified by silica gel chromatography (DCM to DCM+10% 2N ammonia in MeOH) to give a solid, which was dissolved in DCM (1.0 mL), 2N HCl in ether (1.0 mL) was added, kept at room temperature for 10 min, condensed, triturated with hexanes to yield the title compound (88 mg). LCMS: m/z 464 [M+2]. $^1$H NMR (400 MHz, CD$_3$OD) δ 7.83 and 7.93 (1H, s), 7.45-7.55 (4H, m), 7.36-7.40 (2H, m), 7.31-7.35 (1H, m), 7.20-7.24 (2H, m), 5.20 (2H, s), 4.59-4.63 (2H, m), 3.63-3.95 (4H, m), 2.58-3.3 (9H, m), 1.44-1.53 (2H, m), 1.25-1.33 (2H, m), 0.81 (3H, t).

Example 7

(±)-trans-4-(4-Benzyloxy-phenyl)-3-butyl-6-(4-methoxymethyl-1-methyl-pyrrolidin-3-ylmethoxy)-pyridazine dihydrochloride To a stirred solution of (±)-trans-3-[5-(4-benzyloxy-phenyl)-6-butyl-pyridazin-3-yloxymethyl]-4-hydroxymethyl-pyrrolidine-1-carboxylic acid tert-butyl ester (Example 6, 1.0 mmol, 547 mg) in THF (4.0 mL) at 0° C., NaH (60% dispersion in mineral oil, 1.5 mmol, 60 mg) was added and stirring continued for 10 min at room temperature, then methyl iodide (1.5 mmol, 94 µL) was added. The resulting mixture was stirred at room temperature for 2 hour, poured into water, and extracted with ethyl acetate. The organic layers were combined and concentrated under reduced pressure. The product was purified by column chromatography using 50% ethyl acetate in hexanes to give (±)-trans-3-[5-(4-benzyloxy-phenyl)-6-butyl-pyridazin-3-yloxymethyl]-4-methoxymethyl-pyrrolidine-1-carboxylic acid tert-butyl ester, which was dissolved in dichloromethane (1.0 mL), added 4.0 M HCl in dioxane (1.0 mL) and stirred at room temperature for 1 hour. Solvents were evaporated to give (±)-trans-4-(4-benzyloxy-phenyl)-3-butyl-6-(4-methoxymethyl-pyrrolidin-3-yl-methoxy)-pyridazine di hydrochloride.

To a solution of the above pyridazine dihydrochloride (0.5 mmol, 267 mg) in dichloromethane (2.0 mL) was added formaldehyde solution in water (37%, 10 mmol, 1.0 mL), and 2 drops of acetic acid. Then sodium triacetoxyborohydride (10 mmol, 2.12 g) was added. The mixture was stirred at room temperature for 0.5 hour then concentrated. The mixture was then diluted with water/EtOAc, and neutralized with NaHCO$_3$ powder. The organic layers were combined and dried over Na$_2$SO$_4$. The solvent was removed in vacuo, and the residue was purified by silica gel chromatography (DCM to DCM+10% 2N ammonia in MeOH) to give a solid, which was dissolved in DCM (1.0 mL), 2N HCl in ether (1.0 mL) was added, kept at room temperature for 10 min, condensed, triturated with hexanes to provide the title compound (211 mg). LCMS: m/z 477 [M+1]. $^1$H NMR (400 MHz, CD$_3$OD)

δ 7.83 and 7.93 (1H, s), 7.45-7.55 (4H, m), 7.36-7.40 (2H, m), 7.31-7.35 (1H, m), 7.20-7.24 (2H, m), 5.20 (2H, s), 4.59-4.63 (2H, m), 3.63-3.95 (4H, m), 3.44 (3H, s), 2.58-3.23 (9H, m), 1.44-1.53 (2H, m), 1.25-1.33 (2H, m), 0.81 (3H, t).

Example 8

4-{3-[5-(4-Benzyloxy-phenyl)-6-butyl-pyridazin-3-yloxy]-propyl}-morpholine dihydrochloride To a stirred solution of 3-morpholin-4-yl-propan-1-ol (1.0 mmol, 0.145 g) in THF (3 mL) at 0° C. was added sodium hydride (60% dispersion in mineral oil) (1.3 mmol, 0.052 g) and continued stirring for 15 min. The reaction mixture was allowed to come to room temperature. To the mixture was added 4-(4-benzyloxy-phenyl)-3-butyl-6-chloro-pyridazine (Example 1, 0.74 mmol, 0.26 g). After completion of addition, the reaction mixture was warmed to 70° C. for 3 h. The reaction was concentrated onto SiO$_2$ and purified via flash chromatography using 20-50% ethyl acetate in hexanes to give 4-{3-[5-(4-benzyloxy-phenyl)-6-butyl-pyridazin-3-yloxy]-propyl}-morpholine (0.26 g, 75%). The free amine may be dissolved in DCM and 2 N HCl in diethyl ether followed by evaporation of the solvents to provide the title compound. LCMS: m/z 463 [M+1]. $^1$H NMR (400 MHz, CDCl$_3$): δ 7.32-7.49 (5H, m), 7.21-7.26 (2H, m), 7.03-7.09 (2H, m), 6.74 (1H, s), 5.12 (2H, s), 4.58 (2H, t), 3.67-3.76 (4H, m), 2.83-2.91 (2H, m), 2.41-2.56 (6H, m), 1.98-2.08 (2H, m), 1.56-1.68 (2H, m), 1.21-1.33 (2H, m), 0.83 (3H, t).

Example 9

4-(4-Benzyloxy-phenyl)-3-butyl-6-(1-methyl-azetidin-3-ylmethoxy)-pyridazine dihydrochloride To a stirred solution of 3-hydroxymethyl-azetidine-1-carboxylic acid tert-butyl ester (1.5 mmol, 281 mg) in THF (4.0 mL) at 0° C., NaH (60% dispersion in mineral oil, 1.5 mmol, 60 mg) was added and stirring continued for 10 min at room temperature, then 4-(4-benzyloxy-phenyl)-3-butyl-6-chloro-pyridazine (Example 1, 1.0 mmol, 352 mg) was added. The resulting mixture was stirred at 50° C. for 1 hour, poured into water, and extracted with ethyl acetate. The organic layers were combined and concentrated under reduced pressure. The product was purified by column chromatography using 50% ethyl acetate in hexanes to give 3-[5-(4-benzyloxy-phenyl)-6-butyl-pyridazin-3-yloxymethyl]-azetidine-1-carboxylic acid tert-butyl ester, which was dissolved in dichloromethane (1.0 mL), added 4.0 M HCl in dioxane (1.0 mL) and stirred at room temperature for 1 hour. Solvents were evaporated to give 6-(azetidin-3-ylmethoxy)-4-(4-benzyloxy-phenyl)-3-butyl-pyridazine dihydrochloride.

To a solution of the above pyridazine dihydrochloride (0.3 mmol, 143 mg) in dichloromethane (2 mL) was added formaldehyde solution in water (37%, 10 mmol, 1.0 mL), and 2 drops of acetic acid. Then sodium triacetoxyborohydride (10 mmol, 2.12 g) was added. The mixture was stirred at room temperature for 0.5 hour then condensed, diluted with water/EtOAc, and neutralized with NaHCO$_3$ powder. The solvent was removed in vacuo, and the residue was purified by silica gel chromatography (DCM to DCM+10% 2N ammonia in MeOH) to give a solid, which was dissolved in DCM (1.0 mL), 2N HCl in ether (1.0 mL) was added, kept at room temperature for 10 min, condensed, triturated with hexanes to provide the title compound (106 mg). LCMS: m/z 419 [M+1]. $^1$H NMR (400 MHz, CD$_3$OD) δ 7.84 (1H, s), 7.45-7.55 (4H, m), 7.36-7.40 (2H, m), 7.31-7.35 (1H, m), 7.20-7.24 (2H, m), 5.21 (2H, s), 4.42 (2H, d), 3.63-3.68 (2H, m), 3.02-3.17 (4H, m), 2.87 (3H, s), 2.25-2.33 (1H, m), 1.62-1.74 (2H, m), 1.23-1.33 (2H, m), 0.82 (3H, t).

Example 10

4-(4-Benzyloxy-phenyl)-3-butyl-6-(1-methyl-pyrrolidin-3-ylmethoxy)-pyridazine dihydrochloride To a stirred solution of 3-hydroxymethyl-pyrrolidine-1-carboxylic acid tert-butyl ester (1.5 mmol, 302 mg) in THF (4.0 mL) at 0° C., NaH (60% dispersion in mineral oil, 1.5 mmol, 60 mg) was added and stirring continued for 10 min at room temperature, then 4-(4-benzyloxy-phenyl)-3-butyl-6-chloro-pyridazine (Example 1, 1.0 mmol, 352 mg) was added. The resulting mixture was stirred at 50° C. for 1 hour, poured into water and extracted with ethyl acetate. The organic layers were combined and concentrated under reduced pressure. The product was purified by column chromatography using 50% ethyl acetate in hexanes to give 3-[5-(4-benzyloxy-phenyl)-6-butyl-pyridazin-3-yloxymethyl]-pyrrolidine-1-carboxylic acid tert-butyl ester, which was dissolved in dichloromethane (1.0 mL), added 4.0 M HCl in dioxane (1.0 mL) and stirred at room temperature for 1 hour. Solvents were evaporated to provide 4-(4-benzyloxy-phenyl)-3-butyl-6-(pyrrolidin-3-ylmethoxy)-pyridazine dihydrochloride.

To a solution of 4-(4-benzyloxy-phenyl)-3-butyl-6-(pyrrolidin-3-ylmethoxy)-pyridazine dihydrochloride (0.3 mmol, 147 mg) in dichloromethane (2 mL) was added formaldehyde solution in water (37%, 10 mmol, 1.0 mL), and 2 drops of acetic acid. Then sodium triacetoxyborohydride (10 mmol, 2.12 g) was added. And the mixture was stirred at room temperature for 0.5 hour then condensed. It was then diluted with water/EtOAc and neutralized with NaHCO$_3$ powder. The solvent was removed in vacuo and the residue was purified by silica gel chromatography (DCM to DCM+10% 2N NH$_3$ in MeOH) to give a colorless sticky solid, which was dissolved in DCM (1.0 mL), 2N HCl in ether (1.0 mL) was added, kept at room temperature for 10 min, condensed, triturated with hexanes to provide the title compound (117 mg). LCMS: m/z 433 [M+1]. $^1$H NMR (400 MHz, CD$_3$OD) δ 7.82 (1H, s), 7.45-7.55 (4H, m), 7.36-7.40 (2H, m), 7.31-7.35 (1H, m), 7.21-7.24 (2H, m), 5.20 (2H, s), 4.43 (2H, d), 3.57-3.62 (2H, m), 3.05-3.17 (3H, m), 2.87 (3H, s), 2.14-2.30 (2H, m), 1.70-1.81 (2H, m), 1.45-1.53 (2H, m), 1.23-1.33 (2H, m), 0.81 (3H, t).

Example 11

4-[5-(4-Benzyloxy-phenyl)-6-butyl-pyridazin-3-yloxymethyl]-1-methyl-piperidin-4-ol dihydrochloride To a stirred solution of AD mix alpha (4.0 g) in tert-butyl alcohol (20 mL) and water was added 4-methylene-piperidine-1-carboxylic acid tert-butyl ester (8.5 mmol, 1.68 g) dropwise. After stirring the reaction for 48 h, the reaction was quenched with sodium sulfite (5 g) and stirred. The reaction was then poured into ethyl acetate (100 mL). The organic layer was washed with brine, dried, and concentrated to give the crude product (1.8 g, 46%). The compound may be purified by flash chromatography to give 4-hydroxy-4-hydroxymethyl-piperidine-1-carboxylic acid tert-butyl ester.

A stirred solution of the above tert-butyl ester (1.0 mmol) in anhydrous THF at 0° C. may be treated with sodium hydride (60% dispersion in mineral oil) (1.3 mmol). After stirring for 15 min the reaction mixture will come to room temperature. To the solution of the alkoxide may be added 4-(4-benzyloxy-phenyl)-3-butyl-6-chloro-pyridazine (Example 1, 0.74 mmol). After completion of addition, the reaction mixture may be warmed to 50° C. for 3 hours. The reaction may be concentrated onto $SiO_2$ and purified via flash chromatography using 20-50% ethyl acetate in hexanes to provide 4-[5-(4-benzyloxy-phenyl)-6-butyl-pyridazin-3-yloxymethyl]-4-hydroxy-piperidine-1-carboxylic acid tert-butyl ester.

The above tert-butyl ester in DCM may be treated with 4 N HCl in dioxane and stirred for 1 h. The solvent may be removed under reduced pressure, and the salt may be triturated with ethyl ether and filtered to give 4-[5-(4-benzyloxy-phenyl)-6-butyl-pyridazin-3-yloxymethyl]-piperidin-4-ol dihydrochloride.

A suspension of 4-[5-(4-benzyloxy-phenyl)-6-butyl-pyridazin-3-yloxymethyl]-piperidin-4-ol dihydrochloride (0.1 mmol) aqueous formaldehyde (37%, 0.3 mmol) and molecular sieves in anhydrous DCM may be stirred for 20 minutes. To this suspension at room temperature may be added sodium triacetoxyborohydride (0.3 mmol). The reaction mixture may be monitored by LCMS until the reaction is complete. The reaction may be quenched with saturated $NaHCO_3$ and the layers may be separated. The organic layer may be dried and the solvent may be removed under reduced pressure. The crude product may be purified by flash chromatography using with 1-5% (2N ammonia in MeOH) in DCM to give 4-[5-(4-benzyloxy-phenyl)-6-butyl-pyridazin-3-yloxymethyl]-1-methyl-piperidin-4-ol. The neutral amine may be treated with 2N HCl in diethyl ether and DCM. The volatiles may be removed under reduced pressure and the salt triturated with diethyl ether and filtered to provide the title compound. LCMS: m/z 463 [M+1]. $^1$H NMR (400 MHz, $CDCl_3$) δ 7.32-7.49 (5H, m), 7.19-7.25 (2H, m), 7.02-7.09 (2H, m), 6.78 (1H, bs), 5.12 (2H, s), 4.58-4.83 (1H, m), 4.32 (2H, s), 2.54-2.69 (3H, m), 2.40-2.51 (2H, m), 2.27-2.36 (3H, m), 1.71-1.83 (2H, m), 1.59-1.70 (2H, m), 1.18-1.51 (5H, m), 0.81 (3H, t).

Example 12

4-(4-Benzyloxy-phenyl)-6-(1-methyl-piperidin-4-yloxy)-3-propyl-pyridazine dihydrochloride To a stirred solution of 2-(4-benzyloxy-phenyl)-N-methoxy-N-methyl-acetamide (10.51 mmol, 3.0 g) in anhydrous THF at 0° C. was added n-propyl magnesium bromide (2.0 M solution in THF, 20 mL) drop-wise over 30 min. After completion of addition, the reaction mixture was warmed to room temperature and stirred for 30 min. The reaction mixture was cooled to 0° C. and quenched by adding saturated aqueous $NH_4Cl$ drop-wise followed by addition of ethyl acetate. The organic layer was separated, dried, filtered, and concentrated under reduced pressure. The residue was purified by flash column chromatography by eluting with 5% ethyl acetate in hexanes to provide 1-(4-benzyloxy-phenyl)-pentan-2-one.

A mixture of 1-(4-benzyloxy-phenyl)-pentan-2-one (2.98 mmol, 11.4 g), oxo-acetic acid ethyl ester solution in toluene (8 mL, 50% solution in toluene) and triethylamine (2 mL) was stirred at ambient temperature for 24 h. The volatiles were removed under reduced pressure, and the resultant residue was purified by flash silica gel chromatography using by eluting with 30% ethyl acetate in hexanes to provide 3-(4-benzyloxy-phenyl)-2-hydroxy-4-oxo-heptanoic acid ethyl ester.

A mixture of the ethyl ester (1.84 mmol, 0.68 g) and hydrazine hydrate (2 mL) in acetic acid (4 mL) was kept stirring at 120° C. for 3 h. The reaction mixture was cooled to room temperature, added water, the precipitated solid was filtered, and the solid was dried under high vacuum. LCMS: m/z 322.14 [M+2]. The solid was taken in $POCl_3$ (3 mL) and kept the mixture stirring at 90° C. for 1 h. The reaction mixture was concentrated under reduced pressure, to the residue was added ice and stirred for 1 h. This was extracted with DCM (3×25 mL), the combined organic layer was dried over $Na_2SO_4$, filtered, and concentrated under reduced pressure. The resultant residue was purified by flash column chromatography by eluting with 10% ethyl acetate in hexanes to provide 4-(4-benzyloxy-phenyl)-6-chloro-3-propyl-pyridazine.

To a stirred solution of 4-hydroxy-piperidine-1-carboxylic acid tert-butyl ester (0.49 mmol, 0.1 g) in THF (1.5 mL) at room temperature was added NaH (50 mg) followed 4-(4-benzyloxy-phenyl)-6-chloro-3-propyl-pyridazine (0.44 mmol, 0.15 g). The mixture was stirred at 70° C. for 4 h. The reaction mixture was cooled to room temperature, quenched with methanol by drop-wise addition, and removed the volatiles under reduced pressure. The residue was purified by flash silica gel column chromatography by eluting with 20% ethyl acetate to provide 4-[5-(4-benzyloxy-phenyl)-6-propyl-pyridazin-3-yloxy]-piperidine-1-carboxylic acid tert-butyl ester.

To a stirred solution of the above tert-butyl ester (0.178 mmol, 0.09 g) in DCM (1 mL) was added 4N HCl in dioxane (3 mL) and continued stirring at room temperature for 30 min. The volatiles were removed under reduced pressure. The residue was taken in DCM (2 mL) and added formaldehyde solution (2 mL) followed by sodium triacetoxyborohydride (0.3 g) and stirred at room temp for 20 min. The organic layer was separated and purified by flash silica gel flash column chromatography by eluting with ethyl acetate (200 mL) followed by 10% methanolic solution of ammonia (2 M ammonia in methanol) in ethyl acetate to provide 4-(4-benzyloxy-phenyl)-6-(1-methyl-piperidin-4-yloxy)-3-propyl-pyridazine. This was dissolved in DCM (2 mL) then added 4N HCl in dioxane (2 mL). The volatiles were removed, the resultant solid was washed with ether (2 mL) and the solid was dried under vacuum to provide the title compound. LCMS: m/z 420 [M+1]. $^1$H NMR (400 MHz, $CD_3OD$) δ 7.67 and 7.76 (1H, s), 7.44-7.50 (5H, m), 7.31-7.41 (2H, m), 7.19-7.24 (2H, m), 5.54-5.39 (1H, m), 5.19 and 5.2 (2H, s), 3.2-3.74 (4H, m), 3.05-3.14 (2H, m), 2.94 (3H, s), 2.04-2.57 (4H, m), 1.51-1.61 (2H, m), 0.89 (3H, t).

Example 13

4-(4-Benzyloxy-phenyl)-6-(1-methyl-piperidin-4-yloxy)-3-trifluoromethyl-pyridazine dihydrochloride A mixture of (4-benzyloxy-phenyl)-acetic acid methyl ester (11.7 mmol, 3.0 g), trimethyl-trifluoromethyl-silane and cesium fluoride in THF may be stirred at room temperature for 2 h. Hydrochloride may be added upon consumption of ester as indicated by TLC. The mixture may be stirred further at room temperature until the intermediate disappears as indicated by TLC to provide 3-(4-benzyloxy-phenyl)-1,1,1-trifluoro-propan-2-one.

A mixture of 3-(4-benzyloxy-phenyl)-1,1,1-trifluoro-propan-2-one, oxo-acetic acid ethyl ester (1.3 equiv.) and triethyl amine (3 equiv.) in THF may be stirred at room temperature. The reaction mixture may be concentrated in vacuo, and the residue may be heated with hydrazine hydrate and acetic acid at 120° C. to give 5-(4-benzyloxy-phenyl)-6-trifluoromethyl-2H-pyridazin-3-one as white solid.

A mixture of the 5-(4-benzyloxy-phenyl)-6-trifluoromethyl-2H-pyridazin-3-one (0.491 mmol, 170 mg) and phosphorus(V) oxychloride may be heated at 90° C. for 2 h. The reaction mixture may be concentrated in vacuo, and ice may be added to the residue. The mixture may be neutralized with solid sodium bicarbonate and extracted with diethyl ether. Purification by column chromatography on silica gel gives 4-(4-benzyloxy-phenyl)-6-chloro-3-trifluoromethyl-pyridazine as a white solid.

4-[5-(4-Benzyloxy-phenyl)-6-trifluoromethyl-pyridazin-3-yloxy]-piperidine-1-carboxylic acid tert-butyl ester may be obtained from the reaction of 4-(4-benzyloxy-phenyl)-6-chloro-3-trifluoromethyl-pyridazine with 4-hydroxy-piperidine-1-carboxylic acid tert-butyl ester and potassium tert-butoxide in THF.

4-(4-Benzyloxy-phenyl)-6-(piperidin-4-yloxy)-3-trifluoromethyl-pyridazine dihydrochloride may be obtained by treating 4-[5-(4-benzyloxy-phenyl)-6-trifluoromethyl-pyridazin-3-yloxy]-piperidine-1-carboxylic acid tert-butyl ester with 4 N HCl in dioxane. LCMS: m/z 431 [M+1].

4-(4-Benzyloxy-phenyl)-6-(1-methyl-piperidin-4-yloxy)-3-trifluoromethyl-pyridazine dihydrochloride may be obtained by reaction of 4-(4-benzyloxy-phenyl)-6-(piperidin-4-yloxy)-3-trifluoromethyl-pyridazine dihydrochloride with formaldehyde solution in water (37%) and sodium triacetoxyborohydride and subsequently converting to dihydrochloride salt using 4 N HCl in dioxane. LCMS: m/z 446 [M+2]. $^1$H NMR (free base, 400 MHz, CDCl$_3$) δ 7.28-7.47 (7H, m), 7.06 (2H, dd), 6.91 (1H, s), 5.43-5.47 (1H, m), 5.12 (2H, s), 2.75-2.78 (2H, m), 2.33 (5H, m), 2.26-2.15 (2H, m), 1.89-1.97 (2H, m).

Example 14

3-Butyl-4-(4-cyclohexyloxy-phenyl)-6-(1-methyl-piperidin-4-yloxy)-pyridazine dihydrochloride To a sonicated solution of (4-hydroxy-phenyl)-acetic acid methyl ester (601 mmol, 99.9 g), triphenylphosphine (1803 mmol, 473 g), and cyclohexanol (1803 mmol, 180.6 g, 188.5 mL) in anhydrous THF (1800 mL) under N$_2$ atmosphere was added DIAD (1803 mmol, 364.6 g, 355 mL) dropwise over 20 min. After completion of addition, sonication was continued for an additional 30 min. The reaction mixture was concentrated under reduced pressure and filtered through 1 kg SiO$_2$ column using 0-5% ethyl acetate/hexane as an eluant. The resultant product was taken in 600 mL of hexanes, stirred overnight, filtered and the solid was washed with hexanes (3×500 mL). Removal of the solvent gave (4-cyclohexyloxy-phenyl)-acetic acid methyl ester (210 g).

To a stirred solution of the methyl ester (210 g) in THF (1200 mL) and methanol (400 mL), was added 2 N NaOH (~8 mol), and the solution was stirred over night. Most of the volatiles were removed under reduced pressure, the aqueous layer was extracted with ether (3×100 mL), and aqueous layer was diluted with water (300 mL). This was acidified with 6 N HCl to pH ~3 and extracted with ether (3×200 mL). The combined ether layers were washed with brine (100 mL), dried (Na$_2$SO$_4$), filtered, and concentrated to provide (4-cyclohexyloxy-phenyl)-acetic acid.

To a stirred solution of (4-cyclohexyloxy-phenyl)-acetic acid (181 mmol, 42.4 g) in anhydrous DCM (200 mL) at 0° C. was added oxalyl chloride (362 mmol, 36.6 mL) and continued stirring for 12 h during which time the reaction mixture slowly attained room temperature. The reaction mixture was concentrated in vacuo to remove volatile impurities and dried under high vacuum. To a stirred solution of N,O-dimethylhydroxylamine hydrochloride (226 mmol, 22.1 g) and N-methylmorpholine (407 mmol, 44.8 mL) in anhydrous DCM (200 mL) at 0° C. was added the acid chloride obtained above, dissolved in DCM (50 mL) dropwise. The reaction mixture was stirred for 12 h allowing it to slowly attain room temperature. The reaction mixture was washed with water (2×200 mL), brine (100 mL), dried (Na$_2$SO$_4$), filtered, and concentrated under reduced pressure. The residue was purified on a 330 g SiO$_2$ cartridge with 20-30% ethyl acetate in hexanes to provide 2-(4-cyclohexyloxy-phenyl)-N-methoxy-N-methyl-acetamide.

To a stirred solution of the 2-(4-cyclohexyloxy-phenyl)-N-methoxy-N-methyl-acetamide (149 mmol, 41.4 g) in anhydrous THF (150 mL) at −78° C. was added n-butyl lithium (1.6 M in hexanes, 298 mmol, 186 mL) dropwise over 45 minutes. The dry ice/acetone bath was replaced with an ice bath, and the reaction was stirred for an additional 30 min. TLC (30% ethyl acetate in hexanes) analysis indicated complete consumption of starting material. The reaction mixture was quenched by addition of saturated ammonium chloride (100 mL) at 0° C., further diluted with water (125 mL) and extracted with ethyl acetate (2×150 mL). The combined ethyl acetate layers were washed with brine (100 mL), dried (Na$_2$SO$_4$), filtered and concentrated under reduced pressure. The residue was dissolved in 6% ethyl acetate in hexanes and filtered through a 110 g SiO$_2$ column. The column was eluted with 6% ethyl acetate in hexanes to provide 1-(4-cyclohexyloxy-phenyl)hexan-2-one upon evaporation of solvent.

To a stirred solution of 1-(4-cyclohexyloxy-phenyl)-hexan-2-one (86.4 mmol, 23.7 g) and triethylamine (86.4 mmol, 12.1 mL) in THF (10 mL) was added a solution of ethyl glyoxylate (50% in toluene, 432 mmol, 86 mL) and continued stirring for 12 h during which time the starting material was fully consumed as judged by TLC. After removal of volatiles in vacuo, the crude product was purified on a 300 g SiO$_2$ cartridge with 10-15% ethyl acetate in hexanes to afford 3-(4-cyclohexyloxy-phenyl)-2-hydroxy-4-oxo-octanoic acid ethyl ester To a stirred solution of the octanoic acid ethyl ester (105 mmol, 39.5 g) in glacial acetic acid (25.5 mL) was added hydrazine hydrate (525 mmol, 25.5 mL), and the reaction was heated at 100° C. for 12 h. After cooling, the volatiles were removed in vacuo, the residue was dissolved in ethyl acetate (300 mL). The organic layer was washed with water (100 mL), saturated NaHCO$_3$ (3×100 mL), brine (100 mL), dried (Na$_2$SO$_4$), filtered, and concentrated under reduced pressure. The residue was recrystallized from a mixture of ethyl acetate (200 mL) and hexanes (300 mL) to afford 6-butyl-5-(4-cyclohexyloxy-phenyl)-2H-pyridazin-3-one.

A suspension of the pyridazin-3-one (58.4 mmol, 19.1 g) in phosphorous oxychloride (292 mmol, 26.7 mL) was heated at 90° C. for 30 min with stirring during which period the starting material was fully consumed as judged by TLC. The reaction mixture was cooled to room temperature and the volatiles were removed in vacuo. The residue was dissolved in ethyl acetate (200 mL), washed with saturated NaHCO$_3$ (3×100 mL), brine (100 mL), dried (Na$_2$SO$_4$) filtered and concentrated under reduced pressure. The residue was purified on a 330 g SiO$_2$ cartridge eluating with 0-10% ethyl acetate in hexanes to afford 3-butyl-6-chloro-4-(4-cyclohexyloxy-phenyl)-pyridazine.

To a stirred solution of 4-hydroxy-piperidine-1-carboxylic acid tert-butyl ester (94.2 mmol, 18.97 g) in THF (100 mL) at room temperature was added potassium tert-butoxide (87.0 mmol, 9.76 g) and continued stirring for 15 min. The reaction mixture was cooled to 0° C. using an ice bath. To this was added a solution of 3-butyl-6-chloro-4-(4-cyclohexyloxyphenyl)-pyridazine (72.5 mmol, 25.0 g) in THF (100 mL). The reaction mixture was allowed to slowly attain room temperature while stirring overnight. The reaction was poured into a mixture of water (300 mL) and ethyl acetate (300 mL). The mixture was shaken and separated. The aqueous layer was extracted with ethyl acetate (2×100 mL). The combined organic layer was washed with brine (50 mL), dried ($Na_2SO_4$), filtered and concentrated under reduced pressure. The residue was purified on 330 g $SiO_2$ cartridge using an ethyl acetate/hexanes gradient to provide 4-[6-butyl-5-(4-cyclohexyloxy-phenyl)-pyridazin-3-yloxy]-piperidine-1-carboxylic acid tert-butyl ester.

To a solution of the tert-butyl ester (39.2 mmol, 20.0 g) in DCM (50 mL) was added 4 N HCl in dioxane (50 mL), and the reaction was stirred for 45 min. The solvents were removed in vacuo and the residue was triturated with anhydrous ethyl ether (50 mL) and filtered and washed the cake with ethyl ether (50 mL). The off-white solid was dried over night at 50° C. under high vacuum to provide 3-butyl-4-(4-cyclohexyloxy-phenyl)-6-(piperidin-4-yloxy)-pyridazine dihydrochloride.

To a solution of 3-butyl-4-(4-cyclohexyloxy-phenyl)-6-(piperidin-4-yloxy)-pyridazine dihydrochloride (0.2 mmol, 82 mg) in DCM (2 mL) was added formaldehyde solution in water (37%, 2 mmol, 0.2 mL), and 1 drop of acetic acid. Then sodium triacetoxyborohydride (2 mmol, 424 mg) was added, and the mixture was stirred at room temperature for 0.5 hour then condensed. It was then diluted with water/EtOAc and neutralized with $NaHCO_3$ powder. The organic layers were combined and dried over $Na_2SO_4$. The solvent was removed in vacuo and the residue was purified by silica gel chromatography (DCM to DCM+10% 2N ammonia in MeOH) to provide 3-butyl-4-(4-cyclohexyloxy-phenyl)-6-(1-methyl-piperidin-4-yloxy)-pyridazine. The solid was dissolved in 1 mL DCM, 2N HCl in ether (1 mL) was added, kept at room temperature for 10 min, condensed, triturated with hexanes to provide the title compound (79 mg). LCMS: m/z 425 [M+1]. $^1$H NMR (400 MHz, $CD_3OD$): δ 7.78 and 7.86 (1H, s), 7.45-7.50 (2H, m), 7.11-7.15 (2H, m), 5.35-5.53 (1H, m), 4.42-4.49 (1H, m), 3.24-3.69 (4H, m), 3.12-3.17 (2H, m), 2.94 (3H, s), 1.90-2.58 (6H, m), 1.78-1.86 (2H, m), 1.34-1.64 (8H, m), 1.25-1.32 (2H, m), 0.82 (3H, t).

Example 15

3-{4-[6-Butyl-5-(4-cyclohexyloxy-phenyl)-pyridazin-3-yloxy]-piperidin-1-yl}-propionic acid ethyl ester dihydrochloride To a solution of 3-butyl-4-(4-cyclohexyloxy-phenyl)-6-(piperidin-4-yloxy)-pyridazine dihydrochloride (Example 14, 2.0 mmol, 965 mg) in DCM (5 mL) was added ethyl acrylate (6.0 mmol, 0.66 mL), and DIEA (6.0 mmol, 1.05 mL). The mixture was stirred at room temperature over night then condensed. The residue was purified by silica gel chromatography (DCM to DCM+10% 2N $NH_3$ in MeOH) to give a colorless sticky solid, which was dissolved in DCM (2.0 mL), 2N HCl in ether (2.0 mL) was added, kept at room temperature for 10 min, condensed, triturated with hexanes to provide the title compound (792 mg). LCMS: m/z 512 [M+2]. $^1$H NMR (400 MHz, $CD_3OD$): δ 7.30-7.34 (2H, m), 7.01-7.07 (3H, m), 5.47-5.53 (1H, m), 4.37-4.43 (1H, m), 4.20 (2H, q), 3.35-3.70 (5H, m), 2.87-2.95 (5H, m), 2.20-2.35 (4H, m), 1.96-2.03 (2H, m), 1.78-1.84 (2H, m), 1.35-1.64 (7H, m), 1.28 (3H, t), 1.20-1.26 (3H, m), 0.80 (3H, t).

Example 16

3-{4-[6-Butyl-5-(4-cyclohexyloxy-phenyl)-pyridazin-3-yloxy]-piperidin-1-yl}-N,N-dimethyl-propionamide dihydrochloride To a solution of 3-{4-[6-butyl-5-(4-cyclohexyloxy-phenyl)-pyridazin-3-yloxy]-piperidin-1-yl}-propionic acid ethyl ester dihydrochloride (Example 15, 1.0 mmol, 583 mg) in THF-MeOH—$H_2O$ (1:1:1, 3 mL) was added LiOH (20 mmol, 480 mg). The mixture was stirred at 100° C. for 10 min. The mixture was then diluted with water/EtOAc and neutralized with acetic acid. The organic layers combined, dried, and condensed in vacuo, and the residue was dissolved in DMF (2 mL). Dimethylamine hydrochloride (3.0 mmol, 245 mg), HBTU (3.0 mmol, 1.14 g), DIEA (3.0 mmol, 0.53 mL) were added to the mixture, and the mixture was stirred at 100° C. for 2 hours. It was then diluted with water/EtOAc and neutralized with acetic acid. The organic layers were combined, dried, and condensed in vacuo, and the residue was purified by silica gel chromatography (DCM to DCM+10% 2N ammonia in MeOH) to give a colorless sticky solid, which was dissolved in DCM (2 mL), 2N HCl in ether (2 mL) was added, kept at room temperature for 10 min, condensed, triturated with hexanes to provide the title compound (279 mg). LCMS: m/z 510 [M+1]. $^1$H NMR (400 MHz, $CD_3OD$): δ 7.31-7.35 (2H, m), 7.01-7.07 (3H, m), 5.46-5.52 (1H, m), 4.37-4.43 (1H, m), 3.35-3.50 (5H, m), 3.03 (6H, s), 2.87-2.95 (5H, m), 2.20-2.35 (4H, m), 1.96-2.03 (2H, m), 1.78-1.84 (2H, m), 1.27-1.63 (8H, m), 1.20-1.24 (2H, m), 0.80 (3H, t).

Example 17

2-{4-[6-Butyl-5-(4-cyclohexyloxy-phenyl)-pyridazin-3-yloxy]-piperidin-1-yl}-ethanol dihydrochloride To a solution of 3-butyl-4-(4-cyclohexyloxy-phenyl)-6-(piperidin-4-yloxy)-pyridazine dihydrochloride (Example 14, 0.1 mmol, 49 mg) in EtOH (1 mL) was added 2-bromoethanol (0.3 mmol, 22 μL), and potassium carbonate (0.4 mmol, 56 mg). The mixture was stirred at room temperature for 3 hours and then diluted with water/EtOAc. The organic layers were combined, dried, and condensed in vacuo, and the residue was purified by silica gel chromatography (DCM to DCM+10% 2N ammonia in MeOH) to give a colorless sticky solid, which was dissolved in DCM (1 mL), 1N HCl in ether (1 mL) was added, kept at room temperature for 10 min, condensed, triturated with hexanes to provide the title compound (12 mg). LCMS: m/z 456 [M+2]. $^1$H NMR (400 MHz, $CD_3OD$): δ 7.78 (1H, s), 7.45-7.49 (2H, m), 7.12-7.17 (2H, m), 5.38-5.57 (1H, m), 4.41-4.48 (1H, m), 3.91-3.95 (2H, m), 3.60-3.81 (2H, m), 3.32-3.47 (4H, m), 3.12-3.17 (2H, m), 2.10-2.59 (5H, m), 1.98-2.04 (2H, m), 1.78-1.84 (2H, m), 1.35-1.63 (7H, m), 1.26-1.33 (2H, m), 0.82 (3H, t).

Example 18

3-Butyl-4-(4-cyclohexyloxy-phenyl)-6-[1-(2-[1,3] dioxan-2-yl-ethyl)-piperidin-4-yloxy]-pyridazine dihydrochloride To a solution of 3-butyl-4-(4-cyclohexyloxy-phenyl)-6-(piperidin-4-yloxy)-pyridazine dihydrochloride (Example 14, 0.1 mmol, 49 mg) in DMF (1 mL) was added 2-(2-bromoethyl)-1,3-dioxane (0.3 mmol, 40 µL), and potassium carbonate (0.4 mmol, 56 mg). The mixture was stirred at room temperature for 3 hours. It was then diluted with water/EtOAc. The organic layers were combined, dried, and condensed in vacuo and the residue was purified by silica gel chromatography (DCM to DCM+10% 2N ammonia in MeOH) to give a colorless sticky solid, which was dissolved in DCM (1 mL), 1N HCl in ether (1 mL) was added, kept at room temperature for 10 min, condensed, triturated with hexanes to provide the title compound (22 mg). LCMS: m/z 525 [M+1]. $^1$H NMR (400 MHz, CD$_3$OD): δ 7.72 and 7.81 (1H, s), 7.44-7.49 (2H, m), 7.12-7.17 (2H, m), 5.38-5.57 (1H, m), 4.76-4.79 (1H, m), 4.41-4.48 (1H, m), 4.06-4.13 (2H, m), 3.72-3.86 (3H, m), 3.55-3.60 (1H, m), 3.22-3.39 (4H, m), 3.12-3.17 (2H, m), 2.23-2.57 (3H, m), 1.98-2.17 (6H, m), 1.79-1.86 (2H, m), 1.23-1.64 (11H, m), 0.82 (3H, t).

Example 19

3-Butyl-4-[4-(4,4-difluoro-cyclohexyloxy)-phenyl]-6-(1-methyl-piperidin-4-yloxy)-pyridazine dihydrochloride To a solution of 4-(4-benzyloxy-phenyl)-3-butyl-6-(1-methyl-piperidin-4-yloxy)-pyridazine (Example 1, 14 mmol, 6.04 g) in methanol/ethyl acetate (100 mL, 1/1) was added 10% palladium on activated carbon (10% by weight, 0.60 g). The mixture was repeatedly de-gassed under vacuum, filled with hydrogen for 3 times. Then hydrogen balloons were attached to the reaction, which was stirred at room temperature for 2 hours. TLC/LCMS monitored to completion. The mixture was then filtered through celite, the celite cake was washed with 1/1 methanol/ethyl acetate for 3 times, and the organic layers were combined and condensed to give 4-[3-butyl-6-(1-methyl-piperidin-4-yloxy)-pyridazin-4-yl]-phenol as a white powder (4.06 g, 85% yield), which was used directly in the next step.

To a solution of the above phenol (0.5 mmol, 171 mg) in dry THF (1 mL) was added 4,4-difluoro-cyclohexanol (1.5 mmol, 205 mg) and triphenylphosphine (1.5 mmol, 394 mg). While sonicating, diisopropyl azodicarboxylate (1.5 mmol, 296 µL) was added. The mixture was sonicated for another 1 hour and then condensed. The residue was purified by silica gel chromatography (DCM to DCM+10% MeOH) to a colorless sticky solid, which was dissolved in DCM (2.0 mL), 2N HCl in ether (2.0 mL) was added, condensed, triturated with hexanes to provide the title compound (115 mg). LCMS: m/z 461 [M+1]. $^1$H NMR (400 MHz, CD$_3$OD): δ 7.36-7.39 (2H, m), 7.16-7.19 (2H, m), 7.00 (1H, s), 5.43 (1H, bs), 4.62-4.67 (1H, m), 2.90-2.95 (2H, m), 2.78 (3H, s), 2.61-2.69 (2H, m), 2.14-2.42 (9H, m), 1.68-1.98 (3H, m), 1.43-1.55 (3H, m), 1.20-1.38 (3H, m), 0.81 (3H, t).

Example 20

3-Butyl-4-(4-cyclohexyloxy-phenyl)-6-{1-[2-(5-methyl-[1,3,4]oxadiazol-2-yl)-ethyl]-piperidin-4-yloxy}-pyridazine dihydrochloride A mixture of 3-butyl-4-(4-cyclohexyloxy-phenyl)-6-(piperidin-4-yloxy)-pyridazine (Example 14, 0.244 mmol, 100 mg) and acrylic acid tert-butyl ester (2 mL) may be stirred at room temperature for 20 h. The organic solvent may be removed in vacuo and the residue is purified by column chromatography on silica gel using 1-2% of MeOH in DCM to give 3-{4-[6-butyl-5-(4-cyclohexyloxy-phenyl)-pyridazin-3-yloxy]-piperidin-1-yl}-propionic acid tert-butyl ester.

A mixture of the tert-butyl ester (from previous step) may be heated with hydrazine (0.5 mL) and ethanol (2 mL) to give 3-{4-[6-butyl-5-(4-cyclohexyloxy-phenyl)-pyridazin-3-yloxy]-piperidin-1-yl}-propionic acid hydrazide after evaporation of volatiles in vacuo.

A mixture of the hydrazide (from previous step) in 1,1,1-trimethoxy-ethane (2 mL) may be refluxed. The organic volatiles are removed in vacuo and the residue may be purified by column chromatography on silica gel using 1-3% of MeOH in DCM to provide 3-butyl-4-(4-cyclohexyloxy-phenyl)-6-{1-[2-(5-methyl-[1,3,4]oxadiazol-2-yl)-ethyl]-piperidin-4-yloxy}-pyridazine which may be converted to the dihydrochloride salt. $^1$H NMR (free base, 400 MHz, CDCl$_3$) δ 7.20 (2H, dd), 6.96 (2H, dd), 6.72 (1H, s), 5.30-5.36 (1H, m), 4.26-4.32 (1H, m), 3.01-3.04 (2H, m), 2.81-2.87 (6H, m), 2.50 (3H, s), 2.35-2.41 (2H, m), 1.24-2.18 (18H, m), 0.82 (3H, t).

Example 21

3-Butyl-4-(4-cyclohexyloxy-phenyl)-6-{1-[2-(2-methyl-2H-tetrazol-5-yl)-ethyl]-piperidin-4-yloxy}-pyridazine dihydrochloride A mixture of 3-butyl-4-(4-cyclohexyloxy-phenyl)-6-(piperidin-4-yloxy)-pyridazine (Example 14, 0.244 mmol, 100 mg) and acrylonitrile (1 mL) may be stirred at room temperature for 20 h. The organic solvent may be removed in vacuo, and the residue may be purified by column chromatography on silica gel using 1-2% of MeOH in DCM to provide 3-{4-[6-butyl-5-(4-cyclohexyloxy-phenyl)-pyridazin-3-yloxy]-piperidin-1-yl}-propionitrile.

A mixture of the propionitrile (from previous step), sodium azide (2.0 equiv.), zinc bromide (1.0 equiv.) in isopropanol and water may be refluxed for 2 h. The crude product 3-butyl-4-(4-cyclohexyloxy-phenyl)-6-{1-[2-(1H-tetrazol-5-yl)-ethyl]-piperidin-4-yloxy}-pyridazine may be used for next step without further purification.

The pyridazine (from the previous step) may be reacted with (trimethylsilyl)diazomethane, 2 M solution in hexanes (2 mL) for 2 h. The reaction may be quenched with MeOH. The reaction mixture may be partitioned between DCM and water. The DCM layer may be separated and dried over sodium sulfate. Purification by column chromatography provides 3-butyl-4-(4-cyclohexyloxy-phenyl)-6-{1-[2-(2-methyl-2H-tetrazol-5-yl)-ethyl]-piperidin-4-yloxy}-pyridazine (a mixture of two regio-isomers, 20 mg) which may be converted to the dihydrochloride salt. $^1$H NMR (free base, 400 MHz, CDCl$_3$) δ 7.15 (2H, dd), 6.90 (2H, dd), 6.66 (1H, s), 5.25-5.31 (1H, m), 4.21-4.27 (4H, m), 2.97-3.06 (2H, m), 2.74-2.81 (6H, m), 2.31-2.37 (2H, m), 1.18-2.12 (18H, m), 0.76 (3H, t).

Example 22

1-{4-[6-Butyl-5-(4-cyclohexyloxy-phenyl)-pyridazin-3-yloxy]-piperidin-1-yl}-2-methyl-propan-2-ol dihydrochloride To a solution of 3-butyl-4-(4-cyclohexyloxy-phenyl)-6-(piperidin-4-yloxy)-pyridazine dihydrochloride (Example 14, 0.2 mmol, 97 mg) in EtOH (2 mL) was added 1-chloro-2-methyl-2-propanol (0.4 mmol, 44 µL), and potassium carbonate (0.6 mmol, 83 mg). And the mixture was stirred at 50° C. for 4 hours. It was then diluted with water/EtOAc. The organic layers were combined, dried, and condensed in vacuo and the residue was purified by silica gel chromatography (DCM to DCM+10% MeOH) to give a colorless sticky solid, which was dissolved in DCM (2 mL), 1N HCl in ether (2 mL) was added, kept at room temperature for 10 min, condensed, triturated with hexanes to yield 1-{4-[6-butyl-5-(4-cyclohexyloxy-phenyl)-pyridazin-3-yloxy]-piperidin-1-yl}-2-methyl-propan-2-ol dihydrochloride (86 mg, 77% yield). LCMS: m/z 483 [M+1]. $^1$H NMR (400 MHz, CD$_3$OD): δ 7.53 and 7.62 (1H, s), 7.41-7.46 (2H, m), 7.10-7.14 (2H, m), 5.42-5.52 (1H, m), 4.41-4.46 (1H, m), 3.65-3.83 (2H, m), 3.25-3.47 (3H, m), 3.05-3.12 (2H, m), 2.22-2.55 (5H, m), 1.98-2.03 (2H, m), 1.78-1.83 (2H, m), 1.40-1.63 (7H, m), 1.38 (6H, s), 1.22-1.36 (3H, m), 0.81 (3H, t).

Example 23

3-Butyl-4-(4-cyclohexyloxy-phenyl)-6-[1-(2-methoxy-ethyl)-piperidin-4-yloxy]-pyridazine dihydrochloride To a solution of 3-butyl-4-(4-cyclohexyloxy-phenyl)-6-(piperidin-4-yloxy)-pyridazine dihydrochloride (Example 14, 0.2 mmol, 97 mg) in EtOH (2 mL) was added 2-bromoethyl methyl ether (0.6 mmol, 57 µL), and potassium carbonate (0.6 mmol, 83 mg). The mixture was stirred at 60° C. for 3 hours, then cooled to room temperature, and filtered through celite. The celite cake was washed with DCM. The organic layers were combined and condensed in vacuo, and the residue was purified by silica gel chromatography (DCM to DCM+10% 2N NH$_3$ in MeOH) to give a colorless sticky solid, which was dissolved in DCM (2 mL), 1N HCl in ether (2 mL) was added, kept at room temperature for 10 min, condensed, triturated with hexanes to provide the title compound (52 mg). LCMS: m/z 469 [M+1]. $^1$H NMR (400 MHz, CD$_3$OD): δ 7.31-7.40 (3H, m), 7.06-7.10 (2H, m), 5.38-5.57 (1H, m), 4.39-4.44 (1H, m), 3.53-3.78 (4H, m), 3.43 (3H, s), 3.25-3.42 (4H, m), 2.96-3.02 (2H, m), 2.04-2.55 (4H, m), 1.97-2.02 (2H, m), 1.78-1.83 (2H, m), 1.29-1.62 (8H, m), 1.22-1.30 (2H, m), 0.80 (3H, t).

Example 24

(±)-cis-4-[6-Butyl-5-(4-cyclohexyloxy-phenyl)-pyridazin-3-yloxymethyl]-1-methyl-piperidin-3-ol dihydrochloride To a stirred solution of (±)-cis-4-[6-butyl-5-(4-cyclohexyloxy-phenyl)-pyridazin-3-yloxymethyl]-piperidin-3-ol dihydrochloride (Example 35, ~0.2 mmol) in dichloromethane (2.0 mL), was added formaldehyde solution in water (37%, 2.0 mmol, 0.2 mL), and 1 drop of acetic acid. Then sodium triacetoxyborohydride (2.0 mmol, 424 mg) was added. The mixture was stirred at room temperature for 0.5 hour, then condensed, worked up and the solvent was removed in vacuo. The residue was purified by silica gel chromatography (DCM to DCM+10% 2N ammonia in MeOH) to give a colorless sticky solid, which was dissolved in DCM (1.0 mL), 2N HCl in ether (1.0 mL) was added, condensed, triturated with hexanes to provide title compound (51 mg). LCMS: m/z 455 [M+1]. $^1$H NMR (400 MHz, CD$_3$OD) δ 7.48 (1H, s), 7.39-7.43 (2H, m), 7.08-7.12 (2H, m), 4.52-4.59 (1H, m), 4.39-4.48 (2H, m), 4.27 (1H, bs), 3.38-3.54 (2H, m), 3.02-3.26 (4H, m), 2.85 (3H, s), 2.25-2.37 (1H, m), 1.78-2.07 (6H, m), 1.20-1.43 (10H, m), 0.81 (3H, t).

Example 25

(±)-trans-4-[6-Butyl-5-(4-cyclohexyloxy-phenyl)-pyridazin-3-yloxymethyl]-1-methyl-piperidin-3-ol dihydrochloride The title compound may be prepared using a procedure analogous to Example 24 and substituting (±)-trans-4-hydroxymethyl-3-methoxymethoxy-piperidine-1-carboxylic acid tert-butyl ester (Example 36) for (±)-cis-4-hydroxymethyl-3-methoxymethoxy-piperidine-1-carboxylic acid tert-butyl ester. LCMS: m/z 455 [M+1]. $^1$H NMR (400 MHz, CD$_3$OD) δ 7.58 and 7.68 (1H, s), 7.41-7.46 (2H, m), 7.08-7.13 (2H, m), 4.58-4.75 (3H, m), 4.39-4.48 (1H, m), 3.84-3.95 (1H, m), 2.97-3.12 (3H, m), 2.90 (3H, s), 2.82-2.89 (2H, m), 1.78-2.23 (7H, m), 1.21-1.63 (10H, m), 0.81 (3H, t).

Example 26

3-[6-Butyl-5-(4-cyclohexyloxy-phenyl)-pyridazin-3-yloxy]-1-azabicyclo[2.2.2]octane dihydrochloride To a stirred solution of 1-aza-bicyclo[2.2.2]octan-3-ol (0.44 mmol, 0.055 g) in THF (1 mL) at room temperature was added sodium hydride (60% dispersion in mineral oil) (0.58 mmol, 0.023 g) and continued stirring for 15 min. The reaction mixture was cooled to 0° C. using an ice bath. To this was added a solution of 3-butyl-6-chloro-4-(4-cyclohexyloxy-phenyl)-pyridazine (Example 14, 0.29 mmol, 0.1 g) in THF (1 mL). After completion of addition, the reaction mixture was warmed to 50° C. for 1 h. LCMS showed the reaction was about 50% complete, so the temperature was raised to 68° C. and the reaction was stirred over night. The reaction was poured into a mixture of water (3 mL) and ethyl acetate (5 mL). The mixture was shaken and separated. The ethyl acetate layer was washed with brine (2 mL), dried (Na$_2$SO$_4$), filtered and concentrated under reduced pressure. The residue was purified on a 4 g SiO$_2$ cartridge using 4-6% (2N NH3 in MeOH) in DCM to provide 3-[6-butyl-5-(4-cyclohexyloxy-phenyl)-pyridazin-3-yloxy]-1-azabicyclo[2.2.2]octane. The amine was treated with 2N HCl in diethyl ether (2 mL) and DCM (2 mL). The volatiles were removed under reduced pressure and the salt was triturated with diethyl ether and filtered to provide the title compound (0.05 g). LCMS: m/z 437 [M+1]. $^1$H NMR (400 MHz, CD$_3$OD) δ 7.92 (1H, s), 7.51-7.49 (2H, m), 7.10-7.17 (2H, m), 5.49-5.56 (1H, m), 4.41-4.50 (1H, m), 3.99-3.93 (1H, m), 3.61 (1H, d), 3.35-3.51 (4H, m), 3.14-3.21 (2H, m), 2.64-2.71 (1H, m), 2.41-2.34 (1H, m), 1.94-2.25 (5H, m), 1.77-1.87 (2H, m), 1.25-1.65 (10H, m), 0.82 (3H, t).

Example 27 endo-3-[6-Butyl-5-(4-cyclohexyloxy-phenyl)-pyridazin-3-yloxy]-8-methyl-8-aza-bicyclo[3.2.1]octane dihydrochloride The title compound may be prepared using a procedure analogous to Example 26 and substituting 8-methyl-8-aza-bicyclo[3.2.1]octan-3-ol for 1-aza-bicyclo[2.2.2]octan-3-ol. LCMS: m/z 451 [M+1]. $^1$H NMR (400 MHz, CD$_3$OD) δ 7.70 (1H, s), 7.43-7.49 (2H, m), 7.08-7.15 (2H, m), 5.49-5.47 (1H, m), 4.42-4.47 (1H, m), 3.93-3.98 (2H, m), 3.06-3.14 (2H, m), 2.85 (3H, s), 2.22-2.70 (8H, m), 1.96-2.07 (2H, m), 1.76-1.86 (2H, m), 1.23-1.67 (10H, m), 0.82 (3H, t).

Example 28

(1R,9aR)-1-[6-Butyl-5-(4-cyclohexyloxy-phenyl)-pyridazin-3-yloxymethyl]-octahydroquinolizine dihydrochloride The title compound may be prepared using a procedure analogous to Example 26 and substituting (1R,9aR)-1-(octahydro-quinolizin-1-yl)-methanol (0.58 mmol, 0.050 g) in DMF for 1-aza-bicyclo[2.2.2]octan-3-ol in THF. LCMS: m/z 479 [M+1]. $^1$H NMR (400 MHz, CD$_3$OD) δ 7.55-7.71 (1H, m), 7.41-7.45 (2H, m), 7.07-7.14 (2H, m), 4.72-4.86 (1H, m), 4.37-4.57 (2H, m), 3.61-3.90 (1H, m), 3.41-3.51 (2H, m), 3.33-3.36 (1H, m), 2.88-3.17 (4H, m), 2.51-2.71 (1H, m), 1.70-2.22 (13H, m), 1.21-1.70 (10H, m), 0.81 (3H, t).

Example 29

3-Butyl-4-(4-cyclohexyloxy-phenyl)-6-((R)-1-methyl-pyrrolidin-3-yloxy)-pyridazine dihydrochloride The title compound may be prepared using a procedure analogous to Example 26 and substituting (R)-1-methyl-pyrrolidin-3-ol (0.58 mmol, 0.060 g) in DMF (1.0 mL) for 1-aza-bicyclo[2.2.2]octan-3-ol in THF. LCMS: m/z 411 [M+1]. $^1$H NMR (400 MHz, CD$_3$OD) δ 7.53-7.60 (1H, m), 7.41-7.45 (2H, m), 7.08-7.12 (2H, m), 5.75-5.90 (1H, m), 4.38-4.49 (1H, m), 4.00-4.29 (1H, m), 3.73-3.96 (1H, m), 3.39-3.61 (1H, m), 2.95-3.12 (5H, m), 2.76-2.88 (1H, m), 2.52-2.56 (1H, m), 2.34-2.48 (1H, m), 1.99-2.01 (2H, m), 1.80-1.83 (2H, m), 1.22-1.66 (10H, m), 0.81 (3H, t).

Example 30

3-Butyl-4-(4-cyclohexyloxy-phenyl)-6-((S)-1-methyl-pyrrolidin-3-yloxy)-pyridazine dihydrochloride The title compound may be prepared using a procedure analogous to Example 26 and substituting (S)-1-methyl-pyrrolidin-3-ol (0.58 mmol, 0.060 g) in DMF (1.0 mL) for 1-aza-bicyclo[2.2.2]octan-3-ol in THF. LCMS: m/z 411 [M+1]. $^1$H NMR (400 MHz, CD$_3$OD) δ 7.53-7.62 (1H, m), 7.39-7.48 (2H, m), 7.08-7.12 (2H, m), 5.74-5.91 (1H, m), 4.39-4.48 (1H, m), 4.00-4.28 (1H, m), 3.80-3.96 (1H, m), 3.38-3.62 (1H, m), 2.92-3.13 (5H, m), 2.76-2.88 (1H, m), 2.55-2.62 (1H, m), 2.34-2.48 (1H, m), 1.96-2.07 (2H, m), 1.80-1.83 (2H, m), 1.22-1.66 (10H, m), 0.81 (3H, t).

Example 31

(3S,6R)-3-[6-Butyl-5-(4-cyclohexyloxy-phenyl)-pyridazin-3-yloxy]-8-methyl-8-aza-bicyclo[3.2.1]octan-6-ol dihydrochloride To an ice bath cooled, stirred solution of (R)-6-hydroxy-8-methyl-8-aza-bicyclo[3.2.1]octan-3-one (4.08 mmol, 0.634 g), triethylamine (20.4 mmol, 2.86 mL), and DMAP (0.245 mmol, 0.03 g) in dry DCM (3.5 mL) was added acetic anhydride (6.12 mmol, 0.58 mL). The reaction mixture was allowed to come to room temperature and was stirred for 12 hours. The reaction was evaporated and the resulting residue was purified on a 12 g SiO$_2$ cartridge using 0-3% (2N NH$_3$ in MeOH) in DCM to give acetic acid (R)-8-methyl-3-oxo-8-aza-bicyclo[3.2.1]oct-6-yl ester.

To a solution of the above ester (4.11 mmol, 0.811 g) in 95% ethanol (50 mL) was added platinum (IV) oxide (0.354 mmol, 0.081 g), and the reaction was pressurized to 50 psi of H$_2$. The reaction was stirred vigorously for 12 hours. The reaction was filtered through a pad of celite and the celite was washed with portions of ethyl acetate. The solvents were removed under reduced pressure to provide acetic acid (3S, 6R)-3-hydroxy-8-methyl-8-aza-bicyclo[3.2.1]oct-6-yl ester (0.98 g) which was used without further purification in the next step.

The title compound may be prepared using a procedure analogous to Example 26 and substituting acetic acid (3S, 6R)-3-hydroxy-8-methyl-8-aza-bicyclo[3.2.1]oct-6-yl ester (1.16 mmol, 0.231 g) in DMF (1.5 mL) for 1-aza-bicyclo [2.2.2]octan-3-ol in THF. LCMS: m/z 467 [M+1]. $^1$H NMR (400 MHz, CD$_3$OD) δ 7.44-7.49 (1H, m), 7.37-7.43 (2H, m), 7.08-7.12 (2H, m), 6.12-6.28 (1H, m), 4.38-4.47 (1H, m), 4.00-4.29 (3H, m), 2.96-3.12 (5H, m), 2.59-2.69 (1H, m), 2.32-2.58 (3H, m), 2.07-2.23 (1H, m), 1.96-2.07 (2H, m), 1.80-1.83 (2H, m), 1.21-1.66 (11H, m), 0.81 (3H, t).

Example 32

3-Butyl-4-(4-cyclohexyloxy-phenyl)-6-[2-((R)-1-methyl-piperidin-2-yl)-ethoxy]-pyridazine dihydrochloride To a stirred solution of (R)-2-(2-hydroxy-ethyl)-piperidine-1-carboxylic acid tert-butyl ester (0.87 mmol, 0.20 g) in DMF (1.0 mL) at room temperature was added sodium hydride (60% dispersion in mineral oil) (2.61 mmol, 0.104 g) and continued stirring for 15 min. The reaction mixture was cooled to 0° C. using an ice bath. To this was added a solution of 3-butyl-6-chloro-4-(4-cyclohexyloxy-phenyl)-pyridazine (Example 14, 0.435 mmol, 0.15 g) in DMF (1.0 mL). After completion of addition, the reaction mixture was warmed to 50° C. for 12 hour. The reaction was poured into a mixture of water (10 mL) and ethyl acetate (5 mL). The mixture was shaken and separated. The ethyl acetate layer was washed with brine (2 mL), dried (Na$_2$SO$_4$), filtered and concentrated under reduced pressure. The residue was purified on a 12 g SiO$_2$ cartridge using ethyl acetate/hexanes gradient to give (R)-2-{2-[6-butyl-5-(4-cyclohexyloxy-phenyl)-pyridazin-3-yloxy]-ethyl}-piperidine-1-carboxylic acid tert-butyl ester.

To a solution of the above tert-butyl ester in DCM (2 mL) was added 4 N HCl in dioxane (2 mL). The solution was stirred for 1 hour. The solvents were removed with reduced pressure and the salt was triturated with diethyl ether and filtered to give 3-butyl-4-(4-cyclohexyloxy-phenyl)-6-((R)-2-piperidin-2-yl-ethoxy)-pyridazine dihydrochloride.

To a solution of 3-butyl-4-(4-cyclohexyloxy-phenyl)-6-((R)-2-piperidin-2-yl-ethoxy)-pyridazine dihydrochloride (0.065 mmol, 0.033 g) and aqueous formaldehyde (37%, 0.323 mmol, 0.03 mL) in dry DCM (2 mL) was added macroporous resin-bound triacetoxyborohydride (loading 2.36 mmol/gram, 0.39 mmol, 0.165 g). The mixture was shaken for 12 hours. The reaction was filtered and the resin was washed with DCM (5 mL). The solvent was removed under reduced pressure. The crude product was purified on a 4 g SiO$_2$ cartridge with 4-6% (2N NH$_3$ in MeOH) in DCM to give 3-butyl-4-(4-cyclohexyloxy-phenyl)-6-[2-((R)-1-methyl-piperidin-2-yl)-ethoxy]-pyridazine (0.02 g, 73%). The neutral amine was treated with 2N HCl in diethyl ether (1 mL) and DCM (1 mL). The volatiles were removed under reduced pressure and the salt was triturated with diethyl ether and filtered to provide the title compound (0.025 g). LCMS: m/z 453 [M+1]. $^1$H NMR (400 MHz, CD$_3$OD) δ 6.97-7.45 (5H, m), 4.55-4.72 (2H, m), 4.35-4.46 (1H, m), 3.46-3.82 (1H, m), 3.05-3.19 (1H, m), 2.79-3.06 (5H, m), 2.44-2.74 (2H, m), 2.10-2.36 (2H, m), 1.74-2.06 (9H, m), 0.79 (3H, t).

Example 33

3-butyl-4-(4-cyclohexyloxy-phenyl)-6-[2-((S)-1-methyl-piperidin-2-yl)-ethoxy]-pyridazine dihydrochloride The title compound may be prepared using a procedure analogous to Example 32 and substituting (S)-2-(2-hydroxy-ethyl)piperidine-1-carboxylic acid tert-butyl ester for (R)-2-(2-hydroxy-ethyl)piperidine-1-carboxylic acid tert-butyl ester. LCMS: m/z 453 [M+1].

Example 34

2-[6-Butyl-5-(4-cyclohexyloxy-phenyl)-pyridazin-3-yloxymethyl]-4-methyl-morpholine dihydrochloride To a stirred solution of 2-hydroxymethyl-morpholine-4-carboxylic acid tert-butyl ester (0.58 mmol, 0.126 g) in DMF (1.0 mL) at room temperature was added sodium hydride (60% dispersion in mineral oil) (1.74 mmol, 0.07 g) and continued stirring for 15 min. The reaction mixture was cooled to 0° C. using an ice bath. To this was added a solution of 3-butyl-6-chloro-4-(4-cyclohexyloxy-phenyl)-pyridazine (Example 14, 0.29 mmol, 0.10 g) in DMF (0.5 mL). After completion of addition, the reaction mixture was warmed to 50° C. for 12 hour. The reaction was poured into a mixture of water (10 mL) and ethyl acetate (5 mL). The mixture was shaken and separated. The ethyl acetate layer was washed with brine (2 mL), dried ($Na_2SO_4$), filtered and concentrated under reduced pressure. The residue was purified on a 12 g $SiO_2$ cartridge using ethyl acetate/hexanes gradient to give 2-[6-butyl-5-(4-cyclohexyloxy-phenyl)-pyridazin-3-yloxymethyl]-morpholine-4-carboxylic acid tert-butyl ester.

To a solution of the tert-butyl ester in DCM (2 mL) was added 4 N HCl in dioxane (2 mL). The solution was stirred for 1 hour. The solvents were removed with reduced pressure and the salt was triturated with diethyl ether and filtered to give 2-[6-butyl-5-(4-cyclohexyloxy-phenyl)-pyridazin-3-yloxymethyl]-morpholine dihydrochloride.

To a solution of 2-[6-butyl-5-(4-cyclohexyloxy-phenyl)-pyridazin-3-yloxymethyl]-morpholine dihydrochloride (0.067 mmol, 0.031 g) and aqueous formaldehyde (37%, 0.304 mmol, 0.025 mL) in dry DCM (2 mL) was added macroporous resin-bound triacetoxyborohydride (loading 2.36 mmol/gram, 0.364 mmol, 0.154 g). The mixture was shaken for 12 hours. The reaction was filtered and the resin was washed with DCM (5 mL). The solvent was removed under reduced pressure. The crude product was purified on a 4 g $SiO_2$ cartridge with 4-6% (2N $NH_3$ in MeOH) in DCM to give 2-[6-butyl-5-(4-cyclohexyloxy-phenyl)-pyridazin-3-yloxymethyl]-4-methyl-morpholine. The neutral amine was treated with 2N HCl in diethyl ether (1 mL) and DCM (1 mL). The volatiles were removed under reduced pressure and the salt was triturated with diethyl ether and filtered to provide the title compound (0.022 g). LCMS: m/z 441 [M+1]. $^1$H NMR (400 MHz, $CD_3OD$) δ 7.35-7.46 (3H, m), 7.09 (2H, d), 4.56-4.68 (2H, m), 4.38-4.47 (1H, m), 4.13-4.29 (2H, m), 3.91 (1H, t), 3.68 (1H, d), 3.49 (1H, d), 3.12-3.26 (2H, m), 3.00-3.09 (2H, m), 2.97 (3H, s), 1.99-2.02 (2H, m), 1.80-1.82 (2H, m), 1.19-1.66 (10H, m), 0.81 (3H, t).

Example 35

(±)-cis-3-Butyl-4-(4-cyclohexyloxy-phenyl)-6-(3-methoxy-1-methyl-piperidin-4-ylmethoxy)-pyridazine dihydrochloride To a stirred suspension of 1-benzyl-3-oxo-piperidine-4-carboxylic acid ethyl ester hydrochloride salt (25 g) in EtOAc (500 mL) was added saturated sodium bicarbonate solution (200 mL) and continued stirring for 2 h. The organic layer was separated, dried over $Na_2SO_4$, filtered and concentrated to provide ethyl 1-benzyl-3-oxo-piperidine-4-carboxylic acid ethyl ester (22.00 g). To a solution of ethyl 1-benzyl-3-oxo-piperidine-4-carboxylic acid ethyl ester (22 g, 84.18 mmol) in EtOAc (75 mL) was added $(Boc)_2O$ (20.21 g, 92.59 mmol) followed by 10% Pd—C (2.4 g) and the resultant reaction mixture was subjected to hydrogenation at 50 psi of hydrogen for 14 h. The catalyst was filtered by passing through a pad of celite, washed the celite pad with EtOAc (200 mL) and the combined filtrate was concentrated. The residue was purified by flash silica gel column chromatography by eluting with 0.5% ethyl acetate in hexanes to provide ethyl 3-oxo-piperidine-1,4-dicarboxylic acid 1-tert-butyl ester 4-ethyl ester (34 g).

To a stirred solution of 3-Oxo-piperidine-1,4-dicarboxylic acid 1-tert-butyl ester 4-ethyl ester (10 g) in a mixture of THF (100 mL) and MeOH (50 mL) was added $NaBH_4$ in 10 lots over 1 h period. At the end of 1 h, TLC analysis (eluant: EtOAC) showed complete consumption of starting material. Removed solvent under reduced pressure, to the residue was added saturated $NH_4Cl$ solution (200 mL) and stirred for 1 h at rt. The aqueous layer was extracted with DCM (4×100 mL). The combined organic layer was dried over $Na_2SO_4$, filtered and concentrated the filtrate. The product was purified by silica gel column chromatography (Eluant 8:2 EtOAc/Hexanes) to give 3-hydroxy-4-hydroxymethyl-piperidine-1-carboxylic acid tert-butyl ester (6.6 g, cis/trans mixture). The cis/trans mixture (5 g) was separated on ISCO (Combiflash instrument) on a silica gel column (300 g) by eluting with ethyl acetate in hexanes to get (±)-trans-3-hydroxy-4-hydroxymethyl-piperidine-1-carboxylic acid tert-butyl ester (1.5 g, $HR_f$) and (±)-cis-3-hydroxy-4-hydroxymethyl-piperidine-1-carboxylic acid tert-butyl ester (3.0 g, $LR_f$).

To a stirred solution of (±)-cis-3-hydroxy-4-hydroxymethyl-piperidine-1-carboxylic acid tert-butyl ester (50.0 mmol, 11.6 g) in anhydrous DCM (500 mL) at room temperature was added triethylamine (100 mmol, 14.0 mL). The reaction mixture was cooled to 0° C. using an ice bath. To this was added acetic anhydride (50.0 mmol, 4.72 mL) dropwise over 10 minutes. After completion of addition, the reaction was stirred for 12 hours while slowly coming to room temperature. All volatiles were removed under reduced pressure. The residue was dissolved in ethyl acetate (250 mL) and washed with saturated $NaHCO_3$ (2×50 mL), water (50 mL) and brine (50 mL). The organic layer was dried ($Na_2SO_4$), filtered and concentrated under reduced pressure. The residue was purified on a 110 g $SiO_2$ cartridge using ethyl acetate/hexanes gradient to provide (±)-cis-4-acetoxymethyl-3-hydroxy-piperidine-1-carboxylic acid tert-butyl ester (12.3 g).

To a solution of (±)-cis-4-acetoxymethyl-3-hydroxy-piperidine-1-carboxylic acid tert-butyl ester (45.0 mmol, 12.3 g) in anhydrous DCM (100 mL) at room temperature was added N,N-diisopropylethyl amine (180 mmol, 31.4 mL). The reaction mixture was cooled to 0° C. using an ice bath. To this was added chloromethylmethyl ether (135 mmol, 11.4 mL) dropwise over 15 minutes. After completion of addition, the reaction was stirred for 12 hours while coming to room temperature. All volatiles were removed under reduced pressure. The residue was dissolved in ethyl acetate (250 mL) and washed with water (3×50 mL) and brine (50 mL). The organic layer was dried (Na$_2$SO$_4$), filtered and concentrated under reduced pressure. The residue was purified on 110 g SiO$_2$ cartridge using ethyl acetate/hexanes gradient to give (±)-cis-4-acetoxymethyl-3-methoxymethoxy-piperidine-1-carboxylic acid tert-butyl ester (13.3 g).

A solution of (±)-cis-4-acetoxymethyl-3-methoxymethoxy-piperidine-1-carboxylic acid tert-butyl ester (41.9 mmol, 13.3 g) in THF (100 mL), MeOH (25 mL), and 2 N NaOH (25 mL) was stirred for 3 hours at room temperature. The THF and MeOH were removed under reduced pressure. The crude product was extracted from the water layer with ethyl acetate (3×100 mL). The combined ethyl acetate layers were washed with brine, dried (Na$_2$SO$_4$), filtered and concentrated under reduced pressure. The residue was purified on a 110 g SiO$_2$ cartridge using ethyl acetate/hexanes gradient to give (±)-cis-4-hydroxymethyl-3-methoxymethoxy-piperidine-1-carboxylic acid tert-butyl ester (10.2 g).

To a stirred solution of (±)-cis-4-hydroxymethyl-3-methoxymethoxy-piperidine-1-carboxylic acid tert-butyl ester (4.64 mmol, 1.28 g) in DMF (5 mL) at room temperature was added sodium hydride (60% dispersion in mineral oil) (13.9 mmol, 0.56 g) and continued stirring for 15 min. The reaction mixture was cooled to 0° C. using an ice bath. To this was added a solution of 3-butyl-6-chloro-4-(4-cyclohexyloxyphenyl)-pyridazine (Example 14, 2.32 mmol, 0.80 g) in DMF (5 mL). After completion of addition, the reaction mixture was warmed to 50° C. for 2 hours. After cooling to room temperature, the reaction was poured into a mixture of water (100 mL) and ethyl acetate (100 mL). The mixture was shaken and separated. The ethyl acetate layer was washed with brine, dried (Na$_2$SO$_4$), filtered and concentrated under reduced pressure. The residue was purified on a 40 g SiO$_2$ cartridge using a gradient of ethyl acetate/hexanes to provide (±)-cis-4-[6-butyl-5-(4-cyclohexyloxy-phenyl)-pyridazin-3-yloxymethyl]-3-methoxymethoxy-piperidine-1-carboxylic acid tert-butyl ester (0.60 g, 44° A). LCMS: m/z 583.9 [M+1].

To a solution of (±)-cis-4-[6-butyl-5-(4-cyclohexyloxy-phenyl)-pyridazin-3-yloxymethyl]-3-methoxymethoxy-piperidine-1-carboxylic acid tert-butyl ester (1.03 mmol, 0.60 g) in DCM (5 mL) was added 4 N HCl in dioxane (5 mL). The solution was stirred for 2 hours. The solvents were removed with reduced pressure and the salt was triturated with diethyl ether and filtered to give (±)-cis-4-[6-butyl-5-(4-cyclohexyloxy-phenyl)-pyridazin-3-yloxymethyl]-piperidin-3-ol dihydrochloride (0.50 g).

To a solution of (±)-cis-4-[6-butyl-5-(4-cyclohexyloxy-phenyl)-pyridazin-3-yloxymethyl]-piperidin-3-ol dihydrochloride (1.14 mmol, 0.50 g) in DCM and saturated NaHCO$_3$ (1 M, 1:1, v/v), was added di-t-butyl carbonate (3.42 mmol, 0.75 g). The reaction was stirred for 1 hour at room temperature. The reaction was allowed to settle and the layers were separated. The organic layer was dried and the crude product was purified by flash chromatography to give (±)-cis-4-[6-butyl-5-(4-cyclohexyloxy-phenyl)-pyridazin-3-yloxymethyl]-3-hydroxy-piperidine-1-carboxylic acid tert-butyl ester (0.50 g).

To a stirred solution of (±)-cis-4-[6-butyl-5-(4-cyclohexyloxy-phenyl)-pyridazin-3-yloxymethyl]-3-hydroxy-piperidine-1-carboxylic acid tert-butyl ester (0.46 mmol, 0.25 g) in anhydrous DMF (1.5 mL) was added sodium hydride (60% dispersion in mineral oil) (0.92 mmol, 0.037 g) and continued stirring for 15 min. The reaction mixture was cooled to 0° C. using an ice bath. To this was added methyl iodide (0.57 mmol, 0.035 mL) and the reaction was stirred for 12 hours coming to room temperature. The reaction was poured into a mixture of water (5 mL) and ethyl acetate (5 mL). The mixture was shaken and separated. The ethyl acetate layer was washed with brine, dried (Na$_2$SO$_4$), filtered and concentrated under reduced pressure. The residue was purified on 24 g SiO$_2$ cartridge using a gradient of ethyl acetate/hexanes to give (±)-cis-4-[6-butyl-5-(4-cyclohexyloxy-phenyl)-pyridazin-3-yloxymethyl]-3-methoxy-piperidine-1-carboxylic acid tert-butyl ester (0.20 g).

To a solution of (±)-cis-4-[6-butyl-5-(4-cyclohexyloxy-phenyl)-pyridazin-3-yloxymethyl]-3-methoxy-piperidine-1-carboxylic acid tert-butyl ester (0.36 mmol, 0.20 g) in DCM (1 mL) was added 4 N HCl in dioxane (1 mL). The solution was stirred for 1 hour. The solvents were removed with reduced pressure and the salt was triturated with diethyl ether and filtered to give (±)-cis-3-butyl-4-(4-cyclohexyloxy-phenyl)-6-(3-methoxy-piperidin-4-ylmethoxy)-pyridazine dihydrochloride (0.17 g).

To a solution of (±)-3-butyl-4-(4-cyclohexyloxy-phenyl)-6-((cis-3,4)-3-methoxy-piperidin-4-ylmethoxy)-pyridazine dihydrochloride (0.057 mmol, 0.030 g) and aqueous formaldehyde (37%, 0.29 mmol, 0.025 mL) in dry DCM (1.5 mL) was added macroporous resin-bound triacetoxyborohydride (loading 2.36 mmol/gram, 0.34 mmol, 0.145 g). The mixture was shaken for 12 hours. The reaction was filtered and the resin was washed with DCM (5 mL). The solvent was removed under reduced pressure. The crude product was purified on a 4 g SiO$_2$ cartridge with 4-6% (2N NH$_3$ in MeOH) in DCM to give (±)-cis-3-butyl-4-(4-cyclohexyloxy-phenyl)-6-(3-methoxy-1-methyl-piperidin-4-ylmethoxy)-pyridazine. The neutral amine was treated with 2N HCl in diethyl ether (1 mL) and DCM (1 mL). The volatiles were removed under reduced pressure and the salt was triturated with diethyl ether and filtered to provide the title compound (0.020 g). LCMS: m/z 468 [M+1]. $^1$H NMR (400 MHz, CD$_3$OD) δ 7.34 (2H, d), 7.14 (1H, s), 7.06 (2H, d), 4.36-4.57 (3H, m), 3.77-3.90 (2H, m), 3.42-3.54 (4H, m), 3.04-3.18 (2H, m), 2.93-3.01 (2H, m), 2.90 (3H, s), 2.27-2.43 (1H, m), 1.88-2.06 (4H, m), 1.79-1.83 (2H, m), 1.18-1.66 (10H, m), 0.80 (3H, t).

Example 36

(±)-trans-3-Butyl-4-(4-cyclohexyloxy-phenyl)-6-(3-methoxy-1-methyl-piperidin-4-ylmethoxy)-pyridazine dihydrochloride The title compound may be prepared using a procedure analogous to Example 35 with the exception that (±)-trans-3-hydroxy-4-hydroxymethyl-piperidine-1-carboxylic acid tert-butyl ester is substituted for (±)-cis-3-hydroxy-4-hydroxymethyl-piperidine-1-carboxylic acid tert-butyl ester. LCMS: m/z 468 [M+1]. $^1$H NMR (400 MHz, CD$_3$OD) δ 7.33 (2H, d), 7.11 (1H, s), 7.05 (2H, d), 4.52-4.69 (2H, m), 4.35-4.46 (1H, m), 3.78-3.90 (1H, m), 3.19-3.62 (6H, m), 2.75-3.10 (7H, m), 1.76-2.35 (6H, m), 1.17-1.67 (10H, m), 0.80 (3H, t).

Example 37

{4-[6-Butyl-5-(4-cyclohexyloxy-phenyl)-pyridazin-3-yloxy]-cyclohexyl}-methyl-amine dihydrochloride A stirred solution of trans-(4-hydroxy-cyclohexyl)-carbamic acid tert-butyl ester (1.0 mmol) in anhydrous THF at 0° C. may be treated with sodium hydride (60% dispersion in mineral oil) (1.3 mmol). After stirring for 15 min the reaction mixture is allowed to come to room temperature. To the alkoxide solution is added 3-butyl-6-chloro-4-(4-cyclohexyloxy-phenyl)-pyridazine (0.74 mmol). After completion of the addition, the reaction mixture is warmed to 50° C. and is stirred 3 hours. The reaction is concentrated onto $SiO_2$, purification via flash chromatography may be used (20-50% ethyl acetate in hexanes) to provide trans-{4-[6-butyl-5-(4-cyclohexyloxy-phenyl)-pyridazin-3-yloxy]-cyclohexyl}-carbamic acid tert-butyl ester.

A solution of trans-{4-[6-butyl-5-(4-cyclohexyloxy-phenyl)-pyridazin-3-yloxy]-cyclohexyl}-carbamic acid tert-butyl ester (1 mmol) in anhydrous THF at 0° C. may be treated with LAH in THF (1 M, 2 mL). The reaction may be allowed to come to room temperature. The reaction may be quenched with water and extracted with ethyl acetate. The product may be isolated by flash chromatography using ethyl acetate/hexanes mixtures to give trans-N-{4-[6-butyl-5-(4-cyclohexyloxy-phenyl)-pyridazin-3-yloxy]-cyclohexyl}-formamide.

A solution of trans-N-{4-[6-butyl-5-(4-cyclohexyloxy-phenyl)-pyridazin-3-yloxy]-cyclohexyl}-formamide in anhydrous THF at 0° C. may be treated with borane-THF complex in THF (1 M, excess). The reaction may be allowed to come to room temperature and may be monitored by LCMS until the reaction is complete. The reaction may be quenched with MeOH and the solvents may be removed under reduced pressure. The crude product may be purified by flash chromatography using with 1-5% (2N $NH_3$ in MeOH) in DCM to give trans-{4-[6-butyl-5-(4-cyclohexyloxy-phenyl)-pyridazin-3-yloxy]-cyclohexyl}-methyl-amine. The neutral amine may be treated with 2N HCl in diethyl ether and DCM. The volatiles may be removed under reduced pressure and the salt may be triturated with diethyl ether and filtered to provide the title compound. LCMS: m/z 439 [M+1].

Example 38

{4-[6-Butyl-5-(4-cyclohexyloxy-phenyl)-pyridazin-3-yloxy]-1-methyl-piperidin-3-yl}-methanol dihydrochloride To a stirred suspension of ethyl 1-benzyl-4-oxo-piperidine-3-carboxylic acid ethyl ester hydrochloride salt (83.95 mmol, 25 g) in EtOAc (400 mL) was added saturated sodium bicarbonate solution (100 mL) and continued stirring for 1 h. The organic layer was separated, dried over, filtered and concentrated to get ethyl 1-benzyl-4-oxo-piperidine-3-carboxylic acid ethyl ester. To a solution of ethyl 1-benzyl-4-oxo-piperidine-3-carboxylic acid ethyl ester in EtOAc (100 mL) was added $(Boc)_2O$ (27.48 g) followed by 10% Pd—C (5 g) and the resultant reaction mixture was subjected to hydrogenation at 50 psi of hydrogen for 24 h. The catalyst was filtered by passing through a pad of celite, washed the celite pad with EtOAc (200 mL) and the combined filtrate was concentrated. The residue was purified by flash silica gel column chromatography by eluting with 10% ethyl acetate in hexanes to get ethyl 4-oxo-piperidine-1,3-dicarboxylic acid 1-tert-butyl ester 3-ethyl ester (24.2 g).

To a stirred solution of 4-oxo-piperidine-1,3-dicarboxylic acid 1-tert-butyl ester 3-ethyl ester (14 g) in MeOH (300 mL) was added $NaBH_4$ (12 g) in 12 lots over 1 h period. After completion of addition, the reaction mixture was stirred for 30 min. Removed solvent under reduced pressure, to the residue was added saturated $NH_4Cl$ solution (300 mL) and was extracted with EtOAc (300 mL). The organic layer was dried, filtered and concentrated under reduced pressure. The residue was purified by flash silica gel column chromatography by eluting with ethyl acetate to give 4-hydroxy-3-hydroxymethyl-piperidine-1-carboxylic acid tert-butyl ester (10.1 g, cis/trans mixture).

To a solution of the tert-butyl ester (5.2 mmol, 1.2 g) in 50 mL of DCM was added DIEA (16.8 mmol, 3.1 mL) and chloromethyl methyl ether (15.9 mmol, 1.2 mL). The mixture was stirred at room temperature overnight. The resulting mixture was washed with saturated $NaHCO_3$ solution, brine, dried, evaporated, the resulted residue was chromatographed with 9:1 hexane/EtOAc afforded 4-hydroxy-3-methoxymethoxymethyl-piperidine-1-carboxylic acid tert-butyl ester.

To a stirred solution of 4-hydroxy-3-methoxymethoxymethyl-piperidine-1-carboxylic acid tert-butyl ester (0.4 mmol, 0.111 g) in 3 mL of THF was added 60% NaH in mineral oil (2.0 mmol, 0.05 g) at room temperature. The mixture was stirred for 10 mins, then a solution of 3-butyl-6-chloro-4-(4-cyclohexyloxy-phenyl)-pyridazine (Example 14, 0.2 mmol, 0.07 g) in THF was added. The mixture was refluxed for 1 h, then, stirred at room temperature overnight. The mixture was quenched with water, extracted with ethyl acetate, the organic layer was washed with brine, dried ($Na_2SO_4$), filtered and concentrated under reduced pressure, the resulting residue was chromatographed using 10% ethyl acetate in hexane to provide 4-[6-butyl-5-(4-cyclohexyloxy-phenyl)-pyridazin-3-yloxy]-3-methoxymethoxymethyl-piperidine-1-carboxylic acid tert-butyl ester.

The above tert-butyl ester (0.077 mmol, 45 mg) was dissolved in 4.0 M HCl in dioxane (2 mL) and DCM (2 mL), stirred for 1 h at rt. Removed the solvent provide {4-[6-butyl-5-(4-cyclohexyloxy-phenyl)-pyridazin-3-yloxy]-piperidin-3-yl}-methanol dihydrochloride.

A suspension of {4-[6-butyl-5-(4-cyclohexyloxy-phenyl)-pyridazin-3-yloxy]-piperidin-3-yl}-methanol dihydrochloride (0.059 mmol, 30 mg), 37% paraformaldehyde (0.205 mmol, 16 mg), and 1 drop of acetic acid in 3 mL of DCM was stirred for 5 min then added sodium triacetoxyborohydride (0.205 mmol, 43 mg) and continued stirring for 0.5 h at room temperature. Quenched with water, solvent was evaporated, the residue was diluted with ethyl acetate, and then washed with saturated $NaHCO_3$ solution, brine. The organic layer was dried ($Na_2SO_4$), filtered and concentrated under reduced pressure. The resultant residue was purified by column chromatography using 5% methanolic solution of ammonia (2.0 M ammonia in methanol) in DCM to provide {4-[6-butyl-5-(4-cyclohexyloxy-phenyl)-pyridazin-3-yloxy]-1-methyl-piperidin-3-yl}-methanol.

The {4-[6-Butyl-5-(4-cyclohexyloxy-phenyl)-pyridazin-3-yloxy]-1-methyl-piperidin-3-yl}-methanol was dissolved in 4.0 M HCl in dioxane (2 mL) and evaporated the solvent, dried to provide the title compound (26 mg). LCMS: m/z 455 [M+1]. $^1$H NMR (400 MHz, $CD_3OD$) δ 7.32 (2H, d), 7.03 (2H, d), 6.99 (1H, s), 5.58 (1H, s), 4.44-4.38 (1H, m), 3.66-3.62 (1H, m), 3.58-3.49 (1H, m), 2.96-2.80 (4H, m), 2.63-2.20 (7H, m), 2.08-1.90 (3H, m), 1.88-1.78 (2H, m), 1.62-1.20 (11H, m), 0.79 (3H, t,).

Example 39

3-Butyl-4-(4-cyclohexyloxy-phenyl)-6-(4,4-difluoro-1-methyl-piperidin-3-ylmethoxy)-pyridazine dihydrochloride To a solution of 4-hydroxy-3-methoxymethoxymethyl-piperidine-1-carboxylic acid tert-butyl ester (Example 38, 9.1 mmol, 2.5 g) in 50 mL of DCM was added Dess-Martin reagent (10.8 mmol, 4.6 g). The mixture was stirred at room temperature for 2 h, then washed with saturated sodium bicarbonate solution, brine, dried, evaporated, the resulting residue was chromatographed with 9:1 hexane/EtOAc afforded 3-methoxymethoxymethyl-4-oxo-piperidine-1-carboxylic acid tert-butyl ester (2.2 g).

To a solution of 3-methoxymethoxymethyl-4-oxo-piperidine-1-carboxylic acid tert-butyl ester (3.7 mmol, 1.0 g) in 20 mL of DCM was added Deoxo-Fluor (5.43 mmol, 1.0 mL). The mixture was stirred at room temperature overnight. After removing the solvent, the residue was chromatographed with 9:1 hexane/EtOAc to afford 4,4-difluoro-3-methoxymethoxymethyl-piperidine-1-carboxylic acid tert-butyl ester (0.6 g).

A mixture of 4,4-difluoro-3-methoxymethoxymethyl-piperidine-1-carboxylic acid tert-butyl ester (2.0 mmol, 0.6 g) and 4M HCl in dioxane solution (2 mL) in 10 mL of DCM was stirred at room temperature for 2 h. Removal of the solvent afforded the crude (4,4-difluoro-piperidin-3-yl)-methanol hydrochloride salt (360 mg, 98%), which was used directly in the next step.

A mixture of (4,4-difluoro-piperidin-3-yl)-methanol chloride (2.6 mmol, 0.4 g), Boc anhydride (3.2 mmol, 0.7 g) in 6 mL of saturated sodium bicarbonate and 12 mL of DCM was stirred at room temperature for 2 h. The mixture was evaporated, diluted with DCM, washed with brine, dried, evaporated, and the resulting residue was chromatographed with 20:1 hexane/EtOAc afforded 4,4-difluoro-3-hydroxymethyl-piperidine-1-carboxylic acid tert-butyl ester (520 mg).

To a solution of 4,4-difluoro-3-hydroxymethyl-piperidine-1-carboxylic acid tert-butyl ester (0.8 mmol, 0.2 g) in 5 mL of THF was added 60% NaH (4.0 mmol, 96 mg). The mixture was stirred at room temperature for 10 min, then a solution of 3-butyl-6-chloro-4-(4-cyclohexyloxy-phenyl)-pyridazine (Example 14, 0.4 mmol, 0.14 g) was added. The mixture was refluxed for 1 h, quenched with water, extracted with EtOAc. The organic layer was washed with saturated sodium bicarbonate, brine, dried, evaporated, the resulting residue was chromatographed with 20:1 DCM/MeOH to afford 3-[6-butyl-5-(4-cyclohexyloxy-phenyl)-pyridazin-3-yloxymethyl]-4,4-difluoro-piperidine-1-carboxylic acid tert-butyl ester (150 mg).

A mixture of 3-[6-butyl-5-(4-cyclohexyloxy-phenyl)-pyridazin-3-yloxymethyl]-4,4-difluoro-piperidine-1-carboxylic acid tert-butyl ester (0.36 mmol, 0.2 g) and 4M HCl in dioxane solution (3 mL) in 10 mL of DCM was heated at 50° C. for 1 h. Removed the solvent afforded the crude 3-butyl-4-(4-cyclohexyloxy-phenyl)-6-(4,4-difluoro-piperidin-3-ylmethoxy)-pyridazine dihydrochloride as a yellowish solid.

A suspension of 3-butyl-4-(4-cyclohexyloxy-phenyl)-6-(4,4-difluoro-piperidin-3-ylmethoxy)-pyridazine dichloride (0.17 mmol, 90 mg), 37% paraformaldehyde (0.4 mmol, 32 mg), and 1 drop of acetic acid in 5 mL of DCM was stirred for 5 min then added sodium triacetoxyborohydride (0.4 mmol, 85 mg) and continued stirring for 0.5 h at room temperature. Quenched with water, solvent was evaporated; the residue was diluted with ethyl acetate, and then washed with saturated NaHCO$_3$ solution, brine. The organic layer was dried (Na$_2$SO$_4$), filtered and concentrated under reduced pressure. The resultant residue was purified by column chromatography using 5% methanolic solution of ammonia (2.0 M ammonia in methanol) in DCM to get 3-butyl-4-(4-cyclohexyloxy-phenyl)-6-(4,4-difluoro-1-methyl-piperidin-3-ylmethoxy)-pyridazine (52 mg).

3-Butyl-4-(4-cyclohexyloxy-phenyl)-6-(4,4-difluoro-1-methyl-piperidin-3-ylmethoxy)-pyridazine was dissolved in 4.0 M HCl in dioxane (2 mL) and evaporated the solvent to provide the title compound (59 mg). LCMS: m/z 475 [M+1].

$^1$H NMR (400 MHz, CD$_3$OD) δ 7.29 (2H, d), 7.04 (2H, d), 6.97 (1H, s), 4.80 (1H, dd), 4.48-4.36 (2H, m), 3.16-3.06 (1H, m), 2.92-2.86 (3H, m), 2.76-2.60 (1H, m), 2.48-2.32 (5H, m), 2.16-2.04 (2H, m), 2.02-1.98 (2H, m), 1.82-1.78 (2H, m), 1.62-1.20 (10H, m), 0.79 (3H, t).

Example 40

3-Butyl-4-(4-cyclohexyloxy-phenyl)-6-(1-methyl-piperidin-4-yloxy)-pyridazine 2-oxide hydrochloride To a solution of 4-[6-butyl-5-(4-cyclohexyloxy-phenyl)-pyridazin-3-yloxy]-piperidine-1-carboxylic acid tert-butyl ester (Example 14, 0.4 mmol, 204 mg) in DCM (2 mL) at 0° C. was added 3-chloroperbenzoic acid (0.6-0.64 mmol, 148 mg, 70-75%). It was stirred at 0° C. for 75 min. The reaction mixture was partitioned between ethyl acetate (20 mL) and saturated aq. sodium bicarbonate solution (20 mL). The ethyl acetate layer was separated and dried over sodium sulfate. Purification by column chromatography on silica gel using 20-40% of ethyl acetate in hexanes gave 4-[6-butyl-5-(4-cyclohexyloxy-phenyl)-1-oxy-pyridazin-3-yloxy]-piperidine-1-carboxylic acid tert-butyl ester as white solid (129 mg).

To a solution of 4-[6-butyl-5-(4-cyclohexyloxy-phenyl)-1-oxy-pyridazin-3-yloxy]-piperidine-1-carboxylic acid tert-butyl ester (0.231 mmol, 121.3 mg) in DCM (3 mL) was added 4 N HCl in dioxane (1 mL) and the reaction mixture was stirred for 45 min. The organic solvents were removed in vacuo and the residue was triturated with anhydrous diethyl ether and hexanes. The pink solid was dried overnight under high vacuum to give 3-butyl-4-(4-cyclohexyloxy-phenyl)-6-(piperidin-4-yloxy)-pyridazine 2-oxide hydrochloride (63.2 mg).

To a solution of 3-butyl-4-(4-cyclohexyloxy-phenyl)-6-(piperidin-4-yloxy)-pyridazine 2-oxide hydrochloride (0.162 mmol, 74.8 mg) in DCM (1.5 mL) was added formaldehyde solution in water (37%, 0.5 mmol, 0.372 mL), and 1 drop of acetic acid. It was stirred for 80 min. and sodium triacetoxyborohydride (0.65 mmol, 145 mg, 95%) was added. The reaction mixture was stirred at room temperature for 80 min. and partitioned between ethyl acetate (8 mL) and saturated aq. sodium bicarbonate solution (8 mL). The ethyl acetate layer was separated and dried over sodium sulfate. The organic solvent was removed in vacuo and the residue was dissolved in DCM and treated with 4 N HCl in dioxane. The organic solvents were removed in vacuo and the residue was triturated with anhydrous diethyl ether and hexanes. The off-white solid was dried overnight under high vacuum to provide the title compound (69.3 mg). LCMS: m/z 441 [M+1] $^1$H NMR (400 MHz, CD$_3$OD) δ 7.28-7.32 (2H, m), 7.05-7.07 (2H, m), 6.79 and 6.88 (1H, s), 5.15-5.34 (1H, m), 4.38-4.43 (1H, m), 3.23-3.65 (4H, m), 2.92 (3H, s), 2.80-2.84 (2H, m), 2.47-2.56 (1H, m), 2.38 (1H, d), 2.08-2.21 (1H, m), 1.89-2.05 (3H, m), 1.81 (2H, m), 1.21-1.66 (10H, m) 0.82 (3H, t).

Example 41

(±)-trans-3-Butyl-4-(4-cyclohexyloxy-phenyl)-6-(3-fluoro-1-methylpiperidin-4-yloxy)-pyridazine dihydrochloride To a stirred solution of benzyl 4-oxopiperidine-1-carboxylate (4.0 g, 17.2 mmol) in DMF (20 mL) was added TEA (9.0 mL) and TMSCl (4.0 mL, 32 mmol). The mixture was stirred overnight at 80° C., cooled, diluted with hexanes and washed with water. The organics were dried over sodium sulfate, filtered, concentrated, and purified by column chromatography using 10% EtOAc in hexanes to give 4-trimethylsilanyloxy-3,6-dihydro-2H-pyridine-1-carboxylic acid benzyl ester (5 g).

To a stirred solution of 4-trimethylsilanyloxy-3,6-dihydro-2H-pyridine-1-carboxylic acid benzyl ester (5 g, 16.4 mmol) in acetonitrile at 0° C. was added 1-(chloromethyl)-4-fluoro-1,4-diazoniabicyclo[2.2.2]octane ditetrafluoroborate (6.4 g, 18 mmol). The solution was stirred overnight at room temperature, concentrated, diluted with EtOAc and washed with water. The organics were dried over sodium sulfate, filtered, concentrated, and purified by column chromatography using 40-60% EtOAc in hexanes to give 3-fluoro-4-oxo-piperidine-1-carboxylic acid benzyl ester (3.1 g) To a stirred solution of 3-fluoro-4-oxo-piperidine-1-carboxylic acid benzyl ester (500 mg, 2 mmol) in ethanol (6 mL) was added sodium borohydride (100 mg, 2.6 mmol). After 0.5 hr, the mixture was concentrated, diluted with EtOAc and washed with water. The organics were dried over sodium sulfate, filtered, concentrated, and purified by column chromatography using 40-70% EtOAc in hexanes to give (±)-trans-3-fluoro-4-hydroxy-piperidine-1-carboxylic acid benzyl ester (120 mg).

To a stirred solution of (±)-trans-3-fluoro-4-hydroxy-piperidine-1-carboxylic acid benzyl ester (100 mg, 0.4 mmol) at 0° C. in THF (2 mL) was added potassium tert-butoxide (1.0 M in THF, 0.5 mmol, 0.5 mL). After 15 min 3-butyl-6-chloro-4-(4-cyclohexyloxy-phenyl)-pyridazine (120 mg, 0.34 mmol) in THF (2 mL) was added. The solution was stirred overnight at 40° C., diluted with EtOAc and washed with water. The organics were dried over sodium sulfate, filtered, concentrated, and purified by column chromatography using 20-40% EtOAc in hexanes to provide (±)-trans-4-[6-butyl-5-(4-cyclohexyloxy-phenyl)-pyridazin-3-yloxy]-3-fluoro-piperidine-1-carboxylic acid benzyl ester (65 mg).

A mixture of (±)-trans-4-[6-butyl-5-(4-cyclohexyloxy-phenyl)-pyridazin-3-yloxy]-3-fluoro-piperidine-1-carboxylic acid benzyl ester (65 mg, 0.12 mmol) and 10% palladium on carbon (10 mg) in MeOH (5 mL) was stirred under an atmosphere of $H_2$ for 1.5 hrs, filtered through celite and concentrated to provide (±)-trans-3-butyl-4-(4-cyclohexyloxy-phenyl)-6-(3-fluoro-piperidin-4-yloxy)-pyridazine (40 mg).

To a stirred solution of (±)-trans-3-butyl-4-(4-cyclohexyloxy-phenyl)-6-(3-fluoro-piperidin-4-yloxy)-pyridazine (20 mg, 0.047 mmol) in DCM (4 mL) was added 37% aqueous formaldehyde (0.1 mL, 1 mmol) and sodium triacetoxyborohydride (106 mg, 0.5 mmol). After 2 hrs the mixture was diluted with saturated aqueous $NaHCO_3$ and extracted with DCM. The organics were dried over sodium sulfate, filtered, concentrated, and purified by column chromatography using 2-5% methanolic solution of ammonia (2.0 M ammonia in methanol) in DCM to give (±)-trans-3-Butyl-4-(4-cyclohexyloxy-phenyl)-6-(3-fluoro-1-methyl-piperidin-4-yloxy)-pyridazine. The free base was dissolved in DCM, treated with 4.0 M HCl in dioxane and concentrated. The resultant salt was washed with ether and dried to provide the title compound (20 mg). LCMS: m/z 443 [M+1]. $^1$H NMR (400 MHz, $CD_3OD$) δ 7.93 (1H, s), 7.51 (2H, d), 7.14 (2H, d), 5.54-5.60 (1H, m), 5.29 (1H, d), 4.41-4.50 (1H, m), 3.64-3.94 (2H, m), 3.46-3.53 (2H, m), 3.14-3.21 (2H, m), 3.00 (3H, t), 2.40-2.50 (2H, m) 1.96-2.05 (2H, m), 1.77-1.86 (2H, m), 1.23-1.66 (10H, m), 0.82 (3H, t).

Example 42

(±)-cis-3-Butyl-4-(4-cyclohexyloxy-phenyl)-6-(3-fluoro-1-methylpiperidin-4-yloxy)-pyridazine dihydrochloride The title compound may be prepared using a procedure analogous to Example 41 and substituting (±)-cis-3-fluoro-4-hydroxy-piperidine-1-carboxylic acid benzyl ester for (±)-trans-3-fluoro-4-hydroxy-piperidine-1-carboxylic acid benzyl ester. LCMS: m/z 443 [M+1]. $^1$H NMR (400 MHz, $CD_3OD$) δ 8.02 and 7.92 (1H, s), 7.50 (2H, d), 7.13 (2H, d), 5.38-5.64 (2H, m), 4.40-4.50 (1H, m), 3.94-4.04 (1H, m), 3.63-3.79 (2H, m), 3.39-3.53 (1H, m), 3.14-3.22 (2H, m), 2.94-3.08 (3H, m), 2.37-2.54 (2H, m) 1.96-2.06 (2H, m), 1.76-1.86 (2H, m), 1.23-1.66 (10H, m), 0.82 (3H, t).

Example 43

(±)-cis-3-[6-Butyl-5-(4-cyclohexyloxy-phenyl)-pyridazin-3-yloxymethyl]-1-methyl-piperidin-4-ol dihydrochloride To a stirred mixture of 4-oxo-piperidine-1,3-dicarboxylic acid 1-tert-butylester 3-methyl ester (10 mmol, 2.71 g) and DIEA (1 mL) in DCM was added methoxymethyl chloride (1.3 mL) drop-wise and continued stirring for 16 h at room temperature. Volatiles were removed under reduced pressure, the resultant residue was taken up in ethyl acetate (50 mL), washed with water (25 mL), dried the organic layer, filtered and concentrated under reduced pressure. The resultant residue was purified by flash column chromatography using mixture of hexanes and ethyl acetate to provide 4-methoxymethoxy-5,6-dihydro-2H-pyridine-1,3-dicarboxylic acid 1-tert-butyl ester 3-methyl ester.

A stirred mixture of the above methyl ester (5.97 mmol, 1.8 g) and 10% palladium on carbon (0.4 g) in methanol (5 mL) was subjected to catalytic hydrogenation at 55 psi of hydrogen pressure for 16 h. Filtered off the catalyst through a pad of celite, washed the celite pad with methanol and the combined filtrate was concentrated. The resultant residue was purified by flash silica gel chromatography using 20% ethyl acetate in hexanes to provide (±)-cis-4-methoxymethoxy-piperidine-1,3-dicarboxylic acid 1-tert-butylester 3-methyl ester.

To a stirred solution of (±)-cis-4-methoxymethoxy-piperidine-1,3-dicarboxylic acid 1-tert-butylester 3-methyl ester (1.98 mmol, 0.5 g) in ether (5 mL) at 0° C. was added LAH powder (50 mg) in one lot and continued stirring at 0° C. for additional 20 min followed 10 min at room temperature. TLC analysis of an aliquot of the reaction mixture showed complete consumption of starting material. The reaction mixture was diluted with ether (5 mL), cooled to 0° C., added ethyl acetate drop-wise followed by saturated sodium sulfate. The organic layer was separated, dried, filtered and concentrated under reduced pressure. The residue was purified by silica gel flash column chromatography eluting with 50% ethyl acetate in hexanes to provide (±)-cis-3-hydroxymethyl-4-methoxymethoxy-piperidine-1-carboxylic acid tert-butyl ester (0.506 g, 93%) as an oil. To a stirred suspension of sodium hydride (4.16 mmol, 0.1 g) in THF (8 mL) at room temperature was added (±)-cis-3-hydroxymethyl-4-methoxymethoxy-piperidine-1-carboxylic acid tert-butyl ester (1.84 mmol, 0.506 g) followed 3-butyl-6-chloro-4-(4-cyclohexyloxy-phenyl)-pyridazine (Example 14, 1.74 mmol, 0.6 g). The resultant reaction mixture was kept stirring at 50-60° C. for 2 h. The reaction mixture was cooled to room temperature and excess NaH was decomposed by addition of methanol drop-wise. This was diluted with ethyl acetate (20 mL), washed with water (5 mL), separated the organic layer, dried, filtered and concentrated under reduced pressure. The resultant residue was purified by flash silica gel chromatography by eluting with 40% ethyl acetate in hexanes to afford (±)-cis-3-[6-butyl-5-(4-cyclohexyloxy-phenyl)-pyridazin-3-yloxymethyl]-4-methoxymethoxy-piperidine-1-carboxylic acid tert-butyl ester (0.93 g, 82% yield) as a light yellow oil.

To a stirred solution of (±)-cis-3-[6-butyl-5-(4-cyclohexyloxy-phenyl)-pyridazin-3-yloxymethyl]-4-methoxymethoxy-piperidine-1-carboxylic acid tert-butyl ester (1.59 mmol, 0.93 g) in a mixture of methanol (2 mL) and DCM (0.5 mL) was added 4 N HCl in dioxane (5 mL) at room temperature and continued stirring for 1 h. The progress of the reaction was monitored by LCMS analysis of an aliquot of the reaction mixture. The reaction mixture was concentrated under reduced pressure. The residue was dissolved in DCM (5 mL) and added 2 N sodium hydroxide solution (2 mL) followed by di-t-butyl dicarbonate (1 g) and the resultant reaction mixture was stirred at room temperature for 2 h. The organic layer was separated and the aqueous layer was extracted with DCM (5 mL). The combined organic layer was concentrated under reduced pressure and the residue was purified by silica gel flash column chromatography by eluting with 50% ethyl acetate in hexanes to afford (±)-cis-3-[6-butyl-5-(4-cyclohexyloxy-phenyl)-pyridazin-3-yloxymethyl]-4-hydroxy-piperidine-1-carboxylic acid tert-butyl ester.

To a stirred solution of (±)-cis-3-[6-butyl-5-(4-cyclohexyloxy-phenyl)-pyridazin-3-yloxymethyl]-4-hydroxy-piperidine-1-carboxylic acid tert-butyl ester (0.37 mmol, 0.2 g) in DCM (2 mL) was added 4 N HCl in dioxane (4 mL) and continued stirring for 1 h at room temperature. The volatiles were removed under reduced pressure; residue was dissolved in DCM, added hexanes to precipitate the desired HCl salt. Solvent was removed under reduced pressure and the solid was dried under high vacuum to provide (±)-cis-3-[6-butyl-5-(4-cyclohexyloxy-phenyl)-pyridazin-3-yloxymethyl]-piperidin-4-ol.

To a stirred solution of (±)-cis-3-[6-butyl-5-(4-cyclohexyloxy-phenyl)-pyridazin-3-yloxymethyl]-piperidin-4-ol (0.27 mmol, 0.14 g) in DCM (1 mL) was added formaldehyde solution (1 mL) followed by sodium triacetoxyborohydride (0.5 g) and continued stirring the reaction mixture for 2 h at room temperature. The reaction mixture was diluted with DCM, separated the organic layer, dried, filtered and concentrated under reduced pressure. The residue was purified by flash silica gel column chromatography by eluting with DCM (300 mL) followed 10% methanolic solution of ammonia (2 M solution of NH3 in methanol) in DCM to provide (±)-cis-3-[6-butyl-5-(4-cyclohexyloxy-phenyl)-pyridazin-3-yloxymethyl]-1-methyl-piperidin-4-ol which was converted to dihydrochloride salt by treating with 4 N HCl in dioxane. The volatiles were removed under educed pressure, salt was washed with anhydrous ether and solid was dried under high vacuum to provide the title compound (0.121 g). LCMS: m/z 455 [M+1]. $^1$H NMR (400 MHz, CD$_3$OD) δ 7.78 (1H, s), 7.46 (2H, d), 7.12 (2H, d), 4.6-4.73 (1H, m), 4.5-4.58 (2H, m), 4.19 (1H, bs), 3.11-3.53 (6H, m), 2.93 (3H, s), 2.58 (1H, m), 1.99-2.05 (3H, m), 1.8 (2H, m), 1.24-1.60 (11H, m), 0.82 (3H, t).

Example 44

(±)-cis-3-Butyl-4-(4-cyclohexyloxy-phenyl)-6-(4-methoxy-1-methyl-piperidin-3-ylmethoxy)-pyridazine dihydrochloride To a stirred solution of (±)-cis-3-[6-butyl-5-(4-cyclohexyloxy-phenyl)-pyridazin-3-yloxymethyl]-4-hydroxy-piperidine-1-carboxylic acid tert-butyl ester (0.296 mmol, 0.16 g; Example 43) in DMF (2 mL) at 0° C. was added sodium hydride (80 mg) followed by methyl iodide (0.2 mL) and continued stirring at 0° C. for 30 min. The reaction mixture was diluted with ethyl acetate (10 mL) and quenched excess NaH by drop-wise addition of methanol. This was washed with brine (10 mL), organic layer was dried, filtered and concentrated under reduced pressure. The residue was purified by flash silica gel column chromatography by eluating with 20% ethyl acetate in hexanes to afford (±)-cis-3-[6-butyl-5-(4-cyclohexyloxy-phenyl)-pyridazin-3-yloxymethyl]-4-methoxy-piperidine-1-carboxylic acid tert-butyl ester (0.145 g) as an oil.

Using the above tert-butyl ester, the title compound may be prepared using a procedure analogous to the last two steps of the procedure in Example 43 (0.098 g). LCMS: m/z 469 [M+1]. $^1$H NMR (400 MHz, CD$_3$OD) δ 7.81 (1H, s), 7.48 (d, 2H), 7.12 (2H, d), 4.61-4.65 (1H, m), 4.42-4.45 (2H, m), 3.78 (1H, bs) 3.12-3.72 (9H, m), 2.91 (3H, s), 2.67-2.72 (1H, m), 2.39 (1H, m), 1.80-2.02 (4H, m), 1.24-1.63 (11H, m), 0.84 (3H, s).

Example 45

3-Butyl-4-(4-cyclohexyloxy-phenyl)-6-(4-fluoro-1-methyl-piperidin-4-ylmethoxy)-pyridazine dihydrochloride To a stirred solution of 4-fluoro-piperidine-1,4-dicarboxylic acid 1-tert-butyl ester 4-ethyl ester (0.9 mmol, 0.25 g), in anhydrous THF (3 mL) under N$_2$ atmosphere, was added LiBH$_4$ (2.0 mmol, 1.0 mL, 2N solution in THF) dropwise and reaction was stirred at room temperature for 10 h. The reaction was quenched with slow addition of water (1 mL) and the product was extracted with ethyl acetate (2×5 mL), Organic layer was washed with water, (5 mL), brine (5 mL), dried (Na$_2$SO$_4$), filtered and concentrated under reduced pressure. The residue was purified on a SiO$_2$ cartridge with 30% ethyl acetate in hexanes to provide 4-fluoro-4-hydroxymethyl-piperidine-1-carboxylic acid tert-butyl ester (0.182 g).

To a stirred solution of 4-fluoro-4-hydroxymethyl-piperidine-1-carboxylic acid tert-butyl ester (0.5 mmol, 0.116.g) in THF (2 mL) at room temperature was added potassium tert-butoxide (0.5 mmol, 0.5 mL, 1M solution in THF) and continued stirring for 30 min. 3-Butyl-6-chloro-4-(4-cyclohexyloxy-phenyl)-pyridazine (Example 14, 0.5 mmol, 0.172 g) was taken THF (1 mL) and added to the reaction and stirred for 10 h at room temperature. The reaction was quenched with slow addition of water (2 mL) and the product was extracted with ethyl acetate (2×5 mL), Organic layer was washed with water (5 mL), brine (5 mL), dried (Na$_2$SO$_4$), filtered and concentrated under reduced pressure. The residue was purified on a SiO$_2$ cartridge with 30% ethyl acetate in hexanes to provide 4-[6-butyl-5-(4-cyclohexyloxy-phenyl)-pyridazin-3-yloxymethyl]-4-fluoro-piperidine-1-carboxylic acid tert-butyl ester (90 mg).

To a solution of 4-[6-butyl-5-(4-cyclohexyloxy-phenyl)-pyridazin-3-yloxymethyl]-4-fluoro-piperidine-1-carboxylic acid tert-butyl ester (0.15 mmol, 85 mg) in DCM (1 mL) was added 4 N HCl in dioxane (1.5 mL) and the reaction was stirred for 30 min. The volatiles were removed in vacuo and the residue was triturated with anhydrous ethyl ether (2×3 mL) and dried under high vacuum to provide 3-butyl-4-(4-cyclohexyloxy-phenyl)-6-(4-fluoro-piperidin-4-ylmethoxy)-pyridazine dihydrochloride (0.078 g).

To a solution of 3-butyl-4-(4-cyclohexyloxy-phenyl)-6-(4-fluoro-piperidin-4-ylmethoxy)-pyridazine dihydrochloride (0.058 mmol, 30 mg) in DCM (2 mL) was added formaldehyde solution in water (37%, 1 mL), and stirred for 5 min. Sodium triacetoxyborohydride (0.35 mmol, 75 mg) was added stirred at room temperature for 2 h. Reaction was diluted with DCM (5 mL), DCM layer was separated and washed with saturated NaHCO₃ solution, dried (Na₂SO₄), filtered and concentrated under reduced pressure. The residue was purified on a SiO₂ cartridge with 2% (NH₃ in MeOH, 2M) in DCM—6% (NH₃ in MeOH, 2M) in DCM gave 3-butyl-4-(4-cyclohexyloxy-phenyl)-6-(4-fluoro-1-methyl-piperidin-4-yl methoxy)-pyridazine, which was converted to the title compound by treating with 4 N HCl in dioxane (0.5 mL) in DCM (2 mL). The volatiles were removed under reduced pressure, salt was washed with anhydrous ether and solid was dried under high vacuum (24 mg). LCMS: m/z 457 [M+1]. $^1$H NMR (300 MHz, CD₃OD): δ 7.86 (1H, s), 7.45 (2H, d), 7.12 (2H, d), 4.68 (2H, d), 4.44-4.50 (1H, m), 3.50-3.62 (2H, m), 3.24-3.39 (2H, m), 3.13 (2H, t), 2.94 (3H, s), 1.74-2.50 (8H, m), 1.20-1.68 (10H, m), 0.82 (3H, t).

Example 46

(±)-trans-3-Butyl-4-(4-cyclohexyloxy-phenyl)-6-(4-methoxy-1-methyl-piperidin-3-ylmethoxy)-pyridazine dihydrochloride To a stirred mixture of (±)-cis-3-[6-butyl-5-(4-cyclohexyloxy-phenyl)-pyridazin-3-yloxymethyl]-4-hydroxy-piperidine-1-carboxylic acid tert-butyl ester (Example 43, 1.18 mmol, 0.64 g), PPh₃ (1.43 mmol, 0.375 g) and p-nitrobenzoic acid (1.5 mmol, 0.251 g) in anhydrous THF (15 mL) at −60° C. was added DIAD (1.43 mmol. 0.289 mL) over 10 min. The stirring was continued and let the reaction slowly attain room temperature over 3 h. The reaction mixture was diluted with ether (300 mL), washed with water (100 mL) followed by saturated sodium bicarbonate (100 mL). The organic layer was dried, filtered and concentrated under reduced pressure. The residue was purified by flash silica gel flash column chromatography by eluating with 20% ethyl acetate in hexanes to provide (±)-trans-3-[6-butyl-5-(4-cyclohexyloxy-phenyl)-pyridazin-3-yloxymethyl]-4-(4-nitro-benzoyloxy)-piperidine-1-carboxylic acid tert-butyl ester (0.63 g).

To a stirred solution of (±)-trans-3-[6-butyl-5-(4-cyclohexyloxy-phenyl)-pyridazin-3-yloxymethyl]-4-(4-nitro-benzoyloxy)-piperidine-1-carboxylic acid tert-butyl ester (0.914 mmol, 0.63 g) in a mixture of methanol (8 mL) and water (2 mL) was added sodium hydroxide (0.3 g) and continued stirring for 3 h at room temperature. The volatiles were removed under reduced pressure and the residue was dissolved in water (20 mL). This was extracted with ethyl acetate (3×15 mL), combined organic layer was dried, filtered and concentrated. The residue was purified by flash silica gel column chromatography by eluting with 20% ethyl acetate in hexanes to provide (±)-trans-3-[6-butyl-5-(4-cyclohexyloxy-phenyl)-pyridazin-3-yloxymethyl]-4-hydroxy-piperidine-1-carboxylic acid tert-butyl ester (0.395 g) as an white solid.

The title compound may be prepared from using a procedure analogous to Example 44 and substituting (±)-trans-3-[6-butyl-5-(4-cyclohexyloxy-phenyl)-pyridazin-3-yloxymethyl]-4-hydroxy-piperidine-1-carboxylic acid tert-butyl ester for (±)-cis-3-[6-butyl-5-(4-cyclohexyloxy-phenyl)-pyridazin-3-yloxymethyl]-4-hydroxy-piperidine-1-carboxylic acid tert-butyl ester. LCMS: m/z 469 [M+1]. $^1$H NMR (400 MHz, CD₃OD) δ 7.90 and 7.85 (1H, s), 7.48 (2H, d), 7.13 (2H, d), 4.67-4.74 (1H, m), 4.60 (1H, dd), 4.40-4.49 (1H, m), 3.74 (1H, d), 3.46-3.69 (2H, m), 3.4 (3H, s), 3.29-3.33 (1H, m), 3.08-3.24 (3H, m), 2.92 (3H, s), 2.53 (1H, d), 2.34-2.47 (1H, m), 1.99 (2H, bs), 1.76-1.87 (2H, m), 1.22-1.75 (11H, m), 0.82 (3H, t).

Example 47

(±)-trans-3-[6-Butyl-5-(4-cyclohexyloxy-phenyl)-pyridazin-3-yloxymethyl]-1-methyl-piperidin-4-ol dihydrochloride To a stirred solution of (±)-trans-3-[6-butyl-5-(4-cyclohexyloxy-phenyl)-pyridazin-3-yloxymethyl]-4-hydroxy-piperidine-1-carboxylic acid tert-butyl ester (0.157 mmol, 0.85 g; Example 46) in DCM (1 mL) was added 4 N HCl in dioxane (4 mL) and continued stirring for 30 min at room temperature. The volatiles were removed under reduced pressure. The residue was washed with anhydrous ether and the solid was dried under high vacuum to provide (±)-trans-3-[6-butyl-5-(4-cyclohexyloxy-phenyl)-pyridazin-3-yloxymethyl]-piperidin-4-ol.

To a stirred solution of (±)-trans-3-[6-butyl-5-(4-cyclohexyloxy-phenyl)-pyridazin-3-yloxymethyl]-piperidin-4-ol (0.117 mmol, 0.06 g) in DCM (1 mL) was added formaldehyde solution (1 mL) followed by sodium triacetoxyborohydride (0.3 g) and continued stirring the reaction mixture for 3 h at room temperature. The reaction mixture was diluted with DCM (10 mL), washed the organic layer with water, dried the organic layer, filtered and concentrated under reduced pressure. The residue was purified by flash silica gel column chromatography by eluting with DCM (200 mL) followed 10% methanolic solution of ammonia (2 M solution of NH₃ in methanol) in DCM to provide (±)-trans-3-[6-butyl-5-(4-cyclohexyloxy-phenyl)-pyridazin-3-yloxymethyl]-1-methyl-piperidin-4-ol which was treated with 4 N HCl in dioxane. The volatiles were removed under reduced pressure, and the salt was washed with anhydrous ether and dried under high vacuum to provide the title compound (0.058 g). LCMS: m/z 455 [M+1]. $^1$H NMR (400 MHz, CD₃OD) δ 7.81 (1H, s), 7.47 (2H, d), 7.13 (2H, d), 4.6-4.76 (2H, m), 4.42-4.48 (1H, m), 3.52-3.85 (3H, m), 3.12-3.22 (4H, m), 2.92 (3H, s), 2.21-2.36 (2H, m), 1.84-2.04 (4H, m), 1.23-1.64 (11H, m), 0.82 (3H, t).

Example 48

(±)-trans-3-butyl-4-(4-cyclohexyloxy-phenyl)-6-(4-difluoromethyl-1-methyl-piperidin-3-yloxy)-pyridazine dihydrochloride To a stirred solution of (±)-trans-4-hydroxymethyl-3-methoxymethoxy-piperidine-1-carboxylic acid tert-butyl ester (Example 36, 2.17 mmol, 0.75 g) in anhydrous DCM (5 mL) at room temperature was added 1,1,1-tris(acetyloxy)-1,1-dihydro-1,2-benziodoxol-3-(1H)-one (4.35 mmol, 1.85 g). The reaction was stirred for 1 hour. The reaction mixture was pre-absorbed on 6.5 g SiO₂ and purified on 40 g SiO₂ cartridge using a 20-40% ethyl acetate/hexanes gradient to give (±)-trans-4-formyl-3-methoxymethoxy-piperidine-1-carboxylic acid tert-butyl ester (0.69 g).

To a stirred solution of (±)-trans-4-formyl-3-methoxymethoxy-piperidine-1-carboxylic acid tert-butyl ester (2.52 mmol, 0.69 g) in anhydrous DCM (2 mL) cooled in an ice bath was added bis(2-methoxyethyl)aminosulfur trifluoride (9.21 mmol, 1.70 mL) dropwise. After completion of addition, the reaction was stirred for 12 hours while coming slowly to room temperature. The reaction mixture was cooled in an ice bath. The cooled reaction was quenched with water (3 mL) dropwise. The layers were separated and the organic layer was dried (Na₂SO₄), filtered and concentrated under reduced pressure. The residue was purified on a 24 g SiO₂ cartridge using a 20% ethyl acetate/hexanes to give (±)-trans- 4-difluoromethyl-3-methoxymethoxy-piperidine-1-carboxylic acid tert-butyl ester (0.45 g).

To a solution of (±)-trans-4-difluoromethyl-3-methoxymethoxy-piperidine-1-carboxylic acid tert-butyl ester (1.52 mmol, 0.45 g) in DCM (2 mL) was added 4 N HCl in dioxane (3 mL). The solution was stirred for 1 hour. The solvents were removed with reduced pressure. The crude amine hydrochloride was dissolved in DCM (3 mL), and saturated NaHCO$_3$ (3 mL). To this suspension was added di-tert-butyl carbonate (4.12 mmol, 0.90 g) and the reaction was stirred for 30 minutes at room temperature. The layers were separated and the DCM layer was dried (Na$_2$SO$_4$), filtered and concentrated under reduced pressure. The crude product was purified on a 12 g SiO$_2$ cartridge using a 0-30% ethyl acetate/hexanes gradient to give (±)-trans-4-difluoromethyl-3-hydroxy-piperidine-1-carboxylic acid tert-butyl ester (0.14 g).

To a stirred solution of (±)-trans-4-difluoromethyl-3-hydroxy-piperidine-1-carboxylic acid tert-butyl ester (0.52 mmol, 0.13 g) in anhydrous THF (1 mL) at room temperature was added sodium hydride (60% dispersion in mineral oil) (1.08 mmol, 0.043 g) and continued stirring for 10 min. The reaction mixture was cooled to 0° C. using an ice bath. To this was added a solution of 3-butyl-6-chloro-4-(4-cyclohexyloxy-phenyl)-pyridazine (Example 14, 0.43 mmol, 0.15 g) in anhydrous THF (1 mL). After completion of addition, the reaction mixture was warmed to room temperature and stirred for 12 hours. The reaction was quenched with water (2 mL). The reaction was then extracted with ethyl acetate (5 mL). The ethyl acetate layer was dried (Na$_2$SO$_4$), filtered and concentrated under reduced pressure. The residue was purified on a 12 g SiO$_2$ cartridge using a gradient of ethyl acetate/hexanes to give (±)-trans-3-[6-butyl-5-(4-cyclohexyloxy-phenyl)-pyridazin-3-yloxy]-4-difluoromethyl-piperidine-1-carboxylic acid tert-butyl ester (0.18 g). LCMS: m/z 561 [M+1].

To a solution of (±)-trans-3-[6-butyl-5-(4-cyclohexyloxy-phenyl)-pyridazin-3-yloxy]-4-difluoromethyl-piperidine-1-carboxylic acid tert-butyl ester (0.32 mmol, 0.18 g) in DCM (0.75 mL) was added 4 N HCl in dioxane (0.75 mL). The solution was stirred for 1 hour. The solvents were removed with reduced pressure and the salt was triturated with diethyl ether and filtered to give (±)-trans-3-butyl-4-(4-cyclohexyloxy-phenyl)-6-(4-difluoromethyl-piperidin-3-yloxy)-pyridazine dihydrochloride (0.14 g).

To a solution of (±)-trans-3-butyl-4-(4-cyclohexyloxy-phenyl)-6-(4-difluoromethyl-piperidin-3-yloxy)-pyridazine dihydrochloride (0.18 mmol, 0.095 g) and aqueous formaldehyde (37%, 0.89 mmol, 0.075 mL) in dry DCM (2.0 mL) was added macroporous resin-bound triacetoxyborohydride (loading 2.36 mmol/gram, 1.07 mmol, 0.45 g). The mixture was shaken for 4 hours. The reaction was filtered and the resin was washed with DCM (10 mL). The solvent was removed under reduced pressure. The crude product was purified on a 4 g SiO$_2$ cartridge with 4-6% (2N NH$_3$ in MeOH) in DCM to give (±)-3-butyl-4-(4-cyclohexyloxy-phenyl)-6-((trans-3,4)-4-difluoromethyl-1-methyl-piperidin-3-yloxy)-pyridazine. The neutral amine was treated with 2N HCl in diethyl ether (0.5 mL) and DCM (0.5 mL). The volatiles were removed under reduced pressure and the salt was triturated with diethyl ether and filtered to provide the title compound (0.05 g). LCMS: m/z 475 [M+1]. $^1$H NMR (400 MHz, CD$_3$OD) δ 7.30-7.58 (3H, m), 7.08 (2H, d), 6.02-6.42 (1H, m), 5.54-5.94 (1H, m), 4.36-4.50 (1H, m), 3.83-4.19 (1H, m), 3.45-3.78 (1H, m), 2.89-3.35 (6H, m), 2.11-2.87 (3H, m), 1.92-2.08 (3H, m), 1.74-1.89 (2H, m), 1.18-1.67 (10H, m), 0.81 (3H, t).

Example 49

3-Butyl-4-(4-isopropoxy-phenyl)-6-(1-methyl-piperidin-4-yloxy)-pyridazine dihydrochloride To a solution of 4-[3-butyl-6-(1-methyl-piperidin-4-yloxy)-pyridazin-4-yl]-phenol (Example 19, 0.2 mmol, 69 mg) in dry THF (0.5 mL) was added 2-propanol (0.6 mmol, 46 μL) and triphenylphosphine (0.6 mmol, 158 mg). While sonicating, diisopropyl azodicarboxylate (0.6 mmol, 118 μL) was added, and the mixture was sonicated for another 1 hour then condensed. The residue was purified by silica gel chromatography (DCM to DCM+10% MeOH) to a colorless sticky solid, which was dissolved in DCM (1.0 mL), 2N HCl in ether (1.0 mL) was added, condensed, triturated with hexanes to provide the title compound (58 mg). LCMS: m/z 385 [M+1]. $^1$H NMR (400 MHz, CD$_3$OD): δ 7.82 and 7.93 (1H, s), 7.45-7.52 (2H, m), 7.12-7.18 (2H, m), 5.37-5.55 (1H, m), 4.72-4.79 (1H, m), 3.38-3.71 (4H, m), 3.15-3.19 (2H, m), 2.93 (3H, s), 2.08-2.59 (4H, m), 1.46-1.55 (2H, m), 1.35 (6H, d), 1.26-1.34 (2H, m), 0.83 (3H, t).

Example 50

3-butyl-4-[4-(4-chloro-benzyloxy)-phenyl]-6-(1-methyl-piperidin-4-yloxy)-pyridazine dihydrochloride To a solution of 4-[3-butyl-6-(1-methyl-piperidin-4-yloxy)-pyridazin-4-yl]-phenol (Example 19, 0.2 mmol, 69 mg) in dry DMF (1 mL) was added 4-chlorobenzyl bromide (0.4 mmol, 83 mg), and potassium carbonate (0.4 mmol, 56 mg). And the mixture was stirred at 80° C. over night. It was then diluted with water/EtOAc. The organic layers were combined, dried, and condensed in vacuo and the residue was purified by silica gel chromatography (DCM to DCM+10% MeOH) to give a colorless sticky solid, which was dissolved in DCM (1.0 mL), 1N HCl in ether (1.0 mL) was added, kept at room temperature for 10 min, condensed, triturated with hexanes to provide the title compound (69 mg). LCMS: m/z 467 [M+1]. $^1$H NMR (400 MHz, CD$_3$OD): δ 7.44-7.47 (2H, m), 7.38-7.41 (2H, m), 7.32-7.35 (2H, m), 7.12-7.15 (2H, m), 7.02 (1H, s), 5.47-5.53 (1H, m), 5.16 (2H, s), 3.30-3.49 (4H, m), 2.91 (3H, s), 2.89-2.94 (2H, m), 2.22-2.37 (4H, m), 1.44-1.52 (2H, m), 1.18-1.26 (2H, m), 0.79 (3H, t).

Example 51

3-butyl-4-(4-cyclopentyloxy-phenyl)-6-(1-methyl-piperidin-4-yloxy)-pyridazine dihydrochloride The title compound may be prepared using a procedure analogous to Example 49 and substituting cyclopentanol for isopropanol. LCMS: m/z 411 [M+1]. $^1$H NMR (400 MHz, CD$_3$OD): δ 7.62 and 7.75 (1H, s), 7.42-7.48 (2H, m), 7.10-7.15 (2H, m), 5.38-5.55 (1H, m), 4.42-4.48 (1H, m), 3.37-3.68 (4H, m), 3.12-3.17 (2H, m), 2.94 (3H, s), 1.98-2.58 (8H, m), 1.34-1.63 (6H, m), 1.23-1.30 (2H, m), 0.82 (3H, t).

Example 52

3-butyl-4-[4-(2-cyclohexyl-ethoxy)-phenyl]-6-(1-methyl-piperidin-4-yloxy)-pyridazine dihydrochloride The title compound may be prepared using a procedure analogous to Example 50 and substituting 1-bromo-2-cyclohexylethane for 4-chlorobenzyl bromide. LCMS: m/z 453 [M+1]. $^1$H NMR (400 MHz, CD$_3$OD): δ 7.58 (1H, s), 7.40-7.45 (2H, m), 7.08-7.12 (2H, m), 5.36-5.56 (1H, m), 4.08-4.12 (2H, m), 3.28-3.68 (4H, m), 3.03-3.09 (2H, m), 2.93 (3H, s), 2.00-2.58 (4H, m), 1.64-1.83 (7H, m), 1.46-1.58 (3H, m), 1.19-1.33 (5H, m), 0.97-1.07 (2H, m), 0.82 (3H, t).

Example 53

3-butyl-6-(1-methyl-piperidin-4-yloxy)-4-[4-(pyridazin-3-ylmethoxy)-phenyl]-pyridazine trihydrochloride To a solution of 4-[3-butyl-6-(1-methyl-piperidin-4-yloxy)-pyridazin-4-yl]-phenol (Example 19) (0.2 mmol, 69 mg) in dry DMF (1 mL) was added 3-bromomethyl-pyridazine (0.4 mmol, 70 mg), and potassium carbonate (0.4 mmol, 56 mg). And the mixture was stirred at 80° C. over night. It was then diluted with water/EtOAc. The organic layers were combined, dried, and condensed in vacuo and the residue was purified by silica gel chromatography (DCM to DCM+10% MeOH) to give a colorless sticky solid, which was dissolved in DCM (1.0 mL), 1N HCl in ether (1.0 mL) was added, kept at room temperature for 10 min, condensed, triturated with hexanes to provide the title compound (77 mg). LCMS: m/z 435 [M+1]. $^1$H NMR (400 MHz, CD$_3$OD): δ 7.81 and 7.88 (1H, s), 7.46-7.51 (2H, m), 7.30-7.41 (3H, m), 7.20-7.25 (2H, m), 5.37-5.53 (1H, m), 5.20 (2H, s), 3.30-3.53 (4H, m), 3.12-3.17 (2H, m), 2.93 (3H, s), 2.08-2.58 (4H, m), 1.44-1.53 (2H, m), 1.24-1.34 (2H, m), 0.81 (3H, t).

Example 54

3-butyl-6-(1-methyl-piperidin-4-yloxy)-4-[4-(tetrahydro-pyran-4-ylmethoxy)-phenyl]-pyridazine dihydrochloride The title compound may be prepared using a procedure analogous to Example 53 and substituting 4-bromomethyltetrahydropyran for 3-bromomethyl-pyridazine. LCMS: m/z 441 [M+1]. $^1$H NMR (400 MHz, CD$_3$OD): δ 7.74-7.76 (1H, m), 7.66-7.71 (2H, m), 7.57-7.63 (1H, m), 7.44 (1H, s), 5.30-5.50 (1H, m), 4.35 (2H, d), 3.77-3.80 (2H, m), 3.55-3.59 (2H, m), 3.02-3.09 (2H, m), 2.91-2.93 (2H, m), 2.88 (3H, s), 2.67-2.72 (2H, m), 2.10-2.34 (5H, m), 1.52-1.75 (6H, m), 1.39-1.49 (2H, m), 1.03 (3H, t).

Example 55

1-(4-{4-[3-butyl-6-(1-methyl-piperidin-4-yloxy)-pyridazin-4-yl]-phenoxymethyl}-piperidin-1-yl)-ethanone dihydrochloride The compound 3-butyl-6-(1-methyl-piperidin-4-yloxy)-4-[4-(piperidin-4-ylmethoxy)-phenyl]-pyridazine dihydrochloride may be prepared using a procedure analogous to Example 53 and substituting 1-boc-4-bromomethyl piperidine for 3-bromomethyl-pyridazine.
To a solution of 3-butyl-6-(1-methyl-piperidin-4-yloxy)-4-[4-(piperidin-4-ylmethoxy)-phenyl]-pyridazine dihydrochloride (0.2 mmol, 103 mg) in DCM (1 mL) at 0° C. was added acetyl chloride (0.4 mmol, 29 μL), DIEA (0.4 mmol, 70 μL) and DMAP (5 mg). The mixture was stirred at room temperature for 1 hour. The mixture was then condensed in vacuo and the residue was purified by silica gel chromatography (DCM to DCM+10% 2N NH$_3$ in MeOH) to give a colorless sticky solid, which was dissolved in DCM (1.0 mL), 2N HCl in ether (1.0 mL) was added, kept at room temperature for 10 min, condensed, triturated with hexanes to provide the title compound. LCMS: m/z 482 [M+1]. $^1$H NMR (400 MHz, CD$_3$OD): δ 7.63 and 7.75 (1H, s), 7.44-7.50 (2H, m), 7.12-7.17 (2H, m), 5.37-5.54 (1H, m), 4.37 (2H, d), 3.36-3.69 (3H, m), 3.08-3.30 (4H, m), 2.92 (3H, s), 2.11-2.74 (5H, m), 2.10 (3H, s), 1.86-2.08 (4H, m), 1.25-1.54 (7H, m), 0.82 (3H, t).

Example 56

4-{4-[3-butyl-6-(1-methyl-piperidin-4-yloxy)-pyridazin-4-yl]-phenoxymethyl}-cyclohexanecarboxylic acid dimethylamide dihydrochloride The compound 4-{4-[3-butyl-6-(1-methyl-piperidin-4-yloxy)-pyridazin-4-yl]-phenoxymethyl}-cyclohexanecarboxylic acid may be prepared using a procedure analogous to Example 53 and substituting 4-bromomethyl-cyclohexanecarboxylic acid methyl ester for 3-bromomethyl-pyridazine.
To a solution of 4-{4-[3-butyl-6-(1-methyl-piperidin-4-yloxy)-pyridazin-4-yl]-phenoxymethyl}-cyclohexanecarboxylic acid (0.2 mmol, 97 mg) in DMF (1 mL) was added dimethylamine hydrochloride (0.3 mmol, 25 mg), HBTU (0.4 mmol, 152 mg), DIEA (0.4 mmol, 70 μL). The mixture was stirred at 100° C. for 2 hours. The mixture was then diluted with water/EtOAc and neutralized with acetic acid. The organic layers were combined, dried, and condensed in vacuo and the residue was purified by silica gel chromatography (DCM to DCM+10% in MeOH) to give a colorless sticky solid, which was dissolved in DCM (1 mL), 2N HCl in ether (1 mL) was added, kept at room temperature for 10 min, condensed, triturated with hexanes to provide the title compound (89 mg). LCMS: m/z 510 [M+1]. 1H NMR (400 MHz, CD$_3$OD): δ 7.64 and 7.76 (1H, s), 7.45-7.51 (2H, m), 7.13-7.17 (2H, m), 5.37-5.54 (1H, m), 4.30 (2H, d), 3.35-3.69 (3H, m), 3.08-3.30 (4H, m), 2.94 (3H, s), 2.81 (6H, s), 2.21-2.74 (5H, m), 1.86-2.98 (2H, m), 1.25-1.54 (10H, m), 0.82 (3H, t).

Example 57

3-butyl-6-(1-methyl-piperidin-4-yloxy)-4-[4-(6-methyl-pyridazin-3-yloxy)-phenyl]-pyridazine trihydrochloride The title compound may be prepared using a procedure analogous to Example 53 and substituting 3-chloro-6-methyl-pyridazine for 3-bromomethyl-pyridazine and cesium carbonate for potassium carbonate.
LCMS: m/z 435 [M+1]. $^1$H NMR (400 MHz, CD$_3$OD): δ 7.82 and 7.89 (1H, s), 7.45-7.51 (2H, m), 7.35-7.41 (2H, m), 7.29-7.34 (1H, m), 7.19-7.25 (1H, m), 5.37-5.53 (1H, m), 3.30-3.53 (4H, m), 3.12-3.17 (2H, m), 2.93 (3H, s), 2.23-2.58 (4H, m), 2.10 (3H, s), 1.44-1.53 (2H, m), 1.24-1.34 (2H, m), 0.82 (3H, t).

Example 58

3-butyl-4-(4-cyclohexyloxy-phenyl)-6-(1-methyl-piperidin-4-yloxy)-5-trifluoromethyl-pyridazine dihydrochloride To a stirred solution of 1-(4-cyclohexyloxy-phenyl)-hexan-2-one (Example 14, 4.46 mmol, 1.22 g) and triethylamine (4.46 mmol, 0.62 mL) in THF (5 mL) was added a solution of 3,3,3-trifluoro-2-oxo-propionic acid methyl ester (13.4 mmol, 2.09 g) and continued stirring for 12 h at room temperature. After removal of volatiles in vacuo, the crude product was purified on a 40 g $SiO_2$ cartridge with ethyl acetate/hexanes gradient to afford 3-(4-cyclohexyloxy-phenyl)-4-oxo-2-trifluoromethyl-oct-2-enoic acid methyl ester (1.4 g).

To a stirred solution of 3-(4-cyclohexyloxy-phenyl)-4-oxo-2-trifluoromethyl-oct-2-enoic acid methyl ester (3.40 mmol, 1.4 g) in glacial acetic acid (3 mL) was added hydrazine hydrate (61.7 mmol, 3 mL) and the reaction was heated at 100° C. for 12 h. After cooling, the volatiles were under reduced pressure to give 1.6 g of crude 6-butyl-5-(4-cyclohexyloxy-phenyl)-4-trifluoromethyl-2H-pyridazin-3-one. The ketone was treated with phosphorous oxychloride (21.8 mmol, 2.0 mL) and heated at 90° C. for 1 hour with stirring. The reaction mixture was cooled to room temperature and the volatiles were removed under reduced pressure. The residue was dissolved in ethyl acetate (30 mL) and shaken with water (30 mL). The layers were separated and the organic layer was washed with saturated $NaHCO_3$ (2×30 mL), brine (30 mL), dried ($Na_2SO_4$) filtered and concentrated under reduced pressure. The residue was purified on a 40 g $SiO_2$ cartridge eluting with ethyl acetate/hexanes gradient to afford 3-butyl-6-chloro-4-(4-cyclohexyloxy-phenyl)-5-trifluoromethyl-pyridazine (0.65 g).

To a stirred solution of 4-hydroxy-piperidine-1-carboxylic acid tert-butyl ester (1.45 mmol, 0.29 g) in anhydrous DMF (1 mL) at room temperature was added sodium hydride (60% dispersion in mineral oil) (4.36 mmol, 0.175 g) and continued stirring for 10 min. To this was added a solution of 3-butyl-6-chloro-4-(4-cyclohexyloxy-phenyl)-5-trifluoromethyl-pyridazine (72.5 mmol, 25.0 g) in anhydrous DMF (1 mL). After 30 minutes, no starting material was remaining as indicated by LCMS. The reaction was quenched with water (20 mL) and extracted with ethyl acetate (2×20 mL). The combined organic layer was washed with brine (10 mL), dried ($Na_2SO_4$), filtered and concentrated under reduced pressure. The residue was purified on 24 g $SiO_2$ cartridge using an ethyl acetate/hexanes gradient to give 4-[6-butyl-5-(4-cyclohexyloxy-phenyl)-4-trifluoromethyl-pyridazin-3-yloxy]-piperidine-1-carboxylic acid tert-butyl ester (0.17 g).

To a solution of 4-[6-butyl-5-(4-cyclohexyloxy-phenyl)-4-trifluoromethyl-pyridazin-3-yloxy]-piperidine-1-carboxylic acid tert-butyl ester (0.294 mmol, 0.17 g) in DCM (1 mL) was added 4 N HCl in dioxane (0.5 mL) and the reaction was stirred for 1 hour. The solvents were removed with reduced pressure and the salt was triturated with diethyl ether and filtered to give 3-butyl-4-(4-cyclohexyloxy-phenyl)-6-(piperidin-4-yloxy)-5-trifluoromethyl-pyridazine dihydrochloride (0.12 g).

To a solution of 3-butyl-4-(4-cyclohexyloxy-phenyl)-6-(piperidin-4-yloxy)-5-trifluoromethyl-pyridazine dihydrochloride (0.14 mmol, 0.075 g) and aqueous formaldehyde (37%, 0.68 mmol, 0.070 mL) in dry DCM (1.2 mL) was added macroporous resin-bound triacetoxyborohydride (loading 2.36 mmol/gram, 0.82 mmol, 0.35 g). The mixture was shaken for 12 hours. The reaction was filtered and the resin was washed with DCM (10 mL). The solvent was removed under reduced pressure. The crude product was purified on a 4 g $SiO_2$ cartridge with 4-6% (2N $NH_3$ in MeOH) in DCM to give 3-butyl-4-(4-cyclohexyloxy-phenyl)-6-(1-methyl-piperidin-4-yloxy)-5-trifluoromethyl-pyridazine. The neutral amine was treated with 2N HCl in diethyl ether (0.5 mL) and DCM (0.5 mL). The volatiles were removed under reduced pressure and the salt was triturated with diethyl ether and filtered to provide the title compound (0.05 g). LCMS: m/z 493 [M+1]; $^1$H NMR (400 MHz, $CD_3OD$) δ 7.10-7.19 (2H, m), 7.00-7.09 (2H, d), 5.54-5.82 (1H, m), 4.38-4.43 (1H, m), 3.66 (1 h, d), 3.54 (1H, d), 3.10-3.35 (2H, m), 2.89-2.98 (3H, m), 2.64-2.73 (2H, m), 2.58 (1H, d), 2.46 (1H, d), 2.27 (1H, t), 1.96-2.13 (3H, m), 1.78-1.83 (2H, m), 1.14-1.66 (10H, m), 0.77 (3H, t).

Example 59

4-(4-cyclohexyloxy-phenyl)-3-cyclopropyl-6-(1-methyl-piperidin-4-yloxy)-pyridazine dihydrochloride To a stirred solution of 2-(4-cyclohexyloxy-phenyl)-N-methoxy-N-methyl-acetamide (Example 14, 1.31 mmol, 0.36 g) in anhydrous THF (1 mL) at −78° C. was added cyclopropylmagnesium bromide (2 M in diethyl ether, 2.62 mmol, 5.25 mL) dropwise over 5 minutes. The reaction was stirred for 30 minutes at −78° C. The dry ice/acetone bath was replaced with an ice bath and the reaction was stirred for an additional 30 min. The reaction mixture was quenched by addition of saturated ammonium chloride (5 mL) and extracted with ethyl acetate (2×10 mL). The combined ethyl acetate layers were washed with brine (5 mL), dried ($Na_2SO_4$), filtered and concentrated under reduced pressure. The residue was purified on a 12 g $SiO_2$ column with 6-8% ethyl acetate in hexanes to give 2-(4-cyclohexyloxy-phenyl)-1-cyclopropyl-ethanone (0.24 g).

To a stirred solution of 2-(4-cyclohexyloxy-phenyl)-1-cyclopropyl-ethanone (0.86 mmol, 0.22 g) and triethylamine (0.86 mmol, 0.12 mL) in THF (0.5 mL) was added a solution of ethyl glyoxylate (50% in toluene, 4.30 mmol, 0.85 mL) and continued stirring for 12 h during which period the starting material was fully consumed as judged by TLC. After removal of volatiles under reduced pressure, the crude product, 3-(4-cyclohexyloxy-phenyl)-4-cyclopropyl-2-hydroxy-4-oxo-butyric acid ethyl ester (0.83 g), was used in the next step without further purification.

To a stirred solution of 3-(4-cyclohexyloxy-phenyl)-4-cyclopropyl-2-hydroxy-4-oxo-butyric acid ethyl ester (0.86 mmol, 0.31 g) in glacial acetic acid (0.21 mL) was added hydrazine hydrate (4.3 mmol, 0.21 mL) and the reaction was heated at 90° C. for 12h. After cooling, the volatiles were removed in vacuo, the residue was dissolved in ethyl acetate (3 mL). This washed with water (3 mL), saturated $NaHCO_3$ (2×2 mL), brine (2 mL), dried ($Na_2SO_4$), filtered, concentrated and concentrated under reduced pressure. The crude product, 5-(4-cyclohexyloxy-phenyl)-6-cyclopropyl-2H-pyridazin-3-one (0.29 g), was used in the next step without further purification.

A suspension of 5-(4-cyclohexyloxy-phenyl)-6-cyclopropyl-2H-pyridazin-3-one (0.86 mmol, 0.29 g) in phosphorous oxychloride (4.30 mmol, 0.40 mL) was heated at 90° C. for 20 min with stirring during which period the starting material was fully consumed as judged by TLC. The reaction mixture was cooled to room temperature and the volatiles were removed in vacuo. The residue was dissolved in ethyl acetate (5 mL), washed with water (2 mL), saturated $NaHCO_3$ (2×2 mL) and dried ($Na_2SO_4$). The residue was purified on a 12 g $SiO_2$ cartridge eluting with an ethyl acetate/hexanes gradient to afford 6-chloro-4-(4-cyclohexyloxy-phenyl)-3-cyclopropyl-pyridazine (0.082 g).

To a stirred solution of 1-methyl-piperidin-4-ol (0.50 mmol, 0.06 g) in THF (1 mL) at room temperature was added sodium hydride (60% dispersion in mineral oil) (0.75 mmol, 0.03 g) and continued stirring for 15 min. The reaction mixture was cooled to 0° C. using an ice bath. To this was added a solution of 6-chloro-4-(4-cyclohexyloxy-phenyl)-3-cyclopropyl-pyridazine (0.25 mmol, 0.082 g) in THF (0.5 mL).

After completion of addition, the reaction mixture was warmed to 50° C. and stirred for 2 hours. After cooling the reaction to room temperature, the reaction was quenched with water (1 mL) and extracted with ethyl acetate (1×5 mL). The ethyl acetate layer was washed with brine (2 mL), dried ($Na_2SO_4$), filtered and concentrated under reduced pressure. The residue was purified on 4 g $SiO_2$ cartridge 4-6% (2N $NH_3$ in MeOH) in DCM to give 4-(4-cyclohexyloxy-phenyl)-3-cyclopropyl-6-(1-methyl-piperidin-4-yloxy)-pyridazine. The neutral amine was treated with 2N HCl in diethyl ether (0.5 mL) and DCM (0.5 mL). The volatiles were removed under reduced pressure and the salt was triturated with diethyl ether and filtered to provide the title compound (0.030 g). LCMS: m/z 409 [M+1]. $^1$H NMR (400 MHz, $CD_3OD$) δ 7.48-7.58 (2H, m), 7.30-7.48 (1H, m), 7.04-7.14 (2H, m), 5.30-5.54 (1H, m), 4.37-4.48 (1H, m), 3.60-3.70 (1H, m), 3.14-3.51 (3H, m), 2.93 (3H, s), 2.54 (1H, d), 2.41 (1H, d), 2.16-2.31 (2H, m), 1.96-2.10 (3H, m), 1.76-1.89 (2H, m), 1.27-1.67 (6H, m), 1.09-1.24 (4H, m).

Example 60

3-cyclohexyl-4-(4-cyclohexyloxy-phenyl)-6-(1-methyl-piperidin-4-yloxy)-pyridazine dihydrochloride To a sonicated solution of 4-bromophenol (57.8 mmol, 10 g), triphenylphosphine (173 mmol, 45.4 g), and cyclohexanol (173 mmol, 17.4 g, 18.3 mL) in anhydrous THF (120 mL) under $N_2$ atmosphere, was added DIAD (173 mmol, 35.0 g, 34.0 mL) dropwise over 20 min. After completion of addition, sonication was continued for an additional 30 min. The reaction mixture was concentrated under reduced pressure. The crude product was taken in 250 mL of hexanes and stirred for 30 minutes, filtered and the solid was washed with hexanes (500 mL). Removal of the solvent gave crude 1-bromo-4-cyclohexyloxy-benzene which was dissolved in hexanes (50 mL) and loaded onto a 240 g $SiO_2$ cartridge. The column was eluted with 3% ethyl acetate in hexanes to give pure 1-bromo-4-cyclohexyloxy-benzene (4.5 g).

A stirred suspension of 1-bromo-4-cyclohexyloxy-benzene (3.92 mmol, 1.0 g), cyclohexylmethylketone (5.92 mmol, 0.83 mL), (R)-(+)-2,2'-bis(diphenylphosphino)-1,1'-binaphthyl (1.88 mmol, 1.17 g), tris(dibenzylideneacetone)dipalladium(0) (0.78 mmol, 0.72 g), and potassium t-butoxide (7.84 mmol, 0.88 g) were heated to 90° C. for 12 h in a sealed vial. The reaction was cooled and partitioned in water (50 mL) and diethyl ether (50 mL). The mixture was filtered through fluted filter paper and the layers were separated. The aqueous layer was washed with diethyl ether (3×20 mL). The combined organic layers were washed with brine (10 mL), dried ($Na_2SO_4$), filtered, and concentrated under reduced pressure. The crude product was purified on a 24 g $SiO_2$ cartridge using an ethyl acetate/hexanes gradient to give 1-cyclohexyl-2-(4-cyclohexyloxy-phenyl)-ethanone (0.35 g).

To a stirred solution of 1-cyclohexyl-2-(4-cyclohexyloxy-phenyl)-ethanone (1.17 mmol, 0.35 g) and triethylamine (1.17 mmol, 0.16 mL) in THF (1.0 mL) was added a solution of ethyl glyoxylate (50% in toluene, 5.83 mmol, 1.15 mL) and continued stirring for 12 h at room temperature. After removal of volatiles under reduced pressure, the crude product was purified on a 24 g $SiO_2$ cartridge using an ethyl acetate/hexanes gradient to give 4-cyclohexyl-3-(4-cyclohexyloxy-phenyl)-2-hydroxy-4-oxo-butyric acid ethyl ester (0.28 g).

To a stirred solution of 4-cyclohexyl-3-(4-cyclohexyloxy-phenyl)-2-hydroxy-4-oxo-butyric acid ethyl ester (0.62 mmol, 0.27 g) in glacial acetic acid (0.17 mL) was added hydrazine hydrate (3.4 mmol, 0.17 mL) and the reaction was heated at 100° C. for 12 h. After cooling, the volatiles were removed under reduced pressure, and the residue was evaporated with DCM (2×5 mL). The residue was partitioned between DCM (5 mL) and water (5 mL). The layers were separated and the organic layer was dried ($Na_2SO_4$), filtered, and concentrated under reduced pressure. The crude product, 6-cyclohexyl-5-(4-cyclohexyloxy-phenyl)-2H-pyridazin-3-one, was used in the next step without further purification.

A suspension of 6-cyclohexyl-5-(4-cyclohexyloxy-phenyl)-2H-pyridazin-3-one (0.62 mmol, 0.22 g) in phosphorous oxychloride (6.7 mmol, 0.60 mL) was heated at 80° C. for 1 hour. The reaction mixture was cooled to room temperature and the volatiles were removed in vacuo. The residue was dissolved in ethyl acetate (25 mL), washed with water (25 mL), saturated $NaHCO_3$ (2×10 mL) and dried ($Na_2SO_4$). The residue was purified on a 12 g $SiO_2$ cartridge eluting with an ethyl acetate/hexanes gradient to give 6-chloro-3-cyclohexyl-4-(4-cyclohexyloxy-phenyl)-pyridazine (0.102 g).

To a stirred solution of 4-hydroxy-piperidine-1-carboxylic acid tert-butyl ester (0.40 mmol, 0.08 g) in THF (0.45 mL) at room temperature was added sodium hydride (60% dispersion in mineral oil) (0.54 mmol, 0.022 g) and continued stirring for 10 min. The reaction mixture was cooled to 0° C. using an ice bath. To this was added a solution of 6-chloro-3-cyclohexyl-4-(4-cyclohexyloxy-phenyl)-pyridazine (0.27 mmol, 0.10 g) in THF (0.45 mL). After completion of addition, the reaction mixture was warmed to 65° C. and stirred for 2 hours. After cooling the reaction to room temperature, the reaction was quenched with water (1 mL) and extracted with ethyl acetate (1×2 mL). The ethyl acetate layer was dried ($Na_2SO_4$), filtered and concentrated under reduced pressure. The residue was purified on a 4 g $SiO_2$ cartridge eluting with an ethyl acetate/hexanes gradient to give 4-[6-cyclohexyl-5-(4-cyclohexyloxy-phenyl)-pyridazin-3-yloxy]-piperidine-1-carboxylic acid tert-butyl ester (0.12 g, 81%). To a solution of 4-[6-cyclohexyl-5-(4-cyclohexyloxy-phenyl)-pyridazin-3-yloxy]-piperidine-1-carboxylic acid tert-butyl ester (0.22 mmol, 0.12 g) in DCM (1.5 mL) was added 4 N HCl in dioxane (0.5 mL) and the reaction was stirred for 30 min. The solvents were removed under reduced pressure and the residue was triturated with anhydrous ethyl ether (50 mL) and filtered to give 3-cyclohexyl-4-(4-cyclohexyloxy-phenyl)-6-(piperidin-4-yloxy)-pyridazine dihydrochloride (0.095 g).

To a solution of 3-cyclohexyl-4-(4-cyclohexyloxy-phenyl)-6-(piperidin-4-yloxy)-pyridazine dihydrochloride (0.079 mmol, 0.04 g) and aqueous formaldehyde (37%, 0.39 mmol, 0.035 mL) in dry DCM (1 mL) was added macroporous resin-bound triacetoxyborohydride (loading 2.36 mmol/gram, 0.47 mmol, 0.20 g). The mixture was shaken for 2 hours. The reaction was placed directly onto a 4 g $SiO_2$ cartridge and the column was eluted with 4-6% (2N $NH_3$ in MeOH) in DCM to give 3-cyclohexyl-4-(4-cyclohexyloxy-phenyl)-6-(1-methyl-piperidin-4-yloxy)-pyridazine. The neutral amine was treated with 2N HCl in diethyl ether (0.5 mL) and DCM (0.5 mL). The volatiles were removed under reduced pressure and the salt was triturated with diethyl ether and filtered to provide the title compound (0.04 g). LCMS: m/z 451 [M+1]. $^1$H NMR (400 MHz, $CD_3OD$) δ 7.63-7.79 (1H, m), 7.38-7.43 (2H, m), 7.10-7.14 (2H, m), 5.33-5.57 (1H, m), 4.40-4.51 (1H, m), 3.66-3.69 (1H, m), 3.11-3.54 (3H, m), 2.94 (3H, s), 2.37-2.62 (2H, m), 2.20-2.30 (1H, m), 1.20-2.17 (22H, m).

Example 61

3-cyclobutyl-4-(4-cyclohexyloxy-phenyl)-6-(1-methyl-piperidin-4-yloxy)-pyridazine dihydrochloride A stirred suspension of 1-bromo-4-cyclohexyloxy-benzene (Example 60, 4.18 mmol, 1.05 g), cyclobutylmethylketone (5.23 mmol, 0.57 mL), (R)-(+)-2,2'-bis(diphenylphosphino)-1,1'-binaphthyl (0.50 mmol, 0.31 g), tris(dibenzylideneacetone)dipalladium(0) (0.21 mmol, 0.19 g), and potassium t-butoxide (6.27 mmol, 0.70 g) was heated in a single mode microwave synthesizer to 130° C. for 1 h in a 10 mL microwave sealed tube. The reaction was cooled and partitioned in water (20 mL) and diethyl ether (50 mL). The mixture was filtered through fluted filter paper and the layers were separated. The aqueous layer was washed with diethyl ether (50 mL). The combined organic layers were dried ($Na_2SO_4$), filtered, and concentrated under reduced pressure. The crude product was purified on 2×40 g $SiO_2$ cartridges stacked using a 0-20% ethyl acetate/hexanes gradient to give 1-cyclobutyl-2-(4-cyclohexyloxy-phenyl)-ethanone (0.98 g).

To a stirred solution of 1-cyclobutyl-2-(4-cyclohexyloxy-phenyl)-ethanone (3.60 mmol, 0.98 g) and triethylamine (3.60 mmol, 0.51 mL) in THF (2.0 mL) was added a solution of ethyl glyoxylate (50% in toluene, 18.0 mmol, 3.82 mL) and continued stirring for 12 h at room temperature. After removal of volatiles under reduced pressure, the crude product was pre-absorbed onto 10 g $SiO_2$ followed by purification on a 24 g $SiO_2$ cartridge using a 0-30% ethyl acetate/hexanes gradient to give 4-cyclobutyl-3-(4-cyclohexyloxy-phenyl)-2-hydroxy-4-oxo-butyric acid ethyl ester (0.42 g).

To a stirred solution of 4-cyclobutyl-3-(4-cyclohexyloxy-phenyl)-2-hydroxy-4-oxo-butyric acid ethyl ester (1.12 mmol, 0.42 g) in glacial acetic acid (0.56 mL) was added hydrazine hydrate (5.62 mmol, 0.56 mL) and the reaction was heated at 100° C. for 1 h. After cooling, the volatiles were removed under reduced pressure, and the residue was partitioned between DCM (5 mL) and water (5 mL). The layers were separated and the organic layer was dried ($Na_2SO_4$), filtered, and concentrated under reduced pressure. The crude product, 6-cyclobutyl-5-(4-cyclohexyloxy-phenyl)-2H-pyridazin-3-one (0.24 g), was used in the next step without further purification.

A suspension of 6-cyclobutyl-5-(4-cyclohexyloxy-phenyl)-2H-pyridazin-3-one (0.74 mmol, 0.24 g) in phosphorous oxychloride (7.41 mmol, 0.68 mL) was heated at 80° C. for 20 minutes. The reaction mixture was cooled to room temperature and the volatiles were removed under reduced pressure. The residue was partitioned between ethyl acetate (5 mL) and saturated $NaHCO_3$. The layers were separated and the organic layer was washed with saturated $NaHCO_3$ (5 mL), brine (5 mL) and dried ($Na_2SO_4$). The residue was purified on a 12 g $SiO_2$ cartridge eluting with an ethyl acetate/hexanes gradient to give 6-chloro-3-cyclobutyl-4-(4-cyclohexyloxy-phenyl)-pyridazine (0.15 g).

To a stirred solution of 4-hydroxy-piperidine-1-carboxylic acid tert-butyl ester (0.66 mmol, 0.13 g) in anhydrous THF (0.5 mL) at room temperature was added sodium hydride (60% dispersion in mineral oil) (0.88 mmol, 0.035 g) and continued stirring for 10 min. The reaction mixture was cooled to 0° C. using an ice bath. To this was added a solution of 6-chloro-3-cyclobutyl-4-(4-cyclohexyloxy-phenyl)-pyridazine (0.44 mmol, 0.15 g) in THF (0.5 mL). After completion of addition, the reaction mixture was warmed to 65° C. and stirred for 1 hour. After cooling the reaction to room temperature, the reaction was quenched with water (1 mL) and extracted with ethyl acetate (1×3 mL). The ethyl acetate layer was dried ($Na_2SO_4$), filtered and concentrated under reduced pressure. The residue was purified on a 4 g $SiO_2$ cartridge eluting with a 10-30% ethyl acetate/hexanes gradient to give 4-[6-cyclobutyl-5-(4-cyclohexyloxy-phenyl)-pyridazin-3-yloxy]-piperidine-1-carboxylic acid tert-butyl ester (0.18 g).

To a solution of 4-[6-cyclobutyl-5-(4-cyclohexyloxy-phenyl)-pyridazin-3-yloxy]-piperidine-1-carboxylic acid tert-butyl ester (0.35 mmol, 0.18 g) in DCM (1.0 mL) was added 4 N HCl in dioxane (1.0 mL) and the reaction was stirred for 30 min. The solvents were removed under reduced pressure and the residue was triturated with anhydrous ethyl ether and filtered to give 3-cyclobutyl-4-(4-cyclohexyloxy-phenyl)-6-(piperidin-4-yloxy)-pyridazine dihydrochloride (0.14 g).

To a solution of 3-cyclobutyl-4-(4-cyclohexyloxy-phenyl)-6-(piperidin-4-yloxy)-pyridazine dihydrochloride (0.17 mmol, 0.08 g) and aqueous formaldehyde (37%, 0.83 mmol, 0.07 mL) in dry DCM (1 mL) was added macroporous resin-bound triacetoxyborohydride (loading 2.36 mmol/gram, 1.0 mmol, 0.42 g). The mixture was shaken for 12 hours. The reaction was placed directly onto a 4 g $SiO_2$ cartridge and the column was eluted with 0-6% (2N $NH_3$ in MeOH) in DCM to give 3-cyclohexyl-4-(4-cyclohexyloxy-phenyl)-6-(1-methyl-piperidin-4-yloxy)-pyridazine. The neutral amine was treated with 2N HCl in diethyl ether (1 mL) and DCM (1 mL). The volatiles were removed under reduced pressure and the salt was triturated with diethyl ether and filtered to provide the title compound (0.05 g). LCMS: m/z 423 [M+]. $^1$H NMR (400 MHz, $CD_3OD$) δ 7.26-7.47 (3H, m), 7.02-7.11 (2H, m), 5.35-5.60 (1H, m), 4.37-4.48 (1H, m), 3.97-4.13 (1H, m), 3.67 (1H, d), 3.23-3.53 (2H, m), 2.92 (3H, s), 1.95-2.62 (12H, m), 1.75-1.92 (3H, m), 1.29-1.68 (6H, m).

Example 62

N-{5-[3-butyl-6-(1-methyl-piperidin-4-yloxy)-pyridazin-4-yl]-2-cyclohexyloxy-phenyl}-acetamide dihydrochloride To a solution of 3-butyl-4-(4-cyclohexyloxy-phenyl)-6-(1-methyl-piperidin-4-yloxy)-pyridazine (Example 14, 10 mmol, 4.24 g) in TFA (10 mL) was added sodium nitrate (12 mmol, 1.02 g) at 0° C. The mixture was allowed to warm up to room temperature and stirred for 8 hours. The mixture was then diluted with water/EtOAc, neutralized slowly with $NaHCO_3$ powder. The organic layers were combined, dried, and condensed in vacuo and the residue was purified by silica gel chromatography (DCM to DCM+10% MeOH) to give a pale-yellow solid, 3-butyl-4-(4-cyclohexyloxy-3-nitro-phenyl)-6-(1-methyl-piperidin-4-yloxy)-pyridazine (3.09 g).

To a solution of 3-butyl-4-(4-cyclohexyloxy-3-nitro-phenyl)-6-(1-methyl-piperidin-4-yloxy)-pyridazine (5 mmol, 2.34 g) in acetic acid (10 mL) was added iron powder (−325 mesh, 50 mmol, 2.80 g). And the mixture was stirred at 100° C. for 0.5 hour. It was then diluted with water/EtOAc and neutralized slowly with $NaHCO_3$ powder. The solvent was removed in vacuo and the residue was purified by silica gel chromatography (DCM to DCM+10% 2N $NH_3$ in MeOH) to give a colorless sticky solid, which was dissolved in DCM (10 mL), 2N HCl in ether (10 mL) was added, kept at room temperature for 10 min, condensed, triturated with hexanes to provide 5-[3-butyl-6-(1-methyl-piperidin-4-yloxy)-pyridazin-4-yl]-2-cyclohexyloxy-phenylamine trihydrochloride (2.06 g).

To a solution of 5-[3-butyl-6-(1-methyl-piperidin-4-yloxy)-pyridazin-4-yl]-2-cyclohexyloxy-phenylamine trihydrochloride (0.2 mmol, 110 mg) in DCM (1.0 mL) at 0° C. was added acetyl chloride (0.4 mmol, 29 µL), DIEA (0.4 mmol, 70 µL) and DMAP (5 mg). And the mixture was stirred at room temperature for 1 hour. It was then condensed in vacuo and the residue was purified by silica gel chromatography (DCM to DCM+10% 2N $NH_3$ in MeOH) to give a colorless sticky solid, which was dissolved in DCM (1.0 mL), 2N HCl in ether (1.0 mL) was added, kept at room temperature for 10 min, condensed, triturated with hexanes to provide the title compound (61 mg). LCMS: m/z 482 [M+1]. $^1$H NMR (400 MHz, CDCl$_3$): δ 8.43 (1H, s), 7.89 (1H, s), 6.97 (2H, s), 6.81 (1H, s), 5.60 (1H, bs), 4.37-4.43 (1H, m), 3.10-3.45 (4H, m), 2.90-2.95 (2H, m), 2.81 (3H, s), 2.35-2.61 (4H, m), 2.23 (3H, s), 1.25-1.87 (14H, m), 0.83 (3H, t).

Example 63

N-{5-[3-butyl-6-(1-methyl-piperidin-4-yloxy)-pyridazin-4-yl]-2-cyclohexyloxy-phenyl}-N-isobutyl-acetamide dihydrochloride To a solution of 5-[3-butyl-6-(1-methyl-piperidin-4-yloxy)-pyridazin-4-yl]-2-cyclohexyloxy-phenylamine (Example 62, 0.2 mmol, 88 mg) in DCM (2.0 mL) was added isobutyraldehyde (0.3 mmol, 28 µL), and 1 drop of acetic acid. Then sodium triacetoxyborohydride (0.6 mmol, 127 mg) was added. The mixture was stirred at room temperature for 1 hour then condensed. The mixture was then diluted with water/EtOAc. The solvent was removed in vacuo and the residue was again dissolved in DCM (2.0 mL) at 0° C., added acetyl chloride (0.4 mmol, 29 µL), DIEA (0.6 mmol, 105 µL) and DMAP (5 mg). And the mixture was stirred at room temperature for 1 hour. It was then condensed in vacuo and the residue was purified by silica gel chromatography (DCM to DCM+10% 2N NH$_3$ in MeOH) to give a colorless sticky solid, which was dissolved in DCM (1.0 mL), 2N HCl in ether (1.0 mL) was added, kept at room temperature for 10 min, condensed, triturated with hexanes to provide the title compound (41 mg). LCMS: m/z 537 [M+1]. $^1$H NMR (400 MHz, CD$_3$OD): δ 7.40-7.43 (1H, m), 7.28-7.35 (2H, m), 7.07 (1H, s), 5.52 (1H, bs), 4.53-4.59 (1H, m), 3.65-3.71 (1H, m), 3.29-3.47 (7H, m), 2.92-2.97 (2H, m), 2.89 (3H, s), 2.18-2.37 (4H, m), 1.99-2.07 (2H, m), 1.84 (3H, s), 1.25-1.83 (9H, m), 1.18-1.26 (2H, m), 0.91-0.95 (6H, m), 0.80 (3H, t).

Example 64

N-{5-[3-butyl-6-(1-methyl-piperidin-4-yloxy)-pyridazin-4-yl]-2-cyclohexyloxy-phenyl}-N-isobutyl-methanesulfonamide dihydrochloride To a solution of 5-[3-butyl-6-(1-methyl-piperidin-4-yloxy)-pyridazin-4-yl]-2-cyclohexyloxy-phenylamine (Example 62, 0.2 mmol, 88 mg) in DCM (1.0 mL) at 0° C. was added methanesulfonyl chloride (0.3 mmol, 24 µL) and DIEA (0.3 mmol, 53 µL). And the mixture was stirred at room temperature for 1 hour. It was then condensed in vacuo and the residue was purified by silica gel chromatography (DCM to DCM+10% 2N NH$_3$ in MeOH) to give a colorless sticky solid, which was dissolved in DCM (1.0 mL), 2N HCl in ether (1.0 mL) was added, kept at room temperature for 10 min, condensed, triturated with hexanes to afford N-{5-[3-butyl-6-(1-methyl-piperidin-4-yloxy)-pyridazin-4-yl]-2-cyclohexyloxy-phenyl}-methanesulfonamide dihydrochloride (72 mg).

To a solution of N-{5-[3-butyl-6-(1-methyl-piperidin-4-yloxy)-pyridazin-4-yl]-2-cyclohexyloxy-phenyl}-methanesulfonamide dihydrochloride (0.1 mmol, 59 mg) in DMF (1.0 mL) was added isobutyl bromide (0.2 mmol, 22 µL), and potassium carbonate (0.4 mmol, 56 mg). And the mixture was stirred at 90° C. for 2 hours. It was then diluted with water/EtOAc. The solvent was removed in vacuo and the residue was purified by silica gel chromatography (DCM to DCM+10% 2N NH$_3$ in MeOH) to give a colorless sticky solid, which was dissolved in DCM (1.0 mL), 2N HCl in ether (1.0 mL) was added, condensed, triturated with hexanes to provide the title compound (38 mg). LCMS: m/z 574 [M+1]. $^1$H NMR (400 MHz, CD$_3$OD): δ 7.39 (1H, d), 7.31 (1H, s), 7.25 (1H, d), 7.04 (1H, s), 5.42 (1H, bs), 4.46-4.53 (1H, m), 3.42-3.48 (1H, m), 2.98-3.30 (5H, m), 2.95 (3H, s), 2.90-2.94 (2H, m), 2.69 (3H, s), 2.09-2.30 (6H, m), 1.82-1.88 (2H, m), 1.20-1.69 (11H, m), 0.89-0.93 (6H, m), 0.79 (3H, t).

Example 65

3-Butyl-4-(4-cyclohexyloxy-3-oxazol-2-yl-phenyl)-6-(1-methyl-piperidin-4-yloxy)-pyridazine dihydrochloride salt 3-Bromo-4-hydroxy-benzaldehyde (24.8 mmol, 5.0 g), bromo-cyclohexane (37.3 mmol, 6.08 g) and K$_2$CO$_3$ (37.3 mmol, 5.15 g) were suspended in DMF (15 mL) and stirred over night at 90° C. The mixture was cooled to room temperature, and bromo-cyclohexane (36.8 mmol, 6.0 g) and K$_2$CO$_3$ (36.2 mmol, 5.0 g) were added stirred at 90° C. for another 24 h. The mixture was cooled and filtered. The filtrate was extracted with ethyl acetate. The organic layer was washed with 1.0 N NaOH (200 mL), water, and brine, dried (Na$_2$SO$_4$), filtered, and concentrated under reduced pressure to provide 3-bromo-4-cyclohexyloxy-benzaldehyde (2.7 g).

3-bromo-4-cyclohexyloxy-benzaldehyde (13 mmol, 3.7 g), 1-nitro-pentane (19.6 mmol, 2.3 g) and n-butyl amine (2.6 mmol, 0.19 g) were dissolved in toluene (5 mL) and refluxed for 48 h. The reaction mixture was cooled, filtered and evaporated the solvent and purified by column chromatography using 2% ethyl acetate in hexane as an eluents to provide 2-bromo-1-cyclohexyloxy-4-((E)-2-nitro-hex-1-enyl)-benzene (3.5 g).

2-Bromo-1-cyclohexyloxy-4-((E)-2-nitro-hex-1-enyl)-benzene (8.3 mmol, 3.2 g), and iron powder (41.8 mmol, 2.3 g) were dispersed in methanol (20 mL), 3.0 N HCl (20 mL) and heated to reflux for 3.0 h. Cooled the reaction mixture to room temperature, filtered through celite washed with ether. Organic layer separated, dried (Na$_2$SO$_4$) filtered and concentrated under reduced pressure to provide 1-(3-Bromo-4-cyclohexyloxy-phenyl)-hexan-2-one (2.5 g).

A mixture of 1-(3-Bromo-4-cyclohexyloxy-phenyl)-hexan-2-one (7.08 mmol, 2.5 g), oxo-acetic acid ethyl ester solution in toluene (2.8 mL, 50% solution in toluene) and triethylamine (0.5 mL) was stirred at ambient temperature for 16 h. The reaction mixture was diluted with DCM (300 mL), washed with water (3×100 mL), dried the organic layer and concentrated under reduced pressure. The resultant residue was purified by flash silica gel chromatography using mixture of hexanes in ethyl acetate (9:1) to provide 3-(3-bromo-4-cyclohexyloxy-phenyl)-2-hydroxy-4-oxo-octanoic acid ethyl ester (2.0 g).

A mixture of 3-(3-bromo-4-cyclohexyloxy-phenyl)-2-hydroxy-4-oxo-octanoic acid ethyl ester (4.39 mmol, 2.0 g) and hydrazine hydrate (2.0 mL) in acetic acid (10 mL) was kept stirring at 120° C. for 3 h. The reaction mixture was concentrated under reduced pressure and to the residue was added water, extracted with ethyl acetate dried and concentrated under reduced pressure, dried to provide 5-(3-bromo-4-cyclohexyloxy-phenyl)-6-butyl-pyridazin-3-ol (1.7 g).

A suspension of 5-(3-bromo-4-cyclohexyloxy-phenyl)-6-butyl-pyridazin-3-ol (4.18 mmol, 1.7 g) in POCl$_3$ (20 mL) was kept stirring at 70° C. for 2 h. The reaction mixture was concentrated, to the residue water was added, extracted with ethyl acetate washed with sat NaHCO$_3$ solution, water, brine, dried and concentrated under reduced pressure. The resultant residue was purified by silica gel flash chromatography using a mixture of hexanes in ethyl acetate (9:1) to provide 4-(3-bromo-4-cyclohexyloxy-phenyl)-3-butyl-6-chloro-pyridazine (1.5 g).

To a stirred solution of 4-hydroxy-piperidine-1-carboxylic acid tert-butyl ester (5.33 mmol, 1.07 g) in THF at room temperature, NaH (100 mg, 4.5 mmol) was added and stirring continued for 30 min then 4-(3-Bromo-4-cyclohexyloxy-phenyl)-3-butyl-6-chloro-pyridazine (3.50 mmol, 1.5 g) was added. The resulting mixture was stirred at 50° C. for over night, poured into water and extracted with ethyl acetate. The organic layer was washed with water, brine dried ($Na_2SO_4$) filtered and concentrated under reduced pressure. The product was purified by column chromatography using 10-20% ethyl acetate in hexanes to provide 4-[5-(3-bromo-4-cyclohexyloxy-phenyl)-6-butyl-pyridazin-3-yloxy]-piperidine-1-carboxylic acid tert-butyl ester (1.6 g).

4-[5-(3-bromo-4-cyclohexyloxy-phenyl)-6-butyl-pyridazin-3-yloxy]-piperidine-1-carboxylic acid tert-butyl ester (0.34 mmol, 0.2 g), 2-(tri-n-butylstannyl)oxazole (0.68 mmol, 0.24 g), tetrakis(triphenylphosphine)palladium (0.034 mmol, 0.04 g) in dioxane (5.0 mL) were degassed with nitrogen for 10 min and heated at 90° C. over night under nitrogen. Cooled, KF solution (2.0 M, 10 mL) was added, stirred at room temperature for 30 min. extracted with ethyl acetate. The organic layer was washed with water, brine, dried ($Na_2SO_4$) filtered and concentrated under reduced pressure. The product was purified by column chromatography using 25% ethyl acetate in hexanes to get 4-[6-butyl-5-(4-cyclohexyloxy-3-oxazol-2-yl-phenyl)-pyridazin-3-yloxy]-piperidine-1-carboxylic acid tert-butyl ester (0.1 g).

To a stirring solution of 4-[6-Butyl-5-(4-cyclohexyloxy-3-oxazol-2-yl-phenyl)-pyridazin-3-yloxy]-piperidine-1-carboxylic acid tert-butyl ester (0.08 g, 0.13 mmol) in DCM, 2.0 mL of 4.0 M HCl in dioxane was added and stirring continued for 30 min. Solvent evaporated, resulting solid was washed with ether, dried to get 3-butyl-4-(4-cyclohexyloxy-3-oxazol-2-yl-phenyl)-6-(piperidin-4-yloxy)-pyridazine dihydrochloride salt (60 mg)

To a solution of 3-butyl-4-(4-cyclohexyloxy-3-oxazol-2-yl-phenyl)-6-(piperidin-4-yloxy)-pyridazine dihydrochloride (50 mg, 0.091 mmol) in dichloromethane (2.0 mL) was added formaldehyde solution in water (37%, 0.25 mL), and 0.1 mL of acetic acid. Then sodium triacetoxyborohydride (300 mg) was added. And the mixture was stirred at room temperature for 10 min then condensed. It was then diluted with water/DCM, neutralized with sat $NaHCO_3$ powder, organic layer was separated washed with water, brine and dried ($Na_2SO_4$). The solvent was removed in vacuo and the residue was purified by column chromatography using 5% methanolic solution of ammonia (2.0 M ammonia in methanol) in DCM to get 3-butyl-4-(4-cyclohexyloxy-3-oxazol-2-yl-phenyl)-6-(1-methyl-piperidin-4-yloxy)-pyridazine. This compound was dissolved in DCM (2.0 mL) and 1.0 mL of 4.0 M HCl in dioxane was added. Solvents were evaporated resulting solid was washed with ether and dried to provide the title compound (25 mg). LCMS: m/z 492 [M+1].

Example 66

1-{5-[3-Butyl-6-(1-methyl-piperidin-4-yloxy)-pyridazin-4-yl]-2-cyclohexyloxy-phenyl}-ethanone 4-[5-(3-Bromo-4-cyclohexyloxy-phenyl)-6-butyl-pyridazin-3-yloxy]-piperidine-1-carboxylic acid tert-butyl ester (Example 65, 0.34 mmol, 0.2 g), tributyl(1-ethoxyvinyl) tin (0.68 mmol, 0.24 g), tetrakis(triphenylphosphine)palladium (0.034 mmol, 0.04 g) in dioxane (5.0 mL) were degassed with nitrogen for 10 min and heated at 90° C. over night under nitrogen. Cooled, KF solution (2.0 M, 10 mL) was added, stirred at room temperature for 30 min. extracted with ethyl acetate. The organic layer was washed with water, brine, dried ($Na_2SO_4$) filtered and concentrated under reduced pressure. The product was purified by column chromatography using 10-25% ethyl acetate in hexanes to provide 4-[5-(3-acetyl-4-cyclohexyloxy-phenyl)-6-butyl-pyridazin-3-yloxy]-piperidine-1-carboxylic acid tert-butyl ester (0.1 g).

To a stirring solution of 4-[5-(3-acetyl-4-cyclohexyloxy-phenyl)-6-butyl-pyridazin-3-yloxy]-piperidine-1-carboxylic acid tert-butyl ester (0.1 g, 0.17 mmol) in DCM (2.0 mL), 4.0 M HCl in dioxane (2.0 mL) was added and stirring continued for 30 min. Solvent evaporated, resulting solid was washed with ether, dried to provide 1-{5-[3-butyl-6-(piperidin-4-yloxy)-pyridazin-4-yl]-2-cyclohexyloxy-phenyl}-ethanone dihydrochloride salt (60 mg).

To a solution of 1-{5-[3-butyl-6-(piperidin-4-yloxy)-pyridazin-4-yl]-2-cyclohexyloxy-phenyl}-ethanone dihydrochloride (50 mg, 0.095 mmol) in dichloromethane (2.0 mL) was added formaldehyde solution in water (37%, 0.2 mL), and 0.1 mL of acetic acid. Then sodium triacetoxyborohydride (200 mg) was added. And the mixture was stirred at room temperature for 10 min then condensed. It was then diluted with water/DCM, neutralized with sat $NaHCO_3$ powder, organic layer was separated washed with water, brine and dried ($Na_2SO_4$). The solvent was removed in vacuo and the residue was purified by column chromatography using 5% methanolic solution of ammonia (2.0 M ammonia in methanol) in DCM to provide 1-{5-[3-Butyl-6-(1-methyl-piperidin-4-yloxy)-pyridazin-4-yl]-2-cyclohexyloxy-phenyl}-ethanone (30 mg). This compound was dissolved in DCM (2.0 mL) and 1.0 mL of 4.0 M HCl in dioxane was added. Solvents were evaporated resulting solid was washed with ether and dried to provide the title compound (33 mg). LCMS: m/z 467 [M+1]. $^1$H NMR (400 MHz, $CD_3OD$) 7.94 (1H, s), 7.83-7.87 (1H, m), 7.68-7.74 (1H, m), 7.39 (1H, t), 5.35-5.43 (1H, m), 4.65-4.71 (1H, m), 3.65 (1H, d), 3.38-3.50 (2H, m), 3.28-3.30 (2H, m), 3.09-3.14 (2H, m), 2.84 (3H, s), 2.67 (3H, s), 2.5 (1H, d), 2.41 (1H, d), 2.24-2.31 (1H, m), 2.05-2.13 (2H, m), 1.80-1.84 (2H, m) 1.64-1.72 (3H, m), 1.51-1.56 (4H, m), 1.28-1.34 (3H, m), 0.83 (3H, t).

Example 67

5-[3-Butyl-6-(1-methyl-piperidin-4-yloxy)-pyridazin-4-yl]-2-cyclohexyloxy-benzonitrile dihydrochloride 4-[5-(3-Bromo-4-cyclohexyloxy-phenyl)-6-butyl-pyridazin-3-yloxy]-piperidine-1-carboxylic acid tert-butyl ester (Example 65, 0.44 mmol, 0.26 g), Zinc cyanide (0.44 mmol, 0.052 g) in DMF (5.0 mL), water (0.05 mL) were degassed with nitrogen for 10 min then $Pd_2dba_3$ (0.022 mmol, 0.02 g), dppf (0.053 mmol, 0.029 g) was added and then degassed for 10 more min. The reaction mixture was heated at 120° C. for 36 h under nitrogen. Cooled, water was added extracted with ethyl acetate. The organic layer was washed with water, brine, dried ($Na_2SO_4$) filtered and concentrated under reduced pressure. The product was purified by column chromatography using 20% ethyl acetate in hexanes to get 4-[6-butyl-5-(3-cyano-4-cyclohexyloxy-phenyl)-pyridazin-3-yloxy]-piperidine-1-carboxylic acid tert-butyl ester (0.17 g).

To a stirring solution of 4-[6-butyl-5-(3-cyano-4-cyclohexyloxy-phenyl)-pyridazin-3-yloxy]-piperidine-1-carboxylic acid tert-butyl ester (0.025 g, 0.046 mmol) in DCM (2.0 mL), 4.0 M HCl in dioxane (2.0 mL) was added and stirring continued for 30 min. Solvent evaporated, resulting solid was washed with ether, dried to get 5-[3-Butyl-6-(piperidin-4-yloxy)-pyridazin-4-yl]-2-cyclohexyloxy-benzonitrile dihydrochloride (22 mg).

To a solution of 5-[3-butyl-6-(piperidin-4-yloxy)-pyridazin-4-yl]-2-cyclohexyloxy-benzonitrile dihydrochloride (19 mg, 0.037 mmol) in dichloromethane (2.0 mL) was added formaldehyde solution in water (37%, 0.2 mL), and 0.1 mL of acetic acid. Then sodium triacetoxyborohydride (200 mg) was added. And the mixture was stirred at room temperature for 10 min then condensed. It was then diluted with water/DCM, neutralized with sat NaHCO$_3$ powder, organic layer was separated washed with water, brine and dried (Na$_2$SO$_4$). The solvent was removed in vacuo and the residue was purified by column chromatography using 5% methanolic solution of ammonia (2.0 M ammonia in methanol) in DCM to get 5-[3-butyl-6-(1-methyl-piperidin-4-yloxy)-pyridazin-4-yl]-2-cyclohexyloxy-benzonitrile. This compound was dissolved in DCM (2.0 mL) and 1.0 mL of 4.0 M HCl in dioxane was added. Solvents were evaporated resulting solid was washed with ether and dried to provide the title compound (13 mg, 95%). LCMS: m/z 450 [M+1]. 7.75-7.89 (3H, m), 7.40-7.49 (1H, m), 5.40-5.51 (1H, m), 4.68-4.72 (1H, m), 3.65-3.68 (1H, m), 3.39-3.52 (2H, m), 3.10-3.18 (2H, m), 2.94 (3H, s), 2.54 (1H, d), 2.41 (1H, d), 2.21-2.29 (1H, m), 1.98-2.11 (3H, m), 1.81-1.90 (2H, m), 1.60-1.7 (2H, m), 1.41-1.61 (6H, m), 1.28-1.35 (3H, m), 0.83 (3H, t).

Example 68

1-{5-[3-Butyl-6-(1-methyl-piperidin-4-yloxy)-pyridazin-4-yl]-2-cyclohexyloxy-phenyl}-pyrrolidin-2-one dihydrochloride To a solution of 5-[3-butyl-6-(1-methyl-piperidin-4-yloxy)-pyridazin-4-yl]-2-cyclohexyloxy-phenylamine (Example 62, 0.2 mmol, 88 mg) in dry DCM (1.0 mL) was added 4-bromobutyryl chloride (0.4 mmol, 47 µL), DIEA (0.4 mmol, 70 µL), and DMAP (10 mg). And the mixture was stirred at room temperature for 1 hour then condensed. It was then diluted with water/EtOAc. The solvent was removed in vacuo and dried under vacuum over night. The residue was dissolved in dry THF (1.0 mL) at 0° C., NaH (60% dispersion in mineral oil, 0.8 mmol, 32 mg) was added and the mixture was heated at 50° C. for 1 hour. It was then poured into ice-water and extracted with ethyl acetate. The organic layers were combined, condensed and the residue was purified by silica gel chromatography (DCM to DCM+10% 2N NH$_3$ in MeOH) to give a colorless sticky solid, which was dissolved in DCM (1.0 mL), 2N HCl in ether (1.0 mL) was added, kept at room temperature for 10 min, condensed, triturated with hexanes to provide the title compound (25 mg). LCMS: m/z 508 [M+1]. $^1$H NMR (400 MHz, CD$_3$OD): δ 7.56 and 7.67 (1H, s), 7.41-7.48 (1H, m), 7.33-7.37 (1H, m), 7.25-7.31 (1H, m), 5.36-5.55 (1H, m), 4.52-4.58 (1H, m), 3.20-3.70 (8H, m), 3.07-3.13 (2H, m), 2.93 (3H, s), 1.92-2.59 (8H, m), 1.27-1.82 (12H, m), 0.80 (3H, t).

Example 69

3-Butyl-4-[4-cyclohexyloxy-3-(1-methyl-1H-pyrazol-4-yl)-phenyl]-6-(1-methyl-piperidin-4-yloxy)-pyridazine dihydrochloride A mixture of 4-[5-(3-bromo-4-cyclohexyloxy-phenyl)-6-butyl-pyridazin-3-yloxy]-piperidine-1-carboxylic acid tert-butyl ester (Example 65, 0.2 mmol, 118 mg), 1-methyl-4-(4,4,5,5-tetramethyl-[1,3,2]dioxaborolan-2-yl)-1H-pyrazole (0.3 mmol, 65.7 mg), tetrakis(triphenylphosphine)palladium (0) (0.01 mmol, 11.6 mg), 2 N aq sodium carbonate solution (0.5 mL) and DME (1 mL) was heated at 80° C. overnight. 1-Methyl-4-(4,4,5,5-tetramethyl-[1,3,2]dioxaborolan-2-yl)-1H-pyrazole (0.3 mmol, 65.7 mg, 95%) and tetrakis(triphenylphosphine)palladium(0) (0.01 mmol, 11.6 mg) were added to the reaction mixture again, and it was heated at 100° C. for 40 min. The reaction mixture was partitioned between ethyl acetate (20 mL) and saturated aq. sodium bicarbonate solution (20 mL). The aq. layer was separated and extracted again with ethyl acetate (2×20 mL). The combined ethyl acetate extracts were dried over sodium sulfate. Purification by column chromatography on silica gel using ethyl acetate/hexanes 1:2 provided 4-{6-butyl-5-[4-cyclohexyloxy-3-(1-methyl-1H-pyrazol-4-yl)-phenyl]-pyridazin-3-yloxy}-piperidine-1-carboxylic acid tert-butyl ester (66.4 mg).

To a solution of 4-{6-butyl-5-[4-cyclohexyloxy-3-(1-methyl-1H-pyrazol-4-yl)-phenyl]-pyridazin-3-yloxy}-piperidine-1-carboxylic acid tert-butyl ester (0.109 mmol, 64.1 mg) in MeOH (0.5 mL) was added 4 N HCl in dioxane (0.5 mL), and the reaction mixture was stirred for 3 h. The organic solvents were removed in vacuo and the residue was triturated with anhydrous diethyl ether and hexanes. The green-yellow solid was dried overnight under high vacuum to provide 3-butyl-4-[4-cyclohexyloxy-3-(1-methyl-1H-pyrazol-4-yl)-phenyl]-6-(piperidin-4-yloxy)-pyridazine dihydrochloride (61.3 mg).

To a solution of 3-butyl-4-[4-cyclohexyloxy-3-(1-methyl-1H-pyrazol-4-yl)-phenyl]-6-(piperidin-4-yloxy)-pyridazine dihydrochloride (0.094 mmol, 56.3 mg) in DCM (1 mL) was added formaldehyde solution in water (37%, 0.3 mmol, 0.022 mL), and 2 drops of acetic acid. Sodium triacetoxyborohydride (0.4 mmol, 89 mg, 95%) was added. The reaction mixture was stirred at room temperature for 2 h and partitioned between ethyl acetate (20 mL) and saturated aq. sodium bicarbonate solution (20 mL). The ethyl acetate layer was separated and dried over sodium sulfate. The crude product was purified by column chromatography on silica gel using 2 M ammonia in MeOH/DCM 1:19, dissolved in MeOH and treated with 4 N HCl in dioxane. The organic solvents were removed in vacuo and the residue was triturated with anhydrous diethyl ether and hexanes. The yellow solid was dried overnight under high vacuum to provide the title compound (42.8 mg). LCMS: m/z 505 [M+1] $^1$H NMR (400 MHz, CD$_3$OD) δ 8.14 and 8.16 (1H, s), 8.00-8.01 (1H, m), 7.86 and 7.94 (1H, s), 7.75-7.79 (1H, m), 7.36-7.41 (1H, m), 7.26-7.30 (1H, s), 5.38-5.55 (1H, m), 4.57-4.62 (1H, m), 3.96 (3H, d), 3.14-3.70 (6H, m), 2.95 (3H, d), 1.81-2.58 (6H, m), 1.31-1.66 (12H, m), 0.81 (3H, t).

Example 70

3-Butyl-4-[4-cyclohexyloxy-3-(1-methyl-1H-tetrazol-5-yl)-phenyl]-6-(1-methyl-piperidin-4-yloxy)-pyridazine dihydrochloride A mixture of 4-[6-butyl-5-(3-cyano-4-cyclohexyloxy-phenyl)-pyridazin-3-yloxy]-piperidine-1-carboxylic acid tert-butyl ester (Example 67, 0.944 mmol, 505 mg), azidotrimethyltin (3.78 mmol, 802 mg, 97%) and toluene (9 mL) was heated at 110° C. for 48h. More azidotrimethyltin (0.95 mmol, 201 mg, 97%) was added and the reaction mixture was heated at 110° C. for another 24 h. The reaction mixture was stirred with aq. 0.41 N HCl (11.5 mL), diluted with water (30 mL) and extracted with DCM (2×40 mL). The combined DCM extracts were dried over sodium sulfate. Purification by column chromatography on silica gel using 0-7.5% MeOH in DCM gave 4-{6-butyl-5-[4-cyclohexyloxy-3-(1H-tetrazol-5-yl)-phenyl]-pyridazin-3-yloxy}-piperidine-1-carboxylic acid tert-butyl ester as light brown solid (545 mg).

A mixture of 4-{6-butyl-5-[4-cyclohexyloxy-3-(1H-tetrazol-5-yl)-phenyl]-pyridazin-3-yloxy}-piperidine-1-carboxylic acid tert-butyl ester (0.936 mmol, 541 mg), iodomethane (2 mmol, 0.126 mL, 99%), potassium carbonate (2.6 mmol, 359 mg) and DMF (5 mL) was stirred at room temperature overnight. The reaction mixture was partitioned between ethyl acetate (50 mL) and saturated aq. sodium bicarbonate solution (50 mL). The ethyl acetate layer was washed again with water (2×50 mL) and dried over sodium sulfate. Purification by column chromatography on silica gel using 20-50% ethyl acetate in hexanes gave two fractions (regio-isomers) as follows: 4-{6-Butyl-5-[4-cyclohexyloxy-3-(2-methyl-2H-tetrazol-5-yl)-phenyl]-pyridazin-3-yloxy}-piperidine-1-carboxylic acid tert-butyl ester (94.6 mg). $^1$H NMR (400 MHz, CDCl$_3$) δ 7.93 (1H, d), 7.37 (1H, dd), 7.15 (1H, d), 6.82 (1H, s), 5.47-5.53 (1H, m), 4.49-4.51 (1H, m), 4.42 (3H, s), 3.80 (2H, bs), 3.24-3.31 (2H, m), 2.89-2.93 (2H, m), 1.24-2.13 (27H, m), 0.83 (3H, t). 4-{6-Butyl-5-[4-cyclohexyloxy-3-(1-methyl-1H-tetrazol-5-yl)-phenyl]-pyridazin-3-yloxy}-piperidine-1-carboxylic acid tert-butyl ester (311 mg). $^1$H NMR (400 MHz, CDCl$_3$) δ 7.52 (1H, d), 7.49 (1H, dd), 7.17 (1H, d), 6.79 (1H, s), 5.47-5.53 (1H, m), 4.41-4.45 (1H, m), 4.05 (3H, s), 3.81 (2H, bs), 3.24-3.30 (2H, m), 2.86-2.90 (2H, m), 1.24-2.12 (27H, m), 0.84 (3H, t).

To a solution of 4-{6-butyl-5-[4-cyclohexyloxy-3-(1-methyl-1H-tetrazol-5-yl)-phenyl]-pyridazin-3-yloxy}-piperidine-1-carboxylic acid tert-butyl ester (0.52 mmol, 308 mg) in DCM (3 mL) was added 4 N HCl in dioxane (1 mL) and the reaction mixture was stirred for 1 h. The organic solvents were removed in vacuo and the residue was triturated with anhydrous diethyl ether and hexanes. The yellow solid was dried overnight under high vacuum to give 3-butyl-4-[4-cyclohexyloxy-3-(1-methyl-1H-tetrazol-5-yl)-phenyl]-6-(piperidin-4-yloxy)-pyridazine dihydrochloride (229.3 mg).

To a solution of 3-butyl-4-[4-cyclohexyloxy-3-(1-methyl-1H-tetrazol-5-yl)-phenyl]-6-(piperidin-4-yloxy)-pyridazine dihydrochloride (0.379 mmol, 214 mg) in DCM (2 mL) was added formaldehyde solution in water (37%, 1.14 mmol, 0.085 mL) and 2 drops of acetic acid. Sodium triacetoxyborohydride (1.52 mmol, 339 mg, 95%) was added. The reaction mixture was stirred at room temperature for 1 h and partitioned between ethyl acetate (20 mL) and saturated aq. sodium bicarbonate solution (20 mL). The ethyl acetate layer was separated and dried over sodium sulfate. The crude product was purified by column chromatography on silica gel using 2 M ammonia in MeOH/DCM 1:19 to 1:14, dissolved in MeOH and treated with 4 N HCl in dioxane. The organic solvents were removed in vacuo and the residue was triturated with anhydrous diethyl ether. The yellow solid was dried overnight under high vacuum to provide the title compound (188.2 mg). LCMS: m/z 507 [M+1] $^1$H NMR (400 MHz, CD$_3$OD) δ 7.85 and 7.93 (1H, s), 7.79-7.85 (1H, m), 7.69 (1H, dd), 7.49-7.53 (1H, m), 5.38-5.56 (1H, m), 4.64-4.69 (1H, m), 4.05 and 4.06 (3H, s), 3.13-3.69 (6H, m), 2.94 (3H, s), 1.97-2.54 (12H, m), 1.30-1.63 (6H, m), 0.84 (3H, dt).

Example 71

5-[3-Butyl-6-(1-methyl-piperidin-4-yloxy)-pyridazin-4-yl]-2-cyclohexyloxy-benzoic acid methyl ester dihydrochloride A mixture of 4-[5-(3-bromo-4-cyclohexyloxy-phenyl)-6-butyl-pyridazin-3-yloxy]-piperidine-1-carboxylic acid tert-butyl ester (Example 65, 0.816 mmol, 480 mg), [1,1-bis(diphenylphosphino)ferrocene]dichloropalladium(II) complex with dichloromethane (1:1) (0.163 mmol, 133 mg), 1,1'-bis(diphenylphosphino)ferrocene (0.163 mmol, 90.4 mg), triethyl amine (1.63 mL), MeOH (16.3 mL) and DMF (16.3 mL) was heated at 90° C. under carbon monoxide atmosphere (24 psi) overnight. The reaction mixture was partitioned between ethyl acetate (200 mL) and saturated aq. sodium bicarbonate solution (200 mL). The ethyl acetate layer was washed again with saturated aq. sodium bicarbonate solution (2×200 mL) and dried over sodium sulfate. Purification by column chromatography on silica gel using 20-50% ethyl acetate in hexanes gave 4-[6-butyl-5-(4-cyclohexyloxy-3-methoxycarbonyl-phenyl)-pyridazin-3-yloxy]-piperidine-1-carboxylic acid tert-butyl ester as light yellow, thick oil (428 mg).

To a solution of 4-[6-butyl-5-(4-cyclohexyloxy-3-methoxycarbonyl-phenyl)-pyridazin-3-yloxy]-piperidine-1-carboxylic acid tert-butyl ester (0.754 mmol, 428 mg) in DCM (6 mL) was added 4 N HCl in dioxane (2 mL) and the reaction mixture was stirred for 1 h. The organic solvents were removed in vacuo and 5-[3-Butyl-6-(piperidin-4-yloxy)-pyridazin-4-yl]-2-cyclohexyloxy-benzoic acid methyl ester dihydrochloride was obtained as yellow solid, which was used for next reaction directly To a solution of 5-[3-butyl-6-(piperidin-4-yloxy)-pyridazin-4-yl]-2-cyclohexyloxy-benzoic acid methyl ester dihydrochloride in DCM (6 mL) was added formaldehyde solution in water (37%, 2.26 mmol, 0.168 mL) and 2 drops of acetic acid. Sodium triacetoxyborohydride (3.02 mmol, 674 mg, 95%) was added. The reaction mixture was stirred at room temperature for 1 h and partitioned between ethyl acetate (40 mL) and saturated aq. sodium bicarbonate solution (40 mL). The ethyl acetate layer was separated and dried over sodium sulfate. The crude product was purified by column chromatography on basic alumina using 0-4.5% MeOH in DCM to give 5-[3-butyl-6-(1-methyl-piperidin-4-yloxy)-pyridazin-4-yl]-2-cyclohexyloxy-benzoic acid methyl ester. This was converted to the title compound using 4 N HCl in dioxane (296 mg). LCMS: m/z 483 [M+1] $^1$H NMR (400 MHz, CD$_3$OD) δ 7.86-7.93 (2H, m), 7.65-7.71 (1H, m), 7.34-7.38 (1H, m), 5.38-5.55 (1H, m), 4.61-4.65 (1H, m), 3.89 and 3.89 (3H, s), 3.11-3.65 (6H, m), 2.94 (3H, s), 1.16-2.57 (18H, m), 0.83 (3H, dt).

Example 72

3-Butyl-4-(4-cyclohexyloxy-3-isoxazol-4-yl-phenyl)-6-(1-methyl-piperidin-4-yloxy)-pyridazine dihydrochloride The title compound may be prepared using a procedure analogous to Example 69 and substituting 4-(4,4,5,5-tetramethyl-[1,3,2]dioxaborolan-2-yl)isoxazole for 1-methyl-4-(4,4,5,5-tetramethyl-[1,3,2]dioxaborolan-2-yl)-1H-pyrazole. LCMS: m/z 492 [M+1] $^1$H NMR (400 MHz, CD$_3$OD) δ 9.17 (1H, d), 8.96 (1H, d), 7.25-7.86 (4H, m), 5.41-5.56 (1H, m), 4.61-4.67 (1H, m), 3.10-3.70 (6H, m), 2.95 (3H, d), 1.28-2.59 (18H, m), 0.81 (3H, t).

Example 73

3-Butyl-4-(4-cyclohexyloxy-3-methoxy-phenyl)-6-(1-methyl-piperidin-4-yloxy)-pyridazine dihydrochloride To a stirred solution of 4-benzyloxy-3-methoxy-phenylacetic acid (10 mmol, 2.73 g), N,O-dimethylhydroxylamine hydrochloride (12 mmol, 1.17 g) and HBTU (12 mmol, 4.55 g) in DMF (20 mL), was added DIEA (24 mmol, 4.2 mL) drop-wise at room temperature and stirred for 1 hour. This was diluted with ethyl acetate and water. The organic layers were combined and concentrated under reduced pressure to get a pale-yellow solid, which was dissolved in anhydrous THF (20 mL) and cooled to 0° C. n-Butyl magnesium chloride (2.0 M solution in THF, 30 mmol, 15.0 mL) was added drop-wise. The reaction mixture was warmed to room temperature and stirred for 3 hours. It was then poured into ice-water, quenched with 1.0 N HCl, extracted with ethyl acetate/water. The organic layers were combined and condensed. The resultant residue was dissolved in THF (10 mL), a solution of ethyl glyoxalate (50% in toluene, 30 mmol, 6.2 mL) and triethylamine (4.3 mL) was added and the mixture was stirred at room temperature for 16 hours. The reaction mixture was diluted with ethyl acetate and water. The organic layers were combined and concentrated under reduced pressure. The resultant residue in acetic acid (20 mL) was added hydrazine hydrate (10 mL) heated at 120° C. for 4 h. The reaction mixture was then diluted with ethyl acetate and water. The organic layers were combined and concentrated under reduced pressure. The resultant residue in phosphorus (V) oxychloride (10 mL) was kept stirring at 70° C. for 2 h. The reaction mixture was added ice (100 g) and quenched slowly with NaHCO$_3$. This was extracted with ethyl acetate and the combined organic layers were concentrated under reduced pressure. The resultant residue was purified by silica gel flash chromatography using a mixture of hexanes in ethyl acetate (9:1) to yield 4-(4-benzyloxy-3-methoxy-phenyl)-3-butyl-6-chloro-pyridazine (804 mg).

To a stirred solution of 4-hydroxy-piperidine-1-carboxylic acid tert-butyl ester (3.0 mmol, 604 mg) in THF (10 mL) at 0° C., NaH (60% dispersion in mineral oil, 4.0 mmol, 160 mg) was added and stirring continued for 10 min at room temperature, then 4-(4-benzyloxy-3-methoxy-phenyl)-3-butyl-6-chloro-pyridazine (2.0 mmol, 766 mg) was added. The resulting mixture was stirred at 50° C. for 1 hour, poured into ice-water and extracted with ethyl acetate. The organic layers were combined and concentrated under reduced pressure. The product was purified by column chromatography using 50% ethyl acetate in hexanes to give 4-[5-(4-benzyloxy-3-methoxy-phenyl)-6-butyl-pyridazin-3-yloxy]-piperidine-1-carboxylic acid tert-butyl ester, which was dissolved in dichloromethane (2.0 mL), added 4.0 M HCl in dioxane (2.0 mL) and stirred at room temperature for 1 hour. Solvents were evaporated in vacuo to give 4-(4-benzyloxy-3-methoxy-phenyl)-3-butyl-6-(piperidin-4-yloxy)-pyridazine dihydrochloride (635 mg).

To a solution of 4-(4-benzyloxy-3-methoxy-phenyl)-3-butyl-6-(piperidin-4-yloxy)-pyridazine dihydrochloride (1.0 mmol, 520 mg) in dichloromethane (5.0 mL) was added formaldehyde solution in water (37%, 10 mmol, 1.0 mL), and 2 drops of acetic acid. Then sodium triacetoxyborohydride (4.0 mmol, 848 mg) was added. And the mixture was stirred at room temperature for 0.5 hour then condensed. It was then diluted with water/EtOAc and neutralized with NaHCO$_3$ powder. The solvent was removed in vacuo and the residue was purified by silica gel chromatography (DCM to DCM+10% 2N NH$_3$ in MeOH) to give a colorless sticky solid, which was dissolved in DCM (5.0 mL), 2N HCl in ether (5.0 mL) was added, kept at room temperature for 10 min, condensed, triturated with hexanes to afford 4-(4-benzyloxy-3-methoxy-phenyl)-3-butyl-6-(1-methyl-piperidin-4-yloxy)-pyridazine dihydrochloride (444 mg).

To a solution of 4-(4-benzyloxy-3-methoxy-phenyl)-3-butyl-6-(1-methyl-piperidin-4-yloxy)-pyridazine (1.0 mmol, 462 mg) in methanol/ethyl acetate (10 mL, 1/1) was added 10% palladium on activated carbon (70 mg). The mixture was repeatedly de-gassed under vacuum, filled with hydrogen for 3 times. Then hydrogen balloons were attached to the reaction, which was stirred at room temperature for 2 hours. TLC/LCMS monitored to completion. The mixture was then filtered through celite, the celite cake was washed with 1/1 methanol/ethyl acetate for 3 times, and the organic layers were combined and condensed under reduced pressure to give 4-[3-butyl-6-(1-methyl-piperidin-4-yloxy)-pyridazin-4-yl]-2-methoxy-phenol as a white powder (327 mg), which was used directly in the next step.

To a solution of 4-[3-butyl-6-(1-methyl-piperidin-4-yloxy)-pyridazin-4-yl]-2-methoxy-phenol (1.0 mmol, 371 mg) in dry THF (3.0 mL) was added cyclohexanol (3.0 mmol, 317 µL) and triphenylphosphine (3.0 mmol, 787 mg). While sonicating, diisopropyl azodicarboxylate (3.0 mmol, 591 µL) was added. And the mixture was sonicated for another 1 hour then condensed. The residue was purified by silica gel chromatography (DCM to DCM+10% MeOH) to afford a colorless sticky solid, which was dissolved in DCM (5.0 mL), 2N HCl in ether (5.0 mL) was added, condensed, triturated with hexanes to provide the title compound (332 mg). LCMS: m/z 455 [M+1]. $^1$H NMR (400 MHz, CD$_3$OD): δ 7.09 (1H, d), 6.98-7.03 (2H, m), 6.90-6.93 (1H, m), 5.45 (1H, bs), 4.30-4.38 (1H, m), 3.85 (3H, s), 3.10-3.37 (4H, m), 2.90-2.96 (2H, m), 2.79 (3H, s), 2.10-2.35 (4H, m), 1.96-2.03 (2H, m), 1.80-1.87 (2H, m), 1.31-1.63 (8H, m), 1.20-1.29 (2H, m), 0.80 (3H, t).

Example 74

5-[3-Butyl-6-(1-methyl-piperidin-4-yloxy)-pyridazin-4-yl]-2-cyclohexyloxy-phenol dihydrochloride To a stirred solution of 3-butyl-4-(4-cyclohexyloxy-3-methoxy-phenyl)-6-(1-methyl-piperidin-4-yloxy)-pyridazine dihydrochloride (Example 73, 0.2 mmol, 104 mg) in dry DMF (2.0 mL), sodium thiomethoxide (1.0 mmol, 70 mg) was added and the resulting mixture was stirred at 100° C. for 2 hours. At completion, it was poured into water and extracted with ethyl acetate. The solvent was removed in vacuo and the residue was purified by silica gel chromatography (DCM to DCM+10% 2N NH$_3$ in MeOH) to give a colorless sticky solid, which was dissolved in DCM (1.0 mL), 2N HCl in ether (1.0 mL) was added, kept at room temperature for 10 min, condensed, triturated with hexanes to provide the title compound (73 mg). LCMS: m/z 441 [M+1]. $^1$H NMR (400 MHz, CD$_3$OD): δ 7.10 (1H, d), 6.98-7.03 (2H, m), 6.90-6.93 (1H, m), 5.46 (1H, bs), 4.31-4.38 (1H, m), 3.11-3.37 (4H, m), 2.91-2.96 (2H, m), 2.79 (3H, s), 2.11-2.36 (4H, m), 1.97-2.03 (2H, m), 1.80-1.86 (2H, m), 1.32-1.63 (8H, m), 1.20-1.29 (2H, m), 0.80 (3H, t).

Example 75

3-Butyl-4-[4-cyclohexyloxy-3-(1,1-dioxo-1lambda*6*-isothiazolidin-2-yl)-phenyl]-6-(1-methyl-piperidin-4-yloxy)-pyridazine dihydrochloride To a solution of 5-[3-butyl-6-(1-methyl-piperidin-4-yloxy)-pyridazin-4-yl]-2-cyclohexyloxy-phenylamine (Example 62, 0.2 mmol, 88 mg) in dry DCM (1.0 mL) was added 3-chloropropanesulfonyl chloride (0.4 mmol, 71 mg), DIEA (0.4 mmol, 70 µL), and DMAP (10 mg). And the mixture was stirred at room temperature for 1 hour then condensed. It was then diluted with water/EtOAc. The solvent was removed in vacuo and dried under vacuum over night. The residue was dissolved in dry THF (1.0 mL) at 0° C., NaH (60% dispersion in mineral oil, 0.8 mmol, 32 mg) was added and the mixture was heated at 50° C. for 4 hours. It was then poured into ice-water and extracted with ethyl acetate. The organic layers combined, condensed and the residue was purified by silica gel chromatography (DCM to DCM+10% 2N $NH_3$ in MeOH) to give a colorless sticky solid, which was dissolved in DCM (1.0 mL), 2N HCl in ether (1.0 mL) was added, kept at room temperature for 10 min, condensed, triturated with hexanes to provide the title compound (35 mg). LCMS: m/z 544 [M+1]. $^1$H NMR (400 MHz, $CD_3OD$): δ 7.70 and 7.81 (1H, s), 7.01-7.12 (3H, m), 5.37-5.56 (1H, m), 4.52-4.58 (1H, m), 3.21-3.69 (8H, m), 3.06-3.13 (2H, m), 2.93 (3H, s), 1.92-2.59 (8H, m), 1.27-1.82 (12H, m), 0.80 (3H, t).

Example 76

3-Butyl-4-[4-cyclohexyloxy-3-(4,4-dimethyl-4,5-dihydro-oxazol-2-yl)-phenyl]-6-(1-methyl-piperidin-4-yloxy)-pyridazine 2 N aq. lithium hydroxide solution (2.5 mmol, 1.25 mL) was added to a solution of 5-[3-butyl-6-(1-methyl-piperidin-4-yloxy)-pyridazin-4-yl]-2-cyclohexyloxy-benzoic acid methyl ester (Example 71, 0.615 mmol, 296 mg) in THF (5 mL) and MeOH (1.25 mL). It was stirred overnight. Aq. HCl solution was added to adjust pH to neutral. The reaction mixture was partitioned between DCM (20 mL) and water (20 mL). The DCM layer was separated and dried over sodium sulfate. The organic solvents were removed in vacuo to give 5-[3-butyl-6-(1-methyl-piperidin-4-yloxy)-pyridazin-4-yl]-2-cyclohexyloxy-benzoic acid.

To a solution of 5-[3-butyl-6-(1-methyl-piperidin-4-yloxy)-pyridazin-4-yl]-2-cyclohexyloxy-benzoic acid (0.203 mmol, 94.9 mg), HBTU (0.203 mmol, 79.3 mg), diisopropyl ethyl amine (0.34 mmol, 0.0592 mL) in DMF (1 mL) was added 2-amino-2-methyl-propan-1-ol (0.45 mmol, 42.2 mg). It was stirred at room temperature for 20 min. The reaction mixture was partitioned between ethyl acetate (12 mL) and saturated aq. sodium bicarbonate solution (12 mL). The ethyl acetate layer was washed again with saturated aq. sodium bicarbonate solution (2×12 mL) and dried over sodium sulfate. The organic solvents were removed in vacuo to give 5-[3-butyl-6-(1-methyl-piperidin-4-yloxy)-pyridazin-4-yl]-2-cyclohexyloxy-N-(2-hydroxy-1,1-dimethyl-ethyl)-benzamide (87.7 mg).

A mixture of 5-[3-butyl-6-(1-methyl-piperidin-4-yloxy)-pyridazin-4-yl]-2-cyclohexyloxy-N-(2-hydroxy-1,1-dimethyl-ethyl)-benzamide (0.163 mmol, 87.7 mg), copper(II) trifluoromethanesulfonate (0.01 mmol, 3.6 mg), N,N'-diisopropylcarbodiimide (0.163 mmol, 20.6 mg) and dioxane (1 mL) was heated at 100° C. for 1 h. Copper(II) trifluoromethanesulfonate (0.01 mmol, 3.6 mg) and N,N'-diisopropylcarbodiimide (0.163 mmol, 20.6 mg) were added again and the reaction mixture was heated at 100° C. for another 1 h. The crude material was purified by column chromatography on basic alumina using 10-80% ethyl acetate in DCM to provide 3-butyl-4-[4-cyclohexyloxy-3-(4,4-dimethyl-4,5-dihydro-oxazol-2-yl)-phenyl]-6-(1-methyl-piperidin-4-yloxy)-pyridazine (50.4 mg). LCMS: m/z 522 [M+1] $^1$H NMR (400 MHz, $CDCl_3$) δ 7.61 (1H, s), 7.31 (1H, d), 7.05 (1H, dd), 6.79 (1H, d), 5.39 (1H, bs), 4.41 (1H, bs), 4.18 (4H, bs), 4.11 (3H, s), 3.41-3.97 (6H, m), 1.13-2.89 (22H, m), 0.84 (3H, t).

Example 77

1-tert-Butyl-3-{5-[3-butyl-6-(1-methyl-piperidin-4-yloxy)-pyridazin-4-yl]-2-cyclohexyloxy-phenyl}-urea dihydrochloride To a solution of 5-[3-butyl-6-(1-methyl-piperidin-4-yloxy)-pyridazin-4-yl]-2-cyclohexyloxy-phenylamine (Example 62, 0.5 mmol, 219 mg) in dry THF (1.0 mL) was added tert-butyl isocyanate (1.5 mmol, 149 mg), and the mixture was stirred at room temperature over night. It was then condensed in vacuo and the residue was purified by silica gel chromatography (DCM to DCM+10% 2N $NH_3$ in MeOH) to give a colorless sticky solid, which was dissolved in DCM (5.0 mL), 2N HCl in ether (5.0 mL) was added, kept at room temperature for 10 min, condensed, triturated with hexanes to provide the title compound (193 mg). LCMS: m/z 539 [M+1]. $^1$H NMR (400 MHz, $CD_3OD$): δ 8.09-8.12 (1H, m), 7.55 and 7.65 (1H, s), 7.12-7.18 (1H, m), 7.00-7.08 (1H, m), 5.36-5.56 (1H, m), 4.41-4.48 (1H, m), 3.25-3.67 (4H, m), 3.08-3.15 (2H, m), 2.93 (3H, s), 2.02-2.58 (6H, m), 1.83-1.89 (2H, m), 1.40-1.70 (8H, m), 1.38 (9H, s), 1.26-1.36 (2H, m), 0.83 (3H, t).

Example 78

3-Butyl-4-{4-cyclohexyloxy-3-[1-(2-methoxy-ethyl)-1H-pyrazol-4-yl]-phenyl}-6-(1-methyl-piperidin-4-yloxy)-pyridazine dihydrochloride A mixture of 4-[5-(3-bromo-4-cyclohexyloxy-phenyl)-6-butyl-pyridazin-3-yloxy]-piperidine-1-carboxylic acid tert-butyl ester (Example 65, 0.2 mmol, 118 mg), 4-(4,4,5,5-tetramethyl-[1,3,2]dioxaborolan-2-yl)-1H-pyrazole (0.3 mmol, 60 mg, 98%), tetrakis(triphenylphosphine)palladium (0) (0.01 mmol, 11.6 mg), 2 N aq. sodium carbonate solution (0.5 mL) and DME (1 mL) was heated at 80° C. for 7 h and at 90° C. for 2 h. 4-(4,4,5,5-Tetramethyl-[1,3,2]dioxaborolan-2-yl)-1H-pyrazole (0.3 mmol, 60 mg, 98%), tetrakis(triphenylphosphine)palladium(0) (0.01 mmol, 11.6 mg), 2 N aq. sodium carbonate solution (0.5 mL) and DME (1 mL) were added again and it was heated at 85° C. for 1.5 h. The reaction mixture was partitioned between ethyl acetate (15 mL) and saturated aq. sodium bicarbonate solution (15 mL). The ethyl acetate layer was dried over sodium sulfate. Purification by column chromatography on silica gel using ethyl acetate/hexanes 1:3 to 3:1 gave 4-{6-butyl-5-[4-cyclohexyloxy-3-(1H-pyrazol-4-yl)-phenyl]-pyridazin-3-yloxy}-piperidine-1-carboxylic acid tert-butyl ester (21.4 mg, 19% yield).

A mixture of 4-{6-butyl-5-[4-cyclohexyloxy-3-(1H-pyrazol-4-yl)-phenyl]-pyridazin-3-yloxy}-piperidine-1-carboxylic acid tert-butyl ester (0.14 mmol, 80.6 mg), potassium tert-butoxide (0.15 mmol, 17.2 mg, 98%) and THF (1 mL) was stirred at room temperature for 40 min. 1-Bromo-2-methoxy-ethane (0.17 mmol, 0.016 mL) was added and it was stirred for 2.5 h. More potassium tert-butoxide (0.30 mmol, 34.4 mg, 98%) was added and after stirring for 30 min, more 1-bromo-2-methoxy-ethane (0.34 mmol, 0.032 mL) was added. It was stirred overnight. The reaction mixture was partitioned between ethyl acetate (10 mL) and saturated aq. sodium bicarbonate solution (10 mL). The ethyl acetate layer was dried over sodium sulfate. Purification by column chromatography on silica gel using 20-100% ethyl acetate in hexanes to provide 4-(6-butyl-5-{4-cyclohexyloxy-3-[1-(2-methoxy-ethyl)-1H-pyrazol-4-yl]-phenyl}-pyridazin-3-yloxy)-piperidine-1-carboxylic acid tert-butyl ester as colorless solid (59.5 mg).

To a solution of 4-(6-butyl-5-{4-cyclohexyloxy-3-[1-(2-methoxy-ethyl)-1H-pyrazol-4-yl]-phenyl}-pyridazin-3-yloxy)-piperidine-1-carboxylic acid tert-butyl ester (0.107 mmol, 68 mg) in DCM (1.5 mL) was added 4 N HCl in dioxane (0.5 mL) and the reaction mixture was stirred for 40 min. The organic solvents were removed in vacuo and the residue was triturated with anhydrous diethyl ether. The yellow solid was dried overnight under high vacuum to give 3-butyl-4-{4-cyclohexyloxy-3-[1-(2-methoxy-ethyl)-1H-pyrazol-4-yl]-phenyl}-6-(piperidin-4-yloxy)-pyridazine dihydrochloride (59.5 mg).

To a mixture of 3-butyl-4-{4-cyclohexyloxy-3-[1-(2-methoxy-ethyl)-1H-pyrazol-4-yl]-phenyl}-6-(piperidin-4-yloxy)-pyridazine dihydrochloride (0.0776 mmol, 49.9 mg) in DCM (1 mL) was added formaldehyde solution in water (37%, 0.23 mmol, 0.017 mL), and 1 drop of acetic acid. Sodium triacetoxyborohydride (0.31 mmol, 69.2 mg, 95%) was added. The reaction mixture was stirred at room temperature for 1 h and partitioned between ethyl acetate (10 mL) and saturated aq. sodium bicarbonate solution (10 mL). The ethyl acetate layer was separated and dried over sodium sulfate. The crude product was purified by column chromatography on basic alumina using 0-3% MeOH in DCM, dissolved in MeOH and treated with 4 N HCl in dioxane. The organic solvents were removed in vacuo and the residue was triturated with anhydrous diethyl ether. The yellow solid was dried overnight under high vacuum to provide the title compound (30.1 mg). LCMS: m/z 549 [M+1] $^1$H NMR (400 MHz, CD$_3$OD) δ 8.24-8.27 (1H, m), 8.04-8.07 (1H, m), 7.90-7.98 (1H, m), 7.78-7.83 (1H, m), 7.37-7.43 (1H, m), 7.27-7.31 (1H, m), 5.37-5.46 (1H, m), 4.59-4.62 (1H, m), 4.38 (2H, t), 3.77 (2H, t), 3.16-3.66 (9H, m), 2.95 (3H, s), 1.25-2.59 (18H, m), 0.82 (3H, t).

Example 79

3-Butyl-4-[4-cyclohexyloxy-3-(2-methyl-2H-tetrazol-5-yl)-phenyl]-6-(1-methyl-piperidin-4-yloxy)-pyridazine dihydrochloride To a solution of 4-{6-butyl-5-[4-cyclohexyloxy-3-(2-methyl-2H-tetrazol-5-yl)-phenyl]-pyridazin-3-yloxy}-piperidine-1-carboxylic acid tert-butyl ester (Example 70, 0.156 mmol, 92.1 mg) in DCM (1.5 mL) was added 4 N HCl in dioxane (0.5 mL) and the reaction mixture was stirred for 1 h. The organic solvents were removed in vacuo and the residue was triturated with anhydrous diethyl ether and hexanes. The yellow solid was dried overnight under high vacuum to give 3-butyl-4-[4-cyclohexyloxy-3-(2-methyl-2H-tetrazol-5-yl)-phenyl]-6-(piperidin-4-yloxy)-pyridazine dihydrochloride (65.8 mg).

To a solution of 3-butyl-4-[4-cyclohexyloxy-3-(2-methyl-2H-tetrazol-5-yl)-phenyl]-6-(piperidin-4-yloxy)-pyridazine dihydrochloride (0.09 mmol, 50.6 mg) in DCM (1 mL) was added formaldehyde solution in water (37%, 0.27 mmol, 0.020 mL) and 1 drop of acetic acid. Sodium triacetoxyborohydride (0.36 mmol, 80.3 mg, 95%) was added. The reaction mixture was stirred at room temperature for 1.5 h and partitioned between ethyl acetate (10 mL) and saturated aq. sodium bicarbonate solution (10 mL). The ethyl acetate layer was separated and dried over sodium sulfate. The crude product was purified by column chromatography on silica gel using 2 M ammonia in MeOH/DCM 1:19 to 1:14, dissolved in MeOH and treated with 4 N HCl in dioxane. The organic solvents were removed in vacuo and the residue was triturated with anhydrous diethyl ether. The light yellow solid was dried overnight under high vacuum to provide the title compound (41.2 mg). LCMS: m/z 508 [M+1] $^1$H NMR (400 MHz, CD$_3$OD) δ 8.00 and 8.03 (1H, d), 7.77-7.86 (1H, m), 7.63-7.69 (1H, m), 7.39-7.43 (1H, m), 5.38-5.56 (1H, m), 4.65-4.68 (1H, m), 4.44 and 4.44 (3H, s), 3.13-3.69 (6H, m), 2.94 (3H, s), 1.29-2.58 (18H, m), 0.82 (3H, t).

Example 80

5-(4-Benzyloxy-phenyl)-6-butyl-pyridazine-3-carboxylic acid (1-methyl-piperidin-4-yl)-amide dihydrochloride

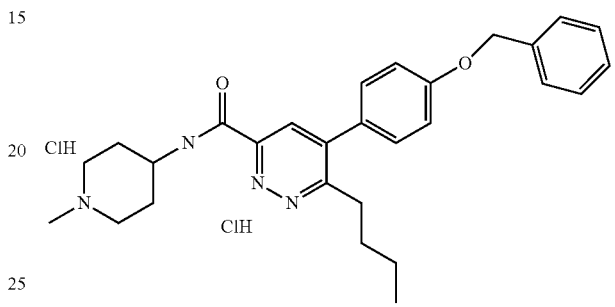

A 5.0 mL vial was charged with 4-(4-benzyloxy-phenyl)-3-butyl-6-chloro-pyridazine (Example 1, 0.3 g, 0.85 mmol), 4-amino-piperidine-1-carboxylic acid tert-butyl ester (0.51 g, 2.5 mmol), Mo(CO)$_6$ (0.22 g, 0.85 mmol), (trans-di-μ-acetobis[2-(di-o-tolylphosphino)benzyl]dipalladium(II) (0.08 g, 0.085 mmol) and THF (3.0 mL). DBU (0.16 g, 1.06 mmol) was added, and the vial was immediately sealed. The reaction mixture was then exposed to microwave heating for 15 min at a pre-selected maximum temperature of 150° C. The reaction was thereafter cooled to room temperature. The mixture was filtered through a small plug of celite, and the plug was washed with DCM. The combined fractions were evaporated under reduced pressure, and the crude product was purified by column chromatography (silica gel) eluting first with DCM and then 5% methanol in DCM. The combined fractions were evaporated and purified by column chromatography (silica gel) eluting with 30% ethyl acetate in hexane to get 4-{[5-(4-benzyloxy-phenyl)-6-butyl-pyridazine-3-carbonyl]-amino}-piperidine-1-carboxylic acid tert-butyl ester (0.120 g). LCMS: m/z 546.4 [M+2].

To a stirring solution of the tert-butyl ester (0.12 g, 0.22 mmol) in DCM, 2.0 mL of 4.0 M HCl in dioxane was added and stirring continued for 30 min. The solvent was evaporated, and the resulting solid was washed with ether, dried to provide 5-(4-benzyloxy-phenyl)-6-butyl-pyridazine-3-carboxylic acid piperidin-4-ylamide dihydrochloride salt (0.1 g) LCMS: m/z 446.4 [M+2].

A solution of 5-(4-benzyloxy-phenyl)-6-butyl-pyridazine-3-carboxylic acid piperidin-4-ylamide dihydrochloride salt (0.096 mmol, 50 mg) and paraformaldehyde (0.96 mmol, 87 mg) in DCM was stirred for 20 min, and then sodium triacetoxyborohydride (0.96 mmol, 204 mg) was added, and stirring continued over night. The solvent was evaporated and to the residue was added saturated NaHCO$_3$ solution, and extracted with ethyl acetate. The organic layer was washed with water, brine, dried (Na$_2$SO$_4$), filtered, and concentrated under reduced pressure. The resultant product was purified by column chromatography using 5% methanolic solution of ammonia (2.0 M ammonia in methanol) in DCM to provide 5-(4-benzyloxy-phenyl)-6-butyl-pyridazine-3-carboxylic acid (1-methyl-piperidin-4-yl)-amide LCMS: m/z 460.3 [M+2].

The amide was dissolved in 4.0 M HCl in dioxane, and the solvent was evaporated. The resultant salt was washed with ether and dried to provide the title compound (30 mg). LCMS: m/z 460.3 [M+1]. $^1$H NMR (400 MHz, CD$_3$OD) δ 8.23 (1H, s), 7.43-7.47 (4H, m), 7.36-7.40 (2H, m), 7.30-7.34 (1H, m), 7.18 (2H, d), 5.18 (2H, S), 4.21-4.27 (1H, m), 3.59 (2H, d), 3.15-3.25 (4H, m), 2.90 (3H, s), 2.25 (2H, d), 1.99-2.09 (2H, m), 1.57-1.65 (2H, m),1.24-1.33 (2H, m), 0.82 (3H, t).

Example 81

5-(4-Benzyloxy-phenyl)-6-butyl-pyridazine-3-carboxylic acid (1-methyl-piperidin-4-ylmethyl)-amide dihydrochloride The title compound may be prepared in a manner similar to that used to prepare Example 80 by substituting 4-aminomethyl-piperidine-1-carboxylic acid tert-butyl ester for 4-amino-piperidine-1-carboxylic acid tert-butyl ester.
LCMS: m/z 474.4 [M+2]. $^1$H NMR (400 MHz, CD$_3$OD) δ 8.38 (1H, s), 7.46-7.49 (4H, m), 7.36-7.40 (2H, m), 7.30-7.34 (1H, m), 7.20 (2H, d), 5.18 (2H, S), 3.52 (2H, d), 3.43 (2H, d), 3.19-3.24 (2H, m), 3.03 (2H, t), 2.91 (3H, s), 2.00-2.07 (3H, m), 1.57-1.64 (4H, m),1.27-1.34 (2H, m), 0.83 (3H, t).

Example 82

5-(4-Benzyloxy-phenyl)-6-butyl-pyridazine-3-carboxylic acid (S)-(1-aza-bicyclo[2.2.2]oct-3-yl)-amide dihydrochloride The title compound may be prepared in a manner similar to that used to prepare Example 80 by substituting (S)-(−)-3-aminoquinuclidine dihydrochloride for 4-amino-piperidine-1-carboxylic acid tert-butyl ester.
LCMS: m/z 472.5 [M+2].

Example 83

5-(4-Benzyloxy-phenyl)-6-butyl-pyridazine-3-carboxylic acid (R)-(1-aza-bicyclo[2.2.2]oct-3-yl)-amide dihydrochloride The title compound may be prepared in a manner similar to that used to prepare Example 80 by substituting (R)-(−)-3-aminoquinuclidine dihydrochloride for 4-amino-piperidine-1-carboxylic acid tert-butyl ester.
LCMS: m/z 472.4 [M+2]. $^1$H NMR (400 MHz, CD$_3$OD) δ 8.59 (1H, s), 7.54 (2H, d), 7.46-7.48 (2H, m), 7.36-7.40 (2H, m), 7.30-7.34 (1H, m), 7.23 (2H, d), 5.20 (2H, S), 4.57-4.62 (1H, m), 3.84 (1H, t), 3.48-3.57 (3H, m), 3.34-3.42 (3H, m) 2.39-2.42 (1H, m), 2.20-2.40 (1H, m), 2.09-2.14 (2H, m), 1.95 (2H, t), 1.71-1.79 (1H, m), 1.56-1.66 (2H, m), 1.27-1.36 (2H, m), 0.83 (3H, t).

Example 84

6-Butyl-5-(4-cyclohexyloxy-phenyl)-pyridazine-3-carboxylic acid (1-methyl-piperidin-4-yl)-amide dihydrochloride The title compound may be prepared in a manner similar to that used to prepare Example 80 by substituting 3-butyl-6-chloro-4-(4-cyclohexyloxy-phenyl)-pyridazine for 4-(4-benzyloxy-phenyl)-3-butyl-6-chloro-pyridazine.
LCMS: m/z 451.0 [M+1]. $^1$H NMR (400 MHz, CD$_3$OD) δ 8.36 (1H, s), 7.44 (2H, d), 7.10 (2H, d), 4.41-4.47 (1H, m), 4.22-4.28 (1H, m), 3.60 (2H, d), 3.17-3.24 (4H, m), 2.90 (3H, s), 2.24 (2H, d) 1.98-2.11 (4H, m), 1.80-1.83 (2H, m), 1.26-1.66 (10H, m), 0.84 (3H, t).

Example 85

(S)-6-Butyl-5-(4-cyclohexyloxy-phenyl)-pyridazine-3-carboxylic acid (1-aza-bicyclo[2.2.2]oct-3-yl)-amide dihydrochloride A mixture of 6-butyl-5-(4-cyclohexyloxy-phenyl)-pyridazine-3-carboxylic acid (Example 93, 0.14 mmol, 50 mg), HBTU (0.18 mmol, 70 mg), DIEA (0.7 mmol, 120 µL) in DMF was stirred for 5 min. (S)-Aminoquinuclidine dihydrochloride (0.37 mmol, 75 mg) was added, and the mixture was stirred for 2 h. Following addition of water, the mixture was extracted with EtOAc. The organic layer was dried (Na$_2$SO$_4$), filtered, and concentrated under reduced pressure. The residue was purified by silica gel column 3%-5% (2M, NH3 in MeOH) in DCM to provide S-6-butyl-5-(4-cyclohexyloxy-phenyl)-pyridazine-3-carboxylic acid (1-aza-bicyclo[2.2.2]oct-3-yl)amide, which was converted to the dihydrochloride salt (25 mg) by treating with HCl (0.5 mL, 4N in dioxane) in DCM (2 mL). All volatiles were removed under reduced pressure and residue was washed with anhydrous diethyl ether, dried in vacuum to provide the title compound (23 mg).
$^1$H NMR (400 MHz, CDCl$_3$) δ 8.46 (1H, d), 8.08 (1H, s), 7.27 (2H, d), 7.01 (2H, d), 4.16-4.38 (2H, m), 3.39-3.51 (1H, m), 3.08 (2H, t) 2.63-3.02 (5H, m), 1.25-2.12 (19H, m), 0.87 (3H, t).

Example 86

(R)-6-Butyl-5-(4-cyclohexyloxy-phenyl)-pyridazine-3-carboxylic acid (1-aza-bicyclo[2.2.2]oct-3-yl)-amide dihydrochloride The title compound may be prepared in a manner similar to that used to prepare Example 85 by substituting (R)-aminoquinuclidine dihydrochloride for (S)-aminoquinuclidine dihydrochloride.
$^1$H NMR (400 MHz, CDCl$_3$) δ 8.46 (1H, d), 8.08 (1H, s), 7.27 (2H, d), 7.01 (2H, d), 4.16-4.38 (2H, m), 3.39-3.51 (1H, m), 3.08 (2H, t) 2.63-3.02 (5H, m), 1.25-2.12 (19H, m), 0.87 (3H, t).

Example 87

6-Butyl-5-(4-cyclohexyloxy-phenyl)-pyridazine-3-carboxylic acid ((S)-3-dimethylamino-2-hydroxy-propyl)-amide dihydrochloride To a mixture of 6-butyl-5-(4-cyclohexyloxy-phenyl)-pyridazine-3-carboxylic acid (Example 93, 0.34 mmol, 0.12 g), HBTU (0.34 mmol, 0.13 g) and (S)-5-aminomethyl-2,2-dimethyl-oxazolidine-3-carboxylic acid tert-butyl ester (0.34 mmol, 0.05 mL) in DMF was added DIEA (1.0 mmol, 0.17 mL). Upon completion of the reaction, the mixture was diluted with ether, and then poured into water. The resulting mixture was extracted, the organic layer was dried. The solvent was removed, and the resulting residue was chromatographed with 4:1 hexane/EtOAc to provide (S)-5-({[6-butyl- 5-(4-cyclohexyloxy-phenyl)-pyridazine-3-carbonyl]-amino}-methyl)-2,2-dimethyl-oxazolidine-3-carboxylic acid tert-butyl ester was used as is in the next step. LCMS: m/z 566.9 [M+1].

A mixture of the oxazolidine and 3 mL of 4.0 M HCl in dioxane in 1 mL of DCM and 0.5 mL of water was stirred at room temperature for 3 h. The solvent was removed, and the resulting 6-butyl-5-(4-cyclohexyloxy-phenyl)-pyridazine-3-carboxylic acid ((R)-3-amino-2-hydroxy-propyl)-amide dihydrochloride was used directly in the next step. LCMS: m/z 426.9[M+1].

A mixture of the above 6-butyl-5-(4-cyclohexyloxy-phenyl)-pyridazine-3-carboxylic acid ((R)-3-amino-2-hydroxy-propyl)-amide dihydrochloride, and 1 mL of 37% formaldehyde in 3 mL of DCM was stirred at room temperature for 10 min, followed by addition of sodium triacetoxyborohydride (3.3 mmol, 0.7 mg). Upon completion, the reaction was quenched with 10% $Na_2CO_3$ solution, extracted, and the organic layer separated and dried. Removal of the solvent afforded the residue which was chromatographed with 4% methanolic solution of ammonia (2.0 M ammonia in methanol) in EtOAc to provide 6-butyl-5-(4-cyclohexyloxy-phenyl)-pyridazine-3-carboxylic acid ((S)-3-dimethylamino-2-hydroxy-propyl)-amide. The corresponding dihydrochloride was formed from HCl solution. LCMS: m/z 455.0 [M+1]. $^1$H NMR (400 MHz, $CD_3OD$) δ 8.22 (1H, s), 7.42 (2H, d), 7.09 (2H, d), 4.46-4.42 (1H, m), 4.26-4.20 (1H, m), 3.62-3.57 (2H, m), 3.30-3.18 (4H, m), 2.94 (3H, s), 2.92 (3H, s), 2.06-2.00 (2H, m), 1.88-1.80 (2H, m), 1.64-1.27 (10H, m), 0.84 (3H, t).

Example 88

6-Butyl-5-(4-cyclohexyloxy-phenyl)-pyridazine-3-carboxylic acid ((R)-3-dimethylamino-2-hydroxy-propyl)-amide dihydrochloride The title compound may be prepared in a manner similar to that used to prepare Example 87 by substituting (R)-5-aminomethyl-2,2-dimethylamino-2,2-dimethyl-oxazolidine-3-carboxylic acid tert-butyl ester for (S)-5-aminomethyl-2,2-dimethyl-oxazolidine-3-carboxylic acid tert-butyl ester.

LCMS: m/z 455.0 [M+1]. $^1$H NMR (400 MHz, $CD_3OD$) δ 8.22 (1H, s), 7.42 (2H, d), 7.11 (2H, d), 4.46-4.40 (1H, m), 4.26-4.20 (1H, m), 3.62-3.58 (2H, m), 3.28-3.18 (4H, m), 2.94 (3H, s), 2.92 (3H, s), 2.04-2.00 (2H, m), 1.86-1.78 (2H, m), 1.63-1.27 (10H, m), 0.84 (3H, t).

Example 89

6-Butyl-5-(4-cyclohexyloxy-phenyl)-pyridazine-3-carboxylic acid (4-methoxy-1-methyl-piperidin-4-ylmethyl)-amide dihydrochloride The title compound may be prepared in a manner similar to that used to prepare Example 87 by substituting 4-aminomethyl-4-methoxy-piperidine-1-carboxylic acid 9H-fluoren-9-ylmethyl ester hydrochloride for (S)-5-aminomethyl-2,2-dimethyl-oxazolidine-3-carboxylic acid tert-butyl ester.

$^1$HNMR (400 MHz, $CDCl_3$) δ 8.39 (1H, t), 8.07 (1H, s), 7.26 (2H, d), 7.00 (2H, d), 4.27-4.37 (1H, m), 3.60 (2H, d), 3.26 (3H, s), 3.07 (2H, d), 2.48-2.58 (2H, m), 2.25-2.39 (5H, m), 1.15-2.11 (18H, m), 0.87 (3H, t).

Example 90

6-Butyl-5-(4-cyclohexyloxy-phenyl)-pyridazine-3-carboxylic acid (morpholin-2-ylmethyl)-amide dihydrochloride To a stirred solution of 6-butyl-5-(4-cyclohexyloxy-phenyl)-pyridazine-3-carboxylic acid pentafluorophenyl ester (oil) in DCM was treated with 1.5 equivalent of anhydrous HCl in ether and stirred for 10 min. The volatiles were removed under reduced pressure and the resultant solid was dried under high vacuum.

To a solution of 6-butyl-5-(4-cyclohexyloxy-phenyl)-pyridazine-3-carboxylic acid pentafluorophenyl ester hydrochloride (0.18 mmol, 0.1 g, Example 90) and 0.1 mL of pyridine in 2 mL of THF was added 2-aminomethyl-morpholine-4-carboxylic acid tert-butyl ester (0.4 mmol, 0.09 g). The mixture was shaken at room temperature, and upon completion of the reaction, the solvent was removed. The residue was chromatographed with 4% methanolic solution of ammonia (2.0 M ammonia in methanol) in EtOAc to provide 2-({[6-butyl-5-(4-cyclohexyloxy-phenyl)-pyridazine-3-carbonyl]-amino}-methyl)-morpholine-4-carboxylic acid tert-butyl ester. LCMS: m/z 553.0 [M+1].

The above tert-butyl ester was treated with 2 mL of 4.0 M HCl in dioxane solution in 2 mL of DCM for 1 h afforded 6-butyl-5-(4-cyclohexyloxy-phenyl)-pyridazine-3-carboxylic acid (morpholin-2-ylmethyl)-amide dihydrochloride. LCMS: m/z 453.0 [M+1]. $^1$H NMR (400 MHz, $CD_3OD$) δ 8.33 (1H, s), 7.44 (2H, d), 7.12 (2H, d), 4.44-4.40 (1H, m), 4.12 (1H, dd), 4.02-3.98 (1H, m), 3.83 (1H, t), 3.65 (2H, d), 3.42-3.35 (1H, m), 3.26-2.22 (4H, m), 3.03-2.99 (1H, m), 2.04-2.00 (2H, m), 1.84-1.80 (2H, m), 1.64-1.28 (10H, m), 0.84 (3H, t).

Example 91

6-Butyl-5-(4-cyclohexyloxy-phenyl)-pyridazine-3-carboxylic acid ((R)-1-ethyl-pyrrolidin-2-ylmethyl)-amide dihydrochloride To a solution of 6-butyl-5-(4-cyclohexyloxy-phenyl)-pyridazine-3-carboxylic acid pentafluorophenyl ester hydrochloride (Example 90, 0.18 mmol, 0.1 g) and 0.1 mL of pyridine in 2 mL of THF was added ((R)-1-ethyl-pyrrolidin-2-yl)-methylamine (0.4 mmol, 0.05 g). The mixture was shaken at room temperature, upon completion, the solvent was removed and the residue was chromatographed with 4% methanolic solution of ammonia (2.0 M ammonia in methanol) in EtOAc afforded 6-butyl-5-(4-cyclohexyloxy-phenyl)-pyridazine-3-carboxylic acid ((R)-1-ethyl-pyrrolidin-2-ylmethyl)-amide. LCMS: m/z 464.9. $^1$H NMR (400 MHz, $CD_3OD$) δ 8.27 (1H, s), 7.42 (2H, d), 7.09 (2H, d), 4.44-4.40 (1H, m), 4.00-3.96 (1H, m), 3.80-3.68 (4H, m), 3.20-3.10 (4H, m), 2.34-2.28 (1H, m), 2.16-2.02 (5H, m), 1.84-1.80 (2H, m), 1.64-1.27 (13H. m), 0.83 (3H, t).

The amide was treated with 2 mL of 4.0 M HCl in dioxane solution in 2 mL of DCM for 1 h to provide the title compound.

Example 92

6-Butyl-5-(4-cyclohexyloxy-phenyl)-pyridazine-3-carboxylic acid ((S)-1-ethyl-pyrrolidin-2-ylmethyl)-amide dihydrochloride The title compound may be prepared in a manner similar to that used to prepare Example 91 by substituting (S)-1-ethyl-pyrrolidin-2-yl)-methylamine for (R)-1-ethyl-pyrrolidin-2-yl)-methylamine.

Example 93

6-Butyl-5-(4-cyclohexyloxy-phenyl)-pyridazine-3-carboxylic acid [2-(4-hydroxy-piperidin-1-yl)-ethyl]-amide dihydrochloride To a stirred solution of 3-butyl-6-chloro-4-(4-cyclohexyloxy-phenyl)-pyridazine (Example 14, 29 mmol, 10.0 g,) in mixture of methanol and DMF (1:1, 100 mL) was added [1,1'-bis(diphenylphosphino)ferrocene]dichloropalladium (II) PdCl$_2$ (10 mol %, 2.2 g), DPPF (10 mol %, 1.6 g) and TEA (72.5 mmol, 10 mL). The reaction was stirred at 90° C. under 40-50 psi pressure of carbon monoxide for 8 h. The solvent was removed, and the crude product was purified using hexane:ethyl acetate on a 330 g ISCO silica gel column to provide 6-butyl-5-(4-cyclohexyloxy-phenyl)-pyridazine-3-carboxylic acid methyl ester (10.0 g).

To a stirred solution of the methyl ester (24.4 mmol, 9.0 g) in methanol (30 mL) and tetrahydrofuran (100 mL) was added 1N NaOH solution (30 mL). The reaction was stirred at room temperature for 2 h. After removing the solvent at 30° C., 1N HCl (100 mL) was added, and the product was extracted with ethyl acetate to provide 6-butyl-5-(4-cyclohexyloxy-phenyl)-pyridazine-3-carboxylic acid (9.5 g).

To a stirred solution of the carboxylic acid (24.4 mmol, 8.6 g) in DCM (100 mL) was added pyridine (81 mmol, 6.4 g) followed pentafluorophenyl trifluoroacetate (40.52 mmol, 11.3 g) drop-wise. The reaction was stirred at 0° C. for 30 min and then at room temperature for 8 h. The reaction was added to 1N HCl (100 mL), and the product was extracted with ethyl acetate. The crude product was purified using a mixture of hexanes in ethyl acetate on a 330 g silica gel ISCO column to provide 6-butyl-5-(4-cyclohexyloxy-phenyl)-pyridazine-3-carboxylic acid pentafluorophenyl ester (9.0 g).

To a stirred solution of the pentafluorophenyl ester (0.18 mmol, 100 mg) in THF (2 mL) and pyridine (0.1 mL) was added 1-(2-amino-ethyl)-piperidin-4-ol (0.36 mmol, 60 mg). After stirring for 1 h, the solution was concentrated, and the residue was purified by column chromatography using 4% methanolic solution of ammonia (2.0 M ammonia in methanol) in EtOAc to provide 6-butyl-5-(4-cyclohexyloxy-phenyl)-pyridazine-3-carboxylic acid [2-(4-hydroxy-piperidin-1-yl)-ethyl]-amide. LCMS: m/z 480.9 [M+1]. $^1$H NMR (400 MHz, CD$_3$OD) δ 8.32 and 8.31 (rotamer A and B, two s, 1H), 7.45 (d, 2H), 7.12 (d, 2H), 4.39-4.49 (m, 1H), 4.06-4.12 (m, 1H), 3.84-3.93 (m, 2H), 3.73-3.83 (m, 1H), 3.52-3.62 (m, 1H), 3.34-3.48 (m, 3H), 3.17-3.25 (m, 2H), 3.05-3.17 (m, 1H), 2.11-2.22 (m, 1H), 1.89-2.09 (m, 4H), 1.70-1.88 (m, 4H), 1.24-1.69 (m, 10H), 0.84 (t, 3H).

The title compound may be prepared by treatment of the amide with a HCl dioxane solution.

Example 94

6-Butyl-5-(4-cyclohexyloxy-phenyl)-pyridazine-3-carboxylic acid (4-hydroxy-1-methyl-piperidin-4-ylmethyl)-amide dihydrochloride A mixture of 1-benzyl-piperidin-4-one (264 mmol, 50.0 g), trimethylsilyl cyanide (291 mmol, 38.75 mL) and zinc iodide (13.2 mmol, 4.2 g) was heated to 80° C. for 2 hours under an atmosphere of N$_2$. The reaction was followed by TLC. The reaction mixture was cooled to room temperature, and the crude 1-benzyl-4-hydroxy-piperidine-4-carbonitrile was added dropwise to an ice bath cooled solution of LAH (343 mmol, 13.0 g) in THF (350 mL). The reaction was stirred for 12 hours allowing it to slowly come to room temperature. The reaction was cooled in an ice bath and quenched with H$_2$O (13.5 mL), 15% NaOH (13.5 mL) and H$_2$O (40.5 mL). The reaction mixture was filtered through a pad of celite and the celite was washed with portions of diethyl ether. The filtrate was washed with brine (50 mL) and dried (Na$_2$SO$_4$). The crude product, 4-aminomethyl-1-benzyl-piperidin-4-ol (71.4 g) was used in the next step without further purification.

To a solution of 4-aminomethyl-1-benzyl-piperidin-4-ol (264 mmol, 58 g) in DCM (200 mL) and saturated NaHCO$_3$ (200 mL) was added di-tert-butylcarbonate (396 mmol, 86.4 g). The reaction mixture was stirred for 12 hours. The layers were separated and the organic layer was washed with brine (50 mL) and evaporated. The product was purified on 1 L of SiO$_2$ using a mixtures of ethyl acetate and DCM to give (1-benzyl-4-hydroxy-piperidin-4-ylmethyl)-carbamic acid tert-butyl ester (31 g).

A solution of the tert-butyl ester (96.7 mmol, 31 g) in ethyl acetate (50 mL) and MeOH (50 mL) and was treated with 10% Pd/C and pressurized to 40-48 psi of H$_2$. After completion, the reaction was filtered through a pad of celite, and the solvent was evaporated to provide (4-hydroxy-piperidin-4-ylmethyl)-carbamic acid tert-butyl ester. A solution of the tert-butyl ester (43.4 mmol, 10.0 g) in DCM (100 mL) and saturated NaHCO$_3$ (100 mL) was treated with 9-fluorenylmethyl chloroformate (65.1 mmol, 16.8 g) and the reaction was stirred for 2 h. The layers were separated, and the DCM was removed under reduced pressure. The crude product was triturated with 20% ethyl acetate in hexanes (100 mL) and filtered. The crude material was then triturated with 50% diethyl ether in hexanes to give 4-(tert-butoxycarbonylamino-methyl)-4-hydroxy-piperidine-1-carboxylic acid 9H-fluoren-9-ylmethyl ester.

A solution of 4-(tert-butoxycarbonylamino-methyl)-4-hydroxy-piperidine-1-carboxylic acid 9H-fluoren-9-ylmethyl ester (42.0 mmol, 19.0 g) in DCM (50 mL) was treated with 4 N HCl in dioxane (80 mL) and stirred for 90 minutes. The solvents were removed under reduced pressure, and the crude salt was triturated with diethyl ether, filtered, and dried to provide 4-aminomethyl-4-hydroxy-piperidine-1-carboxylic acid 9H-fluoren-9-ylmethyl ester hydrochloride.

The title compound may be prepared in a manner similar to that used to prepare Example 87 by substituting 4-aminomethyl-4-hydroxy-piperidine-1-carboxylic acid 9H-fluoren-9-ylmethyl ester hydrochloride for (S)-5-aminomethyl-2,2-dimethyl-oxazolidine-3-carboxylic acid tert-butyl ester.

$^1$H NMR (400 MHz, CDCl$_3$) δ 8.63 (1H, t), 8.07 (1H, s), 7.27 (2H, d), 7.00 (2H, d), 4.26-4.39 (1H, m), 3.60 (2H, d), 3.16 (1H, bs), 3.08 (2H, t), 2.51-2.67 (2H, m), 2.33-2.47 (2H, m), 2.30 (3H, s), 1.97-2.10 (2H, m), 1.14-1.92 (16H, m), 0.85 (3H, m).

Example 95

(±)-(cis)-6-Butyl-5-(4-cyclohexyloxy-phenyl)-pyridazine-3-carboxylic acid (4-dimethylamino-cyclohexyl)-amide dihydrochloride A mixture of 6-butyl-5-(4-cyclohexyloxy-phenyl)-pyridazine-3-carboxylic acid pentafluorophenyl ester hydrochloride (Example 90, 0.234 mmol, 130 mg), (±)-(cis)-(4-amino-cyclohexyl)-carbamic acid tert-butyl ester (0.1 mL), ethyl-diisopropyl-amine (0.3 mL) in THF (2 mL) may be stirred for 3 h. The reaction mixture may be diluted with diethyl ether, washed with water and 2 M aq. sodium hydroxide solution and dried over magnesium sulfate. Purification by column chromatography on silica gel using 10-40% ethyl acetate in hexanes provides (4-{[6-butyl-5-(4-cyclohexyloxy-phenyl)-pyridazine-3-carbonyl]-amino}-cyclohexyl)-carbamic acid tert-butyl ester.

6-Butyl-5-(4-cyclohexyloxy-phenyl)-pyridazine-3-carboxylic acid (4-amino-cyclohexyl)-amide dihydrochloride may be obtained by treating (4-{[6-butyl-5-(4-cyclohexyloxy-phenyl)-pyridazine-3-carbonyl]-amino}-cyclohexyl)-carbamic acid tert-butyl ester with 4 N HCl in dioxane.

To a solution of 6-butyl-5-(4-cyclohexyloxy-phenyl)-pyridazine-3-carboxylic acid (4-amino-cyclohexyl)-amide dihydrochloride in DCM may be added formaldehyde solution in water (37%) and sodium sulfate. After stirring for 20 min., sodium triacetoxyborohydride may be added. The reaction mixture may be stirred at room temperature for 3 h and partitioned between diethyl ether and saturated aq. sodium carbonate solution. The ethyl layer may be separated and dried over magnesium sulfate. The crude product may be purified by column chromatography on silica gel using 2-5% 2 M ammonia in MeOH in DCM and treated with 4 N HCl in dioxane. The organic solvents may be removed under reduced pressure, and the product dried overnight under high vacuum to provide to provide the free base of the title compound (30 mg). $^1$H NMR (free base, 400 MHz, CDCl$_3$) δ 8.37 (1H, d), 8.08 (1H, s), 7.27 (2H, d), 7.00 (2H, d), 4.29-4.36 (1H, m), 4.25 (1H, bs), 3.07 (2H, t), 2.29 (6H, s), 1.30-2.21 (23H, m), 0.86 (3H, t).

The title compound may be prepared by treatment of the amide with a HCl dioxane solution.

Example 96

6-Butyl-5-(4-cyclohexyloxy-phenyl)-pyridazine-3-carboxylic acid (8-methyl-8-aza-bicyclo[3.2.1]oct-3-yl)-amide dihydrochloride A mixture of 6-butyl-5-(4-cyclohexyloxy-phenyl)-pyridazine-3-carboxylic acid pentafluorophenyl ester hydrochloride (Example 90, 0.108 mmol, 60 mg), 8-methyl-8-aza-bicyclo[3.2.1]oct-3-ylamine (0.05 mL), ethyl-diisopropyl-amine (0.2 mL) in THF (2.0 mL) may be stirred at room temperature for 3 h. The reaction mixture may be diluted with diethyl ether, washed with water and 2 M aq. sodium hydroxide solution and dried over magnesium sulfate. The crude product may be purified by column chromatography on silica gel using 2-5% 2 M ammonia in MeOH in DCM and treated with 4 N HCl in dioxane. The organic solvents may be removed under reduced pressure, and the product dried overnight under high vacuum to provide the free base of the title compound. $^1$H NMR (free base, 400 MHz, CDCl$_3$) δ 8.72 (1H, d), 8.09 (1H, s), 7.27 (2H, d), 7.01 (2H, d), 4.30-4.36 (2H, m), 3.20 (2H, bs), 3.08 (2H, t), 2.32 (3H, s), 1.26-2.35 (22H, m), 0.87 (3H, t).

The title compound may be prepared by treatment of the amide with a HCl dioxane solution.

Example 97

[6-Butyl-5-(4-cyclohexyloxy-phenyl)-pyridazin-3-yl]-((S)-2-dimethylaminomethyl-morpholin-4-yl)-methanone dihydrochloride To a stirred mixture of (R)-2-hydroxymethyl-morpholine-4-carboxylic acid tert-butyl ester (25.77 mmol, 5.6 g; prepared in four steps from (R)-3-amino-propane-1,2-diol following the method described in Org. Lett. 2005, 7 (5), 937-939) and TEA (38.65 mmol, 5.2 mL) in DCM (50 mL) at 0° C. was added methanesulfonyl chloride (30.92 mmol, 2.39 mL) drop-wise, and the reaction mixture was stirred for 30 min at 0° C. The reaction mixture was diluted with DCM (50 mL), water was added (50 mL), and the mixture was stirred at room temperature for 20 min. The organic layer was separated, dried, filtered, and concentrated under reduced pressure. The residue was dissolved in DMF (50 mL) and to this was added sodium azide (6.0 g). The resultant reaction mixture was kept stirring at 80° C. for 16 h. The reaction mixture was cooled to room temperature, diluted with ether (300 mL), added water and stirred at room temperature for 30 min. The organic layer was separated, dried, filtered, and concentrated under reduced pressure. The residue was purified by flash silica gel column chromatography with 20% ethyl acetate in hexanes to provide (R)-2-azidomethyl-morpholine-4-carboxylic acid tert-butyl ester (4.6 g). $^1$H NMR (400 MHz, CDCl$_3$) δ 3.8-3.93 (3H, bm), 3.51-3.54 (2H, m), 3.26-3.34 (2H, m), 2.94 (1H, bt), 2.71 (1H, bt), 1.46 (9H, s).

To a stirred solution of (R)-2-azidomethyl-morpholine-4-carboxylic acid tert-butyl ester (0.82 mmol, 0.2 g) in DCM (2 mL) was added 4 N HCl in dioxane (4 mL) and continued stirring at ambient temperature for 45 min. The volatiles were removed under reduced pressure, and the residue was dissolved in NMP (4 mL). To this was added 6-butyl-5-(4-cyclohexyloxy-phenyl)-pyridazine-3-carboxylic acid pentafluorophenyl ester (Example 93, 0.77 mmol, 0.4 g) followed by TEA (0.5 mL) and the reaction mixture was stirred at room temperature for 30 min. The reaction mixture was diluted with ethyl acetate (20 mL) and washed with water, followed by saturated sodium bicarbonate. The organic layer was dried, filtered, and concentrated under reduced pressure. The residue was purified by flash silica gel column chromatography using ethyl 30% acetate in hexanes to provide ((R)-2-azidomethyl-morpholin-4-yl)-[6-butyl-5-(4-cyclohexyloxy-phenyl)-pyridazin-3-yl]-methanone (0.39 g).

To a stirred solution of ((R)-2-azidomethyl-morpholin-4-yl)-[6-butyl-5-(4-cyclohexyloxy-phenyl)-pyridazin-3-yl]-methanone (0.799 mmol, 0.39 g) in ethyl acetate (4 mL) was added 10% palladium on carbon (0.1 g, wet), and the resulting reaction mixture was subjected to catalytic hydrogenation using a balloon full of hydrogen for 3 h. The catalyst was filtered through a pad of celite, and the celite pad was washed with methanol. The combined filtrate was concentrated under reduced pressure. The residue was purified by flash silica gel column chromatography using ethyl acetate followed by 10% methanolic solution of ammonia (2 M ammonia in methanol) in ethyl acetate to provide ((S)-2-aminomethyl-morpholin-4-yl)-[6-butyl-5-(4-cyclohexyloxy-phenyl)-pyridazin-3-yl]-methanone (0.33 g) which was converted into dihydrochloride salt using 4 N HCl in dioxane. LCMS: m/z 452.8 [M+1]. $^1$H NMR (400 MHz, CD$_3$OD) δ 8.12 and 8.13 (1H, s), 7.46 (2H, dd), 7.12 (2H, d), 4.42-4.66 (2H, m), 3.42-4.16 (5H, m), 2.91-3.25 (5H, m), 1.99 (2H, m), 1.83 (2H, m), 1.3-1.69 (10H, m), 0.85 (3H, t)

To a stirred solution of ((S)-2-aminomethyl-morpholin-4-yl)-[6-butyl-5-(4-cyclohexyloxy-phenyl)-pyridazin-3-yl]-methanone dihydrochloride (0.495 mmol, 0.26 g) in DCM (3 mL) was added formaldehyde solution (3 mL) followed by sodium triacetoxyborohydride (0.6 g). The mixture was stirred for 16 h. The reaction mixture was diluted with DCM (5 mL), separated the organic layer, and concentrated under reduced pressure. The residue was purified by flash silica gel column chromatography by eluting with ethyl acetate (200 mL) followed by 10% methanolic solution of ammonia (2 M ammonia in methanol) in ethyl acetate to provide [6-butyl-5-(4-cyclohexyloxy-phenyl)-pyridazin-3-yl]-((S)-2-dimethylaminomethyl-morpholin-4-yl)-methanone (0.12 g) which was converted to dihydrochloride salt using 4N HCl in dioxane. LCMS: m/z 480.8 [M+1]. $^1$H NMR (400 MHz, CD$_3$OD) δ 8.34 (1H, s), 7.53 (2H, m), 7.14 (2H, d), 4.4-4.61 (2H, m), 3.83-4.15 (3H, m), 3.18-3.81 (7H, m), 2.92 (6H, m), 1.99-2.02 (2H, m), 1.82 (2H, m), 1.28-1.68 (10H, m), 0.87 (3H, t).

Example 98

[6-Butyl-5-(4-cyclohexyloxy-phenyl)-pyridazin-3-yl]-((R)-2-dimethylaminomethyl-morpholin-4-yl)-methanone dihydrochloride The title compound may be prepared in a manner similar to that used to prepare Example 97 by substituting (S)-2-hydroxymethyl-morpholine-4-carboxylic acid tert-butyl ester for (R)-2-hydroxymethyl-morpholine-4-carboxylic acid tert-butyl ester.

LCMS: m/z 480.8 [M]. $^1$H NMR (400 MHz, CD$_3$OD) δ 8.24 and 8.25 (1H, s), 7.5 (2H, m), 7.13 (2H, d), 4.2-4.69 (2H, m), 3.95-4.16 (3H, m), 3.35-3.81 (3H, m), 3.17-3.25 (4H, m), 2.97 (6H, m), 2.02 (2H, m), 1.84 (2H, m), 1.29-1.68 (10H, m), 0.87 (3H, t).

Example 99

6-Butyl-5-(4-cyclohexyloxy-phenyl)-pyridazine-3-carboxylic acid (4,4-difluoro-1-methyl-piperidin-3-ylmethyl)-amide dihydrochloride To a stirred solution of 3-azidomethyl-4-hydroxy-piperidine-1-carboxylic acid tert-butyl ester (Example 100, 2.0 mmol, 512 mg) in DCM (15 mL) was added Dess-Martin periodinane (2.4 mmol, 1.02 g). The mixture was stirred for 2.5 hr, diluted with saturated aqueous NaHCO$_3$ and extracted with DCM. The organic layer was dried over sodium sulfate, filtered, concentrated, and purified by column chromatography using 30% EtOAc in hexanes to provide 3-azidomethyl-4-oxo-cyclohexanecarboxylic acid tert-butyl ester.

To a stirred solution of 3-azidomethyl-4-oxo-cyclohexanecarboxylic acid tert-butyl ester (2.0 mmol, 500 mg) in DCM (30 mL) at 0° C. was added Deoxo-Fluor (4.2 mmol, 0.77 mL). After 0.5 hr, the solution was warmed to room temperature, stirred overnight, concentrated, and purified by column chromatography using 20% EtOAc in hexanes to provide 3-azidomethyl-4,4-difluoro-piperidine-1-carboxylic acid tert-butyl ester.

A mixture of 3-azidomethyl-4,4-difluoro-piperidine-1-carboxylic acid tert-butyl ester (1.1 mmol, 300 mg) and 10% palladium on carbon (60 mg) in EtOAc (8 mL) was stirred under an atmosphere of H$_2$ for 2 hrs, filtered through celite, and concentrated to provide 3-aminomethyl-4,4-difluoro-piperidine-1-carboxylic acid tert-butyl ester.

The title compound may be prepared in a manner similar to that used to prepare Example 95 by substituting 3-aminomethyl-4,4-difluoro-piperidine-1-carboxylic acid tert-butyl ester for (±)-(cis)-(4-amino-cyclohexyl)-carbamic acid tert-butyl ester.

LCMS: m/z 501.9 [M+2]. $^1$H NMR (400 MHz, CD$_3$OD) δ 9.41 (t, 1H), 8.46 (s, 1H), 7.48 (d, 2H), 7.14 (d, 2H), 4.42-4.50 (m, 1H), 3.85-3.94 (m, 1H), 3.71-3.81 (m, 1H), 3.58-3.69 (m, 2H), 3.18-3.36 (m, 4H), 2.95 (s, 3H), 2.79-2.94 (m, 1H), 2.27-2.54 (m, 2H), 1.97-2.07 (m, 2H), 1.77-1.88 (m, 2H), 1.25-1.67 (m, 10H), 0.84 (t, 3H).

Example 100

6-Butyl-5-(4-cyclohexyloxy-phenyl)-pyridazine-3-carboxylic acid (4-hydroxy-1-methyl-piperidin-3-ylmethyl)-amide dihydrochloride To a stirred suspension of 1-benzyl-4-oxo-piperidine-3-carboxylic acid ethyl ester hydrochloride (83.95 mmol, 25 g) in ethyl acetate (400 mL) was added saturated sodium bicarbonate solution (100 mL), and stirring was continued for 30 min. The organic layer was separated, dried, and concentrated to provide 1-benzyl-4-oxo-piperidine-3-carboxylic acid ethyl ester. The ethyl ester was dissolved in ethyl acetate (100 mL) and di-tert-butyl dicarbonate (126 mmol, 27.48 g) was added followed by 10% palladium on carbon (5 g, wet). The resultant reaction mixture was subjected to catalytic hydrogenation at 55-60 psi of hydrogen for 24 h with stirring. The catalyst was filtered through a pad of celite, and the pad was washed with ethyl acetate (200 mL). The combined filtrate was concentrated under reduced pressure. The residue was purified by flash column chromatography by eluting with ethyl acetate in hexanes (1:9) to provide 4-oxo-piperidine-1,3-dicarboxylic acid 1-tert-butyl ester 3-ethyl ester.

To a stirred solution of 4-oxo-piperidine-1,3-dicarboxylic acid 1-tert-butyl ester 3-ethyl ester (51.59 mmol, 14 g) in methanol (300 mL) was added sodium borohydride (12 g) in 12 portions over 30 min. The reaction mixture was stirred for additional 30 min, and the volatiles were removed under reduced pressure. To the residue was added saturated ammonium chloride (300 mL). The mixture was extracted with ethyl acetate (300 mL), and the organic layer was dried and concentrated under reduced pressure. The residue was purified on a flash silica gel column eluting with ethyl acetate to provide 4-hydroxy-3-hydroxymethyl-piperidine-1-carboxylic acid tert-butyl ester.

To a stirred solution of 4-hydroxy-3-hydroxymethyl-piperidine-1-carboxylic acid tert-butyl ester (13.39 mmol, 3.1 g) in DCM (30 mL) at 0° C. was added pyridine (3 mL) followed by p-toluenesulfonyl chloride (14.73 mmol, 2.81 g). The reaction mixture was stirred at ambient temperature for 14 h. The mixture was diluted with DCM (200 mL), washed with 0.5 N HCl (200 mL), and the organic layer was dried and concentrated under reduced pressure. The residue was purified by flash silica gel column chromatography eluting with 20% ethyl acetate in hexanes followed by 100% ethyl acetate to provide 4-(toluene-4-sulfonyloxy)-3-(toluene-4-sulfonyloxymethyl)-piperidine-1-carboxylic acid tert-butyl ester.

To a stirred solution of 4-hydroxy-3-(toluene-4-sulfonyloxymethyl)-piperidine-1-carboxylic acid tert-butyl ester (8.56 mmol, 3.3 g) in DMF (20 mL) was added sodium azide (35.28 mmol, 2.34 g), and the reaction mixture was stirred at 80-90° C. for 16 h. The reaction mixture was cooled to room temperature, diluted with DCM (200 mL), washed with water, and the organic layer was dried and concentrated under reduced pressure. The residue was purified by flash silica gel column chromatography by eluting with ethyl acetate in hexanes (1:1) to provide 3-azidomethyl-4-hydroxy-piperidine-1-carboxylic acid tert-butyl ester.

To a stirred solution of 3-azidomethyl-4-hydroxy-piperidine-1-carboxylic acid tert-butyl ester (0.624 mmol, 0.16 g) in ethyl acetate (5 mL) was added 10% palladium on carbon (0.1 g, wet). The resultant reaction mixture was subjected to hydrogenation using a balloon full of hydrogen for 4 h. The catalyst was filtered through a pad of celite and the filtrate was concentrated to provide 3-aminomethyl-4-hydroxy-piperidine-1-carboxylic acid tert-butyl ester.

The title compound may be prepared in a manner similar to that used to prepare Example 95 by substituting 3-aminomethyl-4-hydroxy-piperidine-1-carboxylic acid tert-butyl ester for (±)-(cis)-(4-amino-cyclohexyl)-carbamic acid tert-butyl ester.

$^1$H NMR (400 MHz, CD$_3$OD) δ 8.46 (1H, s), 7.4 (2H, m), 7.13 (2H, m), 4.4-4.46 (1H, m), 4.06 (1H, bd), 3.49-3.62 (2H, m), 2.93-3.31 (6H, m), 2.86 (3H, s), 2.33 (1H, m), 1.29-2.05 (16H, m), 0.84 (3H, t).

Example 101

6-Butyl-5-(4-cyclohexyloxy-phenyl)-pyridazine-3-carboxylic acid (4-methoxy-1-methyl-piperidin-3-ylmethyl)-amide dihydrochloride To a stirred solution of 3-azidomethyl-4-hydroxy-piperidine-1-carboxylic acid tert-butyl ester (2 mmol, 0.512 g; Example 100) in DMF (5 mL) at 0° C. was added NaH (0.1 g, 60% dispersion in mineral oil) and continued stirring at 0° C. for 20 min. To this was Iodomethane (0.5 mL) and stirred at room temperature for 20 min. The volatiles were removed under reduced pressure, residue was dissolved in ethyl acetate (10 mL), washed with water, separated the organic layer, dried and concentrated under reduced pressure. The residue was purified by flash silica gel column chromatography to get 3-azidomethyl-4-methoxy-piperidine-1-carboxylic acid tert-butyl ester (0.41 g, 76% yield).

To a stirred solution of 3-azidomethyl-4-methoxy-piperidine-1-carboxylic acid tert-butyl ester (0.74 mmol, 0.2 g) in ethyl acetate (5 mL) was added 10% palladium on carbon (0.1 g, wet), and the resultant reaction mixture was subjected to hydrogenation using a balloon full of hydrogen for 1 h. The catalyst was filtered through a pad of celite, washed the celite pad with methanol, and the combined filtrate was concentrated under reduced pressure to provide 3-aminomethyl-4-methoxy-piperidine-1-carboxylic acid tert-butyl ester.

The title compound may be prepared in a manner similar to that used to prepare Example 95 by substituting 3-aminomethyl-4-methoxy-piperidine-1-carboxylic acid tert-butyl ester for (±)-(cis)-(4-amino-cyclohexyl)-carbamic acid tert-butyl ester.

LCMS: m/z 495.9 [M+2]. $^1$H NMR (400 MHz, CD$_3$OD) δ 8.53 (1H, s), 7.5 (2H, m), 7.14 (2H, m), 4.43-4.49 (1H, m), 3.06-3.66 (10H, m), 3.42 (3H, s), 2.87 (3H, s), 2.33-2.45 (2H, m), 2.01-2.05 (2H, m), 1.79-1.86 (2H, m), 1.28-1.67 (11H, m), 0.84 (3H, t).

Example 102

(±)-cis-[6-Butyl-5-(4-cyclohexyloxy-phenyl)-pyridazin-3-yl]-((3R,4S)-4-dimethylaminomethyl-3-methoxy-piperidin-1-yl)-methanone dihydrochloride A solution of cis-4-azidomethyl-3-hydroxy-piperidine-1-carboxylic acid tert-butyl ester (1.4 mmol, 360 mg) in dichloromethane (1 mL) and 4N HCl (2 mL) was stirred at room temperature for 2 h. Solvent was evaporated to give cis-4-azidomethyl-piperidin-3-ol and was used without further purification.

To a solution of cis-4-azidomethyl-piperidin-3-ol (1.4 mmol, 272 mg) in DME (4.2 mL) was added triethylamine (5.62 mmol, 0.8 mL) and 6-butyl-5-(4cyclohexyloxy-phenyl)-pyridazine-3-carboxylic acid pentafluorophenyl ester (1.41 mmol, 785 mg). Reaction was stirred at room temperature for 3 h. Upon completion, the reaction was quenched with 0.1 N NaOH (40 mL), extracted, dried and removal of solvent afforded the residue which was chromatographed with hexane:EtOAc gradient to afforded (+)-cis-4-azidomethyl-3-hydroxy-piperidin-1-yl)-[6-butyl-5-(4-cyclohexyloxy-phenyl)-pyridazin-3-yl]-methanone (180 mg, 25% yield).

To a stirred solution of (±)-cis-(4-azidomethyl-3-hydroxy-piperidin-1-yl)-[6-butyl-5-(4-cyclohexyloxy-phenyl)-pyridazin-3-yl]-methanone (0.36 mmol, 180 mg) in dimethylformamide (1 mL) was added sodium hydride (0.5 mmol, 20 mg) and iodomethane (0.54 mmol, 0.033 mL). The reaction was stirred at 0° C. for 1 h and then allowed to warm to room temperature. The reaction was quenched by adding water (1 mL), and product extracted with ethyl acetate (4 mL). The crude product was purified using DCM:ethyl acetate on a 12 g normal phase flash ISCO column to provide (±)-cis-(4-azidomethyl-3-methoxy-piperidin-1-yl)-[6-butyl-5-(4-cyclohexyloxy-phenyl)-pyridazin-3-yl]-methanone.

To a stirred solution of (±)-cis-(4-azidomethyl-3-methoxy-piperidin-1-yl)-[6-butyl-5-(4-cyclohexyloxy-phenyl)-pyridazin-3-yl]-methanone (0.23 mmol, 120 mg) in methanol (1 mL) was added Pd—C (20% by wt., 25 mg). The reaction was hydrogenated at room temperature under balloon pressure for 2.5 h. The reaction was filtered through celite, and the solvent removed under reduced pressure to provide (±)-cis-(4-aminomethyl-3-methoxy-piperidin-1-yl)-[6-butyl-5-(4-cyclohexyloxy-phenyl)-pyridazin-3-yl]-methanone.

To a stirred solution of (±)-cis-(4-aminomethyl-3-methoxy-piperidin-1-yl)-[6-butyl-5-(4-cyclohexyloxy-phenyl)-pyridazin-3-yl]-methanone (0.082 mmol, 40 mg) in DCM (0.5 mL) was added formaldehyde (0.5 mL) and sodium triacetoxyborohydride (0.14 mmol, 30 mg). The reaction was stirred at room temperature for 8 h. The reaction was diluted with DCM (1 mL) and washed with saturated sodium bicarbonate solution (1 mL). The organic layer was dried over anhydrous sodium sulfate and concentrated. The crude compound was purified using DCM:2 M ammonia in methanol to provide (±)-cis-[6-butyl-5-(4-cyclohexyloxy-phenyl)-pyridazin-3-yl]-((3R,4S)-4-dimethylaminomethyl-3-methoxy-piperidin-1-yl)-methanone (27 mg, 65% yield). LCMS: m/z 510.0 [M+1]. $^1$H NMR (400 MHz, CD$_3$OD) δ 8.16-8.21 (1H, m), 7.47-7.52 (2H, m), 7.12-7.14 (2H, m), 4.57-5.01 (1H, m), 4.44-4.50 (1H, m), 3.97-4.15 (1H, m), 3.34-3.48 (4H, m), 3.22-3.26 (2H, m), 3.07-3.16 (3H, m), 2.92-2.94 (6H, m), 2.38-2.45 (1H, m), 2.00-2.04 (2H, m), 1.77-1.84 (3H, m), 1.30-1.66 (12H, m), 0.83-0.87 (3H, t).

The title compound may be prepared from the free base by treatment with HCl in dioxane.

Example 103

6-Butyl-5-(4-cyclohexyloxy-phenyl)-pyridazine-3-carboxylic acid (1-methyl-piperidin-4-ylmethyl)-amide dihydrochloride The title compound may be prepared in similar manner to that used to prepare Example 95 by substituting 4-aminomethyl-piperidine-1-carboxylic acid tert-butyl ester for (±)-(cis)-(4-amino-cyclohexyl)-carbamic acid tert-butyl ester.

LCMS: m/z 465.9 [M+2]. $^1$H NMR (400 MHz, CD$_3$OD) δ 7.99 (1H, s), 7.34 (2H, d), 7.04 (2H, d), 4.42-3.98 (1H, m), 3.40 (2H, d), 3.10 (2H, t), 2.90 (2H, d), 2.26 (3H, s), 2.04-1.98 (4H, m), 1.84-1.78 (4H, m), 1.76-1.22 (14H, m), 0.83 (3H, t).

Example 104

(±)-cis-6-Butyl-5-(4-cyclohexyloxy-phenyl)-pyridazine-3-carboxylic acid (3-methoxy-1-methyl-piperidin-4-ylmethyl)-amide dihydrochloride The title compound may be prepared in a manner similar to that used to prepare Example 101.

LCMS: m/z 495.9 [M+2]. $^1$H NMR (400 MHz, CD$_3$OD) δ 8.47 (1H, s), 7.48 (2H, d), 7.13 (2H, d), 4.46-4.48 (1H, m), 3.66-3.82 (3H, m), 3.24-3.5 (7H, m), 3.01-3.09 (2H, m), 2.87 (3H, s), 2.13-2.17 (1H, m), 1.81-2.05 (6H, m), 1.28-1.67 (10H, m), 0.86 (3H, t).

Example 105

[6-Butyl-5-(4-cyclohexyloxy-phenyl)-pyridazin-3-yl]-(4-dimethylaminomethyl-3,3-difluoro-piperidin-1-yl)-methanone dihydrochloride The title compound may be prepared in a manner similar to that used to prepare Example 99.

LCMS: m/z 515.9 [M+1]. $^1$H NMR (400 MHz, CD$_3$OD): δ 8.12 and 8.10 (1H, s), 7.46 (2H, d), 7.12 (2H, d), 4.14-4.24 and 4.40-4.54 (2H, m), 3.36-3.85 (2H, m), 3.10-3.28 (4H, m) 2.80-3.05 (7H, m), 1.96-2.20 (3H, m), 1.26-1.91 (14H, m), 0.85 (3H, t).

Example 106

[6-Butyl-5-(4-cyclohexyloxy-phenyl)-pyridazin-3-yl]-(3-dimethylaminomethyl-4-hydroxyoxy-piperidin-1-yl)-methanone dihydrochloride The title compound may be prepared in a manner similar to that used to prepare Example 100.

LCMS: m/z 495.9 [M+1]. $^1$H NMR (400 MHz, CD$_3$OD) δ 8.2 and 8.14 (1H, s), 7.48 (2H, d), 7.12 (2H, dd), 4.45 (1H, m), 4.11-4.17 (1H, m), 3.45-3.8 (4H, m), 3.19-3.34 (4H, m), 2.90-2.98 (6H, m), 2.4-2.52 (1H, m), 1.81-2.03 (4H, m), 1.29-1.71 (12H, m), 0.85 (3H, t).

Example 107

6-Butyl-5-(4-cyclohexyloxy-phenyl)-pyridazine-3-carboxylic acid (3-methoxy-1-methyl-piperidin-4-yl)-amide dihydrochloride The title compound may be prepared in a manner similar to that used to prepared Example 101.

LCMS: m/z 482.0 [M+1]. $^1$H NMR (400 MHz, CD$_3$OD) δ 7.97 (1H, s), 7.32 (2H, d), 7.04 (2H, d), 4.34-4.42 (1H, m), 4.12-4.21 (1H, d), 3.60 (1H, s), 3.46 (3H, s), 3.03-3.11 (2H, m), 2.94 (1H, d), 2.34-2.96 (5H, m), 1.74-2.13 (7H, m), 1.20-1.67 (11H, m), 0.83 (3H, t).

Example 108

6-Butyl-5-(4-cyclohexyloxy-phenyl)-pyridazine-3-carboxylic acid (1-methyl-1,2,3,6-tetrahydro-pyridin-4-ylmethyl)-amide dihydrochloride To a solution of cis (±)-4-azidomethyl-3-hydroxy-piperidine-1-carboxylic acid tert-butyl ester (1.95 mmol, 0.5 g) was added bis(2-methoxyethyl)aminosulfur trifluoride (2.34 mmol, 0.52 g) slowly and stirred for 12. The reaction mixture was diluted with DCM (10 mL), washed with aq.NaHCO$_3$ solution, dried (Na$_2$SO$_4$), filtered, and concentrated under reduced pressure. The residue was purified by flash silica gel column chromatography using ethyl acetate:hexanes (2:8) to get 4-azidomethyl-3,6-dihydro-2H-pyridine-1-carboxylic acid tert-butyl ester.

To a solution of 4-azidomethyl-3,6-dihydro-2H-pyridine-1-carboxylic acid tert-butyl ester (0.97 mmol, 0.25 g) in THF (4 mL) was added triphenylphosphine (1.1 mmol, 0.3 g) and stirred for 12 h at room temperature. Water (2 mL) was added to the reaction mixture and stirred for 4 h. The reaction mixture was diluted with EtOAc (10 mL), and the organic layer was washed with water, brine, dried (Na$_2$SO$_4$), filtered and concentrated under reduced pressure to provide 4-aminomethyl-3,6-dihydro-2H-pyridine-1-carboxylic acid tert-butyl ester.

A mixture of the tert-butyl ester in DCM (2 mL) and 6-butyl-5-(4-cyclohexyloxy-phenyl)-pyridazine-3-carboxylic acid pentafluorophenyl ester (Example 93, 0.23 mmol, 0.12 g) and TEA (0.5 mL) was stirred at room temperature for 3 h. The reaction mixture was diluted with ethyl acetate (6 mL), washed with NaOH (0.5 M) solution, water, and brine, dried (Na$_2$SO$_4$), filtered, and concentrated under reduced pressure. The residue was purified by flash silica gel column chromatography using ethyl acetate:hexanes (4:6) to provide 4-({[6-butyl-5-(4-cyclohexyloxy-phenyl)-pyridazine-3-carbonyl]-amino}-methyl)-3,6-dihydro-2H-pyridine-1-carboxylic acid tert-butyl ester.

To a solution of 4-({[6-butyl-5-(4-cyclohexyloxy-phenyl)-pyridazine-3-carbonyl]-amino}-methyl)-3,6-dihydro-2H-pyridine-1-carboxylic acid tert-butyl ester (70 mg) in DCM (2 mL) was added 4 N HCl in dioxane (1.0 mL) at 0° C., and the reaction was stirred for 1 h at room temperature. The volatiles were removed under reduced pressure, and the residue was triturated with anhydrous ethyl ether and dried under high vacuum to provide 6-butyl-5-(4-cyclohexyloxy-phenyl)-pyridazine-3-carboxylic acid (1,2,3,6-tetrahydro-pyridin-4-yl-methyl)-amide dihydrochloride.

To a solution of 6-butyl-5-(4-cyclohexyloxy-phenyl)-pyridazine-3-carboxylic acid (1,2,3,6-tetrahydro-pyridin-4-ylmethyl)-amide dihydrochloride (30 mg) in DCM (2 mL) was added formaldehyde solution in water (37%, 1 mL), and stirred for 5 min. Sodium triacetoxyborohydride (0.47 mmol, 0.1 g) was added and stirred at room temperature for 2 h. The reaction was diluted with DCM (5 mL), and the DCM layer was separated and washed with saturated NaHCO$_3$ solution, dried (Na$_2$SO$_4$), filtered and concentrated under reduced pressure. The residue was purified on a SiO$_2$ cartridge with 2% (NH$_3$ in MeOH, 2M) in DCM -6% (NH$_3$ in MeOH, 2M) in DCM to provide 6-Butyl-5-(4-cyclohexyloxy-phenyl)-pyridazine-3-carboxylic acid (1-methyl-1,2,3,6-tetrahydro-pyridin-4-ylmethyl)-amide, which was converted to dihydrochloride salt by treating with 4 N HCl in dioxane (0.5 mL) in DCM (2 mL). The volatiles were removed under reduced pressure, and the salt was washed with anhydrous ether and solid was dried under high vacuum (38 mg). LCMS: m/z 464.1 [M+1]. $^1$H NMR (400 MHz, CD$_3$OD): δ 8.38 (1H, s), 7.46 (2H, d), 7.12 (2H, d), 5.71 (1H, s), 4.40-4.50 (1H, m), 4.11 (2H, s) 3.88 (1H, d), 3.55-3.70 (2H, m), 3.17-3.28 (3H, m), 2.94 (3H, s), 2.52-2.66 (1H, m), 2.44 (1H, d), 1.97-2.10 (2H, m),1.75-1.88 (2H, m), 1.25-1.70 (10H, m), 0.84 (3H, t).

Example 109

6-Butyl-5-(4-cyclohexyloxy-phenyl)-pyridazine-3-carboxylic acid (4-fluoro-1-methyl-piperidin-4-ylmethyl)-amide dihydrochloride 4-Fluoro-piperidine-1,4-dicarboxylic acid 1-tert-butyl ester 4-ethyl ester (1.8 mmol, 0.5 g) was taken in 7M NH$_3$ in MeOH (5 mL) and stirred at room temperature for 12 h in a sealed vial. All volatiles were removed under reduced pressure to provide 4-carbamoyl-4-fluoro-piperidine-1-carboxylic acid tert-butyl ester as white solid.

To a solution of 4-carbamoyl-4-fluoro-piperidine-1-carboxylic acid tert-butyl ester (1.01 mmol, 0.25 g) in THF (4.0 mL), was added BH$_3$:THF (2 mL, 1M solution in THF) and stirred for 12 h. All volatiles were removed under reduced pressure. The residue was taken in DCM (2 mL) and 6-butyl-5-(4-cyclohexyloxy-phenyl)-pyridazine-3-carboxylic acid pentafluorophenyl ester (Example 93, 0.29 mmol, 0.15 g) was added followed by TEA (0.5 mL), and the reaction mixture was stirred at room temperature for 3 h. The reaction mixture was diluted with ethyl acetate (20 mL), and washed with NaOH (0.5 M) solution (2×5 mL) water (2×5 mL), brine, dried (Na$_2$SO$_4$), filtered and concentrated under reduced pressure. The residue was purified by flash silica gel column chromatography using ethyl acetate:hexanes (3:7) to provide 4-({[6-butyl-5-(4-cyclohexyloxy-phenyl)-pyridazine-3-carbonyl]-amino}-methyl)-4-fluoro-piperidine-1-carboxylic acid tert-butyl ester.

To a solution of 4-({[6-butyl-5-(4-cyclohexyloxy-phenyl)-pyridazine-3-carbonyl]-amino}-methyl)-4-fluoro-piperidine-1-carboxylic acid tert-butyl ester (70 mg) in DCM (2 mL) was added 4 N HCl in dioxane (1.0 mL), and the reaction was stirred for 1 h. The volatiles were removed under reduced pressure, and the residue was triturated with anhydrous ethyl ether and dried under high vacuum to provide 6-butyl-5-(4-cyclohexyloxy-phenyl)-pyridazine-3-carboxylic acid (4-fluoro-piperidin-4-ylmethyl)-amide dihydrochloride.

To a solution of 6-butyl-5-(4-cyclohexyloxy-phenyl)-pyridazine-3-carboxylic acid (4-fluoro-piperidin-4-ylmethyl)-amide dihydrochloride (45 mg) in DCM (2 mL) was added formaldehyde solution in water (37%, 1 mL), and stirred for 5 min. Sodium triacetoxyborohydride (0.47 mmol, 0.1 g) was added and stirred at room temperature for 2 h. The reaction was diluted with DCM (5 mL), and the DCM layer was separated and washed with saturated NaHCO$_3$ solution, dried (Na$_2$SO$_4$), filtered and concentrated under reduced pressure. The residue was purified on a SiO$_2$ cartridge with 2% (NH$_3$ in MeOH, 2M) in DCM -6% (NH$_3$ in MeOH, 2M) in DCM to provide 6-butyl-5-(4-cyclohexyloxy-phenyl)-pyridazine-3-carboxylic acid (3,3-difluoro-1-methyl-piperidin-4-ylmethyl)-amide, which was converted to dihydrochloride salt by treating with 4 N HCl in dioxane (0.5 mL) in DCM (2 mL). The volatiles were removed under reduced pressure. The salt was washed with anhydrous ether and the solid was dried under high vacuum (38 mg). LCMS: m/z 484.1 [M+1]. $^1$H NMR (400 MHz, CD$_3$OD): δ 9.40 (1H, t), 8.30 (1H, s), 7.44 (2H, d), 7.11 (2H, d), 4.40-4.50 (1H, m), 3.71-3.88 (2H, m), 3.44-3.68 (2H, m), 3.14-3.26 (3H, s), 2.92 (3H, s), 2.50-2.75 (1H, m), 1.75-2.45 (8H, m) 1.23-1.70 (10H, m), 0.84 (3H, t).

Example 110

(±)-cis-6-Butyl-5-(4-cyclohexyloxy-phenyl)-pyridazine-3-carboxylic acid (3-fluoro-1-methyl-piperidin-4-ylmethyl)-amide dihydrochloride To a stirred solution of (±)-trans-4-azidomethyl-3-hydroxy-piperidine-1-carboxylic acid tert-butyl ester (1.35 mmol, 350 mg) in dichloromethane (6 mL) was added bis-(2-methoxyethy)aminosulfur trifluoride (1.62 mmol, 358 mg) at −40° C. After stirring the reaction at −40° C. for 3 h, saturated sodium bicarbonate solution (6 mL) was added, and the product was extracted with dichloromethane (6 mL). The organic layer was dried over sodium sulfate and concentrated. The crude product was purified using hexane:ethyl acetate to provide (±)-cis-4-azidomethyl-3-fluoro-piperidine-1-carboxylic acid tert-butyl ester.

To a stirred solution of (±)-cis-4-azidomethyl-3-fluoro-piperidine-1-carboxylic acid tert-butyl ester (0.68 mmol, 160 mg) in methanol (1.5 mL) was added Pd—C (20% by wt., 35 mg). The reaction was hydrogenated under balloon pressure for 2 h at room temperature. The reaction was filtered through a bed of celite. The solvent was evaporated to provide (±)-cis-4-aminomethyl-3-fluoro-piperidine-1-carboxylic acid tert-butyl ester.

To a stirred solution of (±)-cis-4-aminomethyl-3-fluoro-piperidine-1-carboxylic acid tert-butyl ester (0.65 mmol, 150 mg) in dichloromethane (3 mL) was added 6-butyl-5-(4-cyclohexyloxy-phenyl)-pyridazine-3-carboxylic acid pentafluorophenyl ester (Example 93, 0.75 mmol, 400 mg) and TEA (1.3 mmol, 0.2 mL). After stirring the reaction at room temperature for 8 h, dichloromethane (5 mL) was added. The reaction was washed with saturated sodium bicarbonate solution (5 mL). The organic layer was dried over anhydrous sodium sulfate and concentrated. Crude product was purified using hexane:ethyl acetate on 12 g normal phase ISCO flash column to provide (±)-cis-4-({[6-butyl-5-(4-cyclohexyloxy-phenyl)-pyridazine-3-carbonyl]-amino}-methyl)-3-fluoro-piperidine-1-carboxylic acid tert-butyl ester.

(±)-cis-4-({[6-Butyl-5-(4-cyclohexyloxy-phenyl)-pyridazine-3-carbonyl]-amino}-methyl)-3-fluoro-piperidine-1-carboxylic acid tert-butyl ester (0.47 mmol, 266 mg) was stirred in 4 M HCl/dioxane (2 mL) for 20 min at room temperature. The solvent was evaporated to provide (±)-cis-6-butyl-5-(4-cyclohexyloxy-phenyl)-pyridazine-3-carboxylic acid (3-fluoro-piperidin-4-ylmethyl)-amide dihydrochloride. The crude product was used without further purification.

To a stirred solution of (±)-cis-6-butyl-5-(4-cyclohexyloxy-phenyl)-pyridazine-3-carboxylic acid (3-fluoro-piperidin-4-ylmethyl)-amide dihydrochloride (220 mg, 0.47 mmol) in dichloromethane (1 mL) was added formaldehyde (1 mL) and sodium triacetoxyborohydride (1 mmol, 210 mg). The reaction was stirred at room temperature for 3 h. Reaction was diluted with dichloromethane (5 mL) and washed with saturated sodium bicarbonate solution (5 mL). The organic layer was dried over anhydrous sodium sulfate and concentrated. The crude product was purified using dichloromethane:2 M ammonia in methanol to give (±)-cis-6-butyl-5-(4-cyclohexyloxy-phenyl)-pyridazine-3-carboxylic acid (3-fluoro-1-methyl-piperidin-4-ylmethyl)-amide.

(±)-cis-6-Butyl-5-(4-cyclohexyloxy-phenyl)-pyridazine-3-carboxylic acid (3-fluoro-1-methyl-piperidin-4-ylmethyl)-amide (0.35 mmol, 160 mg) was stirred in 4 M HCl/dioxane (1 mL) for 20 min at room temperature. After evaporating the solvent, dichloromethane (0.2 mL) and hexane (1 mL) was added to precipitate (±)-cis-6-butyl-5-(4-cyclohexyloxy-phenyl)-pyridazine-3-carboxylic acid (3-fluoro-1-methyl-piperidin-4-ylmethyl)-amide dihydrochloride. LCMS: m/z 484 [M+1]. $^1$H NMR (400 MHz, CD$_3$OD) δ 8.51 (1H, s), 7.50-7.51 (2H, m), 7.13-7.15 (2H, m), 4.44-4.48 (1H, m), 3.43-3.76 (5H, m), 2.97-3.03 (1H, m), 2.89-2.90 (3H, m), 2.80-2.85 (1H, m), 2.08-2.34 (1H, m), 1.99-2.04 (2H, m), 1.81-1.84 (3H, m), 1.30-1.63 (13H, m), 0.83-0.87 (3H, t).

Example 111

6-Butyl-5-(4-cyclohexyloxy-phenyl)-pyridazine-3-carboxylic acid (3-hydroxymethyl-1-methyl-pyrrolidin-3-yl)-amide dihydrochloride To a mixture of 3-amino-3-hydroxymethyl-pyrrolidine-1-carboxylic acid tert-butyl ester (1.0 mmol, 0.21 g) in anhydrous DCE (2 mL), 6-butyl-5-(4-cyclohexyloxy-phenyl)-pyridazine-3-carboxylic acid pentafluorophenyl ester (Example 93, 0.5 mmol, 0.26 g) and TEA (0.5 mL) was stirred at room temperature for 3 h. The reaction mixture was diluted with ethyl acetate (10 mL) and washed with NaOH (0.5 M) solution, water, and brine, dried (Na$_2$SO$_4$), filtered and concentrated under reduced pressure. The residue was purified by flash silica gel column chromatography using ethyl acetate: hexanes (7:3) to provide 3-{[6-butyl-5-(4-cyclohexyloxyphenyl)-pyridazine-3-carbonyl]-amino}-3-hydroxymethyl-pyrrolidine-1-carboxylic acid tert-butyl ester.

To a solution of 3-{[6-butyl-5-(4-cyclohexyloxy-phenyl)-pyridazine-3-carbonyl]-amino}-3-hydroxymethyl-pyrrolidine-1-carboxylic acid tert-butyl ester (55 mg) in DCM (2 mL) was added 4 N HCl in dioxane (1.0 mL) at 0° C., and the reaction was stirred for 1 h at room temperature. The volatiles were removed under reduced pressure, and the residue was triturated with anhydrous ethyl ether and dried under high vacuum to provide 6-butyl-5-(4-cyclohexyloxy-phenyl)-pyridazine-3-carboxylic acid (3-hydroxymethyl-pyrrolidin-3-yl)-amide dihydrochloride.

To a solution of 6-butyl-5-(4-cyclohexyloxy-phenyl)-pyridazine-3-carboxylic acid (3,3-difluoro-piperidin-4-ylmethyl)-amide dihydrochloride (20 mg) in DCM (2 mL) was added formaldehyde solution in water (37%, 1 mL), and stirred for 5 min. Sodium triacetoxyborohydride (0.47 mmol, 0.1 g) was added and stirred at room temperature for 2 h. The reaction was diluted with DCM (5 mL), and the DCM layer was separated and washed with saturated NaHCO$_3$ solution, dried (Na$_2$SO$_4$), filtered and concentrated under reduced pressure. The residue was purified on a SiO$_2$ cartridge with 2% (NH$_3$ in MeOH, 2M) in DCM -6% (NH$_3$ in MeOH, 2M) in DCM to provide 6-butyl-5-(4-cyclohexyloxy-phenyl)-pyridazine-3-carboxylic acid (3-hydroxymethyl-1-methyl-pyrrolidin-3-yl)-amide, which was converted to dihydrochloride salt by treating with 4 N HCl in dioxane (0.5 mL) in DCM (2 mL). The volatiles were removed under reduced pressure, the salt was washed with anhydrous ether, and the solid was dried under high vacuum. LCMS: m/z 467.7 [M+1]. $^1$H NMR (400 MHz, CD$_3$OD): δ 8.13 and 8.16 (1H, s), 7.39 (2H, d), 7.10 (2H, d), 4.36-4.50 (1H, m), 3.45-4.20 (4H, m), 3.10-3.20 (3H, m), 3.00 (3H, s), 2.48-2.58 (2H, m), 1.96-2.08 (2H, m), 1.75-1.90 (2H, m), 1.20-1.70 (11H, m), 0.84 (3H, t).

Example 112

(±)-cis-6-Butyl-5-(4-cyclohexyloxy-phenyl)-pyridazine-3-carboxylic acid (3-hydroxy-1-methyl-piperidin-4-yl)-amide dihydrochloride To a stirred solution of 3,6-dihydro-2H-pyridine-1-carboxylic acid tert-butyl ester (19.1 mmol, 3.5 g), in DCM (50 mL) cooled at 0° C., was added m-CPBA (32.2 mmol, 5.95 g (70%)) portion wise. The reaction was stirred at room temperature for 4 h. The reaction was diluted with DCM (50 mL) and washed with sat. Na$_2$S$_2$O$_3$, sat. NaHCO$_3$, water and brine, dried (Na$_2$SO$_4$), filtered and concentrated under reduced pressure. The residue was purified on a SiO$_2$ cartridge (5% EtOAc in hexane -25% EtOAc in hexane) to provide 7-oxa-3-aza-bicyclo[4.1.0]heptane-3-carboxylic acid tert-butyl ester.

To a stirred solution of 7-oxa-3-aza-bicyclo[4.1.0]heptane-3-carboxylic acid tert-butyl ester (15.5 mmol, 3.1 g) in DMF (25 mL) was added a solution of sodium azide (23.3 mmol, 1.5 g) in acetone-water (2:1, 30 mL) (WO 2005/066176). The reaction mixture was heated at 80° C. for 12 h. The reaction mixture was cooled to room temperature, and EtOAc (100 mL) was added. The organic layer was washed with water and brine, dried (Na$_2$SO$_4$), filtered and concentrated under reduced pressure. The residue was purified on a SiO$_2$ cartridge (5% EtOAc in hexane -25% EtOAc in hexane) to provide (±)-trans-4-azido-3-hydroxy-piperidine-1-carboxylic acid tert-butyl ester (2.3 g) (faster moving compound) $^1$H NMR (400 MHz, CDCl$_3$) δ 4.12 (1H, dd), 3.95 (1H, bs), 3.50 (1H, bs), 3.30-3.42 (1H, m), 2.90 (1H, bs), 2.79 (1H, dd), 2.30-2.70 (1H, bs), 1.96-2.05 (1H, m), 1.48-1.6 (1H, m), 1.46 (9H, s). and (±)-trans-3-azido-4-hydroxy-piperidine-1-carboxylic acid tert-butyl ester (0.57 g) (slower moving compound) $^1$H NMR (400 MHz, CDCl$_3$) δ 4.21 (1H, bs), 4.00 (1H, d), 3.56 (1H, bs), 3.21-3.35 (1H, m), 2.55-2.95 (2H, m), 2.24 (1H, bs), 1.92-2.04 (1H, m), 1.49-1.6 (1H, m), 1.47 (9H, s)

To a stirred solution of (±)-trans-4-azido-3-hydroxy-piperidine-1-carboxylic acid tert-butyl ester (10 mmol, 2.42 g) in methanol (25 mL) was added 10% palladium on carbon (0.5 g, wet), and the resultant reaction mixture was subjected to hydrogenation using a balloon full of hydrogen for 8 h. The catalyst was filtered through a pad of celite, and the pad was washed with methanol (25 mL). The combined filtrate was concentrated under reduced pressure to provide (±)-trans-4-amino-3-hydroxy-piperidine-1-carboxylic acid tert-butyl ester.

To a stirred solution of (±)-trans-4-amino-3-hydroxy-piperidine-1-carboxylic acid tert-butyl ester (9.48 mmol, 2.05 g) in a biphasic mixture of DCM (10 mL) and saturated sodium bicarbonate (10 mL) at 0° C. was added benzyl chloroformate (2.0 mL) drop-wise and continued stirring at 0-5° C. for 1 h. The organic layer was separated, and the aqueous layer was extracted with DCM. The combined organic layers were dried, filtered and concentrated under reduced pressure. The residue was purified by flash silica gel column chromatography by eluting with 50% ethyl acetate in hexanes to provide (±)-trans-4-benzyloxycarbonylamino-3-hydroxy-piperidine-1-carboxylic acid tert-butyl ester.

To a stirred mixture of (±)-trans-4-benzyloxycarbonylamino-3-hydroxy-piperidine-1-carboxylic acid tert-butyl ester (1 mmol, 0.35 g), triphenylphosphine (1.5 mmol, 0.393 g) and p-nitrobenzoic acid (1.5 mmol, 0.25 g) in anhydrous THF (6 mL) at −60° C. was added DIAD drop-wise over 5 min period. After completion of addition, the reaction mixture was stirred for 4 h during which period the reaction mixture was slowly let attain room temperature. The reaction mixture was diluted with ether (100 mL) and washed with saturated sodium bicarbonate solution (2×50 mL). The organic layer was dried, filtered and concentrated under reduced pressure. The residue was purified by flash silica gel column chromatography by eluting with 30% ethyl acetate in hexanes to get (±)-cis-4-benzyloxycarbonylamino-3-(4-nitro-benzoyloxy)-piperidine-1-carboxylic acid tert-butyl ester.

To a stirred solution of (±)-cis-4-benzyloxycarbonylamino-3-(4-nitro-benzoyloxy)-piperidine-1-carboxylic acid tert-butyl ester (0.63 mmol, 0.315 g) in THF (5 mL) at 0° C. was added LiOH (0.16 g) dissolved in water (1.5 mL) and continued stirring at 0° C. for 30 min followed by 2 h at room temperature. The reaction mixture was concentrated under reduced pressure. The residue was dissolved in water (10 mL) and extracted with ethyl acetate. The combined organic layers were dried, filtered and concentrated under reduced pressure. The residue was purified by silica gel flash column chromatography to provide (±)-cis-4-benzyloxycarbonylamino-3-hydroxy-piperidine-1-carboxylic acid tert-butyl ester.

To a stirred solution of (±)-cis-4-benzyloxycarbonylamino-3-hydroxy-piperidine-1-carboxylic acid tert-butyl ester (0.365 mmol, 0.128 g)) in methanol (3 mL) was added 10% palladium on carbon (0.07 g, wet). The resultant reaction mixture was subjected to hydrogenation using a balloon full of hydrogen for 2 h. The catalyst was filtered through a pad of celite. The pad was washed with methanol (10 mL), and the combined filtrate was concentrated under reduced pressure to get (±)-cis-4-amino-3-hydroxy-piperidine-1-carboxylic acid tert-butyl ester.

The title compound may be prepare in a manner similar to that used to prepare Example 95 by substituting (±)-cis-4-amino-3-hydroxy-piperidine-1-carboxylic acid tert-butyl ester for (±)-(cis)-(4-amino-cyclohexyl)-carbamic acid tert-butyl ester.

LCMS: m/z 468 [M+1]. $^1$H NMR (400 MHz, CD$_3$OD) δ 8.40 (1H, s), 7.45-7.48 (2H, m), 7.11-7.14 (2H, m), 4.42-4.48 (1H, m), 4.3-4.35 (1H, m), 4.24 (1H, bs), 3.52 (2H, m), 3.18-3.38 (4H, m), 2.9 (3H, s), 2.32-2.38 (1H, m), 1.98-2.08 (3H, m), 1.81-1.85 (2H, m), 1.27-1.67 (10H, m), 0.84 (3H, t)

Example 113

6-Butyl-5-(4-cyclohexyloxy-phenyl)-pyridazine-3-carboxylic acid (3,3-difluoro-1-methyl-piperidin-4-yl)-amide dihydrochloride To a solution of (±)-trans[3-azido-4-hydroxy-piperidine-1-carboxylic acid tert-butyl ester (Example 112, 1.24 mmol, 0.3 g) in DCM (4 mL) at 0° C. was added Dess-Martin periodinane (1.48 mmol, 0.63 g) portion wise, and the reaction was stirred for 8 h. The reaction was diluted with DCM (5 mL), cooled to 0° C., and quenched with Na$_2$S$_2$O$_3$ solution, organic layer was separated and washed with saturated NaHCO$_3$ solution, water, brine and dried (Na$_2$SO$_4$), filtered and concentrated under reduced pressure. The residue was purified on a SiO$_2$ cartridge with 5% ethyl acetate in hexanes –30% ethylacetate in hexanes to provide 3-azido-4-oxo-piperidine-1-carboxylic acid tert-butyl ester.

To a solution of 3-azido-4-oxo-piperidine-1-carboxylic acid tert-butyl ester (1.08 mmol, 0.26 g) in DCM (6 mL) was added bis(2-methoxyethyl)aminosulfur trifluoride (2.38 mmol, 0.52 g), at 0° C. and stirred for 8 h at room temperature. The reaction was diluted with DCM (10 mL) and washed with saturated NaHCO$_3$ solution, water, brine, dried (Na$_2$SO$_4$), filtered and concentrated under reduced pressure. The residue was purified on a SiO$_2$ cartridge with 5% ethyl acetate in hexanes -20% ethyl acetate in hexanes to provide 3-azido-4,4-difluoro-piperidine-1-carboxylic acid tert-butyl ester.

To a solution of 3-azido-4,4-difluoro-piperidine-1-carboxylic acid tert-butyl ester (0.68 mmol, 0.18 g) in MeOH (4.0 mL), was added Pd—C (10% by wt, 30 mg) and stirred under H$_2$ atmosphere (balloon) for 3 h. The catalyst was filtered and washed with DCM, and the filtrate was concentrated under reduced pressure to provide 3-amino-4,4-difluoro-piperidine-1-carboxylic acid tert-butyl ester.

The title compound may be prepared in a manner similar to that used to prepare Example 95 by substituting 3-amino-4,4-difluoro-piperidine-1-carboxylic acid tert-butyl ester for (±)-(cis)-(4-amino-cyclohexyl)-carbamic acid tert-butyl ester.

LCMS: m/z 487.9 [M+1]. $^1$H NMR (400 MHz, CD$_3$OD): δ 8.29 (1H, s), 7.44 (2H, d), 7.10 (2H, d), 4.98-5.16 (1H, m), 4.37-4.50 (2H, m), 3.34-3.86 (4H, m), 3.17 (2H, t), 3.05 (3H, s), 2.40-2.72 (2H, m), 1.96-2.09 (2H, m), 1.76-1.89 (2H, m), 1.22-1.71 (10H, m), 0.82 (3H, t).

Example 114

6-Butyl-5-(4-cyclohexyloxy-phenyl)-pyridazine-3-carboxylic acid methyl-(1-methyl-piperidin-4-yl)-amide dihydrochloride The title compound may be prepared in a manner similar to that used to prepare Example 95 by substituting 4-methylamino-piperidine-1-carboxylic acid tert-butyl ester for (±)-(cis)-(4-amino-cyclohexyl)-carbamic acid tert-butyl ester.

LCMS: m/z 465.9 [M+2]. $^1$H NMR (400 MHz, CD$_3$OD) δ 7.78 (1H, s), 7.38 (2H, d), 7.07 (2H, d), 4.48-4.55 (1H, m), 4.30-4.40 (1H, m), 3.31-3.52 (4H, m), 3.09-3.14 (2H, m), 2.99 (3H, s), 2.88 (3H, s), 1.99-2.05 (2H, m), 1.79-1.86 (2H, m), 1.26-1.66 (14H, m), 0.83 (3H, t).

Example 115

6-Butyl-5-(4-cyclohexyloxy-phenyl)-pyridazine-3-carboxylic acid cyclopropyl-(1-methyl-piperidin-4-yl)-amide dihydrochloride The title compound may be prepared in a manner similar to that used to prepare Example 95 by substituting 1-tert-butoxycarbonyl-4-(cyclopropylamino)piperidine for (±)-(cis)-(4-amino-cyclohexyl)-carbamic acid tert-butyl ester.

LCMS: m/z 492.0 [M+1]. $^1$H NMR (400 MHz, CD$_3$OD) δ 8.20 (1H, s), 7.47-7.52 (2H, m), 7.10-7.15 (2H, m), 4.42-4.48 (1H, m), 4.25-4.35 (1H, m), 3.60-3.67 (2H, m), 3.18-3.26 (4H, m), 2.96-3.02 (1H, m), 2.90 (3H, s), 2.56-2.67 (2H, m), 2.22-2.27 (2H, m), 1.98-2.03 (2H, m), 1.78-1.84 (2H, m), 1.26-1.63 (10H, m), 0.85 (3H, t), 0.61-0.75 (4H, m).

Binding Assay

The following assay method may be used to identify compounds of Formula (I) or pharmaceutically acceptable salts thereof which are useful as inhibitors of binding of physiological RAGE ligands, such as S100b and β-amyloid, to RAGE.

S100b, β-amyloid, or CML (500 ng/100 μL/well) in 100 mM sodium bicarbonate/sodium carbonate buffer (pH 9.8) is loaded onto the wells of a NUNC Maxisorp flat bottom 96-well microtitre plate. The plate is incubated at 4° C. overnight. The wells are aspirated and treated with 50 mM imidazole buffer saline (pH 7.2) (with 5 mM CaCl$_2$/MgCl$_2$) containing 1% bovine serum albumin (BSA) (300 μL/well) for 1 h at RT. The wells are aspirated.

Test compounds are dissolved in nanopure water (concentration: 10-100 μM). DMSO may be used as co-solvent. 25 μL of test compound solution in 4% DMSO is added, along with 75 μL sRAGE (6 nM FAC) to each well and samples are incubated for 1 h at 37° C. The wells are washed several times with 155 mM NaCl pH 7.2 buffer saline and are soaked for several seconds between each wash.

Non-radioactive detection is performed by adding:

10 μL Biotinylated goat F(ab')2 Anti-mouse IgG. (8.0× 10-4 mg/mL, FAC), 5 μL Alk-phos-Streptavidin (3×10-3 mg/mL FAC), 0.42 μL per 5 mL Monoclonal antibody for sRAGE (FAC 6.0×10-3 mg/mL) to 5 mL 50 mM imidazole buffer saline (pH 7.2) containing 0.2% bovine serum albumin and 5 mM CaCl$_2$. The mixture is incubated for 30 minutes at RT.

100 μL of complex is added to each well and incubation is allowed to proceed at rt for 1 h. Wells are washed several times with wash buffer and soaked several seconds between each wash. 100 μL 1 mg/mL (pNPP) in 1 M diethanolamine (pH adjusted to 9.8 with HCl) is added. Color is allowed to develop in the dark for 30 min to 1 h at rt. The reaction is quenched with 10 μL of stop solution (0.5-1.0 N NaOH in 50% ethanol) and the absorbance is measured spectrophotometrically with a microplate reader at 405 nm.

The Examples 1-115 (hydrochloride salt form) were tested according to the assay method described above, employing S100b or β-amyloid as the RAGE ligand, and were found to possess IC50 concentrations shown below. The IC50 (μM) value in the ELISA assay represents the concentration of compound at which 50% signal has been inhibited.

| Ex. | IC50 (S100b) (μM) | IC50 (β-amyloid) (μM) |
|---|---|---|
| 1 | 0.95 | 1.09 |
| 2 | 1.32 | 1.23 |
| 3 | 2.49 | 2.28 |
| 4 | 1.14 | 1.24 |
| 5 | 3.11 | 6.28 |
| 6 | 2.13 | 2.33 |
| 7 | 2.33 | 1.52 |
| 8 | 4.84 | 3.72 |
| 9 | 2.70 | 3.14 |
| 10 | 1.52 | 1.63 |
| 11 | 5.74 | 3.23 |
| 12 | 1.19 | 1.54 |
| 13 | 2.57 | 2.62 |
| 14 | 0.81 | 0.82 |
| 15 | 0.64 | 0.66 |
| 16 | 2.17 | 2.07 |
| 17 | 0.81 | 0.82 |
| 18 | 0.83 | 0.60 |
| 19 | 0.64 | 0.87 |
| 20 | 1.46 | 2.23 |
| 21 | 1.34 | 1.53 |
| 22 | 1.38 | 1.12 |
| 23 | 0.78 | 1.11 |
| 24 | 2.64 | 2.90 |
| 25 | 1.37 | 1.54 |
| 26 | 2.08 | 1.90 |
| 27 | 2.69 | 2.52 |
| 28 | 1.75 | 1.66 |
| 29 | 1.72 | 2.36 |
| 30 | 1.82 | 2.59 |
| 31 | 0.89 | 1.18 |
| 32 | 2.78 | 1.78 |
| 33 | 2.63 | 1.48 |
| 34 | 2.93 | 2.58 |
| 35 | 0.74 | 0.74 |
| 36 | 0.96 | 0.96 |
| 37 | 1.87 | 1.65 |
| 38 | 2.62 | 2.47 |
| 39 | 1.22 | 1.50 |
| 40 | 2.98 | 2.18 |
| 41 | 2.19 | 4.04 |
| 42 | 2.21 | 1.80 |
| 43 | 2.07 | 0.83 |
| 44 | 0.48 | 0.32 |
| 45 | 1.15 | 0.50 |
| 46 | 1.35 | 1.25 |
| 47 | 2.93 | 2.50 |
| 48 | 2.60 | 8.96 |
| 49 | 3.94 | 6.26 |
| 50 | 1.42 | 1.96 |
| 51 | 2.94 | 2.62 |
| 52 | 0.65 | 0.69 |
| 53 | 2.51 | 2.02 |
| 54 | 3.65 | 5.45 |
| 55 | 3.68 | 9.18 |
| 56 | 1.80 | 2.43 |
| 57 | 3.27 | 4.56 |
| 58 | 0.74 | 0.76 |
| 59 | 4.79 | 3.16 |
| 60 | 1.13 | 1.83 |
| 61 | 3.40 | 3.72 |
| 62 | 3.63 | 5.00 |
| 63 | 0.84 | 0.68 |
| 64 | 0.88 | 0.84 |
| 65 | 2.12 | 1.78 |
| 66 | 1.47 | 1.83 |
| 67 | 1.70 | 3.20 |
| 68 | 2.04 | 2.49 |
| 69 | 0.73 | 0.79 |
| 70 | 2.17 | 2.94 |
| 71 | 1.13 | 1.59 |
| 72 | 1.69 | 1.20 |
| 73 | 1.74 | 1.04 |
| 74 | 1.64 | 1.16 |
| 75 | 2.19 | 2.85 |
| 76 | 2.07 | 6.78 |
| 77 | 0.68 | 0.66 |
| 78 | 0.50 | 1.16 |
| 79 | 1.47 | 1.49 |
| 80 | 1.25 | 1.25 |
| 81 | 1.82 | 1.54 |
| 82 | 1.27 | 1.29 |
| 83 | 1.18 | 1.13 |
| 84 | 1.56 | 1.96 |
| 85 | 1.49 | 1.97 |
| 86 | 1.92 | 1.02 |
| 87 | 1.97 | 2.43 |
| 88 | 2.03 | 2.46 |
| 89 | 2.73 | 2.01 |
| 90 | 1.54 | 1.78 |
| 91 | 1.14 | 1.39 |
| 92 | 1.75 | 1.02 |
| 93 | 1.69 | 2.51 |
| 94 | 2.55 | 1.95 |
| 95 | 0.69 | 1.05 |
| 96 | 1.16 | 0.94 |
| 97 | 1.89 | 1.72 |
| 98 | 1.99 | 1.62 |
| 99 | 1.82 | 1.81 |
| 100 | 0.59 | 1.16 |
| 101 | 0.66 | 0.94 |
| 102 | 2.61 | 1.46 |
| 103 | 1.77 | 1.11 |
| 104 | 1.12 | 1.61 |
| 105 | 1.39 | 2.12 |
| 106 | 2.18 | 1.75 |
| 107 | 0.97 | 0.56 |
| 108 | 1.17 | 0.86 |
| 109 | 5.84 | 5.83 |
| 110 | 1.04 | 1.34 |
| 111 | 2.12 | 2.92 |
| 112 | 1.44 | 1.47 |
| 113 | 1.84 | 2.62 |
| 114 | 1.08 | 0.97 |
| 115 | 1.12 | 1.00 |

Functional Assay

Previously the literature has cited that THP-1 cells in response to RAGE ligands secrete TNF alpha (Yeh C—H, et al. Diabetes. Vol. 50, June 2001, pp. 1495-1504). The following assay method may be used to identify compounds of Formula (I) or pharmaceutically acceptable salts thereof which are useful as antagonists of RAGE signaling.

The myeloid cell line, THP-1 (ATTC # TIB-202), may be cultured in RPMI-1640 media (ATCC, Cat #30-2001) supplemented with fetal bovine serum to a final concentration of 10% by volume and Penicillin-Streptomycin (Gibco, Cat #. 15140-122). Alternatively, media may be formulated using RPMI 1640 (Bio-Whitaker #12-702F) supplemented with 2 mM L-glutamine (Gibco #12381-018) adjusted to contain 1.5 g/L sodium bicarbonate (Gibco #25080-094), 4.5 g/L glucose, 10 mM HEPES (Cellgro #25-060-L1) and 1.0 mM sodium pyruvate (Gibco #11360-070) and supplemented with 0.05 mM 2-mercaptoethanol, 90% fetal bovine serum, 10% per ATCC instructions. During culture, the culture cells are maintained at a density between $5 \times 10^4$ and $1 \times 10^6$ viable cells/mL. The cell doubling time is approximately 20 hours and the cells should be passed every 3-4 days.

THP1 cells are first harvested by centrifugation and then washed 1 time with RPMI containing Pen Strep without serum. The cells are resuspended to a final concentration of between $5 \times 10^5$ and $1 \times 10^6$ cells/mL in RPMI without serum. The cells are dispensed into a 96-well tissue culture plate (Corning, CSL3599) at 50,000-100,000 cells per well in 100 μL of RPMI. Following plating of cells, compounds are dispensed and serially diluted using DMSO. DMSO and compound concentrations are adjusted with RPMI to give a final concentration of DMSO no greater than 0.5% in the cell culture. Typically, compounds are diluted into 50 μL of RPMI prior to addition to culture. Compounds are incubated with the cells for 30 minutes at 37° C. and 5% $CO_2$ to equilibrate the compound in culture. After the 30 minute preincubation, the cells are stimulated with bovine S100b at a final concentration of 100 pg/mL. This material is prepared by dissolving bovine S100b (Calbiochem, #559290) in RPMI to a final concentration of 0.4 mg/mL. Assays may be run in the presence of a RAGE fusion protein or with sRAGE as a positive control or a human IgG (Sigma #14506) as a negative control.

The amount of TNF-alpha secreted by the THP-1 cells was measured 24 hours after the addition of the stimulant proteins to the cell culture using a commercially available ELISA kit (R&D Systems, Minneapolis, Minn. # DY210). All reagents and standards are prepared as directed by the manufacturer. Then, 100 μL of standards, media controls or media samples are added to the appropriate ELISA well. The plate is incubated at room temperature (22-25° C.). for 2 hours. The plate is then aspirated and washed with 400 μL of wash buffer (PBS+0.1% Tween-20) and repeated three more times for a total of four washes. Next, 100 μL of TNF-alpha detection conjugate is added to each ELISA well and allowed to incubate at room temperature for one hour. The plate is then aspirated and washed with 400 μL of wash buffer and repeated three more times for a total of four washes. Next, 100 μL of a preparation of streptavidin conjugated to horseradish peroxidase is added to each well and allowed to incubate for 20 minutes. The plate is then aspirated and washed with 400 μL of wash buffer and repeated three more times for a total of four washes. Color development is initiated by the addition of 100 uL of TMB Substrate Solution (Sigma, T0440-1L)) and incubated for 10-20 minutes. The color development is stopped by addition of 100 μL of 1M phosphoric acid. The plate is read at 450 nm within 30 minutes. With S100b stimulation, 125-250 pg/mL are seen above background.

Example 14 had an EC50 for TNF expression of 1.26 μM. Thus, the cell based assay demonstrated a correlation with the binding assay data for Example 14 which had an IC50 of 0.82 μM in the binding assay.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for RAGE-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:

1. A method of treating Alzheimer's disease comprising administering to a subject in need thereof a compound of Formula (I) or a pharmaceutically acceptable salt thereof

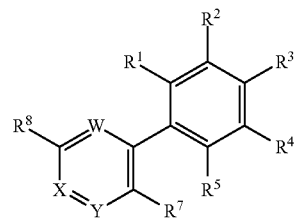

(I)

wherein
W is $CR^6$, and X and Y are N, and $R^6$ is —H,
$R^1$, $R^2$, $R^4$, and $R^5$ are —H,
$R^3$ is the group —$X^1$-$L^1$-$R^{13}$ wherein
    $X^1$ is selected from the group consisting of a direct bond and —O—,
    $L^1$ is selected from the group consisting of a direct bond, —$CH_2$—, and —$CH_2CH_2$—, and
    $R^{13}$ is selected from the group consisting of -phenyl and -cyclohexyl, wherein the cyclohexyl and phenyl groups of $R^{13}$ are optionally substituted one or more times with $R^{14}$, wherein each $R^{14}$ is independently selected from the group consisting of -halogen, —($C_1$-$C_6$)alkyl, and —($C_1$-$C_6$)haloalkyl,
$R^7$ is the group -$L^2$-$X^2$—$R^{15}$ wherein
    $L^2$ is —($C_1$-$C_4$)alkylene-,
    $X^2$ is selected from the group consisting of a direct bond and —O—, and
    $R^{15}$ is selected from the group consisting of —($C_1$-$C_4$)alkyl, optionally substituted one or more times with $R^{16}$, wherein each $R^{16}$ is independently selected from the group consisting of -halogen,
$R^8$ is the group —$X^3$-$L^3$-$R^{17}$, wherein
    $X^3$ is selected from the group consisting of direct bond, —O—, and —C(O)NH—,
    $L^3$ is selected from the group consisting of a direct bond and —$CH_2$—,
    $R^{17}$ is

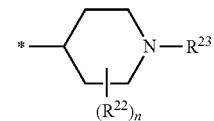

wherein
each $R^{22}$ may be attached to any of the ring carbon atoms of $R^{17}$, and wherein
each $R^{22}$ is independently selected from the group consisting of -halogen, $X^4$—$R^{24}$, —($C_1$-$C_6$)alkylene-$R^{24}$, —($C_1$-$C_6$)alkylene-$X^5$—$R^{24}$, and —$X^4$—($C_1$-$C_6$)alkylene-$NR^{25}R^{26}$, wherein
    $X^4$ and $X^5$ are independently selected from the group consisting of: direct bond, —O—, and —N($R^{27}$)—, wherein $R^{27}$ is selected from the group consisting of —H and —($C_1$-$C_6$)alkyl,
    $R^{24}$ is selected from the group consisting of —H, and —($C_1$-$C_6$)alkyl, wherein the alkyl groups of $R^{24}$ is optionally substituted one or more times with $R^{28}$, wherein each $R^{28}$ is independently selected from the group consisting of halogen,
    $R^{25}$ and $R^{26}$ are independently selected from the group consisting of —H, and —($C_1$-$C_6$)alkyl, $R^{23}$ is selected from the group consisting of —H and —$(C_1-C_6)$alkyl, and n is 0, 1, 2, or 3.

2. The method of claim 1, wherein the compound is selected from the group consisting of:
- 4-(4-Benzyloxy-phenyl)-6-(1-methyl-piperidin-4-yloxy)-3-propyl-pyridazine;
- 3-Butyl-4-[4-(4,4-difluoro-cyclohexyloxy)-phenyl]-6-(1-methylpiperidin-4-yloxy)-pyridazine;
- cis-(±)-4-[6-Butyl-5-(4-cyclohexyloxy-phenyl)-pyridazin-3-yloxymethyl]-1-methyl-piperidin-3-ol;
- cis-(±)-3-Butyl-4-(4-cyclohexyloxy-phenyl)-6-(−3-methoxy-1-methyl-piperidin-4-ylmethoxy)-pyridazine;
- trans-(±)-3-Butyl-4-(4-cyclohexyloxy-phenyl)-6-(3-methoxy-1-methyl-piperidin-4-ylmethoxy)-pyridazine;
- {4-[6-Butyl-5-(4-cyclohexyloxy-phenyl)-pyridazin-3-yloxy]-1-methyl-piperidin-3-yl}-methanol;
- trans-(±)-3-Butyl-4-(4-cyclohexyloxy-phenyl)-6-(3-fluoro-1-methyl-piperidin-4-yloxy)-pyridazine;
- cis-(±)-3-Butyl-4-(4-cyclohexyloxy-phenyl)-6-(−3-fluoro-1-methyl-piperidin-4-yloxy)-pyridazine;
- 3-Butyl-4-[4-(4-chloro-benzyloxy)-phenyl]-6-(1-methyl-piperidin-4-yloxy)-pyridazine;
- 3-Butyl-4-[4-(2-cyclohexyl-ethoxy)-phenyl]-6-(1-methyl-piperidin-4-yloxy)-pyridazine;
- 5-(4-Benzyloxy-phenyl)-6-butyl-pyridazine-3-carboxylic acid (1-methyl-piperidin-4-ylmethyl)-amide;
- 6-Butyl-5-(4-cyclohexyloxy-phenyl)-pyridazine-3-carboxylic acid (1-methyl-piperidin-4-yl)-amide;
- 6-Butyl-5-(4-cyclohexyloxy-phenyl)-pyridazine-3-carboxylic acid (1-methyl-piperidin-4-ylmethyl)-amide;
- (±)-cis-6-Butyl-5-(4-cyclohexyloxy-phenyl)-pyridazine-3-carboxylic acid (3-methoxy-1-methyl-piperidin-4-ylmethyl)-amide;
- 6-Butyl-5-(4-cyclohexyloxy-phenyl)-pyridazine-3-carboxylic acid (3-methoxy-1-methyl-piperidin-4-yl)-amide;
- 6-Butyl-5-(4-cyclohexyloxy-phenyl)-pyridazine-3-carboxylic acid (4-fluoro-1-methyl-piperidin-4-ylmethyl)-amide;
- (±)-cis-6-Butyl-5-(4-cyclohexyloxy-phenyl)-pyridazine-3-carboxylic acid (3-fluoro-1-methyl-piperidin-4-ylmethyl)-amide; and
- (±)-cis-6-Butyl-5-(4-cyclohexyloxy-phenyl)-pyridazine-3-carboxylic acid (3-hydroxy-1-methyl-piperidin-4-yl)-amide;

or a pharmaceutically acceptable salt thereof.

3. The method of claim 1, wherein the compound is 4-(4-Benzyloxy-phenyl)-3-butyl-6-(1-methyl-piperidin-4-yloxy)-pyridazine or a pharmaceutically acceptable salt thereof.

4. The method of claim 1, wherein the compound is 4-(4-Benzyloxy-phenyl)-3-butyl-6-(1-methyl-piperidin-4-ylmethoxy)-pyridazine or a pharmaceutically acceptable salt thereof.

5. The method of claim 1, wherein the compound is 3-Butyl-4-(4-cyclohexyloxy-phenyl)-6-(1-methyl-piperidin-4-yloxy)-pyridazine or a pharmaceutically acceptable salt thereof.

6. The method of claim 1, wherein the compound is 3-Butyl-4-(4-cyclohexyloxy-phenyl)-6-(piperidin-4-yloxy)-pyridazine or a pharmaceutically acceptable salt thereof.

7. The method of claim 1, wherein the compound is 2-{4-[6-Butyl-5-(4-cyclohexyloxy-phenyl)-pyridazin-3-yloxy]-piperidin-1-yl}-ethanol or a pharmaceutically acceptable salt thereof.

8. The method of claim 1, wherein the compound is 5-(4-Benzyloxy-phenyl)-6-butyl-pyridazine-3-carboxylic acid (1-methyl-piperidin-4-yl)-amide or a pharmaceutically acceptable salt thereof.

* * * * *